(12) United States Patent
Siu et al.

(10) Patent No.: US 8,329,722 B2
(45) Date of Patent: *Dec. 11, 2012

(54) INHIBITORS OF JANUS KINASES AND/OR 3-PHOSPHOINOSITIDE-DEPENDENT PROTEIN KINASE-1

(75) Inventors: Tony Siu, Brookline, MA (US); Jonathan Young, Southborough, MA (US); Michael Altman, Cambridge, MA (US); Alan Northrup, Reading, MA (US); Ekaterina Kozina, Evanston, IL (US); Christopher Dinsmore, Newton, MA (US); David J. Guerin, Natick, MA (US); Kevin A. Keenan, Newton, MA (US); Joon O. Jung, Newton, MA (US); Solomon Kattar, Arlington, MA (US); Rachel N. MacCoss, Brookline, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 452 days.

This patent is subject to a terminal disclaimer.

(21) Appl. No.: 12/530,648

(22) PCT Filed: Mar. 10, 2008

(86) PCT No.: PCT/US2008/003206
§ 371 (c)(1),
(2), (4) Date: Sep. 10, 2009

(87) PCT Pub. No.: WO2008/112217
PCT Pub. Date: Sep. 18, 2008

(65) Prior Publication Data
US 2010/0160309 A1    Jun. 24, 2010

Related U.S. Application Data

(60) Provisional application No. 60/906,753, filed on Mar. 13, 2007.

(51) Int. Cl.
*C07D 487/14* (2006.01)
*A61K 31/4375* (2006.01)

(52) U.S. Cl. .......................................... 514/290; 546/80
(58) Field of Classification Search .................... 546/80; 514/290
See application file for complete search history.

(56) References Cited

U.S. PATENT DOCUMENTS

| 6,265,410 B1 | 7/2001 | Bridges et al. |
| 2004/0038979 A1 | 2/2004 | Schmidt |
| 2004/0209894 A1 | 10/2004 | Bold et al. |
| 2005/0153996 A1 | 7/2005 | Auerbach et al. |

FOREIGN PATENT DOCUMENTS

| WO | WO03/011285 | 2/2003 |
| WO | WO2005105814 | 11/2005 |
| WO | WO2007008502 | 1/2007 |

OTHER PUBLICATIONS

Dorwald F. A. Side Reactions in Organic Synthesis, 2005, Wiley: VCH, Weinheim p. IX of Preface.*
Freshney ( Culture of Animal Cells, A Manual of Basic Technique, Alan R. Liss, Inc., 1983, New York, p4.*
Dermer (Bio/Technology, 1994, 12:320.*
Kaushansky K. Hematology, 2005.*
Thompson, JE et al., Bioorganic & Medicinal Chemistry Letters, vol. 12, pp. 1219-1223 (2002), "Photochemical preparation of a pyridone containing tetracycle: A Jak protein kinase inhibitor".
Matsui, T et al., Journal of Medicinal Chemistry, vol. 35, No. 18, pp. 3307-3319 (1992), "Novel 5-HT3 antagonists. Isoquinolinones and 3-aryl-2-pyridones".

* cited by examiner

*Primary Examiner* — Rita Desai
(74) *Attorney, Agent, or Firm* — Laura M. Ginkel; David A. Muthard

(57) ABSTRACT

The instant invention provides for compounds that inhibit JAK2 tyrosine kinase and/or PDK1. The invention also provides for compositions comprising such inhibitory compounds and methods of inhibiting JAK2 tyrosine kinase activity and/or PDK1 kinase inhibitory activity by administering the compound to a patient in need of treatment or prevention of myeloproliferative disorders or cancer.

9 Claims, No Drawings

INHIBITORS OF JANUS KINASES AND/OR 3-PHOSPHOINOSITIDE-DEPENDENT PROTEIN KINASE-1

CROSS REFERENCE TO RELATED APPLICATIONS

This application is a U.S. National Phase application under 35 U.S.C. §371 of PCT Application No. PCT/US2008/003206 filed Mar. 10, 2008, which claims priority from U.S. Provisional Application Ser. No. 60/906,753, filed Mar. 13, 2007.

BACKGROUND OF THE INVENTION

Janus kinase (JAK) is a family of intracellular non-receptor tyrosine kinases, ranging from 120-140 kDa, that transduce cytokine-mediated signals via the JAK-STAT pathway. The JAK family plays a role in the cytokine-dependent regulation of proliferation and function of cells involved in immune response. Currently, there are four known mammalian JAK family members: JAK1, JAK2, JAK3 and TYK2.

JAK1, JAK2 and TYK2 are ubiquitously expressed whereas JAK3 is expressed in the myeloid and lymphoid lineages. The JAK family members are non-receptor tyrosine kinases that associate with many hematopoietin cytokines, receptor tyrosine kinases and GPCR's. JAK1−/− mice were found to be developmentally similar to the JAK1+/+ although they weighed 40% less than the wild-type and failed to nurse at birth. These pups were not viable and died within 24 hours of birth (Meraz et al Cell, 1998, 373-383). JAK1 deficiency led to reduced number of thymocytes, pre-B cells and mature T and B lymphocytes. TYK2(−/−) mice, on the other hand, are viable, demonstrating subtle defects in their response to IFN-α/β and IL-10 and profound defects to the response of IL-12 and LPS.

The breast cancer susceptibility protein (BRCA1) acts as a tumor suppressor and contributes to cell proliferation, cycle regulation, as well as DNA damage and repair. BRCA1 (−/−) mice develop normally but die by 7.5 days post embryo suggesting a key role of BRCA1 for development. Mice in which the BRCA1 protein was overexpressed led to inhibition of cell growth and sensitized cells to cytotoxic reagents. In the human prostate cancer cell line Du-145 (Gao FEBS Letters 2001, 488, 179-184), enhanced expression of BRCA1 was found to correlate with constitutive activation of STAT3 as well as activation of JAK1 and JAK2. Moreover, antisense oligonucleotides selective for STAT3 led to significant inhibition of cell proliferation and apoptosis in Du-145 cells. This data supports the potential utility of JAK1 and JAK2 inhibitors in the treatment of prostate cancer.

Campbell et al (Journal of Biological Chemistry 1997, 272, 2591-2594) as reported that STAT3 is constitutively activated v-Src transformed cells. To test whether STAT3 activation resulted via signaling through the JAK-STAT pathway, three fibroblast cell lines (NIH3T3, Balb/c, and 3Y1) were transformed with v-Src. The level of JAK1 phosphorylation in NIH3T3 cells was markedly increased in cells overexpressed with v-Src or mutant c-Src (Y527F) compared to those in the less transforming c-Src. This result correlated with increased JAK1 enzymatic activity. Similar results were observed with JAK2 albeit to a lesser extent. These results are consistent with constitutive activation of JAK1 and possibly JAK2 which contribute to the hyperactivation of STAT3 in Src-transformed cells.

Asthma is a disease that is increasing in prevalence and results in "airway obstruction, airway hyperresponsiveness, and airway inflammation and remodeling" (Pernis The Journal of Clinical Investigation 2002, 109, 1279-1283). A common cause is the inappropriate immune responses to environmental antigens usually involving CD4+ T helper cells (TH2) which are triggered from cytokines IL-4, IL-5, IL-6, IL-10, and IL-13 which signal through JAK1/JAK3-STAT6 pathway. Th1 cells are thought to be involved with the "delayed-type hypersensitivity responses" which secrete IL-2, IFN-γ, and TNF-β and signal through the JAK2/TYK2-STAT4 pathway. STAT6 (−/−) mice were protected from AHR when challenged with environmental antigens and showed no increase in IgE levels or the quantity of mucous containing cells.

JAK2 is a cytoplasmic protein-tyrosine kinase that catalyzes the transfer of the gamma-phosphate group of adenosine triphosphate to the hydroxyl groups of specific tyrosine residues in signal transduction molecules. JAK2 mediates signaling downstream of cytokine receptors after ligand-induced autophosphorylation of both receptor and enzyme. The main downstream effectors of JAK2 are a family of transcription factors known as signal transducers and activators of transcription (STAT) proteins. Studies have disclosed an association between an activating JAK2 mutation (JAK2V617F) and myeloproliferative disorders. The myeloproliferative disorders, a subgroup of myeloid malignancies, are clonal stem cell diseases characterized by an expansion of morphologically mature granulocyte, erythroid, megakaryocyte, or monocyte lineage cells. Myeloproliferative disorders (MPD) include polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), juvenile myelomonocytic leukemia (JMML) and systemic mast cell disease (SMCD). It has been suggested that abnormalities in signal transduction mechanisms, including constitutive activation of protein tyrosine kinases, initiate MPD.

JAK3 associates with the common gamma chain of the extracellular receptors for the following interleukins: IL-2, IL-4, IL-7, IL-9 and IL-15. A JAK3 deficiency is associated with an immune compromised (SCID) phenotype in both rodents and humans. The SCID phenotype of JAK3−/− mammals and the lymphoid cell specific expression of JAK3 are two favorable attributes of a target for an immune suppressant. Data suggests that inhibitors of JAK3 could impede T-cell activation and prevent rejection of grafts following transplant surgery, or to provide therapeutic benefit to patients suffering autoimmune disorders.

3-Phosphoinositide-dependent protein kinase-1 (PDK1) is a 556-amino acid containing enzyme comprised of a C-terminal Pleckstrin homology (PH) domain (residues 459-550) and an N-terminal kinase domain (residues 70-359). The PH domain of PDK1 binds phosphatidylinositols (e.g., phosphatidylinositol 4,5-bisphosphate and phosphatidylinositol 3,4,5-triphosphate) produced by phosphatidylinositol kinases, such as phosphatidylinositol 3-kinase (PI3K) and whose levels are, in part, controlled by phosphatases such as PTEN (phosphatase and tensin homologue). PDK1 plays a central role in the PI3K/Akt pathway and has been called a "master regulator" kinase due to its role as a critical upstream activating kinase that phosphorylates the so-called T-loop phosphorylation site for multiple kinases in the AGC family of kinases including but not limited to all three isoforms of PKB (PKBα, PKBβ, PKBγ, also known as Akt1, Akt2, and Akt3, respectively), RSK (three isoforms RSK1, RSK2, RSK3, also known as p90RSK), p70S6K (two isoforms, S6K1 and S61 (2), PKN (three isoforms PKN1, PKN2, and PKN3), SGK1 and PKC.

Signals from several peptide growth factors including insulin, insulin-like growth factor-1, vascular endothelial growth factor and platelet-derived growth factor are transduced by PKB. Like PDK1, PKB contains a PH domain that binds phosphatidyl 3,4,5-triphosphate. PKB is translocated to the plasma membrane and phosphorylated by PDK1 at residue T-308/309 (the two phosphosites correspond to different human isoforms) in response to the second messenger phosphatidyl 3,4,5-triphosphate produced by PI3K. Activation of PKB in tumor cells results in increased cellular survival via anti-apoptotic signals and also proliferation. PKBβ amplification has been observed in a proportion of several tumor types including ovarian, breast and pancreatic cancers. Similarly, PKBα amplification has been observed in a percentage of gastric adenocarcinoma samples. Recently, an activated mutant form of PKBα (E17K) was detected in a number of breast (8%), colorectal (6%), and ovarian (2%) cancers. PDK1 kinase inhibitors are useful as treatments for diseases linked to PKB signaling (such as cancer, Cowden syndrome, Lhermitte-Dudos disease and Bannayan-Zonana syndrome) by preventing activation of PKB signaling by PDK1.

Similarly, PDK1 kinase inhibitors are useful for treating cancer or other proliferative disorders by blocking the activation of p70S6K by PDK1. There are several substrates of p70S6K, such as ribosomal S6 protein, eIF4B, PDCD4 etc., that are involved in translation inhibition complex formation or ribosomal protein synthesis Inhibition of protein synthesis via inhibition of phosphorylation of ribosomal S6 protein is believed to inhibit the proliferation of tumor cells by mTOR inhibitors (e.g., rapamycin). p70S6K gene amplification has been observed in breast tumor specimens, simultaneous amplification of p70S6K and HER-2 correlates with poor survival in cancer patients. Hyperactivation of p70S6K (as measured by phosphorylation of T389) has been observed by immunohistochemical analysis of breast, head and neck squamous cell carcinoma (HNSCC), glioblastoma, lung and liver primary tumor specimens.

Likewise, PDK1 kinase inhibitors are useful for the treatment of cancer by blocking the activation of RSK1 (also known as p90RSK) by PDK1. RSK1 transduces anti-apoptotic and proliferative signals be mediating phosphorylation directly or indirectly of BAD, LKB1, TSC2, NFkB, mTOR. Ras/MAPK pathway is activated in >50% of primary tumors. RSK1 activity is correlated with MAPK activity. RSK1 is overexpressed in primary breast and prostate cancer samples.

PDK1 signaling regulates multiple critical steps in angiogenesis. Inhibitors of the activity of PDK1 are thus useful in the treatment of cancer (both primary tumors and metastases).

In particular, PDK1 is a key signaling molecule in cancers associated with deregulated activity of the PTEN/PI3K pathway including, but not limited to PTEN loss of function mutations, PI3K gain of function mutations and receptor tyrosine kinase gain of function mutations. Thus, inhibitors of PDK1 are especially useful in the treatment of cancers with aberrant signaling of the PTEN/PI3K pathway.

PDK1 signaling has also been implicated in tumorigenesis and a PDK1 inhibitor is useful for the tumor prevention or for the prevention of tumor recurrence. Mice with a PTEN heterozygous (PTEN$^{+/-}$) genotype are well-known to spontaneously develop tumors. Alessi and co-workers found that PDK1 hypomorphic PTEN$^{+/-}$ mice expressing <30% of normal PDK1 protein levels showed a significant delay in tumor formation as compared to littermate controls expressing normal levels of PDK1 protein (Current Biology, 2005, 15, 1839-1846)

SGK1 (serum and glucocorticoid-regulated kinase-1) activity is critical for insulin-mediated Na+ retention and hypertensive effects Inhibition of SGK1 activity by a PDK1 kinase inhibitor is useful in treating hypertension and/or hypoinsulinemia.

SUMMARY OF THE INVENTION

The instant invention provides for compounds that inhibit the four known mammalian JAK kinases (JAK1, JAK2, JAK3 and TYK2) and PDK1. The invention also provides for compositions comprising such inhibitory compounds and methods of inhibiting the activity of JAK1, JAK2, JAK3 TYK2 and PDK1 by administering the compound to a patient in need of treatment for myeloproliferative disorders or cancer. One embodiment of the invention is illustrated by a compound of the following formula, and the pharmaceutically acceptable salts and stereoisomers thereof:

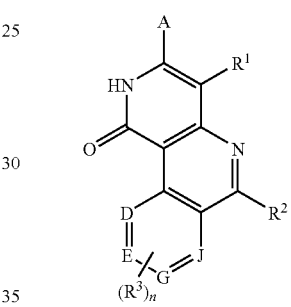

DETAILED DESCRIPTION OF THE INVENTION

The instant invention provides for compounds that inhibit the four known mammalian JAK kinases (JAK1, JAK2, JAK3 and TYK2) and PDK1. The invention also provides for compositions comprising such inhibitory compounds and methods of inhibiting the activity of JAK1, JAK2, JAK3, TYK2 and PDK1 by administering the compound to a patient in need of treatment for myeloproliferative disorders or cancer. One embodiment of the invention is illustrated by a compound of the formula

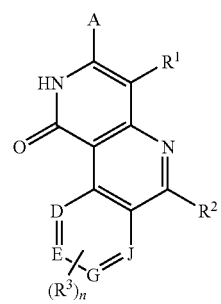

wherein D is CH, N, or NO;
E is CH, N, or NO;
G is CH, N, or NO;
J is CH, N, or NO;

$R^1$ is
- (a) hydrogen;
- (b) $C_{1-6}$ alkyl, which is optionally substituted with halo, hydroxyl, $C_{3-6}$ cycloalkyl, amino, phenyl, heterocyclyl, $C_{1-6}$ alkyl or $R^{10}$;
- (c) $C_{2-6}$ alkenyl, which is optionally substituted with halo, hydroxyl, amino, phenyl, heterocyclyl or $C_{1-6}$ alkyl;
- (d) $C_{2-6}$ alkynyl, which is optionally substituted with one to two substituents independently selected from halo, hydroxyl, amino, phenyl (which is optionally substituted with $C_{1-6}$ alkyl), heteroaryl (which is optionally substituted with $C_{1-6}$ alkyl or $O(C_{1-6}$ alkyl)), heterocyclyl, $C_{1-6}$ alkyl, $C_{3-6}$ cycloalkyl, $(C=O)NR^{13}R^{14}$, $NR^{13}R^{14}$ or $Si(CH_3)_3$;
- (e) $C_{3-10}$ cycloalkyl, which is optionally substituted with $C_{1-6}$ alkyl, $OR^{13}$, $NR^{13}R^{14}$, phenyl (which is optionally substituted with $C_{1-6}$ alkyl, $OR^{13}$ or $NR^{13}R^{14}$), halo, $R^{10}$ or heterocyclyl;
- (f) —$(C=O)R^{13}$;
- (g) —$(C=O)OR^{13}$;
- (h) —$SO_mR^{13}$;
- (i) —$(CO)NR^{13}NR^{14}$;
- (j) —$(C=O)NHR^{13}$;
- (k) —$(C=O)NR^{13}NHR^9$;
- (l) $C_{4-10}$ heterocyclyl, which is optionally substituted on either the carbon or the heteroatom with $C_{1-6}$ alkyl, halo, $R^{10}$, —$OR^{13}$, —$NR^{13}R^{14}$, phenyl (which is optionally substituted with $C_{1-6}$ alkyl, —$OR^{14}$ or —$NR^{13}R^{14}$), —$(C=O)R^9$ or —$(C=O)NR^{13}R^{14}$;
- (m) —$OR^{13}$;
- (n) —$NR^{13}R^{14}$;
- (o) —$NO_2$;
- (p) halo;
- (q) cyano;
- (r) Aryl, which is optionally substituted with one to three groups independently selected from $C_{1-6}$ alkyl (which is optionally substituted with one to three halo), $O(C_{1-6}$ alkyl), halo or $R^{10}$;
- (s) Heteroaryl, which is optionally substituted on either the carbon or the heteroatom with one to three groups independently selected from $C_{1-6}$ alkyl (which is optionally substituted with one to three halo), halo or $R^{10}$;
- (t) —$O(aryl)$, which is optionally substituted with one to three groups independently selected from $C_{1-6}$ alkyl, halo or $R^{10}$; or
- (u) —$O(C_{1-6}$ alkyl), which is optionally substituted with one to three groups independently selected from $C_{1-6}$ alkyl, halo or $R^{10}$;

$R^2$ is $NR^5R^6$, $CR^4R^6R^7$, $SR^5$, $OR^5$, $C_{2-6}$ alkenyl, $C_{3-6}$ cycloalkyl (which is optionally substituted with one or two halo), heteroaryl or heterocyclyl, wherein said heteroaryl or heterocyclyl groups are optionally substituted on either the carbon or the heteroatom with one to three substituents independently selected from $R^8$;

$R^3$ is
- (a) hydrogen;
- (b) $C_{1-6}$ alkyl, which is optionally substituted with halo, hydroxyl, amino, phenyl, heterocyclyl, $C_{1-6}$ alkyl or $R^{10}$;
- (c) $C_{2-6}$ alkenyl, which is optionally substituted with halo, hydroxyl, amino, phenyl, heterocyclyl or $C_{1-6}$ alkyl;
- (d) $C_{2-6}$ alkynyl, which is optionally substituted with one or two substituents independently selected from halo, hydroxyl, amino, phenyl (which is optionally substituted with $C_{1-6}$ alkyl), heterocyclyl, heteroaryl, $C_{1-6}$ alkyl or $Si(CH_3)_3$;
- (e) $C_{3-10}$ cycloalkyl, which is optionally substituted with $C_{1-6}$ alkyl, —$OR^{13}$, —$NR^{13}R^{14}$; phenyl (which is optionally substituted with $C_{1-6}$ alkyl, —$OR^{13}$ or —$NR^{13}R^{14}$), halo, $R^{10}$ or heterocyclyl;
- (f) —$(C=O)R^{11}$;
- (g) —$(C=O)NR^9R^{13}$;
- (h) —$(C=O)NHNH(C=O)R^{11}$;
- (i) $C_{4-10}$ heterocyclyl, which is optionally substituted on either the carbon or the heteroatom with $C_{1-6}$ alkyl, halo, $R^{10}$, —$OR^{13}$, —$NR^{13}R^{14}$, phenyl (which is optionally substituted with $C_{1-6}$ alkyl, $OR^{13}$ or $NR^{13}R^{14}$), —$(C=O)R^9$ or —$(C=O)NR^{13}R^{14}$;
- (j) —$OR^{13}$;
- (k) —$NH(C=O)R^{11}$;
- (l) halo;
- (m) Aryl, which is optionally substituted with one to three groups independently selected from $C_{1-6}$ alkyl (which is optionally substituted with one to three halo, cyano or heterocyclyl), halo, heterocyclyl, or $R^{10}$;
- (n) Heteroaryl, which is optionally substituted on either the carbon or the heteroatom with one to three groups independently selected from $C_{1-6}$ alkyl (which is optionally substituted with one to three halo or hydroxy), halo, heterocyclyl, $R^{10}$ or $R^{11}$;
- (o) —$O(aryl)$, which is optionally substituted with one to three groups independently selected from $C_{1-6}$ alkyl, halo or $R^{10}$;
- (p) —$O(C_{1-6}$ alkyl), which is optionally substituted with one to three groups independently selected from $C_{1-6}$ alkyl, halo or $R^{10}$;
- (q) —$SO_m(C_{1-6}$ alkyl); or
- (r) —$SO_m(aryl)$;

$R^4$ is
- (a) hydrogen;
- (b) $C_{1-6}$ alkyl, which is optionally substituted with halo, hydroxyl, amino, aryl or heterocyclyl;

$R^5$ is
- (a) hydrogen;
- (b) $C_{1-6}$ alkyl, which is optionally substituted with one to three substituents independently selected from halo, cyano, $C_{1-6}$ alkyl, $C_{3-10}$ cycloalkyl, $C_{1-6}$ haloalkyl, aryl, —$NR^{13}R^{14}$, $Si(CH_3)_3$, $SO_m(C_{1-6}$ alkyl), —$(C=O)OR^{13}$, $OR^{13}$ or hydroxyl;
- (c) $C_{3-10}$ cycloalkyl, which is optionally substituted with one to three substitutents independently selected from halo, aryl, $(C_{1-6}$ alkyl)OH or $C_{1-6}$ alkyl;
- (d) aryl, which is optionally substituted with one to three substituents independently selected from halo, $C_{1-6}$ alkyl, aryl, hydroxyl, $O(heteroaryl)$, $C_{1-6}$ haloalkyl or heteroaryl;
- (e) heteroaryl;
- (f) $(C_{1-6}$ alkyl)(aryl), which is optionally substituted on the alkyl and aryl groups with one to three substituents independently selected from halo, cyano, $C_{1-6}$ alkyl, $C_{1-6}$ haloalkyl, $C_{3-10}$ cycloalkyl or $O(C_{1-6}$ alkyl);
- (g) $(C_{1-6}$ alkyl)(heteroaryl), which is optionally substituted on the alkyl and heteroaryl groups with one to three substituents independently selected from halo, $C_{1-6}$ haloalkyl or $C_{1-6}$ alkyl;
- (h) $(C_{1-6}$ alkyl)(heterocyclyl);
- (i) —$SO_m(heterocyclyl)$;
- (j) —$SO_mNR^7R^{13}$;
- (k) heterocyclyl, which is optionally substituted with one to four substituents independently selected from halo, $R^7$, $(C_{1-6}$ alkyl)$R^7$, $(C=O)R^7$, $(C=O)OR^7$, $(C=O)NHR^7$, $(SO_m)R^9$
- (l) $C_{1-6}$ alkyl)($C_{3-10}$ cycloalkyl) which is optionally substituted on the alkyl with aryl;
- (m) $C_{1-6}$ alkyl$(C=O)OH$;

$R^6$ is
- (a) hydrogen;
- (b) $C_{1-8}$ alkyl, which is optionally substituted with one to three substituents independently selected from halo, hydroxyl, cyano, amino, aryl (which is optionally substituted with one to three halo), heteroaryl, cycloalkyl, heterocyclyl, $-SO_2NR^{13}R^{14}$ or $-NR^{13}R^{14}$;
- (c) $C_{3-10}$ cycloalkyl, which is optionally substituted with halo, $C_{1-6}$ alkyl, haloalkyl, $(C_{1-6}$ alkyl)aryl, $(C_{1-6}$ alkyl)$OR^9$, $-OR^{13}$, $-NR^{13}R^{14}$ or phenyl (which is optionally substituted with $C_{1-6}$ alkyl, $-OR^{13}$, $-NR^{13}R^{14}$, heterocyclyl, $-(CO)R^9$ or $-(CO)-NR^{13}R^{14}$);

$R^7$ is
- (a) hydrogen;
- (b) $C_{1-6}$ alkyl, which is optionally substituted with halo, cyano, hydroxyl, amino, aryl (which is optionally substituted with halo, $C_{1-6}$ alkyl, $O(C_{1-6}$ alkyl) or $NR^8R^9$), heterocyclyl, $C_{3-10}$ cycloalkyl, $C_{1-6}$ haloalkyl, $NH(C=O)R^{13}$, $SO_mNR^{13}R^{14}$ or $NR^{13}R^{14}$;
- (c) $C_{3-10}$ cycloalkyl, which is optionally substituted with one to three substituents independently selected from halo, hydroxyl, $C_{1-6}$ alkyl, $C_{1-6}$ haloalkyl, $-OR^4$, $-NR^8R^4$ or phenyl (which is optionally substituted with $C_{1-6}$ alkyl, $-OR^4$, $-NR^8R^4$, heterocyclyl, $-(CO)R^8$ or $-(CO)NR^8R^9$);
- (d) $C_{4-10}$ heterocyclyl which is optionally substituted on either the carbon or the heteroatom with one to three substituents independently selected from halo, $C_{1-6}$ alkyl, $-OR^{13}$, $-NR^{13}R^{14}$, phenyl (which is optionally substituted with $C_{1-6}$ alkyl, $-OR^{13}$, $-NR^{13}R^{14}$, heterocyclyl, $-(CO)R^9$ or $-(CO)-NR^{13}R^{14}$);
- (e) Aryl, which is optionally substituted with one to three substituents independently selected from halo, $NR^{13}R^{14}$ or $C_{1-6}$ haloalkyl;
- (f) Heteroaryl, which is optionally substituted on either the carbon or heteroatom with $NR^{13}R^{14}$;

$R^8$ is hydrogen, $C_{1-6}$ alkyl, $(C_{1-6}$ alkyl)aryl, $(C_{1-6}$ alkenyl)aryl, $(C_{1-6}$ alkyl)$OR^9$, $-OR^{13}$, $-NR^{13}R^{14}$, $-(CO)NR^{13}R^{14}$, heterocyclyl or phenyl (which is optionally substituted with $C_{1-6}$ alkyl, $-OR^{13}$, $-NR^{13}R^{14}$, heterocyclyl, $-(CO)R^9$ or $-(CO)-NR^{13}R^{14}$);

$R^9$ is hydrogen, $C_{1-6}$ alkyl, $(C_{1-6}$ alkyl)aryl, $(C_{1-6}$ alkyl)heterocyclyl, heteroaryl, heterocyclyl, $C_{3-6}$ cycloalkyl or $-NR^{13}NR^{14}$;

$R^{10}$ is:
- (a) hydrogen;
- (b) $-OR^{11}$,
- (c) $-O(C_{1-6}$ haloalkyl);
- (b) $-CO_2R^{11}$;
- (c) $-(C=O)R^{11}$;
- (d) $-NHR^{11}$;
- (e) $-NR^{11}R^{12}$;
- (f) $-NHS(O)_2R^{11}$;
- (g) $-NH(C=O)R^{11}$;
- (h) $-NH(C=O)OR^{11}$;
- (i) $-NH-C=(NH)NH_2$;
- (j) $-NH(C=O)NH_2$;
- (k) $-NH(C=O)NHR^{11}$;
- (l) $-NH(C=O)NR^{11}R^{12}$;
- (m) $-NHC_{3-6}$cycloalkyl;
- (n) $-(C=O)NHR^{11}$;
- (o) $-(C=O)NR^{11}R^{12}$;
- (p) $-SO_2NHR^{11}$;
- (q) $-SO_2NH(C=O)R^{12}$; or
- (r) $-SO_2R^{11}$;
- (s) heterocyclyl;

$R^{11}$ is selected from the group consisting of:
- (a) hydrogen,
- (b) $C_{3-6}$cycloalkyl, which is optionally substituted with aryl, heteroaryl or one to five halo;
- (c) $C_{1-6}$alkyl, which is optionally substituted with aryl, heteroaryl, heterocyclyl, cyano, $NR^{13}R^{14}$, $OR^{13}$ or one to five halo;
- (d) Aryl, which is optionally substituted with one to five halo;
- (e) Heteroaryl (wherein the heteroaryl has 5 or 6 members in which 1, 2, 3 or 4 of the atoms is a heteroatom selected from N, S and O), which is optionally substituted on either the carbon or the heteroatom with one to five halo;
- (f) Heterocyclyl, which is optionally substituted with $(C_{1-6}$alkyl)OH;

$R^{12}$ is selected from the group consisting of:
- (a) hydrogen,
- (b) $C_{1-6}$alkyl, which is optionally substituted with aryl, heteroaryl or one to five halo;
- (c) $C_{3-6}$cycloalkyl, which is optionally substituted with aryl, heteroaryl or one to five halo;
- (d) Aryl, which is optionally substituted with one to five halo;
- (e) Heteroaryl (wherein the heteroaryl has 5 or 6 members in which 1, 2 3 or 4 of the atoms is a heteroatom selected from N, S and O), which is optionally substituted on either the carbon or the heteroatom with one to five halo;

$R^{13}$ is hydrogen or $C_{1-6}$ alkyl;
$R^{14}$ is hydrogen or $C_{1-6}$ alkyl;

A is:
- (a) hydrogen;
- (b) $C_{1-6}$ alkyl, which is optionally substituted with halo, hydroxyl, amino, phenyl, heterocyclyl, $C_{1-6}$ alkyl or $R^{10}$;
- (c) $C_{2-6}$ alkenyl, which is optionally substituted with halo, hydroxyl, amino, phenyl, heterocyclyl, $C_{1-6}$ alkyl;
- (d) $C_{2-6}$ alkynyl, which is optionally substituted with halo, hydroxyl, amino, phenyl, heterocyclyl, $C_{1-6}$ alkyl or;
- (e) $C_{3-10}$ cycloalkyl, which is optionally substituted with $C_{1-6}$ alkyl, $OR^{13}$, $NR^{13}R^{14}$, phenyl (which is optionally substituted with $C_{1-6}$ alkyl, $OR^{13}$ or $NR^{13}R^{14}$), halo, $R^{10}$ or heterocyclyl;
- (f) $-(CO)R^9$;
- (g) $-(CO)NR^{13}R^{14}$;
- (h) $C_{4-10}$ heterocyclyl, which is optionally substituted on either the carbon or the heteroatom with $C_{1-6}$ alkyl, halo, $R^{10}$, $-OR^{13}$, $-NR^{13}R^{14}$, phenyl (which is optionally substituted with $C_{1-6}$ alkyl, $-OR^{13}$ or $-NR^{13}R^{14}$), $-(CO)R^9$ or $-(CO)NR^{13}R^{14}$;
- (i) $-OR^{13}$;
- (j) $-NR^{13}R^{14}$;
- (k) halo;
- (l) Aryl, which is optionally substituted with one to three groups independently selected from $C_{1-6}$ alkyl (which is optionally substituted with one to three halo), $O(C_{1-6}$ alkyl), halo or $R^{10}$;
- (m) Heteroaryl, which is optionally substituted on either the carbon or the heteroatom with one to three groups independently selected from $C_{1-6}$ alkyl (which is optionally substituted with one to three halo), halo or $R^{10}$;
- (n) $-O$(aryl), which is optionally substituted with one to three groups independently selected from $C_{1-6}$ alkyl, halo or $R^{10}$; or
- (o) $-O(C_{1-6}$ alkyl), which is optionally substituted with one to three groups independently selected from $C_{1-6}$ alkyl, halo or $R^{10}$;

m is 0, 1 or 2;
n is 0, 1, 2 or 3;
or a pharmaceutically acceptable salt or stereoisomer thereof.

An embodiment of the invention is illustrated by a compound of the formula

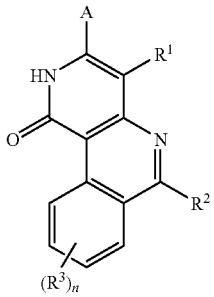

wherein all variables are as defined above.

An embodiment of the invention is illustrated by a compound of the formula

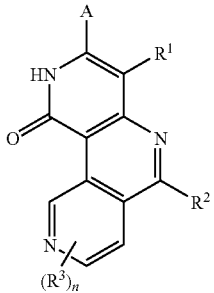

wherein all variables are as defined above.

In an embodiment of the invention, D is CH.

In an embodiment of the invention, E is CH. In an embodiment of the invention, E is N.

In an embodiment of the invention, G is CH.

In an embodiment of the invention, J is CH.

In an embodiment of the invention $R^1$ is
(a) hydrogen;
(b) halo;
(c) Aryl, which is optionally substituted with one to three groups independently selected from $C_{1-6}$ alkyl (which is optionally substituted with one to three halo), —O($C_{1-6}$ alkyl), halo or $R^{10}$;
(d) Heteroaryl, which is optionally substituted on either the carbon or the heteroatom with one to three groups independently selected from $C_{1-6}$ alkyl (which is optionally substituted with one to three halo), halo or $R^{10}$;

In a class of the invention, $R^1$ is Heteroaryl, which is optionally substituted on either the carbon or the heteroatom with one to three groups independently selected from $C_{1-6}$ alkyl (which is optionally substituted with one to three halo), halo or $R^{10}$. In a subclass of the invention, $R^1$ is Heteroaryl.

In another embodiment of the invention, $R^1$ is
(a) $C_{2-6}$ alkynyl, which is optionally substituted with one to two substituents independently selected from halo, hydroxyl, amino, phenyl (which is optionally substituted with $C_{1-6}$ alkyl), heteroaryl (which is optionally substitiuted with $C_{1-6}$ alkyl or O($C_{1-6}$ alkyl)), heterocyclyl, $C_{1-6}$ alkyl, $C_{3-6}$ cycloalkyl, (C=O)$NR^{13}R^{14}$, $NR^{13}R^{14}$ or Si(CH$_3$)$_3$;
(b) —(CO)$NR^{13}NR^9$;
(c) $C_{4-10}$ heterocyclyl, which is optionally substituted on either the carbon or the heteroatom with $C_{1-6}$ alkyl, halo, $R^{10}$, —OR$^{13}$, —NR$^{13}$R$^{14}$, phenyl (which is optionally substituted with $C_{1-6}$ alkyl, —OR$^{14}$ or —NR$^{13}$R$^{14}$), —(CO)R$^9$ or —(CO)NR$^{13}$R$^{14}$.

In an embodiment of the invention $R^2$ is —NR$^5$R$^6$.

In an embodiment of the invention $R^3$ is hydrogen; halo or heteroaryl, which is optionally substituted on either the carbon or the heteroatom with one to three groups independently selected from $C_{1-6}$ alkyl (which is optionally substituted with one to three halo), halo or $R^{10}$. In a class of the invention, $R^3$ is halo or heteroaryl, which is optionally substituted on either the carbon or the heteroatom with one to three groups independently selected from $C_{1-6}$ alkyl (which is optionally substituted with one to three halo), halo or $R^{10}$.

In an embodiment of the invention, $R^5$ is (a) $C_{1-6}$ alkyl, which is optionally substituted with one to three substituents independently selected from halo, $C_{1-6}$ alkyl, $C_{3-6}$ cycloalkyl, $C_{1-6}$ haloalkyl, aryl, —NR$^{13}$R$^{14}$ or hydroxyl; or (b) aryl, which is optionally substituted with one to three substituents independently selected from halo, $C_{1-6}$ alkyl, aryl, hydroxyl, —O(heteroaryl) or heteroaryl. In a class of the invention, $R^5$ is $C_{1-6}$ alkyl, which is substituted with one to three substituents independently selected from halo or $C_{1-6}$ haloalkyl. In a subclass of the invention, $R^5$ is $C_{1-6}$ alkyl, which is substituted with trifluoromethyl. In another subclass of the invention, $R^5$ is trifluoromethyl. In another class of the invention, $R^5$ is aryl, which is optionally substituted with one to three halo.

In an embodiment of the invention, A is hydrogen.

Reference to the preferred embodiments set forth above is meant to include all combinations of particular and preferred groups unless stated otherwise.

Specific embodiments of the present invention include, but are not limited to:

9-bromo-6-{[(1R)-2-methyl-1-(trifluoromethyl)propyl]amino}benzo[c]-1,6-naphthyridin-1(2H)-one;

6-[(2,6-difluorophenyl)amino]-9-fluorobenzo[c]-1,6-naphthyridin-1(2H)-one;

6-[(2,2-dimethylpropyl)amino]-9-fluorobenzo[c]-1,6-naphthyridin-1(2H)-one;

6-{[(1R)-2-methyl-1-(trifluoromethyl)propyl]amino}pyrido[4,3-c]-1,6-naphthyridin-1(2H)-one;

9-(1-methyl-1H-pyrazol-4-yl)-6-(pyridin-3-ylamino)benzo[c]-1,6-naphthyridin-1(2H)-one;

9-(1-methyl-1H-pyrazol-4-yl)-6-[(1,3-thiazol-2-ylmethyl)amino]benzo[c]-1,6-naphthyridin-1(2H)-one;

6-(cyclobutylamino)-9-fluorobenzo[c]-1,6-naphthyridin-1(2H)-one;

6-{[(1S)-1,2-dimethylpropyl]amino}-9-fluorobenzo[c]-1,6-naphthyridin-1(2H)-one;

6-{[(1R)-1,2-dimethylpropyl]amino}-9-fluorobenzo[c]-1,6-naphthyridin-1(2H)-one;

9-fluoro-6-[(1,2,2-trimethylpropyl)amino]benzo[c]-1,6-naphthyridin-1(2H)-one;

9-fluoro-6-(isopropylamino)benzo[c]-1,6-naphthyridin-1(2H)-one;

6-{[2-(dimethylamino)ethyl]amino}-9-fluorobenzo[c]-1,6-naphthyridin-1(2H)-one;

6-{[1-(2,4-dichloro-5-fluorophenyl)ethyl]amino}pyrido[4,3-c]-1,6-naphthyridin-1(2H)-one;

6-{[3-(dimethylamino)-2,2-dimethylpropyl]amino}-9-fluorobenzo[c]-1,6-naphthyridin-1(2H)-one;

9-fluoro-6-(isobutylamino)benzo[c]-1,6-naphthyridin-1(2H)-one;

6-[(2,6-dichlorobenzyl)amino]-9-fluorobenzo[c]-1,6-naphthyridin-1(2H)-one;

9-fluoro-6-[(3-hydroxy-2,2-dimethylpropyl)amino]benzo[c]-1,6-naphthyridin-1(2H)-one;

9-fluoro-6-[(pyridin-2-ylmethyl)amino]benzo[c]-1,6-naphthyridin-1(2H)-one;

9-fluoro-6-{[(3-fluoropyridin-2-yl)methyl]amino}benzo[c]-1,6-naphthyridin-1(2H)-one;

6-[(3,3-difluorocyclobutyl)amino]-9-fluorobenzo[c]-1,6-naphthyridin-1(2H)-one;

6-(cyclopropylamino)-9-fluorobenzo[c]-1,6-naphthyridin-1(2H)-one;

6-(cyclopropylamino)-9-bromobenzo[c]-1,6-naphthyridin-1(2H)-one;

9-fluoro-6-[isobutyl (3-morpholin-4-ylpropyl)amino]benzo[c]-1,6-naphthyridin-1(2H)-one;

9-fluoro-6-[(1,7,7-trimethylbicyclo[2.2.1]hept-2-yl)amino]benzo[c]-1,6-naphthyridin-1(2H)-one;

6-[(3,5-dimethylphenyl)amino]-9-fluorobenzo[c]-1,6-naphthyridin-1(2H)-one;

9-fluoro-6-[(1-methyl-2-pyridin-2-ylethyl)amino]benzo[c]-1,6-naphthyridin-1(2H)-one;

9-fluoro-6-{[(1S)-1-phenylethyl]amino}benzo[c]-1,6-naphthyridin-1(2H)-one;

6-[(2,2-difluoro-1-phenylethyl)amino]-9-fluorobenzo[c]-1,6-naphthyridin-1(2H)-one;

9-fluoro-6-[(3-fluorophenyl)amino]benzo[c]-1,6-naphthyridin-1(2H)-one;

9-fluoro-6-[(4-fluorophenyl)amino]benzo[c]-1,6-naphthyridin-1(2H)-one;

6-(biphenyl-2-ylamino)-9-fluorobenzo[c]-1,6-naphthyridin-1(2H)-one;

9-fluoro-6-{[1-(2-fluorophenyl)ethyl]amino}benzo[c]-1,6-naphthyridin-1(2H)-one;

6-{[1-(3,5-difluorophenyl)ethyl]amino}-9-fluorobenzo[c]-1,6-naphthyridin-1(2H)-one;

6-{[(3R)-1-benzylpiperidin-3-yl]amino}-9-fluorobenzo[c]-1,6-naphthyridin-1(2H)-one;

9-fluoro-6-[(2,2,6,6-tetramethylpiperidin-4-yl)amino]benzo[c]-1,6-naphthyridin-1(2H)-one;

9-fluoro-6-{[(1R)-1-phenylethyl]amino}benzo[c]-1,6-naphthyridin-1(2H)-one;

6-[(2-adamantylmethyl)amino]-9-fluorobenzo[c]-1,6-naphthyridin-1(2H)-one;

6-(biphenyl-3-ylamino)-9-fluorobenzo[c]-1,6-naphthyridin-1(2H)-one;

9-fluoro-6-{[(1R)-2,2,2-trifluoro-1-phenylethyl]amino}benzo[c]-1,6-naphthyridin-1(2H)-one;

9-fluoro-6-{[(1S)-2,2,2-trifluoro-1-phenylethyl]amino}benzo[c]-1,6-naphthyridin-1(2H)-one;

9-fluoro-6-[(4-methoxybenzyl)amino]benzo[c]-1,6-naphthyridin-1(2H)-one;

9-fluoro-6-{[1-(3-fluorophenyl)ethyl]amino}benzo[c]-1,6-naphthyridin-1(2H)-one;

9-fluoro-6-[(1-phenylcyclopropyl)amino]benzo[c]-1,6-naphthyridin-1(2H)-one;

6-[cyclopropyl(1-methylpiperidin-4-yl)amino]-9-fluorobenzo[c]-1,6-naphthyridin-1(2H)-one;

9-fluoro-6-{[1-(hydroxymethyl)cyclopropyl]amino}benzo[c]-1,6-naphthyridin-1(2H)-one;

9-fluoro-6-{[(1-phenylcyclopentyl)methyl]amino}benzo[c]-1,6-naphthyridin-1(2H)-one;

6-{[(1,1-dioxidotetrahydro-3-thienyl)methyl]amino}-9-fluorobenzo[c]-1,6-naphthyridin-1(2H)-one;

9-bromo-6-[(1,2,2-trimethylpropyl)amino]benzo[c]-1,6-naphthyridin-1(2H)-one;

9-fluoro-6-{[2-fluoro-6-(trifluoromethyl)phenyl]amino}benzo[c]-1,6-naphthyridin-1(2H)-one;

9-bromo-6-{[(1S)-1,2,2-trimethylpropyl]amino}benzo[c]-1,6-naphthyridin-1(2H)-one;

9-bromo-6-{[(1R)-1,2,2-trimethylpropyl]amino}benzo[c]-1,6-naphthyridin-1(2H)-one;

6-[(4-chloro-2,6-difluorophenyl)amino]-9-fluorobenzo[c]-1,6-naphthyridin-1(2H)-one;

9-bromo-6-[(pyridin-2-ylmethyl)amino]benzo[c]-1,6-naphthyridin-1(2H)-one;

9-bromo-6-(ethylamino)benzo[c]-1,6-naphthyridin-1(2H)-one;

6-anilino-9-bromobenzo[c]-1,6-naphthyridin-1(2H)-one;

6-{[(1R)-2-methyl-1-(trifluoromethyl)propyl]amino}pyrido[4,3-c]-1,6-naphthyridin-1(2H)-one;

6-{[1-(2-chlorophenyl)-2,2,2-trifluoroethyl]amino}pyrido[4,3-c]-1,6-naphthyridin-1(2H)-one;

9-chloro-6-[(1,2,2-trimethylpropyl)amino]benzo[c]-1,6-naphthyridin-1(2H)-one;

6-[(1,2,2-trimethylpropyl)amino]benzo[c]-1,6-naphthyridin-1(2H)-one;

9-chloro-6-{[(1R)-2-methyl-1-(trifluoromethyl)propyl]amino}benzo[c]-1,6-naphthyridin-1(2H)-one;

9-fluoro-6-{[(1S)-2-methyl-1-(trifluoromethyl)propyl]amino}benzo[c]-1,6-naphthyridin-1(2H)-one;

6-[(2-chloro-4,6-difluorophenyl)amino]-9-fluorobenzo[c]-1,6-naphthyridin-1(2H)-one;

6-[(2,6-dichlorophenyl)amino]-9-fluorobenzo[c]-1,6-naphthyridin-1(2H)-one;

6-{[(1R)-1-(2,6-dichlorophenyl)ethyl]amino}-9-fluorobenzo[c]-1,6-naphthyridin-1(2H)-one;

9-fluoro-6-{[(1R)-1-(2-naphthyl)ethyl]amino}benzo[c]-1,6-naphthyridin-1(2H)-one;

9-fluoro-6-{[2,2,2-trifluoro-1-(2-fluorophenyl)ethyl]amino}benzo[c]-1,6-naphthyridin-1(2H)-one;

9-fluoro-6-[(5-fluoro-2-hydroxyphenyl)amino]benzo[c]-1,6-naphthyridin-1(2H)-one;

9-fluoro-6-{[3-fluoro-5-(pyridin-3-yloxy)phenyl]amino}benzo[c]-1,6-naphthyridin-1(2H)-one;

9-fluoro-6-{[3-(1,3-thiazol-4-yl)phenyl]amino}benzo[c]-1,6-naphthyridin-1(2H)-one;

6-[(1,2,2-trimethylpropyl)amino]pyrido[4,3-c]-1,6-naphthyridin-1(2H)-one;

9-fluoro-6-{[(1R)-2-methyl-1-(trifluoromethyl)propyl]amino}benzo[c]-1,6-naphthyridin-1(2H)-one;

9-chloro-6-[(2,4,6-trifluorophenyl)amino]benzo[c]-1,6-naphthyridin-1(2H)-one;

6-[[3-(dimethylamino)propyl](pyridin-2-ylmethyl)amino]-9-fluorobenzo[c]-1,6-naphthyridin-1(2H)-one;

6-[(2,2,2-trifluoroethyl)amino]pyrido[4,3-c]-1,6-naphthyridin-1(2H)-one;

9-fluoro-6-[(2,2,2-trifluoro-1,1-dimethylethyl)amino]benzo[c]-1,6-naphthyridin-1(2H)-one;

9-chloro-6-[(2,4,6-trifluorophenyl)amino]benzo[c]-1,6-naphthyridin-1(2H)-one;

9-chloro-6-{[(1R)-2-methyl-1-(trifluoromethyl)propyl]amino}benzo[c]-1,6-naphthyridin-1(2H)-one;

9-fluoro-6-{[(trimethylsilyl)methyl]amino}benzo[c]-1,6-naphthyridin-1(2H)-one;

9-fluoro-6-{[2,2,2-trifluoro-1-(2-furyl)ethyl]amino}benzo[c]-1,6-naphthyridin-1(2H)-one;

trans-9-fluoro-6-[(3-methylpiperidin-4-yl)amino]benzo[c]-1,6-naphthyridin-1(2H)-one;

9-(1-methyl-1H-pyrazol-4-yl)-6-[(3S)-piperidin-3-ylamino]benzo[c]-1,6-naphthyridin-1(2H)-one;

9-(1-methyl-1H-pyrazol-4-yl)-6-[(3-thienylmethyl)amino]benzo[c]-1,6-naphthyridin-1(2H)-one;

9-(1-methyl-1H-pyrazol-4-yl)-6-[(pyridin-4-ylmethyl)amino]benzo[c]-1,6-naphthyridin-1(2H)-one;

6-{[(5-methylisoxazol-3-yl)methyl]amino}-9-(1-methyl-1H-pyrazol-4-yl)benzo[c]-1,6-naphthyridin-1(2H)-one;

9-(1-methyl-1H-pyrazol-4-yl)-6-[(pyridazin-3-ylmethyl) amino]benzo[c]-1,6-naphthyridin-1(2H)-one;
6-(benzylamino)-9-(1-methyl-1H-pyrazol-4-yl)benzo[c]-1, 6-naphthyridin-1(2H)-one;
9-(1-methyl-1H-pyrazol-4-yl)-6-[(pyridin-3-ylmethyl) amino]benzo[c]-1,6-naphthyridin-1(2H)-one;
6-[(2-furylmethyl)amino]-9-(1-methyl-1H-pyrazol-4-yl) benzo[c]-1,6-naphthyridin-1(2H)-one;
9-phenyl-6-[(pyridin-3-ylmethyl)amino]benzo[c]-1,6-naphthyridin-1(2H)-one;
9-(1-methyl-1H-pyrazol-4-yl)-6-[(pyridin-2-ylmethyl) amino]benzo[c]-1,6-naphthyridin-1(2H)-one;
9-(1-methyl-1H-pyrazol-4-yl)-6-[(2-pyridin-4-ylethyl) amino]benzo[c]-1,6-naphthyridin-1(2H)-one;
6-(ethylamino)-9-(1-methyl-1H-pyrazol-4-yl)benzo[c]-1,6-naphthyridin-1(2H)-one;
6-[(3-thienylmethyl)amino]pyrido[4,3-c]-1,6-naphthyridin-1(2H)-one;
6-[(3-hydroxypropy)amino]-9-(1-methyl-1H-pyrazol-4-yl) benzo[c]-1,6-naphthyridin-1(2H)-one;
9-(1-methyl-1H-pyrazol-4-yl)-6-(pyridin-2-ylamino)benzo [c]-1,6-naphthyridin-1(2H)-one;
6-[(1,3-thiazol-2-ylmethyl)amino]pyrido[4,3-c]-1,6-naphthyridin-1(2H)-one;
4-({[9-(1-methyl-1H-pyrazol-4-yl)-1-oxo-1,2-dihydrobenzo [c]-1,6-naphthyridin-6-yl]amino}methyl)benzonitrile;
9-phenyl-6-(pyridin-3-ylamino)benzo[c]-1,6-naphthyridin-1(2H)-one;
6-[(1,2,2-trimethylpropyl)amino]pyrido[4,3-c]-1,6-naphthyridin-1(2H)-one;
9-(1-methyl-1H-pyrazol-4-yl)-6-{[2-(methylsulfonyl)ethyl] amino}benzo[c]-1,6-naphthyridin-1(2H)-one;
9-(1-methyl-1H-pyrazol-4-yl)-6-(pyridin-4-ylamino)benzo [c]-1,6-naphthyridin-1(2H)-one;
9-(1-methyl-1H-pyrazol-4-yl)-6-{[(1-methyl-1H-pyrazol-4-yl)methyl]amino}benzo[c]-1,6-naphthyridin-1(2H)-one;
N-[9-(1-methyl-1H-pyrazol-4-yl)-1-oxo-1,2-dihydrobenzo [c]-1,6-naphthyridin-6-yl]-beta-alanine;
3-{[9-(1-methyl-1H-pyrazol-4-yl)-1-oxo-1,2-dihydrobenzo [c]-1,6-naphthyridin-6-yl]amino}propanenitrile;
6-[(pyridin-2-ylmethyl)amino]pyrido[4,3-c]-1,6-naphthyridin-1(2H)-one;
6-{[(5-methylisoxazol-3-yl)methyl]amino}pyrido[4,3-c]-1, 6-naphthyridin-1(2H)-one;
6-[(3-aminopropyl)amino]-9-(1-methyl-1H-pyrazol-4-yl) benzo[c]-1,6-naphthyridin-1(2H)-one;
tert-butyl (3S)-3-[(1-oxo-1,2-dihydropyrido[4,3-c]-1,6-naphthyridin-6-yl)amino]piperidine-1-carboxylate;
9-fluoro-6-[(pyridin-2-ylmethyl)amino]benzo[c]-1,6-naphthyridin-1(2H)-one;
9-bromo-6-{[(1R)-1,2,2-trimethylpropyl]amino}benzo[c]-1,6-naphthyridin-1(2H)-one;
9-bromo-6-[(1S)-1,2,2-trimethylpropyl]amino benzo[c]-1,6-naphthyridin-1(2H)-one;
6-[(2,4-dimethoxybenzyl)amino]-9-fluorobenzo[c]-1,6-naphthyridin-1(2H)-one;
tert-butyl trans-3-fluoro-4-[(9-fluoro-1-oxo-1,2-dihydrobenzo[c]-1,6-naphthyridin-6-yl)amino]piperidine-1-carboxylate;
9-bromo-6-{[(1-methyl-1H-pyrazol-3-yl)methyl] amino}benzo[c]-1,6-naphthyridin-1(2H)-one;
9-Bromo-6-[(3-methyl-3,1-imidazol-4-ylmethyl)-amino]-2H-benzo[c][1,6]naphthyridin-1-one;
9-Bromo-6-[(pyrimidin-2-ylmethyl)-amino]-2H-benzo[c] [1,6]naphthyridin-1-one;
9-Bromo-6-[(pyrazin-2-ylmethyl)-amino]-2H-benzo[c][1,6] naphthyridin-1-one;
9-Bromo-6-[(isoxazol-5-ylmethyl)-amino]-2H-benzo[c][1, 6]naphthyridin-1-one;
9-Bromo-6-[(2-methyl-2H-pyrazol-3-ylmethyl)-amino]-2H-benzo[c][1,6]naphthyridin-1-one;
9-Bromo-6-(1-pyridin-2-yl-ethylamino)-2H-benzo[c][1,6] naphthyridin-1-one;
9-Bromo-6-[(1H-pyrazol-3-ylmethyl)-amino]-2H-benzo[c] [1,6]naphthyridin-1-one;
9-Bromo-6-[(pyrimidin-5-ylmethyl)-amino]-2H-benzo[c] [1,6]naphthyridin-1-one;
9-Bromo-6-[(1-methyl-1H-imidazol-2-ylmethyl)-amino]-2H-benzo[c][1,6]naphthyridin-1-one;
6-(benzylamino)pyrido[4,3-c]-1,6-naphthyridin-1(2H)-one;
6-(methylamino)pyrido[4,3-c]-1,6-naphthyridin-1(2H)-one;
6-(dimethylamino)pyrido[4,3-c]-1,6-naphthyridin-1(2H)-one;
6-(benzylamino)pyrido[4,3-c]-1,6-naphthyridin-1(2H)-one;
6-{[(1R)-1,2,2-trimethylpropyl]amino}pyrido[4,3-c]-1,6-naphthyridin-1(2H)-one;
6-{[(1S)-1,2,2-trimethylpropyl]amino}pyrido[4,3-c]-1,6-naphthyridin-1(2H)-one;
3-{(3R)-3-[(9-fluoro-1-oxo-1,2-dihydrobenzo[c]-1,6-naphthyridin-6-yl)amino]piperidin-1-yl}-3-oxopropanenitrile;
3-{(3S)-3-[(9-fluoro-1-oxo-1,2-dihydrobenzo[c]-1,6-naphthyridin-6-yl)amino]piperidin-1-yl}-3-oxopropanenitrile;
9-fluoro-6-(piperidin-4-ylamino)benzo[c]-1,6-naphthyridin-1(2H)-one;
3-{4-[(9-fluoro-1-oxo-1,2-dihydrobenzo[c]-1,6-naphthyridin-6-yl)amino]piperidin-1-yl}-3-oxopropanenitrile;
3-{(3S,4S)-3-fluoro-4-[(9-fluoro-1-oxo-1,2-dihydrobenzo [c]-1,6-naphthyridin-6-yl)amino]piperidin-1-yl}-3-oxopropanenitrile;
9-fluoro-6-{[(3R,4S)-3-fluoropiperidin-4-yl]amino}benzo [c]-1,6-naphthyridin-1(2H)-one;
3-{(3R,4S)-3-fluoro-4-[(9-fluoro-1-oxo-1,2-dihydrobenzo [c]-1,6-naphthyridin-6-yl)amino]piperidin-1-yl}-3-oxopropanenitrile;
3-{(1R,5S)-6-[(9-fluoro-1-oxo-1,2-dihydrobenzo[c]-1,6-naphthyridin-6-yl)amino]-3-azabicyclo[3.1.0]hex-3-yl}-3-oxopropanenitrile;
6-({(3R)-1-[(2,4-difluorophenyl)acetyl]piperidin-3-yl}amino)-9-fluorobenzo[c]-1,6-naphthyridin-1(2H)-one;
6-(8-azabicyclo[3.2.1]oct-3-ylamino)-9-fluorobenzo[c]-1,6-naphthyridin-1(2H)-one;
9-fluoro-6-({(3R)-1-[(4-methylmorpholin-2-yl)carbonyl]piperidin-3-yl}amino)benzo[c]-1,6-naphthyridin-1(2H)-one;
4-{(3R)-3-[(9-fluoro-1-oxo-1,2-dihydrobenzo[c]-1,6-naphthyridin-6-yl)amino]piperidin-1-yl}-4-oxobutane-1-sulfonamide;
6-{[(3R)-1-(N,N-dimethyl-b-alanyl)piperidin-3-yl]amino}-9-fluorobenzo[c]-1,6-naphthyridin-1(2H)-one;
9-fluoro-6-({(3R)-1-[3-(2-oxopyrrolidin-1-yl)propanoyl]piperidin-3-yl}amino)benzo[c]-1,6-naphthyridin-1(2H)-one;
6-({(3R)-1-[(1,1-dioxidotetrahydro-3-thienyl)carbonyl]piperidin-3-yl}amino)-9-fluorobenzo[c]-1,6-naphthyridin-1 (2H)-one;
3-{3-[(9-fluoro-1-oxo-1,2-dihydrobenzo[c]-1,6-naphthyridin-6-yl)amino]-8-azabicyclo[3.2.1]oct-8-yl}-3-oxopropanenitrile;
9-fluoro-6-{[(3R)-1-(2-thienylcarbonyl)piperidin-3-yl]amino}benzo[c]-1,6-naphthyridin-1(2H)-one;
6-{[(3R)-1-(2,6-dichlorobenzoyl)piperidin-3-yl]amino}-9-fluorobenzo[c]-1,6-naphthyridin-1(2H)-one;
9-fluoro-6-({(3R)-1-[(1-hydroxycyclopropyl)carbonyl]piperidin-3-yl}amino)benzo[c]-1,6-naphthyridin-1(2H)-one;

9-fluoro-6-({(3R)-1-[(1-methylpiperidin-4-yl)carbonyl]piperidin-3-yl}amino)benzo[c]-1,6-naphthyridin-1(2H)-one;
6-({(3R)-1-[(5-amino-4H-1,2,4-triazol-3-yl)carbonyl]piperidin-3-yl}amino)-9-fluorobenzo[c]-1,6-naphthyridin-1(2H)-one;
6-({(3R)-1-[(4,4-difluorocyclohexyl)carbonyl]piperidin-3-yl}amino)-9-fluorobenzo[c]-1,6-naphthyridin-1(2H)-one;
9-fluoro-6-{[(3R)-1-(pyrimidin-4-ylcarbonyl)piperidin-3-yl]amino}benzo[c]-1,6-naphthyridin-1(2H)-one;
9-fluoro-6-[((3R)-1-{[1-(trifluoromethyl)cyclobutyl]carbonyl}piperidin-3-yl)amino]benzo[c]-1,6-naphthyridin-1(2H)-one;
9-fluoro-6-{[(3R)-1-(isoquinolin-8-ylcarbonyl)piperidin-3-yl]amino}benzo[c]-1,6-naphthyridin-1(2H)-one;
N-(3-{(3R)-3-[(9-fluoro-1-oxo-1,2-dihydrobenzo[c]-1,6-naphthyridin-6-yl)amino]piperidin-1-yl}-3-oxopropyl)acetamide;
9-fluoro-6-({(3R)-1-[(1-methyl-1H-pyrazol-4-yl)carbonyl]piperidin-3-yl}amino)benzo[c]-1,6-naphthyridin-1(2H)-one;
6-({(3R)-1-[(3,3-difluorocyclobutyl)carbonyl]piperidin-3-yl}amino)-9-fluorobenzo[c]-1,6-naphthyridin-1(2H)-one;
9-fluoro-6-{[(3R)-1-(tetrahydro-2H-pyran-4-ylcarbonyl)piperidin-3-yl]amino}benzo[c]-1,6-naphthyridin-1(2H)-one;
9-fluoro-6-({(3R)-1-[(5-oxopyrrolidin-3-yl)carbonyl]piperidin-3-yl)amino}benzo[c]-1,6-naphthyridin-1(2H)-one;
3-{(3R)-3-[(9-fluoro-1-oxo-1,2-dihydrobenzo[c]-1,6-naphthyridin-6-yl)amino]pyrrolidin-1-yl}-3-oxopropanenitrile;
6-{[(1R)-1,2-dimethylpropyl]amino}-9-fluoro-4-(3-thienyl)benzo[c]-1,6-naphthyridin-1(2H)-one;
9-fluoro-4-(1H-pyrazol-4-yl)-6-[(1,2,2-trimethylpropyl)amino]benzo[c]-1,6-naphthyridin-1(2H)-one;
9-fluoro-4-(4-methoxyphenyl)-6-[(1,2,2-trimethylpropyl)amino]benzo[c]-1,6-naphthyridin-1(2H)-one;
9-chloro-4-(1H-pyrazol-4-yl)-6-[(1,2,2-trimethylpropyl)amino]benzo[c]-1,6-naphthyridin-1(2H)-one;
9-chloro-4-(1H-indol-3-yl)-6-[(1,2,2-trimethylpropyl)amino]benzo[c]-1,6-naphthyridin-1(2H)-one;
9-chloro-4-(1-methyl-1H-pyrazol-4-yl)-6-[(1,2,2-trimethylpropyl)amino]benzo[c]-1,6-naphthyridin-1(2H)-one;
9-chloro-6-{[(1R)-2-methyl-1-(trifluoromethyl)propyl]amino}-4-(1H-pyrazol-4-yl)benzo[c]-1,6-naphthyridin-1(2H)-one;
6-[(1-cyclopropylethyl)amino]-9-fluoro-4-(1H-pyrazol-4-yl)benzo[c]-1,6-naphthyridin-1(2H)-one;
6-{[(1R)-2-methyl-1-(trifluoromethyl)propyl]amino}-9-(1H-pyrazol-5-yl)benzo[c]-1,6-naphthyridin-1(2H)-one;
6-(cyclopropylamino)-9-(1H-pyrazol-5-yl)benzo[c]-1,6-naphthyridin-1(2H)-one;
6-(cyclopropylamino)-9-phenylbenzo[c]-1,6-naphthyridin-1(2H)-one;
6-(cyclopropylamino)-9-(1-methyl-1H-pyrazol-4-yl)benzo[c]-1,6-naphthyridin-1(2H)-one;
6-(cyclopropylamino)-9-(1H-pyrazol-4-yl)benzo[c]-1,6-naphthyridin-1(2H)-one;
6-{[(1R)-2-methyl-1-(trifluoromethyl)propyl]amino}-9-(1H-pyrrol-2-yl)benzo[c]-1,6-naphthyridin-1(2H)-one;
N-(2-cyanoethyl)-4-(6-{[(1R)-2-methyl-1-(trifluoromethyl)propyl]amino}-1-oxo-1,2-dihydrobenzo[c]-1,6-naphthyridin-9-yl)benzamide;
9-(1H-pyrazol-4-yl)-6-[(1,2,2-trimethylpropyl)amino]benzo[c]-1,6-naphthyridin-1(2H)-one;
9-(1H-pyrazol-5-yl)-6-[(1,2,2-trimethylpropyl)amino]benzo[c]-1,6-naphthyridin-1(2H)-one;
9-(1H-indol-2-yl)-6-[(1,2,2-trimethylpropyl)amino]benzo[c]-1,6-naphthyridin-1(2H)-one;
9-(1-methyl-1H-pyrazol-4-yl)-6-[(1,2,2-trimethylpropyl)amino]benzo[c]-1,6-naphthyridin-1(2H)-one;
N-[2-(dimethylamino)ethyl]-4-(6-{[(1R)-2-methyl-1-(trifluoromethyl)propyl]amino}-1-oxo-1,2-dihydrobenzo[c]-1,6-naphthyridin-9-yl)benzamide;
4-(6-{[(1R)-2-methyl-1-(trifluoromethyl)propyl]amino}-1-oxo-1,2-dihydrobenzo[c]-1,6-naphthyridin-9-yl)-N-(2-morpholin-4-ylethyl)benzamide
6-{[(1R)-2-methyl-1-(trifluoromethyl)propyl]amino}-9-(1H-pyrazol-5-yl)benzo[c]-1,6-naphthyridin-1(2H)-one;
N-(2-methoxyethyl)-4-(6-{[(1R)-2-methyl-1-(trifluoromethyl)propyl]amino}-1-oxo-1,2-dihydrobenzo[c]-1,6-naphthyridin-9-yl)benzamide;
N-(2-cyanoethyl)-4-(6-{[(1R)-2-methyl-1-(trifluoromethyl)propyl]amino}-1-oxo-1,2-dihydrobenzo[c]-1,6-naphthyridin-9-yl)benzamide;
N-[2-(dimethylamino)ethyl]-3-(6-{[(1R)-2-methyl-1-(trifluoromethyl)propyl]amino}-1-oxo-1,2-dihydrobenzo[c]-1,6-naphthyridin-9-yl)benzamide;
9-(4-{[4-(2-hydroxyethyl)piperazin-1-yl]carbonyl}phenyl)-6-{[(1R)-2-methyl-1-(trifluoromethyl)propyl]amino}benzo[c]-1,6-naphthyridin-1(2H)-one;
6-{[(1R)-2-methyl-1-(trifluoromethyl)propyl]amino}-9-(4-morpholin-4-ylphenyl)benzo[c]-1,6-naphthyridin-1(2H)-one;
9-[6-(hydroxymethyl)pyridin-3-yl]-6-{[(1R)-2-methyl-1-(trifluoromethyl)propyl]amino}benzo[c]-1,6-naphthyridin-1(2H)-one;
9-imidazo[1,2-a]pyridin-6-yl-6-{[(1R)-2-methyl-1-(trifluoromethyl)propyl]amino}benzo[c]-1,6-naphthyridin-1(2H)-one;
2-fluoro-N-(2-hydroxyethyl)-5-(6-{[(1R)-2-methyl-1-(trifluoromethyl)propyl]amino}-1-oxo-1,2-dihydrobenzo[c]-1,6-naphthyridin-9-yl)benzamide;
6-{[(1R)-2-methyl-1-(trifluoromethyl)propyl]amino}-9-[4-(morpholin-4-ylsulfonyl)phenyl]benzo[c]-1,6-naphthyridin-1(2H)-one;
9-[4-fluoro-3-(morpholin-4-ylcarbonyl)phenyl]-6-{[(1R)-2-methyl-1-(trifluoromethyl)propyl]amino}benzo[c]-1,6-naphthyridin-1(2H)-one;
6-{[(1R)-2-methyl-1-(trifluoromethyl)propyl]amino}-9-(6-morpholin-4-ylpyridin-3-yl)benzo[c]-1,6-naphthyridin-1(2H)-one;
6-{[(1R)-2-methyl-1-(trifluoromethyl)propyl]amino}-9-[4-(morpholin-4-ylcarbonyl)phenyl]benzo[c]-1,6-naphthyridin-1(2H)-one;
9-bromo-4-nitro-6-[(1,2,2-trimethylpropyl)amino]benzo[c]-1,6-naphthyridin-1(2H)-one;
4-iodo-6-[(1,2,2-trimethylpropyl)amino]pyrido[4,3-c]-1,6-naphthyridin-1(2H)-one;
9-bromo-6-[(2-chloro-4,6-difluorophenyl)amino]-4-iodobenzo[c]-1,6-naphthyridin-1(2H)-one;
9-bromo-4-iodo-6-[(1,2,2-trimethylpropyl)amino]benzo[c]-1,6-naphthyridin-1(2H)-one;
9-bromo-4-iodo-6-{[(1S)-1,2,2-trimethylpropyl]amino}benzo[c]-1,6-naphthyridin-1(2H)-one;
9-bromo-4-iodo-6-{[(1R)-1,2,2-trimethylpropyl]amino}benzo[c]-1,6-naphthyridin-1(2H)-one;
9-bromo-4-iodo-6-[(3S)-piperidin-3-ylamino]benzo[c]-1,6-naphthyridin-1(2H)-one;
9-bromo-4-iodo-6-{[(5-methylisoxazol-3-yl)methyl]amino}benzo[c]-1,6-naphthyridin-1(2H)-one;
9-bromo-6-(ethylamino)-4-iodobenzo[c]-1,6-naphthyridin-1(2H)-one;

9-bromo-4-iodo-6-[(pyridazin-3-ylmethyl)amino]benzo[c]-1,6-naphthyridin-1(2H)-one;
9-bromo-4-iodo-6-[(pyridin-2-ylmethyl)amino]benzo[c]-1,6-naphthyridin-1(2H)-one;
4-iodo-6-[(1,3-thiazol-2-ylmethyl)amino]pyrido[4,3-c]-1,6-naphthyridin-1(2H)-one;
4-iodo-6-[(2,2,2-trifluoroethyl)amino]pyrido[4,3-c]-1,6-naphthyridin-1(2H)-one;
4-iodo-6-{[(5-methylisoxazol-3-yl)methyl]amino}pyrido[4,3-c]-1,6-naphthyridin-1(2H)-one;
tert-butyl (3S)-3-[(4-iodo-1-oxo-1,2-dihydropyrido[4,3-c]-1,6-naphthyridin-6-yl)amino]piperidine-1-carboxylate;
4-iodo-6-[(pyridin-2-ylmethyl)amino]pyrido[4,3-c]-1,6-naphthyridin-1(2H)-one;
tert-butyl trans-3-fluoro-4-[(9-fluoro-4-iodo-1-oxo-1,2-dihydrobenzo[c]-1,6-naphthyridin-6-yl)amino]piperidine-1-carboxylate;
9-bromo-4-iodo-6-{[(3S)-1-(4-(dimethylamino)benzyl)piperidin-3-yl]amino}-benzo[c]-1,6-naphthyridin-1(2H)-one;
9-bromo-4-iodo-6-{[(3S)-1-(4-(trifluoromethyl)benzyl)piperidin-3-yl]amino}-benzo[c]-1,6-naphthyridin-1(2H)-one;
9-bromo-4-iodo-6-{[(3S)-1-(propyl)piperidin-3-yl]amino}-benzo[c]-1,6-naphthyridin-1(2H)-one;
9-bromo-4-iodo-6-{[(3S)-1-(methylnaphthyridinyl)piperidin-3-yl]amino}-benzo[c]-1,6-naphthyridin-1(2H)-one;
9-bromo-4-iodo-6-{[(3S)-1-(methylcyclohexyl)piperidin-3-yl]amino}-benzo[c]-1,6-naphthyridin-1(2H)-one;
9-bromo-4-iodo-6-{[(3S)-1-(ethyl)piperidin-3-ylcarbonyl]amino}-benzo[c]-1,6-naphthyridin-1(2H)-one;
9-bromo-4-iodo-6-{[(3S)-1-(4-(dimethylamino)phenyl)piperidin-3-ylcarbonyl]amino}-benzo[c]-1,6-naphthyridin-1(2H)-one;
9-bromo-4-iodo-6-{[(3S)-1-(3-(4-isopropylphenyl)ethyl)piperidin-3-ylcarbonyl]amino}-benzo[c]-1,6-naphthyridin-1(2H)-one;
9-bromo-4-iodo-6-{[(3S)-1-(2-pyridyl)piperidin-3-ylcarbonyl]amino}-benzo[c]-1,6-naphthyridin-1(2H)-one;
9-bromo-4-iodo-6-{[(3S)-1-(methyl)piperidin-3-ylcarbonyl]amino}-benzo[c]-1,6-naphthyridin-1(2H)-one;
9-bromo-4-iodo-6-{[(3S)-1-(methanesulfonyl)piperidin-3-yl]amino}-benzo[c]-1,6-naphthyridin-1(2H)-one;
9-bromo-4-iodo-6-{[(3S)-1-(ethanesulfonyl)piperidin-3-yl]amino}-benzo[c]-1,6-naphthyridin-1(2H)-one;
9-bromo-4-iodo-6-{[(3S)-1-(cyclopropylsulfonyl)piperidin-3-yl]amino}-benzo[c]-1,6-naphthyridin-1(2H)-one;
9-bromo-4-iodo-6-{[(3S)-1-(2-(thiophenylsulfonyl))piperidin-3-yl]amino}-benzo[c]-1,6-naphthyridin-1(2H)-one;
9-bromo-4-iodo-6-{[(3S)-1-(propylamino)piperidin-3-ylcarbonyl]amino}-benzo[c]-1,6-naphthyridin-1(2H)-one;
9-bromo-4-iodo-6-{[(3S)-1-(tert-butylamino)piperidin-3-ylcarbonyl]amino}-benzo[c]-1,6-naphthyridin-1(2H)-one;
9-bromo-4-iodo-6-{[(3S)-1-(4-fluorophenyl)piperidin-3-ylcarbonyl]amino}-benzo[c]-1,6-naphthyridin-1(2H)-one;
9-bromo-4-iodo-6-{[(3S)-1-(4-methoxybenzyl)piperidin-3-ylcarbonyl]amino}-benzo[c]-1,6-naphthyridin-1(2H)-one;
9-bromo-4-iodo-6-{[(3S)-1-(methyl)piperidin-3-ylcarboxylate]amino}-benzo[c]-1,6-naphthyridin-1(2H)-one;
9-bromo-4-iodo-6-{[(3S)-1-(ethyl)piperidin-3-ylcarboxylate]amino}-benzo[c]-1,6-naphthyridin-1(2H)-one;
9-bromo-4-iodo-6-{[(3S)-1-(phenyl)piperidin-3-ylcarboxylate]amino}-benzo[c]-1,6-naphthyridin-1(2H)-one;
9-bromo-4-iodo-6-{[(3S)-1-(isobutyl)piperidin-3-ylcarboxylate]amino}-benzo[c]-1,6-naphthyridin-1(2H)-one;
9-bromo-1-oxo-6-[(1,2,2-trimethylpropyl)amino]-1,2-dihydrobenzo[c]-1,6-naphthyridine-4-carbonitrile;
9-bromo-4-(methylsulfonyl)-6-[(1,2,2-trimethylpropyl)amino]benzo[c]-1,6-naphthyridin-1(2H)-one;
9-bromo-4-nitro-6-[(1,2,2-trimethylpropyl)amino]benzo[c]-1,6-naphthyridin-1(2H)-one;
9-bromo-4-[cyclopropyl(hydroxy)methyl]-6-[(1,2,2-trimethylpropyl)amino]benzo[c]-1,6-naphthyridin-1(2H)-one;
9-bromo-4-[cyclopropyl(hydroxy)methyl]-6-[(1,2,2-trimethylpropyl)amino]benzo[c]-1,6-naphthyridin-1(2H)-one;
3-[9-bromo-6-(ethylamino)-1-oxo-1,2-dihydrobenzo[c]-1,6-naphthyridin-4-yl]prop-2-ynamide;
9-bromo-4-(cyclopropylethynyl)-6-[(1,2,2-trimethylpropyl)amino]benzo[c]-1,6-naphthyridin-1(2H)-one;
9-bromo-4-(cyclopropylethynyl)-6-[(3S)-piperidin-3-ylamino]benzo[c]-1,6-naphthyridin-1(2H)-one;
9-bromo-4-(3-hydroxylprop-1-yn-1-yl)-6-[(3S)-piperidin-3-ylamino]benzo[c]-1,6-naphthyridin-1(2H)-one;
3-{9-bromo-1-oxo-6-[(3S)-piperidin-3-ylamino]-1,2-dihydrobenzo[c]-1,6-naphthyridin-4-yl}prop-2-ynamide;
9-bromo-4-[(3S)-3-hydroxybut-1-yn-1-yl]-6-[(3S)-piperidin-3-ylamino]benzo[c]-1,6-naphthyridin-1(2H)-one;
9-bromo-4-[(3R)-3-hydroxybut-1-yn-1-yl]-6-[(3S)-piperidin-3-ylamino]benzo[c]-1,6-naphthyridin-1(2H)-one;
9-bromo-6-[(3S)-piperidin-3-ylamino]-4-(pyridin-4-ylethynyl)benzo[c]-1,6-naphthyridin-1(2H)-one;
3-[9-bromo-6-(ethylamino)-1-oxo-1,2-dihydrobenzo[c]-1,6-naphthyridin-4-yl]prop-2-ynamide;
9-bromo-6-[(5-methylisoxazol-3-yl)methyl]amino-4-(pyridin-2-ylethynyl)benzo[c]-1,6-naphthyridin-1(2H)-one;
9-bromo-4-(cyclopropylethynyl)-6-{[(3S)-1-(methylsulfonyl)piperidin-3-yl]amino}benzo[c]-1,6-naphthyridin-1(2H)-one;
9-bromo-4-[(3R)-3-hydroxybut-1-yn-1-yl]-6-{[(5-methylisoxazol-3-yl)methyl]amino}benzo[c]-1,6-naphthyridin-1(2H)-one;
9-bromo-6-[(3S)-piperidin-3-ylamino]-4-(pyridin-2-ylethynyl)benzo[c]-1,6-naphthyridin-1(2H)-one;
9-bromo-4-[(1-methyl-1H-imidazol-5-yl)ethynyl]-6-{[(5-methylisoxazol-3-yl)methyl]amino}benzo[c]-1,6-naphthyridin-1(2H)-one;
9-bromo-6-{[(5-methylisoxazol-3-yl)methyl]amino}-4-(pyridin-3-ylethynyl)benzo[c]-1,6-naphthyridin-1(2H)-one;
9-bromo-4-[(3S)-3-hydroxybut-1-yn-1-yl]-6-{[(5-methylisoxazol-3-yl)methyl]amino}benzo[c]-1,6-naphthyridin-1(2H)-one;
9-bromo-6-{[(3S)-1-(methylsulfonyl)piperidin-3-yl]amino}-4-(pyridin-3-ylethynyl)benzo[c]-1,6-naphthyridin-1(2H)-one;
9-bromo-6-{[(3S)-1-(methylsulfonyl)piperidin-3-yl]amino}-4-(pyridin-4-ylethynyl)benzo[c]-1,6-naphthyridin-1(2H)-one;
9-bromo-6-{[(3S)-1-(methylsulfonyl)piperidin-3-yl]amino}-4-(pyridin-2-ylethynyl)benzo[c]-1,6-naphthyridin-1(2H)-one;
9-bromo-6-[(2-chloro-4,6-difluorophenyl)amino]-4-(cyclopropylethynyl)benzo[c]-1,6-naphthyridin-1(2H)-one;
9-bromo-6-[(2-chloro-4,6-difluorophenyl)amino]-4-(pyridin-3-ylethynyl)benzo[c]-1,6-naphthyridin-1(2H)-one;
9-bromo-6-[(2-chloro-4,6-difluorophenyl)amino]-4-(phenylethynyl)benzo[c]-1,6-naphthyridin-1(2H)-one;
9-bromo-6-[(2-chloro-4,6-difluorophenyl)amino]-4-[(trimethylsilyl)ethynyl]benzo[c]-1,6-naphthyridin-1(2H)-one;
6-[(2-chloro-4,6-difluorophenyl)amino]-4,9-bis[(trimethylsilyl)ethynyl]benzo[c]-1,6-naphthyridin-1(2H)-one;

9-bromo-6-[(2-chloro-4,6-difluorophenyl)amino]-4-[(trimethylsilyl)ethynyl]benzo[c]-1,6-naphthyridin-1(2H)-one;
9-bromo-4-(pyridin-3-ylethynyl)-6-[(1,2,2-trimethylpropyl)amino]benzo[c]-1,6-naphthyridin-1(2H)-one;
9-bromo-4-(pyridin-4-ylethynyl)-6-[(1,2,2-trimethylpropyl)amino]benzo[c]-1,6-naphthyridin-1(2H)-one;
9-bromo-4-(pyridin-2-ylethynyl)-6-[(1,2,2-trimethylpropyl)amino]benzo[c]-1,6-naphthyridin-1(2H)-one;
9-bromo-4-(3-hydroxyprop-1-yn-1-yl)-6-[(1,2,2-trimethylpropyl)amino]benzo[c]-1,6-naphthyridin-1(2H)-one;
4,9-bis(3-hydroxyprop-1-yn-1-yl)-6-[(1,2,2-trimethylpropyl)amino]benzo[c]-1,6-naphthyridin-1(2H)-one;
4-(3-aminoprop-1-yn-1-yl)-9-bromo-6-[(1,2,2-trimethylpropyl)amino]benzo[c]-1,6-naphthyridin-1(2H)-one;
9-bromo-4-(cyclohex-1-en-1-ylethynyl)-6-[(1,2,2-trimethylpropyl)amino]benzo[c]-1,6-naphthyridin-1(2H)-one;
9-bromo-4-[(4-methoxyphenyl)ethynyl]-6-[(1,2,2-trimethylpropyl)amino]benzo[c]-1,6-naphthyridin-1(2H)-one;
9-bromo-4-[(3-methylphenyl)ethynyl]-6-[(1,2,2-trimethylpropyl)amino]benzo[c]-1,6-naphthyridin-1(2H)-one;
4,9-bis(3-methylbut-1-yn-1-yl)-6-[(1,2,2-trimethylpropyl)amino]benzo[c]-1,6-naphthyridin-1(2H)-one;
4,9-bis(cyclohex-1-en-1-ylethynyl)-6-[(1,2,2-trimethylpropyl)amino]benzo[c]-1,6-naphthyridin-1(2H)-one;
9-bromo-4-(cyclohexylethynyl)-6-[(1,2,2-trimethylpropyl)amino]benzo[c]-1,6-naphthyridin-1(2H)-one;
4,9-bis(3,3-dimethylbut-1-yn-1-yl)-6-[(1,2,2-trimethylpropyl)amino]benzo[c]-1,6-naphthyridin-1(2H)-one;
9-bromo-4-(3,3-dimethylbut-1-yn-1-yl)-6-[(1,2,2-trimethylpropyl)amino]benzo[c]-1,6-naphthyridin-1(2H)-one;
9-bromo-4-[(2-methylphenyl)ethynyl]-6-[(1,2,2-trimethylpropyl)amino]benzo[c]-1,6-naphthyridin-1(2H)-one;
4,9-bis(4-methylpent-1-yn-1-yl)-6-[(1,2,2-trimethylpropyl)amino]benzo[c]-1,6-naphthyridin-1(2H)-one;
9-bromo-4-(3,3-dimethylbut-1-yn-1-yl)-6-[(1,2,2-trimethylpropyl)amino]benzo[c]-1,6-naphthyridin-1(2H)-one;
4,9-bis[(3-methylphenyl)ethynyl]-6-[(1,2,2-trimethylpropyl)amino]benzo[c]-1,6-naphthyridin-1(2H)-one;
9-bromo-4-[(1-methyl-1H-imidazol-2-yl)ethynyl]-6-[(1,2,2-trimethylpropyl)amino]benzo[c]-1,6-naphthyridin-1(2H)-one;
9-bromo-4-[(3S)-3-hydroxybut-1-yn-1-yl]-6-[(1,2,2-trimethylpropyl)amino]benzo[c]-1,6-naphthyridin-1(2H)-one;
9-bromo-4-[(3R)-3-hydroxybut-1-yn-1-yl]-6-[(1,2,2-trimethylpropyl)amino]benzo[c]-1,6-naphthyridin-1(2H)-one;
9-[(3R)-3-hydroxybut-1-yn-1-yl]-4-[(3S)-3-hydroxybut-1-yn-1-yl]-6-[(1,2,2-trimethylpropyl)amino]benzo[c]-1,6-naphthyridin-1(2H)-one;
9-bromo-4-[(3S)-3-hydroxy-3-phenylprop-1-yn-1-yl]-6-[(1,2,2-trimethylpropyl)amino]benzo[c]-1,6-naphthyridin-1(2H)-one;
9-bromo-4-[(3R)-3-hydroxy-3-phenylprop-1-yn-1-yl]-6-[(1,2,2-trimethylpropyl)amino]benzo[c]-1,6-naphthyridin-1(2H)-one;
9-bromo-4-(3-hydroxy-3-methylbut-1-yn-1-yl)-6-[(1,2,2-trimethylpropyl)amino]benzo[c]-1,6-naphthyridin-1(2H)-one;
4,9-bis(3-hydroxy-3-methylbut-1-yn-1-yl)-6-[(1,2,2-trimethylpropyl)amino]benzo[c]-1,6-naphthyridin-1(2H)-one;
3-{9-bromo-1-oxo-6-[(pyridin-2-ylmethyl)amino]-1,2-dihydrobenzo[c]-1,6-naphthyridin-4-yl}prop-2-ynamide;
9-bromo-4-(cyclopropylethynyl)-6-[(pyridin-2-ylmethyl)amino]benzo[c]-1,6-naphthyridin-1(2H)-one;
4-(pyridin-3-ylethynyl)-6-[(2,2,2-trifluoroethyl)amino]pyrido[4,3-c]-1,6-naphthyridin-1(2H)-one;
4-(pyridin-3-ylethynyl)-6-[(1,2,2-trimethylpropyl)amino]pyrido[4,3-c]-1,6-naphthyridin-1(2H)-one;
9-bromo-4-(cyclopropylethynyl)-6-[(pyridazin-3-ylmethyl)amino]benzo[c]-1,6-naphthyridin-1(2H)-one;
4-(cyclopropylethynyl)-6-[(1,2,2-trimethylpropyl)amino]pyrido[4,3-c]-1,6-naphthyridin-1(2H)-one;
4-(cyclopropylethynyl)-6-[(2,2,2-trifluoroethyl)amino]pyrido[4,3-c]-1,6-naphthyridin-1(2H)-one;
tert-butyl (3S)-3-{[4-(cyclopropylethynyl)-1-oxo-1,2-dihydropyrido[4,3-c]-1,6-naphthyridin-6-yl]amino}piperidine-1-carboxylate;
4-(cyclopropylethynyl)-6-{[(5-methylisoxazol-3-yl)methyl]amino}pyrido[4,3-c]-1,6-naphthyridin-1(2H)-one;
4-(cyclopropylethynyl)-6-[(pyridin-2-ylmethyl)amino]pyrido[4,3-c]-1,6-naphthyridin-1(2H)-one;
4-(pyridin-2-ylethynyl)-6-[(1,2,2-trimethylpropyl)amino]pyrido[4,3-c]-1,6-naphthyridin-1(2H)-one;
9-bromo-4-(cyclopropylethynyl)-6-{[(1R)-1,2,2-trimethylpropyl]amino}benzo[c]-1,6-naphthyridin-1(2H)-one;
9-bromo-4-(cyclopropylethynyl)-6-{[(1S)-1,2,2-trimethylpropyl]amino}benzo[c]-1,6-naphthyridin-1(2H)-one;
tert-butyl trans-4-{[4-(cyclopropylethynyl)-9-fluoro-1-oxo-1,2-dihydrobenzo[c]-1,6-naphthyridin-6-yl]amino}-3-fluoropiperidines-1-carboxylate;
tert-butyl trans-3-fluoro-4-[(9-fluoro-1-oxo-1,2-dihydrobenzo[c]-1,6-naphthyridin-6-yl)amino]piperidine-1-carboxylate;
4-(cyclopropylethynyl)-9-fluoro-6-[(trans-3-fluoropiperidin-4-yl)amino]benzo[c]-1,6-naphthyridin-1(2H)-one;
4-(cyclopropylethynyl)-6-[(3S)-piperidin-3-ylamino]pyrido[4,3-c]-1,6-naphthyridin-1(2H)-one;
4-(cyclopropylethynyl)-9-(1H-pyrazol-4-yl)-6-[(1,2,2-trimethylpropyl)amino]benzo[c]-1,6-naphthyridin-1(2H)-one;
4-(cyclopropylethynyl)-9-(1H-pyrazol-4-yl)-6-[(pyridin-2-ylmethyl)amino]benzo[c]-1,6-naphthyridin-1(2H)-one;
4-(cyclopropylethynyl)-9-(1H-pyrazol-5-yl)-6-[(pyridin-2-ylmethyl)amino]benzo[c]-1,6-naphthyridin-1(2H)-one;
3-{1-oxo-9-(1H-pyrazol-5-yl)-6-[(pyridin-2-ylmethyl)amino]-1,2-dihydrobenzo[c]-1,6-naphthyridin-4-yl}prop-2-ynamide;
9-bromo-4-[(1-methyl-1H-imidazol-5-yl)ethynyl]-6-[(3S)-piperidin-3-ylamino]benzo[c]-1,6-naphthyridin-1(2H)-one;
3-[1-oxo-6-[(pyridin-2-ylethyl)amino]-9-(3-thienyl)-1,2-dihydrobenzo[c]-1,6-naphthyridin-4-yl]prop-2-ynamide;
3-{9-[4-(ethylsulfonyl)phenyl]-1-oxo-6-[(pyridin-2-ylmethyl)amino]-1,2-dihydrobenzo[c]-1,6-naphthyridin-4-yl}prop-2-ynamide;
3-[6-(ethylamino)-1-oxo-9-(1H-pyrazol-5-yl)-1,2-dihydrobenzo[c]-1,6-naphthyridin-4-yl]prop-2-ynamide;
3-{9-[4-(cyanomethyl)phenyl]-1-oxo-6-[(pyridin-2-ylmethyl)amino]-1,2-dihydrobenzo[c]-1,6-naphthyridin-4-yl}prop-2-ynamide;
3-{9-(4-methoxyphenyl)-1-oxo-6-[(pyridin-2-ylmethyl)amino]-1,2-dihydrobenzo[c]-1,6-naphthyridin-4-yl}prop-2-ynamide;
3-{9-(1-methyl-1H-pyrazol-4-yl)-1-oxo-6-[(pyridin-2-ylmethyl)amino]-1,2-dihydrobenzo[c]-1,6-naphthyridin-4-yl}prop-2-ynamide;
3-{6-(ethylamino)-9-[4-(1-morpholin-4-ylethyl)phenyl]-1-oxo-1,2-dihydrobenzo[c]-1,6-naphthyridin-4-yl}prop-2-ynamide;

3-{9-[3-(hydroxymethyl)phenyl]-1-oxo-6-[(pyridin-2-ylmethyl)amino]-1,2-dihydrobenzo[c]-1,6-naphthyridin-4-yl}prop-2-ynamide;
3-{9-(6-methoxypyridin-3-yl)-1-oxo-6-[(pyridin-2-ylmethyl)amino]-1,2-dihydrobenzo[c]-1,6-naphthyridin-4-yl}prop-2-ynamide;
3-[6-(ethylamino)-1-oxo-9-(3-thienyl)-1,2-dihydrobenzo[c]-1,6-naphthyridin-4-yl]prop-2-ynamide;
3-[1-oxo-6-[(pyridin-2-ylmethyl)amino]-9-(2-thienyl)-1,2-dihydrobenzo[c]-1,6-naphthyridin-4-yl]prop-2-ynamide;
3-{9-(3-hydroxyphenyl)-1-oxo-6-[(pyridin-2-ylmethyl)amino]-1,2-dihydrobenzo[c]-1,6-naphthyridin-4-yl}prop-2-ynamide;
3-{9-[4-(methylsulfonyl)phenyl]-1-oxo-6-[(pyridin-2-ylmethyl)amino]-1,2-dihydrobenzo[c]-1,6-naphthyridin-4-yl}prop-2-ynamide;
3-{9-(1H-indol-6-yl)-1-oxo-6-[(pyridin-2-ylmethyl)amino]-1,2-dihydrobenzo[c]-1,6-naphthyridin-4-yl}prop-2-ynamide;
3-{6-(ethylamino)-9-[4-(methylsulfonyl)phenyl]-1-oxo-1,2-dihydrobenzo[c]-1,6-naphthyridin-4-yl}prop-2-ynamide;
3-{9-(5-methyl-2-thienyl)-1-oxo-6-[(pyridin-2-ylmethyl)amino]-1,2-dihydrobenzo[c]-1,6-naphthyridin-4-yl)}prop-2-ynamide;
3-{9-(2-hydroxyphenyl)-1-oxo-6-[(pyridin-2-ylmethyl)amino]-1,2-dihydrobenzo[c]-1,6-naphthyridin-4-yl}prop-2-ynamide;
3-{9-(1,3-benzodioxol-5-yl)-1-oxo-6-[(pyridin-2-ylmethyl)amino]-1,2-dihydrobenzo[c]-1,6-naphthyridin-4-yl}prop-2-ynamide;
3-[6-(ethylamino)-9-(3-hydroxyphenyl)-1-oxo-1,2-dihydrobenzo[c]-1,6-naphthyridin-4-yl]prop-2-ynamide;
3-{6-(ethylamino)-1-oxo-9-[3-(1-pyrrolidin-1-ylethyl)phenyl]-1,2-dihydrobenzo[c]-1,6-naphthyridin-4-yl}prop-2-ynamide;
3-{6-(ethylamino)-9-[3-(hydroxymethyl)phenyl]-1-oxo-1,2-dihydrobenzo[c]-1,6-naphthyridin-4-yl}prop-2-ynamide;
3-{9-(3-methoxyphenyl)-1-oxo-6-[(pyridin-2-ylmethyl)amino]-1,2-dihydrobenzo[c]-1,6-naphthyridin-4-yl}prop-2-ynamide;
3-[9-(1,3-benzodioxol-5-yl)-6-(ethylamino)-1-oxo-1,2-dihydrobenzo[c]-1,6-naphthyridin-4-yl]prop-2-ynamide;
3-{9-(3-methyl-2-thienyl)-1-oxo-6-[(pyridin-2-ylmethyl)amino]-1,2-dihydrobenzo[c]-1,6-naphthyridin-4-yl)}prop-2-ynamide;
3-{9-(2-methoxypyrimidin-5-yl)-1-oxo-6-[(pyridin-2-ylmethyl)amino]-1,2-dihydrobenzo[c]-1,6-naphthyridin-4-yl}prop-2-ynamide;
3-{9-(2,3-dimethoxyphenyl)-1-oxo-6-[(pyridin-2-ylmethyl)amino]-1,2-dihydrobenzo[c]-1,6-naphthyridin-4-yl}prop-2-ynamide;
3-{1-oxo-6-[(pyridin-2-ylmethyl)amino]-9-[4-(trifluoromethoxy)phenyl]-1,2-dihydrobenzo[c]-1,6-naphthyridin-4-yl}prop-2-ynamide;
3-[9-(2,3-dimethoxyphenyl)-6-(ethylamino)-1-oxo-1,2-dihydrobenzo[c]-1,6-naphthyridin-4-yl]prop-2-ynamide;
3-[6-(ethylamino)-9-(2-fluoro-3-methoxyphenyl)-1-oxo-1,2-dihydrobenzo[c]-1,6-naphthyridin-4-yl]prop-2-ynamide;
3-{9-(2-ethoxyphenyl)-1-oxo-6-[(pyridin-2-ylmethyl)amino]-1,2-dihydrobenzo[c]-1,6-naphthyridin-4-yl}prop-2-ynamide;
3-[9-(2-ethoxyphenyl)-6-(ethylamino)-1-oxo-1,2-dihydrobenzo[c]-1,6-naphthyridin-4-yl]prop-2-ynamide;
4-(cyclopropylethynyl)-9-[4-(methylsulfonyl)phenyl]-6-[(1,2,2-trimethylpropyl)amino]benzo[c]-1,6-naphthyridin-1(2H)-one;
4-(cyclopropylethynyl)-9-[4-(ethylsulfonyl)phenyl]-6-[(1,2,2-trimethylpropyl)amino]benzo[c]-1,6-naphthyridin-1(2H)-one;
3-{1-oxo-9-(1H-pyrazol-5-yl)-6-[(pyridazin-3-ylmethyl)amino]-1,2-dihydrobenzo[c]-1,6-naphthyridin-4-yl}prop-2-ynamide;
4-(cyclopropylethynyl)-9-(1H-pyrazol-5-yl)-6-[(1,2,2-trimethylpropyl)amino]benzo[c]-1,6-naphthyridin-1(2H)-one;
3-{9-(3-cyanophenyl)-1-oxo-6-[(pyridazin-3-ylmethyl)amino]-1,2-dihydrobenzo[c]-1,6-naphthyridin-4-yl}prop-2-ynamide;
4-(cyclopropylethynyl)-9-(1-methyl-1H-pyrazol-4-yl)-6-[(1,2,2-trimethylpropyl)amino]benzo[c]-1,6-naphthyridin-1(2H)-one;
3-{9-[4-(hydroxymethyl)phenyl]-1-oxo-6-[(pyridazin-3-ylmethyl)amino]-1,2-dihydrobenzo[c]-1,6-naphthyridin-4-yl}prop-2-ynamide;
4-(cyclopropylethynyl)-9-(1-methyl-1H-pyrazol-4-yl)-6-[(pyridazin-3-ylmethyl)amino]benzo[c]-1,6-naphthyridin-1(2H)-one;
4-(cyclopropylethynyl)-9-(6-methoxypyridin-3-yl)-6-[(1,2,2-trimethylpropyl)amino]benzo[c]-1,6-naphthyridin-1(2H)-one;
9-(1H-pyrazol-4-yl)-6-{[(1R)-1,2,2-trimethylpropyl]amino}benzo[c]-1,6-naphthyridin-1(2H)-one
4-(cyclopropylethynyl)-9-(1H-pyrazol-4-yl)-6-{[(1R)-1,2,2-trimethylpropyl]amino)}benzo[c]-1,6-naphthyridin-1(2H)-one;
4-(cyclopropylethynyl)-9-(1H-pyrazol-4-yl)-6-{[(1S)-1,2,2-trimethylpropyl]amino}benzo[c]-1,6-naphthyridin-1(2H)-one;
4-(cyclopropylethynyl)-6-{[(1R)-1,2,2-trimethylpropyl]amino}benzo[c]-1,6-naphthyridin-1(2H)-one;
9-bromo-1-oxo-6-[(1,2,2-trimethylpropyl)amino]-1,2-dihydrobenzo[c]-1,6-naphthyridine-4-carboxamide;
N-acetyl-9-bromo-1-oxo-6-[(1,2,2-trimethylpropyl)amino]-1,2-dihydrobenzo[c]-1,6-naphthyridine-4-carbohydrazide;
9-bromo-N-methyl-1-oxo-6-[(1,2,2-trimethylpropyl)amino]-1,2-dihydrobenzo[c]-1,6-naphthyridine-4-carboxamide;
9-bromo-N-methyl-1-oxo-6-[(1,2,2-trimethylpropyl)amino]-1,2-dihydrobenzo[c]-1,6-naphthyridine-4-carboxamide;
9-bromo-N-cyclopropyl-1-oxo-6-[(1,2,2-trimethylpropyl)amino]-1,2-dihydrobenzo[c]-1,6-naphthyridine-4-carboxamide;
N-benzyl-9-bromo-1-oxo-6-[(1,2,2-trimethylpropyl)amino]-1,2-dihydrobenzo[c]-1,6-naphthyridine-4-carboxamide;
6-{[(1R)-2-methyl-1-(trifluoromethyl)propyl]amino}pyrido[4,3-c]-1,6-naphthyridin-1(2H)-one 9-oxide;
6-[(1,2,2-trimethylpropyl)amino]pyrido[4,3-c]-1,6-naphthyridin-1(2H)-one 9-oxide;
N-(9-fluoro-1-oxo-1,2-dihydrobenzo[c]-1,6-naphthyridin-6-yl)piperidine-1-sulfonamide;
9-fluoro-6-(1H-indol-3-yl)benzo[c]-1,6-naphthyridin-1(2H)-one;
6-(1-benzyl-1H-pyrazol-4-yl)-9-fluorobenzo[c]-1,6-naphthyridin-1(2H)-one;
N-(6-{[(1R)-2-methyl-1-(trifluoromethyl)propyl]amino}-1-oxo-1,2-dihydrobenzo[c]-1,6-naphthyridin-9-yl)nicotinamide;

N-(6-{[(1R)-2-methyl-1-(trifluoromethyl)propyl]amino}-1-oxo-1,2-dihydrobenzo[c]-1,6-naphthyridin-9-yl)isonicotinamide;
9-bromo-3-methyl-6-[(pyridin-2-ylmethyl)amino]benzo[c]-1,6-naphthyridin-1(2H)-one;
6-[(1,2,2-trimethylpropyl)amino]-9-[(trimethylsilyl)ethynyl]benzo[c]-1,6-naphthyridin-1(2H)-one;
9-ethynyl-6-[(1,2,2-trimethylpropyl)amino]benzo[c]-1,6-naphthyridin-1(2H)-one;
9-(phenylethynyl)-6-[(1,2,2-trimethylpropyl)amino]benzo[c]-1,6-naphthyridin-1(2H)-one;
9-(1H-1,2,3-triazol-4-yl)-6-[(1,2,2-trimethylpropyl)amino]benzo[c]-1,6-naphthyridin-1(2H)-one;
9-(1-benzyl-1H-1,2,3-triazol-4-yl)-6-[(1,2,2-trimethylpropyl)amino]benzo[c]-1,6-naphthyridin-1(2H)-one;
9-bromo-6-isopropylbenzo[c]-1,6-naphthyridin-1(2H)-one;
9-bromo-6-methylbenzo[c]-1,6-naphthyridin-1(2H)-one;
9-bromo-6-ethylbenzo[c]-1,6-naphthyridin-1(2H)-one;
9-bromo-6-(tetrahydro-2H-pyran-4-yl)benzo[c]-1,6-naphthyridin-1(2H)-one;
9-bromo-6-cyclobutylbenzo[c]-1,6-naphthyridin-1(2H)-one;
9-bromo-6-(3,3-difluorocyclobutyl)benzo[c]-1,6-naphthyridin-1(2H)-one;
9-bromo-6-(2,2-dimethylpropyl)benzo[c]-1,6-naphthyridin-1(2H)-one;
9-bromo-6-sec-butylbenzo[c]-1,6-naphthyridin-1(2H)-one;
9-bromo-6-(1,1-dioxidotetrahydro-2-thienyl)benzo[c]-1,6-naphthyridin-1(2H)-one;
6-isopropylpyrido[4,3-c]-1,6-naphthyridin-1(2H)-one;
N-methyl-1-(1-oxo-1,2-dihydropyrido[4,3-c]-1,6-naphthyridin-6-yl)-N-phenylmethanesulfonamide;
6-isopropyl-9-(1-methyl-1H-pyrazol-4-yl)benzo[c]-1,6-naphthyridin-1(2H)-one;
9-(1-methyl-1H-pyrazol-4-yl)-6-(tetrahydro-2H-pyran-4-yl)benzo[c]-1,6-naphthyridin-1(2H)-one;
6-ethyl-9-(1-methyl-1H-pyrazol-4-yl)benzo[c]-1,6-naphthyridin-1(2H)-one;
6-(3,3-difluorocyclobutyl)-9-(1-methyl-1H-pyrazol-4-yl)benzo[c]-1,6-naphthyridin-1(2H)-one;
6-isopropyl-9-(morpholin-4-ylmethyl)benzo[c]-1,6-naphthyridin-1(2H)-one;
6-isopropylbenzo[c]-1,6-naphthyridin-1(2H)-one;
6-isopropyl-9-(pyrrolidin-1-ylmethyl)benzo[c]-1,6-naphthyridin-1(2H)-one;
6-isopropyl-9-(morpholin-4-ylcarbonyl)benzo[c]-1,6-naphthyridin-1(2H)-one;
9-[(1,1-dioxidothiomorpholin-4-yl)carbonyl]-6-isopropylbenzo[c]-1,6-naphthyridin-1(2H)-one;
6-isopropyl-N,N-dimethyl-1-oxo-1,2-dihydrobenzo[c]-1,6-naphthyridine-9-carboxamide;
6-isopropyl-1-oxo-N-[3-(2-oxoazepan-1-yl)propyl]-1,2-dihydrobenzo[c]-1,6-naphthyridine-9-carboxamide;
6-isopropyl-1-oxo-1,2-dihydrobenzo[c]-1,6-naphthyridine-9-carboxamide;
N-acetyl-6-isopropyl-1-oxo-1,2-dihydrobenzo[c]-1,6-naphthyridine-9-carbohydrazide;
6-isopropyl-9-(5-methyl-1,3,4-oxadiazol-2-yl)benzo[c]-1,6-naphthyridin-1(2H)-one;
9-(5-cyclopropyl-1,3,4-oxadiazol-2-yl)-6-isopropylbenzo[c]-1,6-naphthyridin-1(2H)-one;
3-(9-bromo-6-isopropyl-1-oxo-1,2-dihydrobenzo[c]-1,6-naphthyridin-4-yl)prop-2-ynamide;
3-[6-isopropyl-9-(1-methyl-1H-pyrazol-4-yl)-1-oxo-1,2-dihydrobenzo[c]-1,6-naphthyridin-4-yl]prop-2-ynamide;
9-bromo-4-(pyridin-3-ylethynyl)-6-(tetrahydro-2H-pyran-4-yl)benzo[c]-1,6-naphthyridin-1(2H)-one;
9-bromo-4-(pyridin-2-ylethynyl)-6-(tetrahydro-2H-pyran-4-yl)benzo[c]-1,6-naphthyridin-1(2H)-one;
9-bromo-4-(pyridine-4-ylethynyl)-6-(tetrahydro-2H-pyran-4-yl)benzo[c]-1,6-naphthyridin-1(2H)-one;
9-fluoro-6-isopropoxybenzo[c]-1,6-naphthyridin-1(2H)-one;
6-(cyclopropylmethoxy)-9-fluorobenzo[c]-1,6-naphthyridin-1(2H)-one;
9-fluoro-6-(2,2,2-trifluoroethoxy)benzo[c]-1,6-naphthyridin-1(2H)-one;
9-fluoro-6-(2-methoxyethoxy)benzo[c]-1,6-naphthyridin-1(2H)-one;
9-hydroxy-6-isopropoxybenzo[c]-1,6-naphthyridin-1(2H)-one;
9-(methylsulfonyl)-6-[(1,2,2-trimethylpropyl)amino]benzo[c]-1,6-naphthyridin-1(2H)-one;
9-fluoro-6-isopropenylbenzo[c]-1,6-naphthyridin-1(2H)-one;
9-fluoro-6-isopropylbenzo[c]-1,6-naphthyridin-1(2H)-one;
9-fluoro-6-(1-hydroxy-1-methylethyl)benzo[c]-1,6-naphthyridin-1(2H)-one;
6-(1,2-dihydroxy-1-methylethyl)-9-fluorobenzo[c]-1,6-naphthyridin-1(2H)-one;
9-fluoro-6-(1-methyl-2-morpholin-4-ylethyl)benzo[c]-1,6-naphthyridin-1(2H)-one;
N-(6-{[(1R)-2-methyl-1-(trifluoromethyl)propyl]amino}-1-oxo-1,2-dihydrobenzo[c]-1,6-naphthyridin-9-yl)-2-morpholin-4-ylacetamide;
or a pharmaceutically acceptable salt or stereoisomer thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted. For example the following is within the scope of the instant invention:

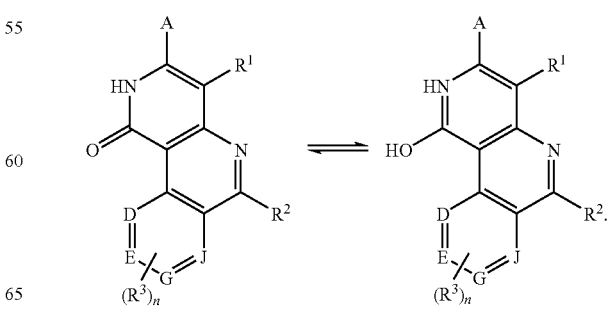

Pyridones exist as a mixture of 1H/2H tautomers. The tautomeric forms of the pyridone moiety are also within the scope of the instant invention.

When any variable (e.g. $R^3$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to four substituents, and the more preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "($C_1$-$C_{10}$)alkyl" is defined to include groups having 1, 2, 3, 4, 5, 6, 7, 8, 9 or 10 carbons in a linear or branched arrangement. For example, "($C_1$-$C_{10}$)alkyl" specifically includes methyl, ethyl, n-propyl, i-propyl, n-butyl, t-butyl, i-butyl, pentyl, hexyl, heptyl, octyl, nonyl, decyl, and so on.

As used herein, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "($C_2$-$C_6$)alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" shall mean a substituting univalent group derived by conceptual removal of one hydrogen atom from a straight or branched-chain acyclic unsaturated hydrocarbon containing at least one triple bond (i.e., —C≡CH, —CH$_2$C≡CH, —C≡CCH$_3$, —CH$_2$C≡CCH$_2$(CH$_3$)$_2$, etc.).

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

The term "haloalkyl" means an alkyl radical as defined above, unless otherwise specified, that is substituted with one to five, preferably one to three halogen. Representative examples include, but are not limited to trifluoromethyl, dichloroethyl, and the like.

"Alkoxy" represents either a cyclic or non-cyclic alkyl group of indicated number of carbon atoms attached through an oxygen bridge. "Alkoxy" therefore encompasses the definitions of alkyl and cycloalkyl above.

In certain instances, substituents may be defined with a range of carbons that includes zero, such as ($C_0$-$C_6$)alkylaryl. If aryl is taken to be phenyl, this definition would include phenyl itself as well as —CH$_2$Ph, —CH$_2$CH$_2$Ph, CH(CH$_3$) CH$_2$CH(CH$_3$)Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively. Such heteroaryl moieties for substituent Q include but are not limited to: 2-benzimidazolyl, 2-quinolinyl, 3-quinolinyl, 4-quinolinyl, 1-isoquinolinyl, 3-isoquinolinyl and 4-isoquinolinyl.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin- 2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro (Cl), fluoro (F), bromo (Br) and iodo (I).

Whenever the term "alkyl," "aryl," "cycloalkyl," heterocyclyl" or "heteroaryl" or either of their prefix roots appear in a name of a substituent (e.g., ($C_{1-6}$ alkyl)aryl or ($C_{1-6}$ alkyl)($C_{3-6}$ cycloalkyl)) it shall be interpreted as including those limitations given above for "alkyl," "aryl," "cycloalkyl," heterocyclyl" or "heteroaryl." Designated numbers of carbon atoms (e.g., $C_{1-6}$) shall refer independently to the number of carbon atoms in an alkyl or cyclic alkyl moiety or to the alkyl portion of a larger substituent in which alkyl appears as its prefix root.

Included in the instant invention is the free form of compounds of the instant invention, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of the instant invention. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Utility

The compounds of the present invention are inhibitors of JAK 1, JAK2, JAK 3, TYK2 and PDK1, and are therefore useful to treat or prevent myeloproliferative disorders or cancer in mammals, preferably humans.

An embodiment of the invention provides a method for inhibiting JAK1 tyrosine kinase, comprising administering to the mammal a therapeutically effective amount of any of the compounds or any of the pharmaceutical compositions described above.

An embodiment of the invention provides a method for inhibiting JAK2 tyrosine kinase, comprising administering to the mammal a therapeutically effective amount of any of the compounds or any of the pharmaceutical compositions described above.

An embodiment of the invention provides a method for inhibiting JAK3 tyrosine kinase, comprising administering to the mammal a therapeutically effective amount of any of the compounds or any of the pharmaceutical compositions described above.

An embodiment of the invention provides a method for inhibiting TYK2 tyrosine kinase, comprising administering to the mammal a therapeutically effective amount of any of the compounds or any of the pharmaceutical compositions described above.

An embodiment of the invention provides a method for inhibiting PDK1 tyrosine kinase, comprising administering to the mammal a therapeutically effective amount of any of the compounds or any of the pharmaceutical compositions described above.

An embodiment of the invention provides a method for inhibiting wild type or mutant JAK2 tyrosine kinase, comprising administering to the mammal a therapeutically effective amount of any of the compounds or any of the pharmaceutical compositions described above.

An embodiment of the invention provides a method for inhibiting JAK2V617F tyrosine kinase, comprising administering to the mammal a therapeutically effective amount of any of the compounds or any of the pharmaceutical compositions described above.

The compounds, compositions and methods provided herein are particularly deemed useful for the treatment of myeloproliferative disorder(s). Myeloproliferative disorders that may be treated include polycythemia vera (PV), essential thrombocythemia (ET), myeloid metaplasia with myelofibrosis (MMM), chronic myelogenous leukemia (CML), myelomonocytic leukemia (CMML), hypereosinophilic syndrome (HES), juvenile myelomonocytic leukemia (JMML), and systemic mast cell disease (SMCD).

It is known in the literature that inhibitors of JAK2 are useful in the treatment and/or prevention of myeloproliferative disorders. See, e.g., Tefferi, A. and Gilliland, D. G. *Mayo Clin. Proc.* 80(7): 947-958 (2005); Fernandez-Luna, J. L. et al. *Haematologica* 83(2): 97-98 (1998); Harrison, C. N. *Br. J. Haematol.* 130(2): 153-165 (2005); *Leukemia* (2005) 19, 1843-1844; and Tefferi, A. and Barbui, T. Mayo *Clin. Proc.* 80(9): 1220-1232 (2005).

The compounds, compositions and methods provided herein are also deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma; and Adrenal glands: neuroblastoma. Thus, the term "cancerous cell" as provided herein, includes a cell afflicted by any one of the above-identified conditions.

The compounds, compositions and methods of the invention may also be useful in treating the following disease states: keloids and psoriasis.

Cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

Cancers that may be treated by the compounds, compositions and methods of the invention include: breast, prostate, colon, ovarian, colorectal and lung (non-small cell lung).

Cancers that may be treated by the compounds, compositions and methods of the invention include: breast, colon, colorectal and lung.

Cancers that may be treated by the compounds, compositions and methods of the invention include: lymphoma and leukemia.

The compounds of the instant invention are also inhibitors of the activity of PDK1 and are thus useful in the treatment of cancer, in particular cancers associated with deregulated activity of the PTEN/PI3K pathway including, but not limited to PTEN loss of function mutations, PI3K gain of function mutations and receptor tyrosine kinase gain of function mutations. Such cancers include, but are not limited to, ovarian, pancreatic, breast and prostate cancer, as well as cancers (including glioblastoma) where the tumor suppressor PTEN is mutated. See, Feldman, Richard I., et al., "Novel Small Molecule Inhibitors of 3-Phosphoinositide-dependent Kinase-1," *The Journal of Biological Chemistry*, Vol. 280, No. 20, Issue of May 20, pp. 19867-19874, 2005.

PDK1 signaling regulates multiple critical steps in angiogenesis. See, Mora, Alfonso et al., "PDK1, the master regulator of AGC kinase signal transduction," *Seminars in Cell & Developmental Biology* 15 (2004) 161-170. The utility of angiogenesis inhibitors in the treatment of cancer is known in the literature, see J. Rak et al. *Cancer Research*, 55:4575-4580, 1995 and Dredge et al., *Expert Opin. Biol. Ther.* (2002) 2(8):953-966, for example. The role of angiogenesis in cancer has been shown in numerous types of cancer and tissues: breast carcinoma (G. Gasparini and A. L. Harris, *J. Clin.*

*Oncol.,* 1995, 13:765-782; M. Toi et al., *Japan. J. Cancer Res.,* 1994, 85:1045-1049); bladder carcinomas (A. J. Dickinson et al., *Br. J. Urol.,* 1994, 74:762-766); colon carcinomas (L. M. Ellis et al., *Surgery,* 1996, 120(5):871-878); and oral cavity tumors (J. K. Williams et al., *Am. J. Surg.,* 1994, 168:373-380). Other cancers include, advanced tumors, hairy cell leukemia, melanoma, advanced head and neck, metastatic renal cell, non-Hodgkin's lymphoma, metastatic breast, breast adenocarcinoma, advanced melanoma, pancreatic, gastric, glioblastoma, lung, ovarian, non-small cell lung, prostate, small cell lung, renal cell carcinoma, various solid tumors, multiple myeloma, metastatic prostate, malignant glioma, renal cancer, lymphoma, refractory metastatic disease, refractory multiple myeloma, cervical cancer, Kaposi's sarcoma, recurrent anaplastic glioma, and metastatic colon cancer (Dredge et al., *Expert Opin. Biol. Ther.* (2002) 2(8): 953-966). Thus, the PDK1 inhibitors disclosed in the instant application are also useful in the treatment of these angiogenesis related cancers.

Tumors which have undergone neovascularization show an increased potential for metastasis. In fact, angiogenesis is essential for tumor growth and metastasis. (S. P. Cunningham, et al., *Can. Research,* 61: 3206-3211(2001)). The PDK1 inhibitors disclosed in the present application are therefore also useful to prevent or decrease tumor cell metastasis.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge et al., *Expert Opin. Biol. Ther.* (2002) 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

Further included within the scope of the invention is a method of treating hyperproliferative disorders such as restenosis, inflammation, autoimmune diseases and allergy/asthma.

Further included within the scope of the instant invention is the use of the instant compounds to coat stents and therefore the use of the instant compounds on coated stents for the treatment and/or prevention of restenosis (WO03/032809).

Further included within the scope of the instant invention is the use of the instant compounds for the treatment and/or prevention of osteoarthritis (WO03/035048).

Further included within the scope of the invention is a method of treating hypoinsulinism.

An embodiment of the invention provides a method for inhibiting JAK3 tyrosine kinase, comprising administering to the mammal a therapeutically effective amount of any of the compounds or any of the pharmaceutical compositions described above.

An embodiment of the invention provides a method for inhibiting TYK2 tyrosine kinase, comprising administering to the mammal a therapeutically effective amount of any of the compounds or any of the pharmaceutical compositions described above.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropymethyl-cellulose or hydroxypropycellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropymethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compounds of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropymethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

When a composition according to this invention is administered into a human subject, the daily dosage will normally be determined by the prescribing physician with the dosage generally varying according to the age, weight, and response of the individual patient, as well as the severity of the patient's symptoms.

In an embodiment, a suitable amount of an inhibitor of JAK2 is administered to a mammal undergoing treatment for cancer. Administration occurs in an amount of inhibitor of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of inhibitor of JAK2. In another embodiment, the dosage comprises from about 1 mg to about 1000 mg of inhibitor of JAK2.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341(Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5a,6,8,8a,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)

amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823,U.S. Pat. No. 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\beta_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Opthalmol. Vis.* 2000; 41:2309-2317).

More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119: 709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671(including LY-450139).

A compound of the instant invention may also be useful for treating or preventing cancer in combination with inhibitors of Akt. Such inhibitors include compounds described in, but not limited to, the following publications: WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469.

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak); dexrazoxane (Zinecard); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofring); procarbazine (Matulane®); quinacrine (Atabrine®); Rasburicase (Elitek®); Rituximab (Rituxan®); sargramostim (Leukine®); Sargramostim (Prolcine); sorafenib (Nexavar); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/1-131 tositumomab (Bexxar®); Trastuzumab (Herceptin®); tretinoin, ATRA (Vesanoid); Uracil Mustard (Uracil Mustard Capsules®); valrubicin (Valstar®); vinblastine (Velban®); vincristine (Oncovin®); vinorelbine (Navelbine®); and zoledronate (Zometa®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration"

and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

All patents, publications and pending patent applications identified are hereby incorporated by reference.

Abbreviations used in the description of the chemistry and in the Examples that follow are:
sec-BuLi sec-butyl lithium
CH$_2$Cl$_2$ methylene chloride
DMF dimethyl formamide
DMSO dimethyl sulfoxide
Et$_{20}$ diethyl ether
EtOAc ethyl acetate
HATU O-(7-Azabenzotriazol-1-yl)-N,N,N,N-tetramethyluronium hexafluorophosphate
HCl hydrochloric acid
HPLC high-performance liquid chromatography
HRMS high resolution mass spectrum
LDA lithium diisopropylamide
LRMS low resolution mass spectrum
MeCN acetonitrile
MgSO$_4$ magnesium sulfate
NaHCO$_3$ sodium bicarbonate
Na$_2$CO$_3$ sodium carbonate
NaHMDS sodium bis(trimethylsilyl)amide
NBS N-bromo succinimide
NIS N-iodo succinimide
NMR (nuclear magnetic resonance);
Pd(PPH$_3$)$_4$ tetrakis(triphenylphosphine) palladium (0)
POCl$_3$ phosphorous oxychloride
TEA triethylamine
THF tetrahydrofuran
TMEDA tetramethylethylenediamine The compounds of the present invention can be prepared according to the following general schemes, using appropriate materials, and are further exemplified by the subsequent specific examples. The compounds illustrated in the examples are not, however, to be construed as forming the only genus that is considered as the invention. The illustrative Examples below, therefore, are not limited by the compounds listed or by any particular substituents employed for illustrative purposes. Those skilled in the art will readily understand that known variations of the conditions and processes of the following preparative procedures can be used to prepare these compounds. All temperatures are degrees Celsius unless otherwise noted.

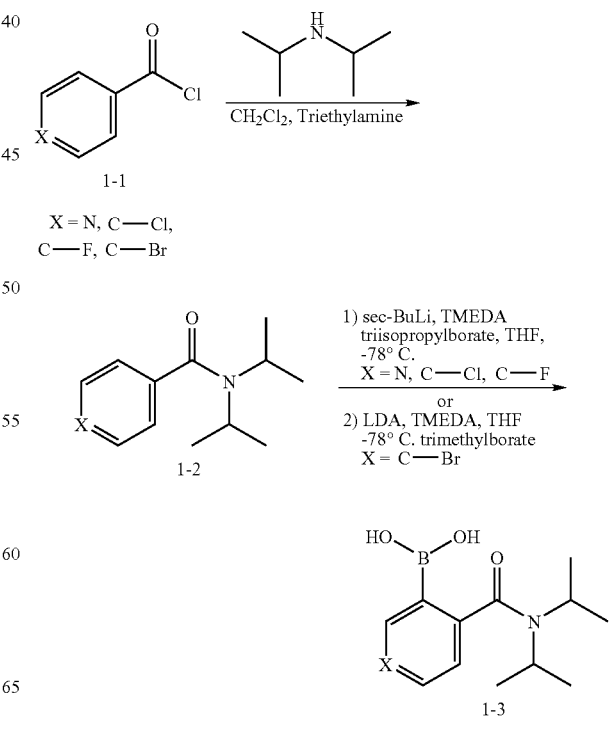

-continued

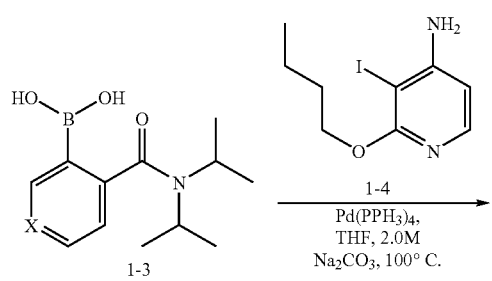

1-3

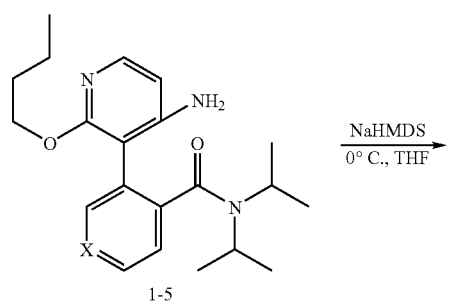

1-5

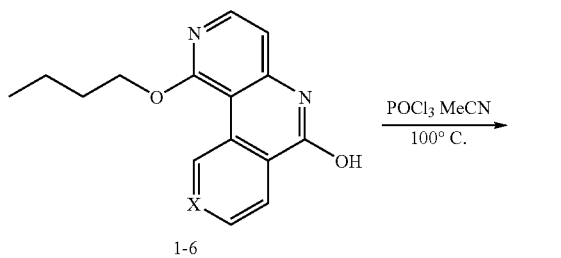

1-6

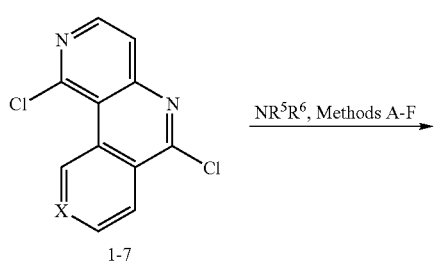

1-7

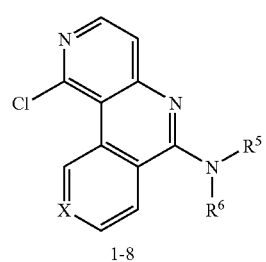

1-8

-continued

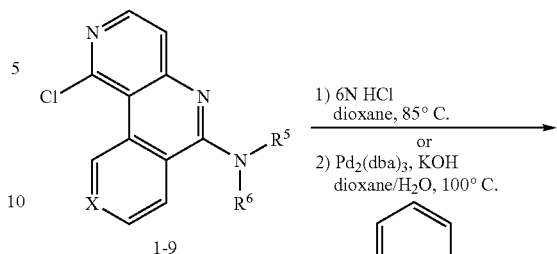

1-9

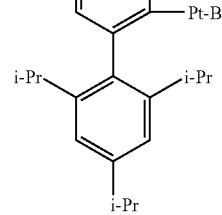

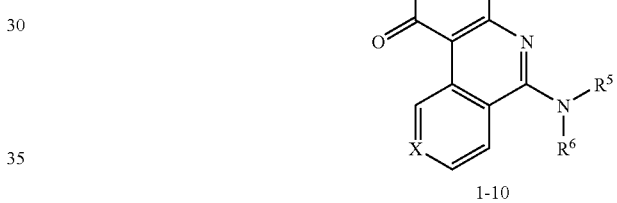

1-10

The synthesis of the tricyclic core 1-6 was based on modified reactions described in International Publication WO2005105814, which published on Nov. 10, 2005, to Incyte. Acyl chloride 1-1 was converted to the diisopropyl amide under basic conditions. Ortho lithiation of amide 1-2 with sec-butyl lithium followed by trapping with triisopropyl borate afforded the boronic acid for Suzuki reaction. In the case where X═C—Br, the ortho lithiation was accomplished using LDA followed by trapping with trimethylborate. Suzuki cross coupling with 2-butoxy-3-iodo-4-aminipyridine (see International Publication WO2005105814, which published on Nov. 10, 2005, to Incyte) and intermediate 1-3 provided biaryl intermediate 1-5. Base induced ring closure with NaHMDS gave the tricyclic core 1-6. Heating tricyclic 1-6 in POCl₃ resulted in the double chlorination intermediate 1-7. A variety of amines were added into the core either via thermally at high temperature, microwave induced addition at high temperature, or acid catalyzed addition at high temperature, or base induced addition at elevated temperature. In the majority of cases the amine added to 1-7 to provide the desired regioisomer as shown in 1-8. Acid hydrolysis or cross coupling, following the procedure of *J. Am. Chem. Soc.* 2006, 128, 1094-10695, of intermediate 1-9 afforded pyridone 1-10.

SCHEME 2

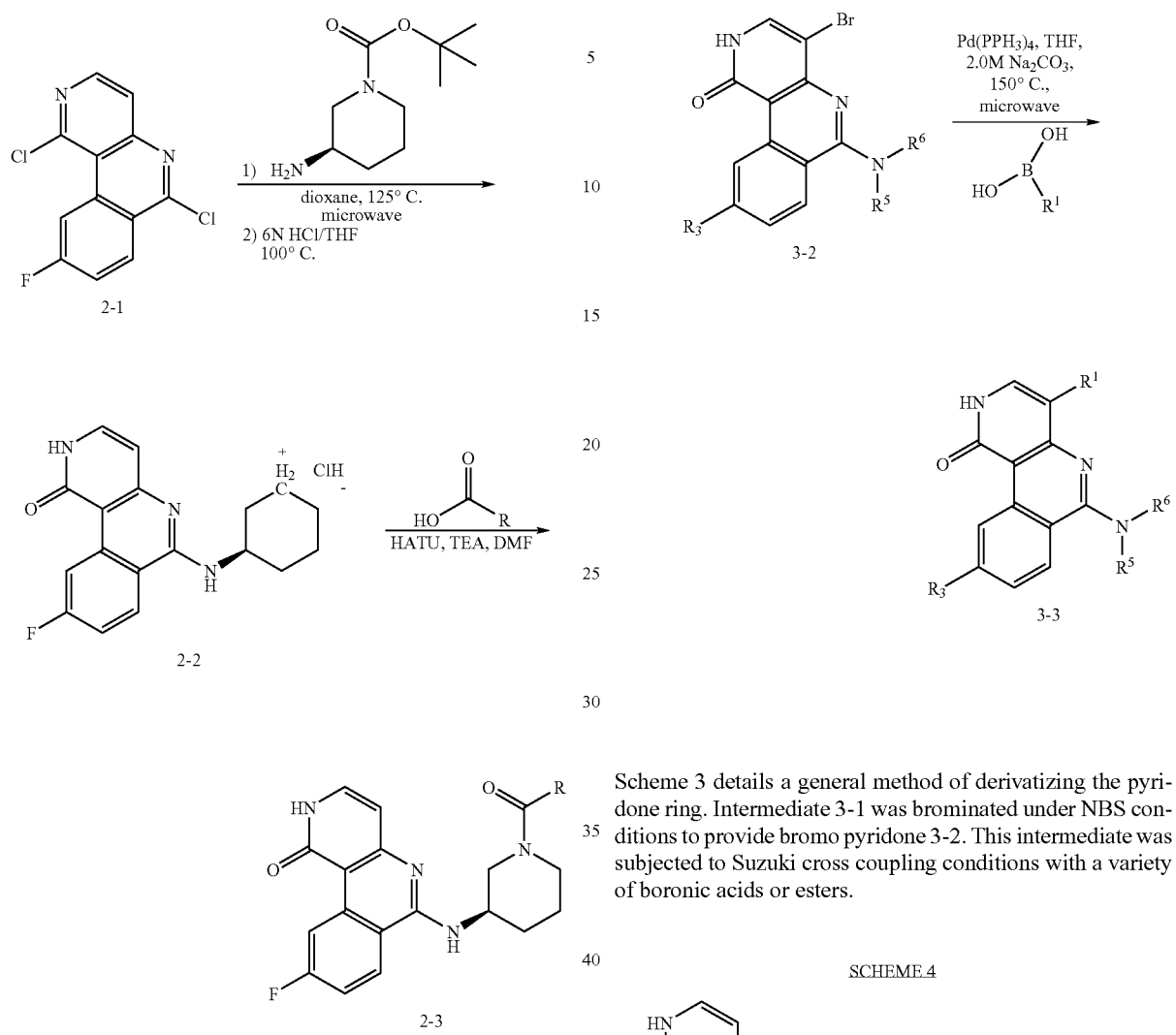

Scheme 2 describes a general method to synthesize analogs of compound 2-3. Intermediate 2-1 was heated with (3R)-3-aminopiperidine-1-carboxylate in a microwave reactor followed by acid hydrolysis to provide intermediate 2-2 as a salt. Amide bond formation with a variety of amides were achieved using HATU (O-(7-Azabenzotriazol-1-yl)-N,N,N,N-tetramethyluronium hexafluorophosphate) as the coupling reagent.

SCHEME 3

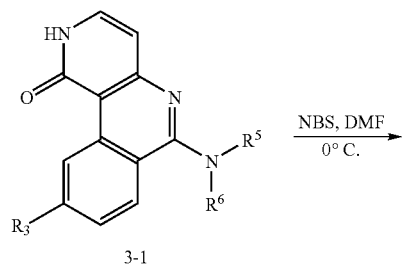

Scheme 3 details a general method of derivatizing the pyridone ring. Intermediate 3-1 was brominated under NBS conditions to provide bromo pyridone 3-2. This intermediate was subjected to Suzuki cross coupling conditions with a variety of boronic acids or esters.

SCHEME 4

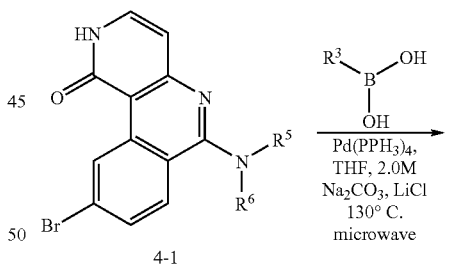

Scheme 4 details a general method for derivatizing the phenyl ring of intermediate 4-1. Suzuki reaction with a variety of boronic acids and boronate esters provided intermediate 4-2.

SCHEME 5

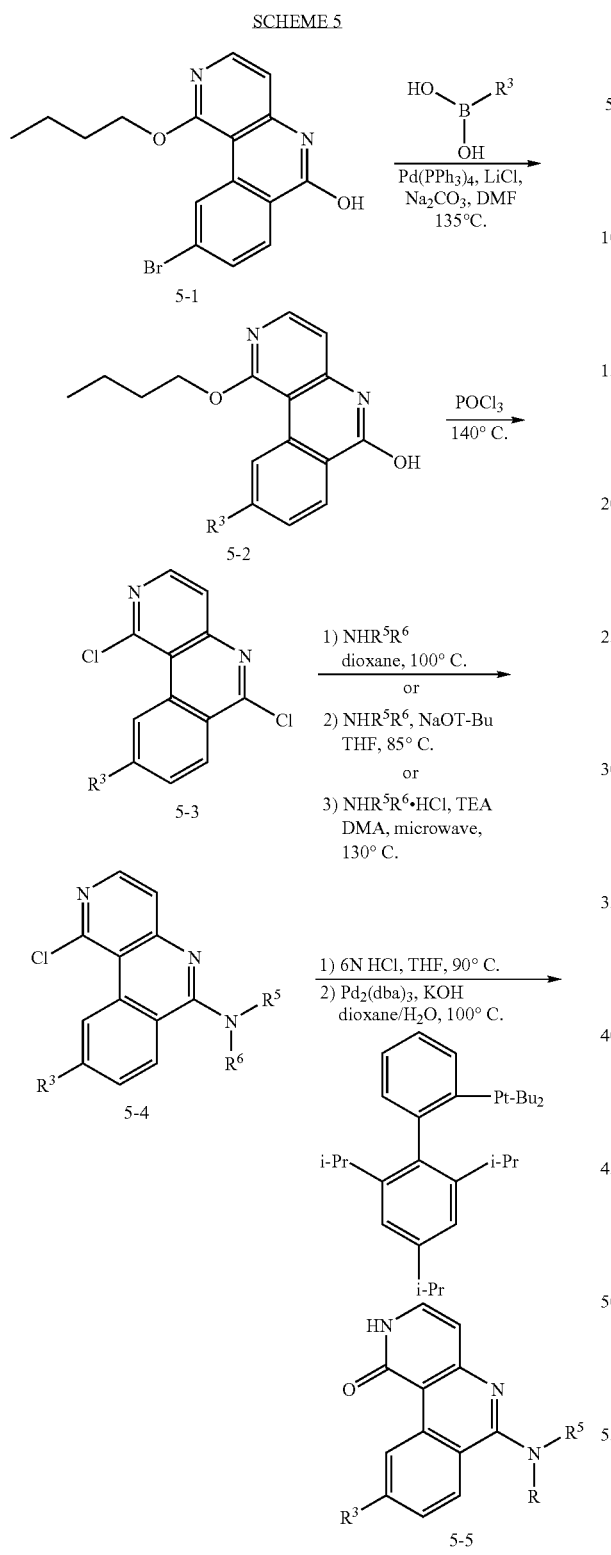

Scheme 5 shows a route for obtaining derivatives of the tricyclic scaffold. Bromide 5-1 is subjected to Suzuki cross-coupling conditions to afford intermediate 5-2. This intermediate 5-2 is then chlorinated with phosphorus oxychloride to provide the dichloride 5-3. An amine is added to this dichloride with heat, base catalysis and heat, or triethylamine and microwave heating (for amine salts). This reaction affords chloride intermediate 5-4, which is then hydrolyzed to pyridone 5-5 by acid hydrolysis or cross-coupling conditions.

SCHEME 6

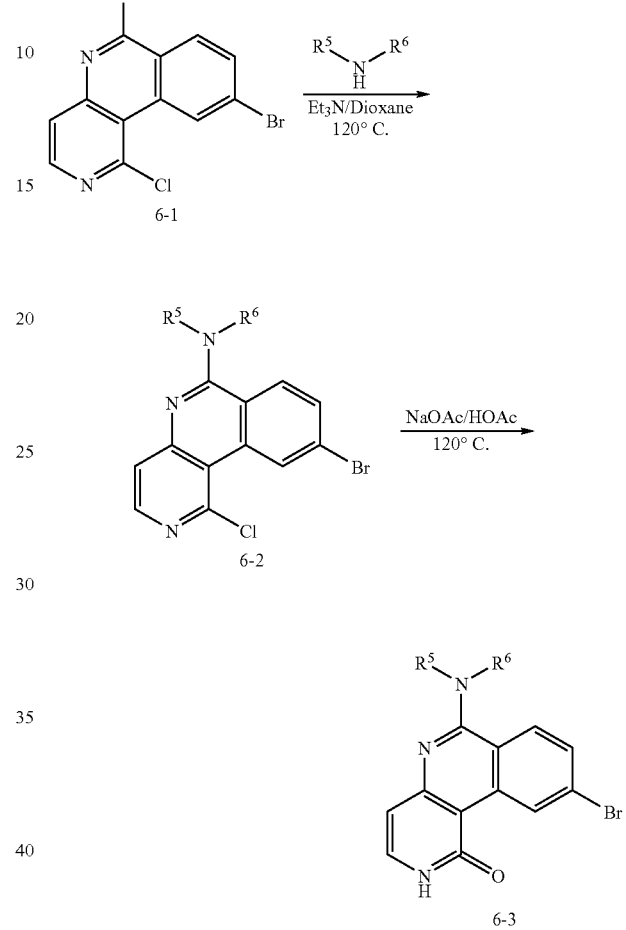

Scheme 5 shows a route for obtaining derivatives of the tricyclic scaffold. Amines are added to dichloride 6-1 under basic conditions at elevated temperatures to afford adduct 6-2. Hydrolysis of chloride 6-2 to pyridone 6-3 is accomplished under acidic conditions at elevated temperatures

SCHEME 7

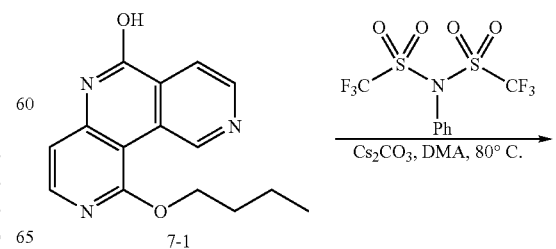

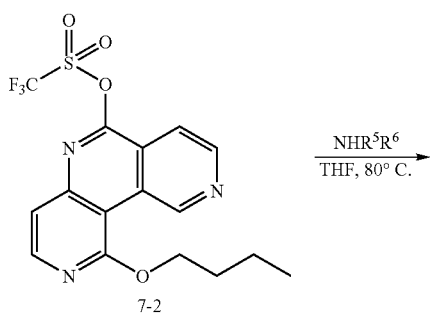

7-2

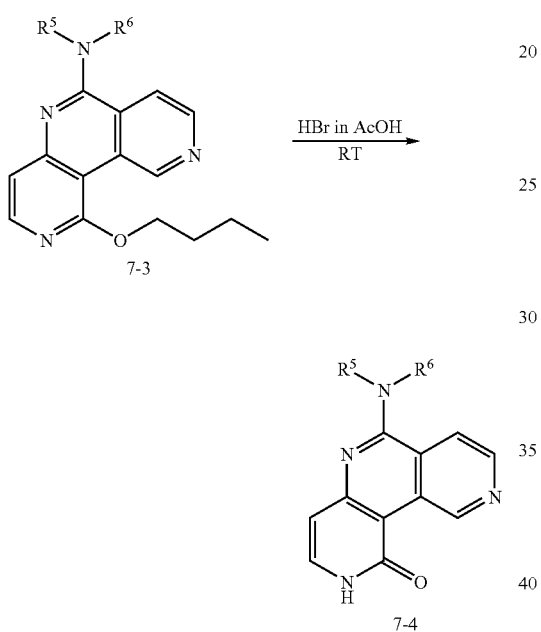

7-3

7-4

Scheme 7 shows a general method for derivatizing the tricyclic scaffold. Intermediate 7-1 was converted to the triflate 7-2 by heating with N-phenylbis(trifluoromethanesulfonimide) and cesium carbonate. A Various amines were added to intermediate 7-2 with heat, and the resulting butoxy-protected intermediate 7-3 was deprotected with acid to afford pyridone 7-4.

SCHEME 8

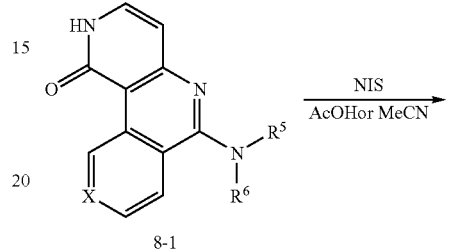

8-1

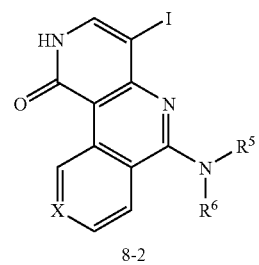

8-2

Scheme 8 shows a general method for derivatizing the tricyclic scaffold where X=N or C—$R^3$. Intermediate 8-1 was converted to iodide 8-2 using an electrophilic iodine source, such as NIS in solvents such as acetic acid or acetonitrile at room temperature or elevated temperature.

SCHEME 9

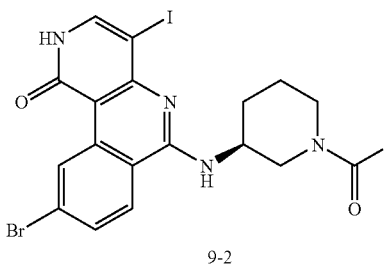

9-2

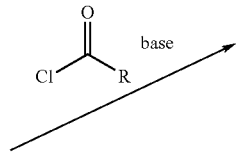

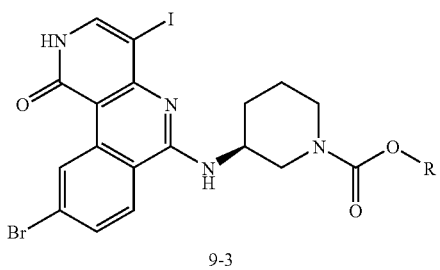

9-3

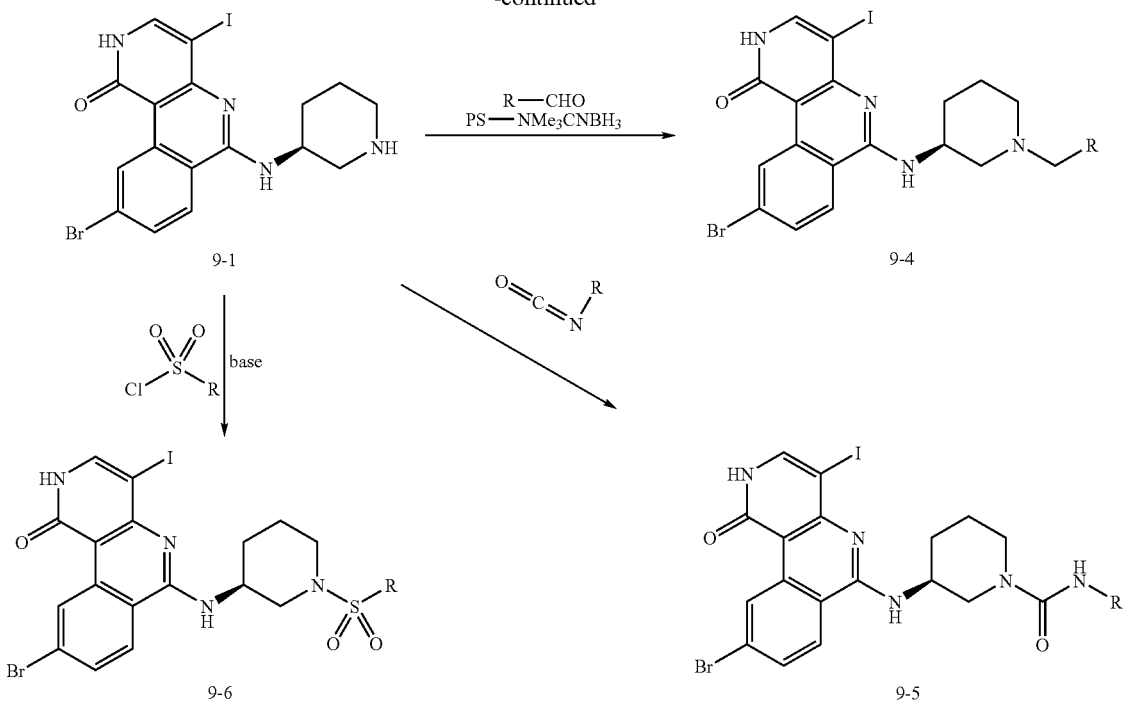

Scheme 9 shows several general methods for derivatizing the tricyclic scaffold. Intermediate 9-1 was converted to carbamate 9-2 using substituted chloroformates. 9-1 was also acylated with acid chlorides in the presence of base to afford acylpiperidine 9-3. Versatile intermediate 9-1 was homologated to alkylpiperidine 9-4 via reductive amination utilizing a solid-supported hydride reagent and a substituted aldehyde. 9-1 was transformed into urea 9-5 by treatment with isocyanates. 9-1 was further transformed into sulfonamides 9-6 by the action of sulfonyl chlorides.

SCHEME 10

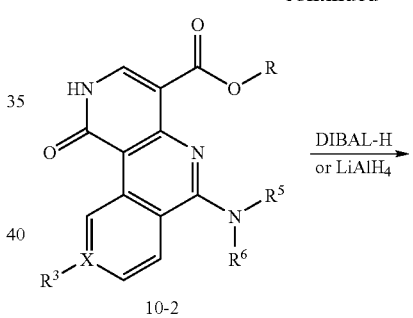

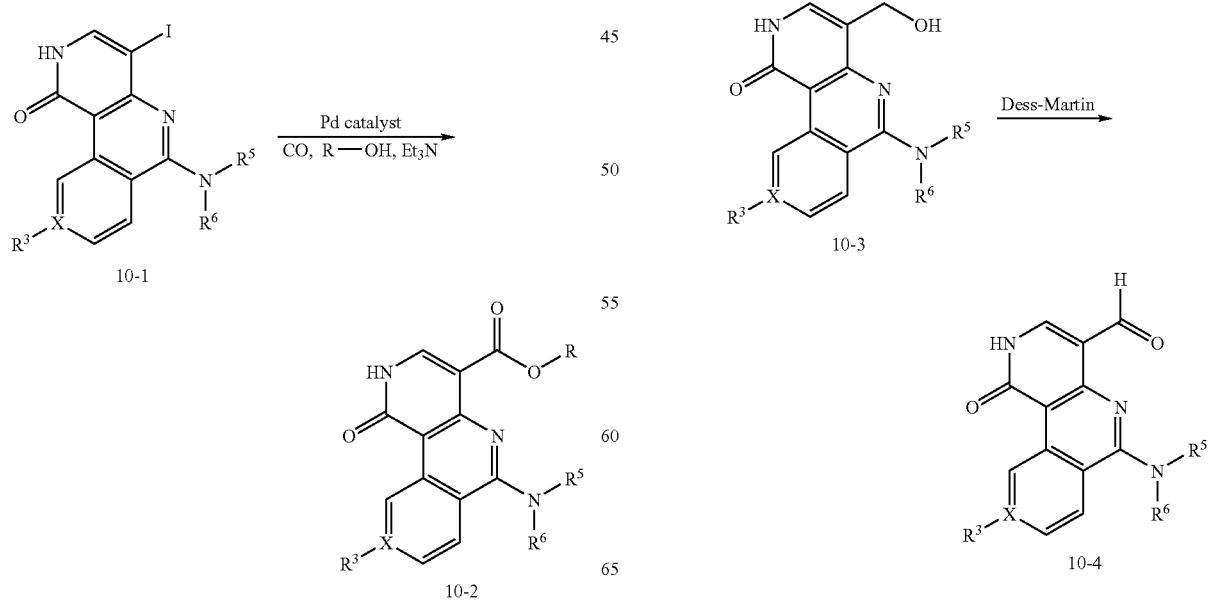

Scheme 10 shows several general methods for derivatizing the tricyclic scaffold wherein X—R3 is either N—R³ or C—R³. Iodides 10-1 can be carbonylated in the presence of either alcohols or water to provide esters or acid 10-2, respectively. Ester or acid 10-2 can be reduced with a suitable hydride reagent such as DIBAL-H or LiAlH₄ to afford alcohol 10-3 which can be oxidized to afford aldehyde 10-4.

SCHEME 11

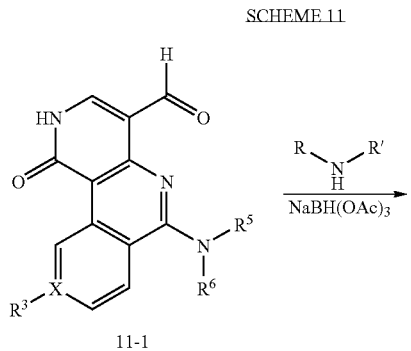

11-1

11-2

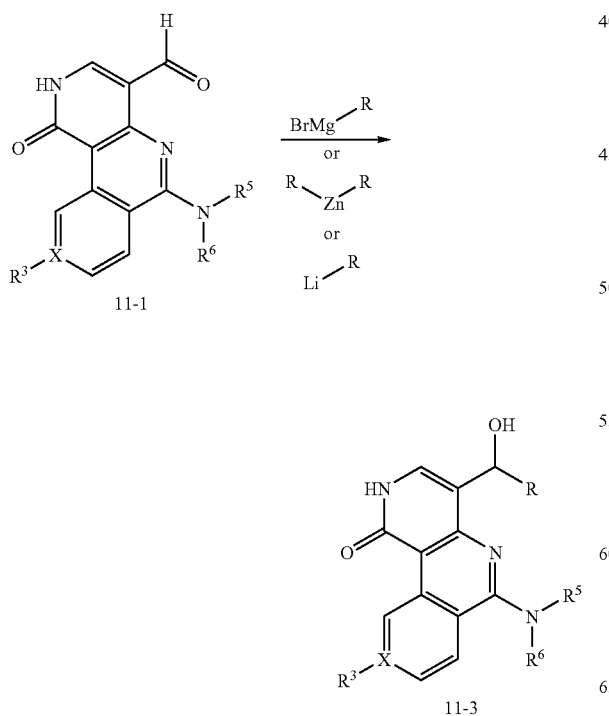

11-1

11-3

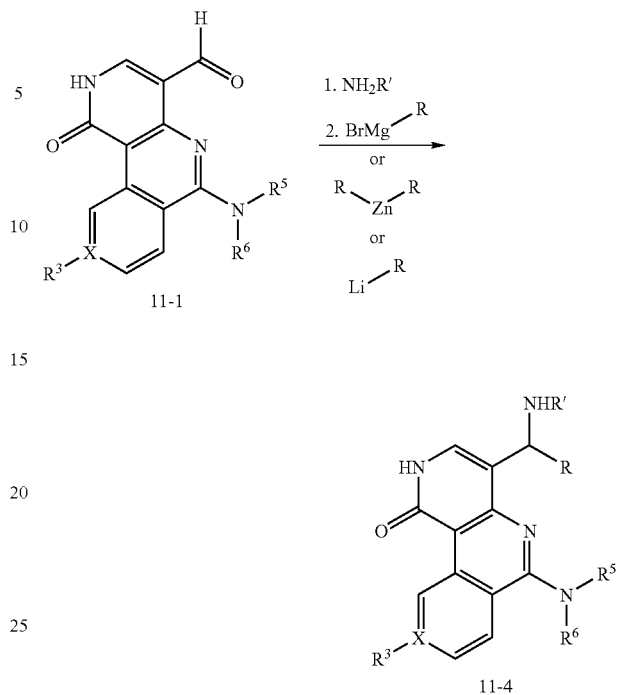

11-1

11-4

Scheme 11 shows several general methods for derivatizing the tricyclic scaffold wherein X—R3 is either N—R³ or C—R³. Aldehyde 11-1 can be treated with an amine and a reducing agent, such as sodium triacetoxyborohydride to afford product 11-2. Alternatively, aldehyde 11-1 can be treated with an organometallic reagent, such as an organomagnesium, organozinc or organolithium reagent to afford alcohol 11-3. Additionally, aldehyde 11-1 can be transformed into an imine by the action of an amine and then treated with an organometallic reagent to afford amine 11-4.

SCHEME 12

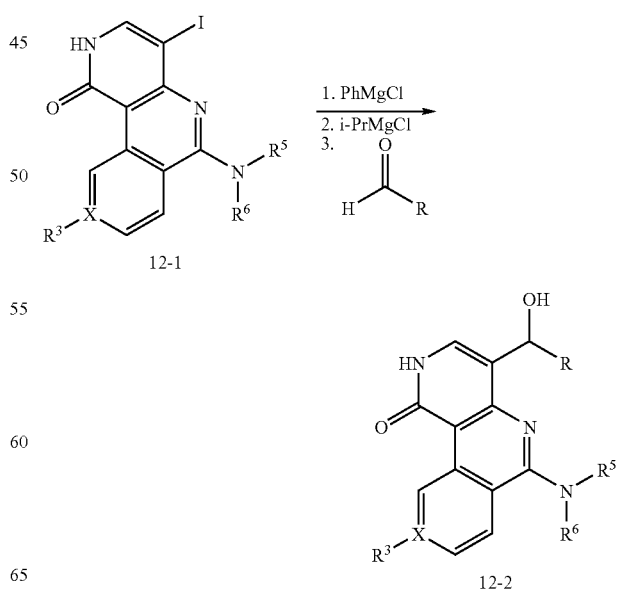

12-1

12-2

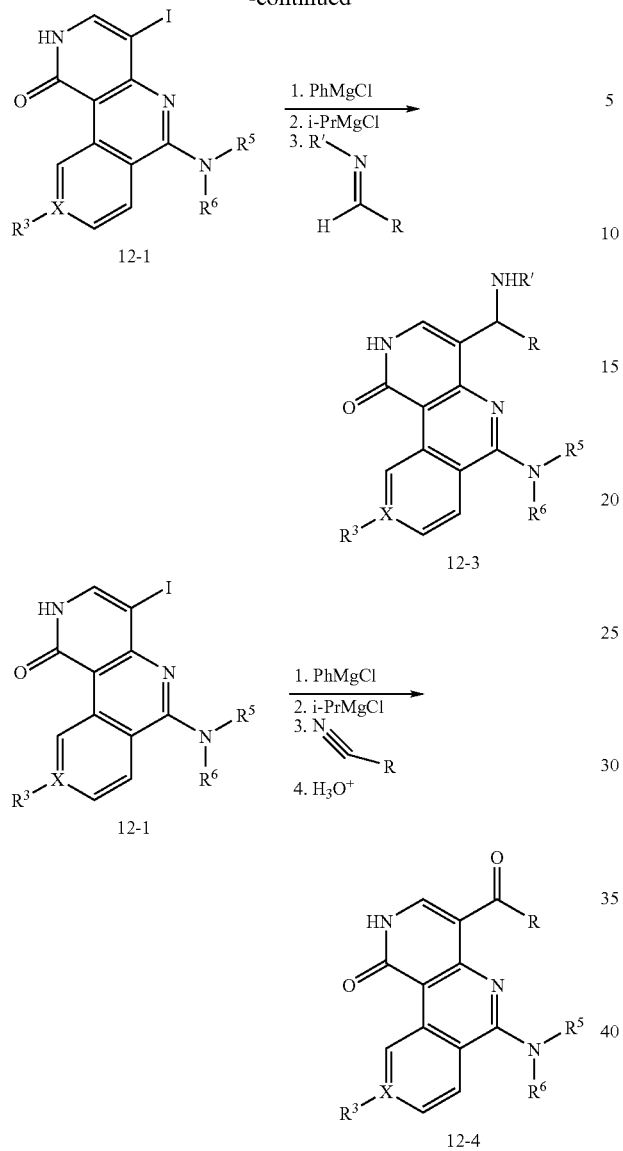
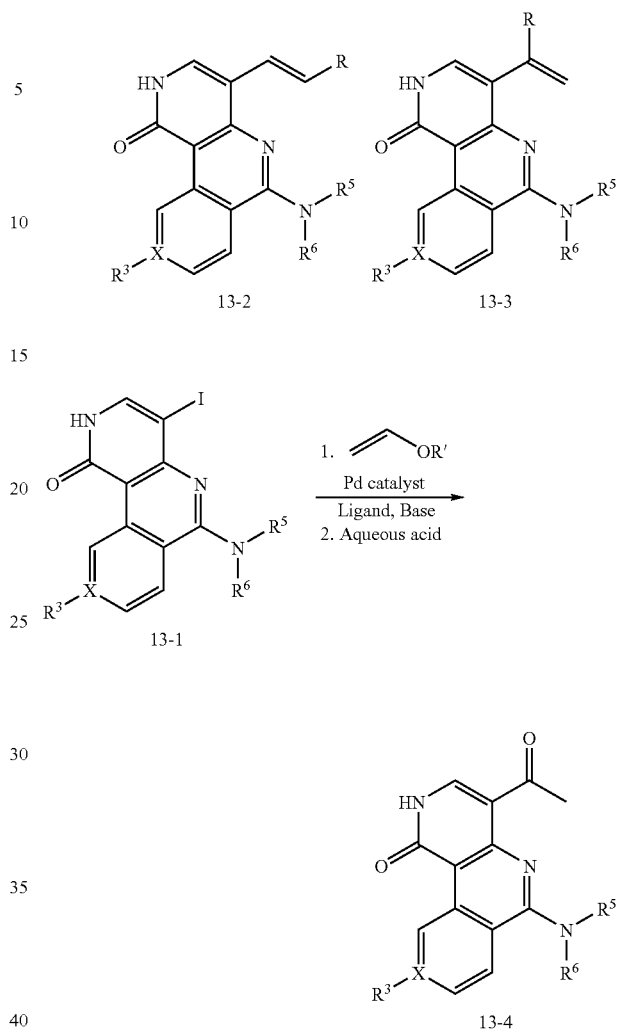

Scheme 12 shows several general methods for derivatizing the tricyclic scaffold wherein X—R3 is either N—R$^3$ or C—R$^3$. Iodide 12-1 can be transformed into an organomagnesium reagent via iodo-magnesium exchange that can be used as a nucleophile to added to aldehydes (to afford alcohol 12-2), imines (to afford amine 12-3) or nitriles (to afford ketone 12-4 after acidic workup).

Scheme 13 shows several general methods for derivatizing the tricyclic scaffold wherein X—R3 is either N—R$^3$ or C—R$^3$. Iodide 13-1 can be alkenylated using a Heck reaction protocol to afford either or both regioisomer 13-2 and/or 13-3. In the special case of a vinyl ether being emplyed in the Heck reaction of 13-1, ketone 13-4 is provided following treatment of the intermediate vinyl ether with aqueous acid.

SCHEME 13

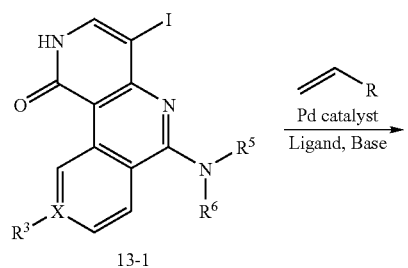

SCHEME 14

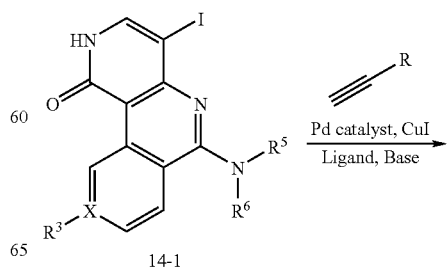

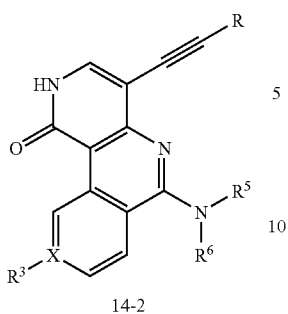

14-2

Scheme 14 shows a method for derivatizing the tricyclic core. Iodide 14-1 can be treated with an alkyne, copper (I) iodide, a suitable palladium catalyst, ligand and base to afford alkyne 14-2.

Scheme 16 shows a method for derivatizing the tricyclic core. Iodide 16-1 can be treated with an amine, a carbon monoxide source (either CO or $MoCO_6$), a suitable palladium catalyst, ligand and base to afford amide 16-2.

SCHEME 15

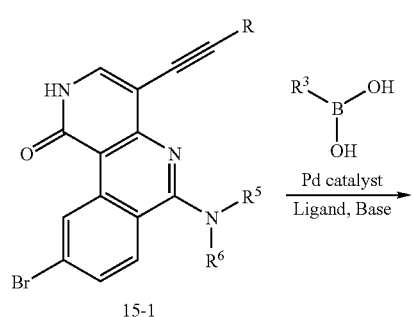

15-1

15-2

Scheme 15 shows a method for derivatizing the tricyclic core. Bromide 15-1 can be treated with a boronic acid, boronic ester, or trifluoroborate salt, a suitable palladium catalyst, ligand and base to afford 15-2.

SCHEME 16

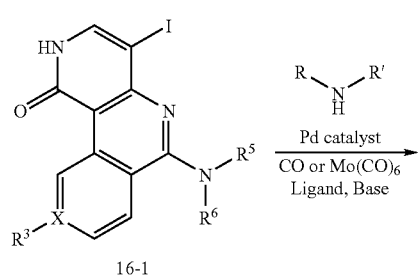

16-1

SCHEME 17

17-1

17-2

Scheme 17 shows primary amide cross couplings of bromide 17-1 that were performed using a modified procedure from *Org. Lett,* 2 (8), 1101-1104, 2000 by Buchwald et al. to provide amides 17-2.

SCHEME 18

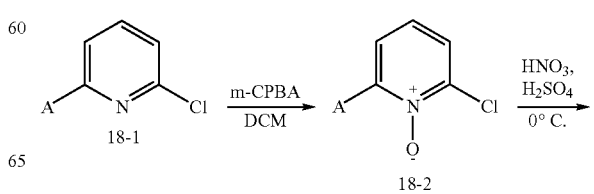

18-1

18-2

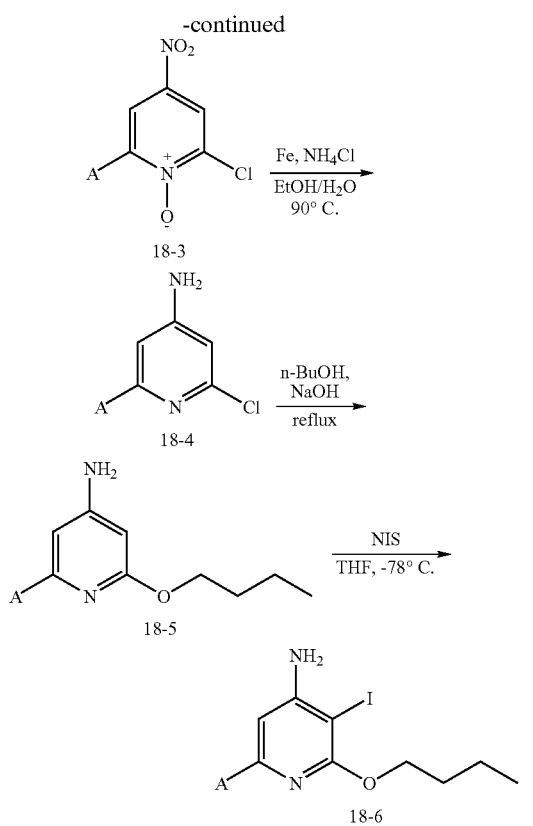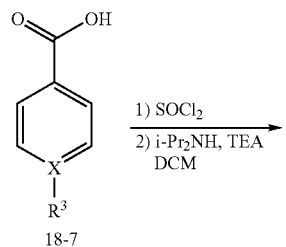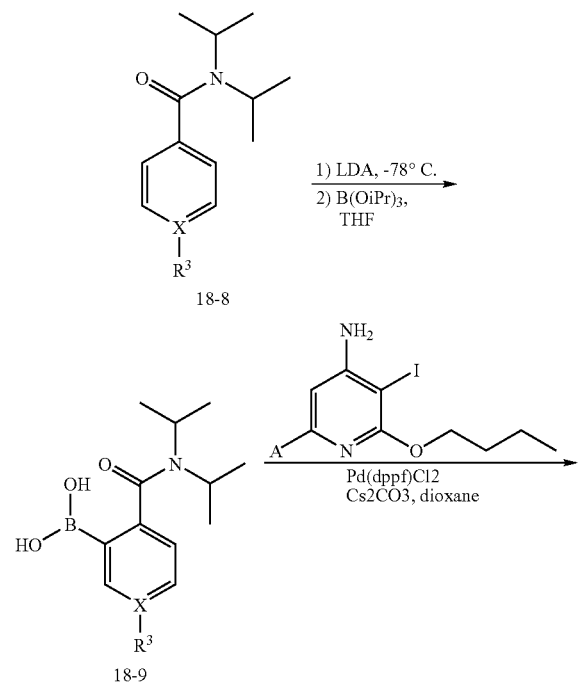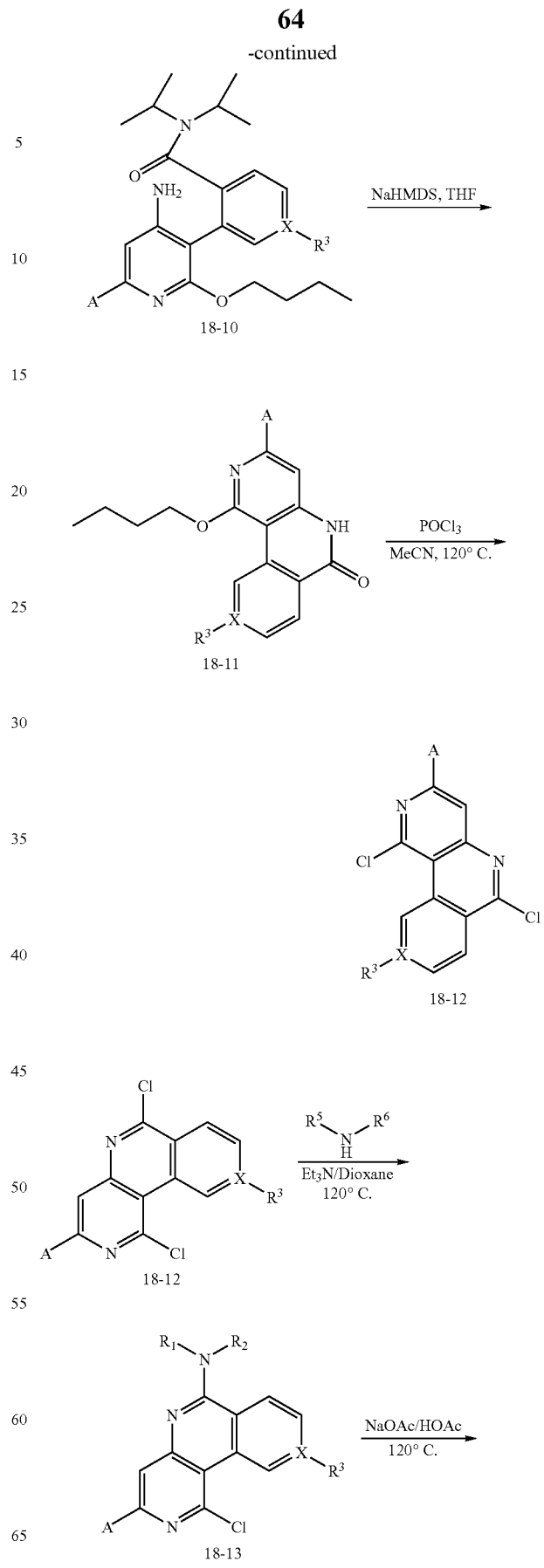

-continued

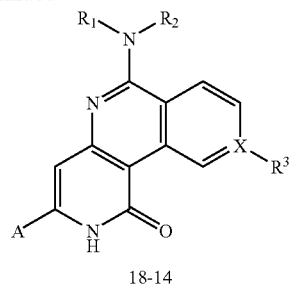

18-14

Scheme 18 shows a method for the preparation of tricyclic pyridones containing substitutent A (e.g., 18-14). Various 2-chloro-6-A pyridines 18-1 are commercially available or are readily prepared from 2,6-dichloropyridine. Compounds 18-1 can be converted to iodopyridine 18-6 in a five step sequence that involves formation of N-oxide 18-2, nitration to form 18-3, reduction of the nitro functionality to form aniline 18-4, protection as the butyl ether 18-5, and finally iodination with N-iodosuccinimide to form 18-6. Boronic acid 18-9 can be prepared in four steps from acid 18-7 by forming the acid chloride of 18-7, amidating with and N,N-diisopropylamine to form 18-8, litiathing 18-8 with LDA and quenching with triisopropylborate. Boronic acid 18-9 and iodide 18-6 are then coupled via Suzuki reaction to form biaryl 18-10, that is then transformed into tricycle 18-11 by the action of NaH-MDS. Tricycle 18-11 is chlorinated with $POCl_3$ to form dichloride 18-12 that is then treated with an amine to form 18-13. Monochloride 18-13 is then hydrolyzed to pyridone 18-14 using sodium acetate in acetic acid at elevated temperature.

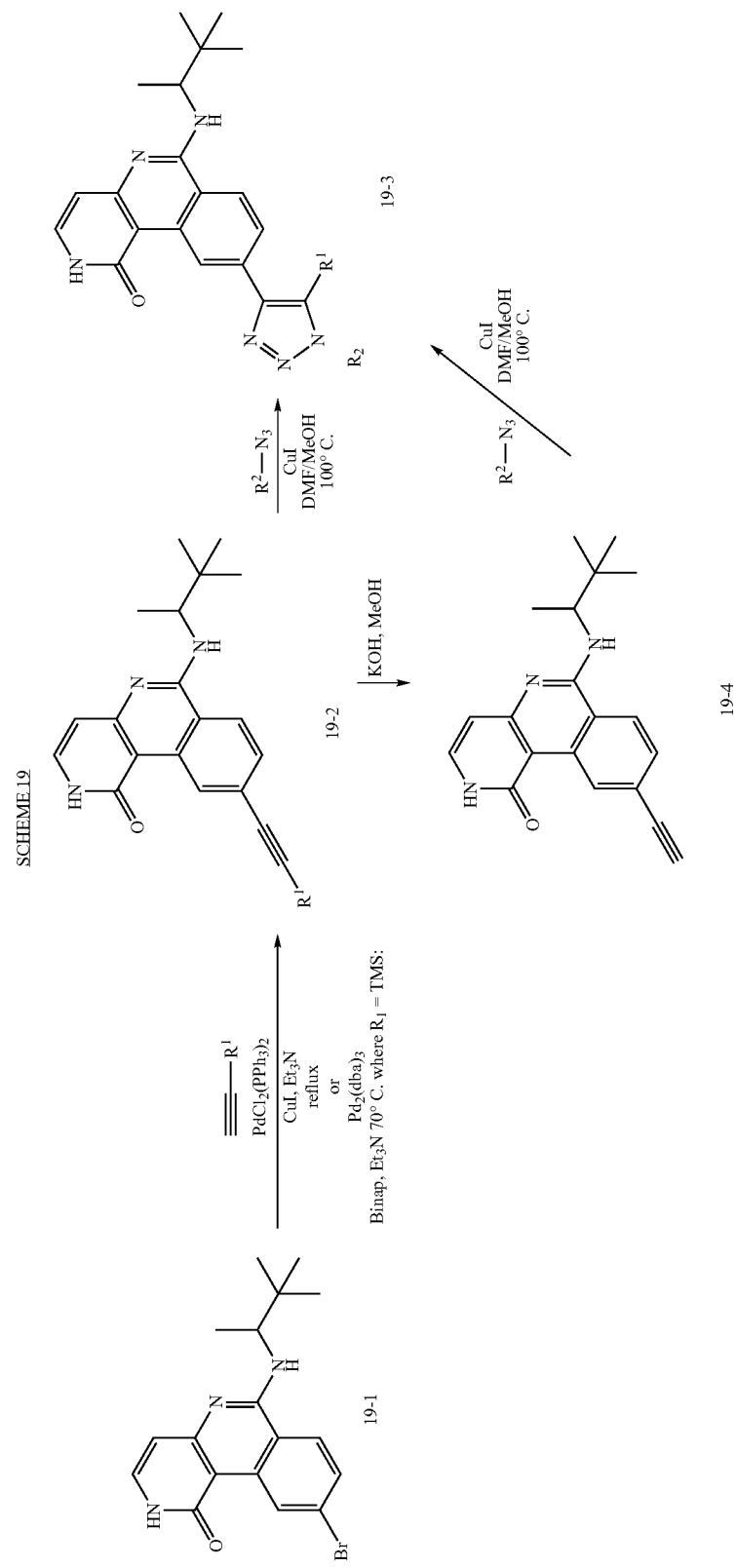

Scheme 19 shows a method for derivatizing the tricyclic scaffold. Bromide 19-1 was subjected to Sonogashira coupling conditions to afford alkyne 19-2 that was either treated with an azide and a copper salt to form triazole 19-3 or first modified to terminal acetylene 19-4 (where $R^1$=trimethylsilyl).

SCHEME 20

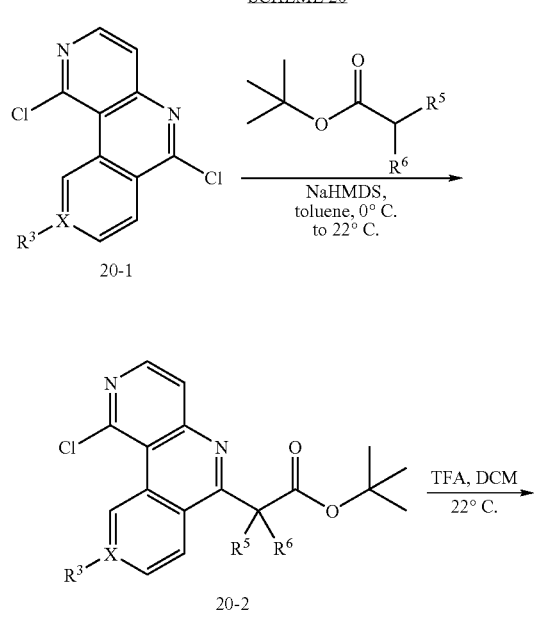

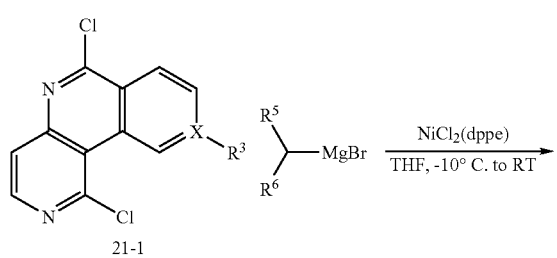

Scheme 20 shows a general method for derivatizing the tricyclic scaffold where X—$R^3$=N, or C—$R^3$. Dichloride 20-1 was alkylated at ambient or sub-ambient temperatures using ester enolates derived from esters and a strong base, such as NaHMDS to afford 20-2. Pyridyl chloride 20-2 was then hydrolyzed with concomitant decarboxylation of the ester moiety to provide pyridone 20-3 by the action of TFA in dichloromethane.

SCHEME 21

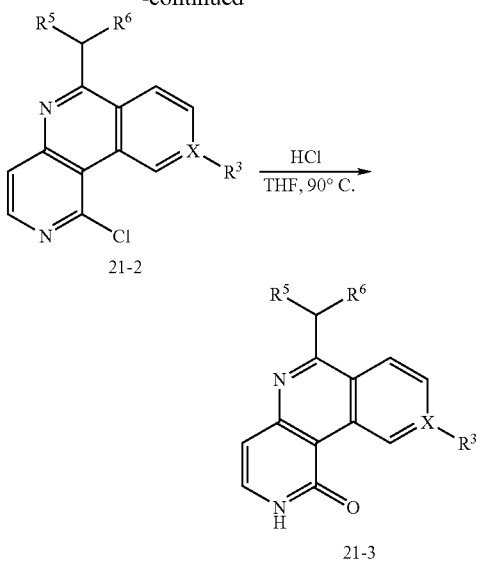

Scheme 21 shows a general method for derivatizing the central ring of the tricyclic core by the formation of a carbon-carbon bond. The dichloride 21-1 is coupled with a Grignard reagent under Kumada coupling conditions to form the chloride 21-2. Under acidic conditions at elevated temperatures, chloride 21-2 is hydrolyzed to the pyridone 21-3.

SCHEME 22

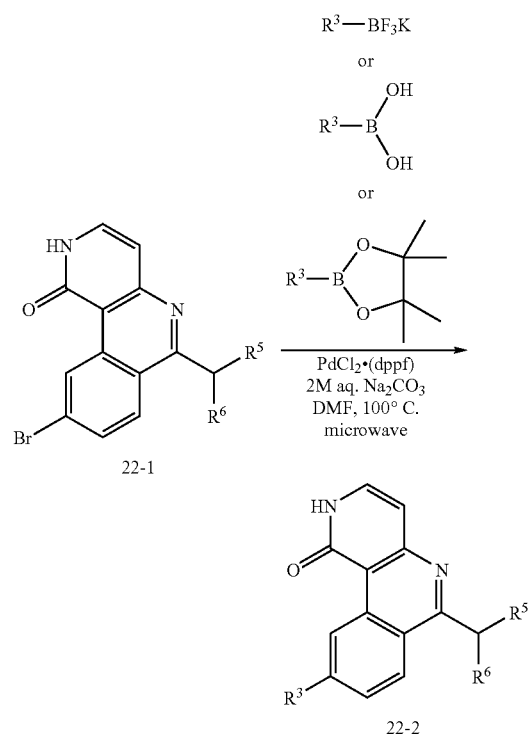

Scheme 22 shows a general method for derivatizing the tricyclic core. Bromide 22-1 was subjected to Suzuki cross-coupling conditions with a boronic acid or ester to afford 22-2.

SCHEME 23
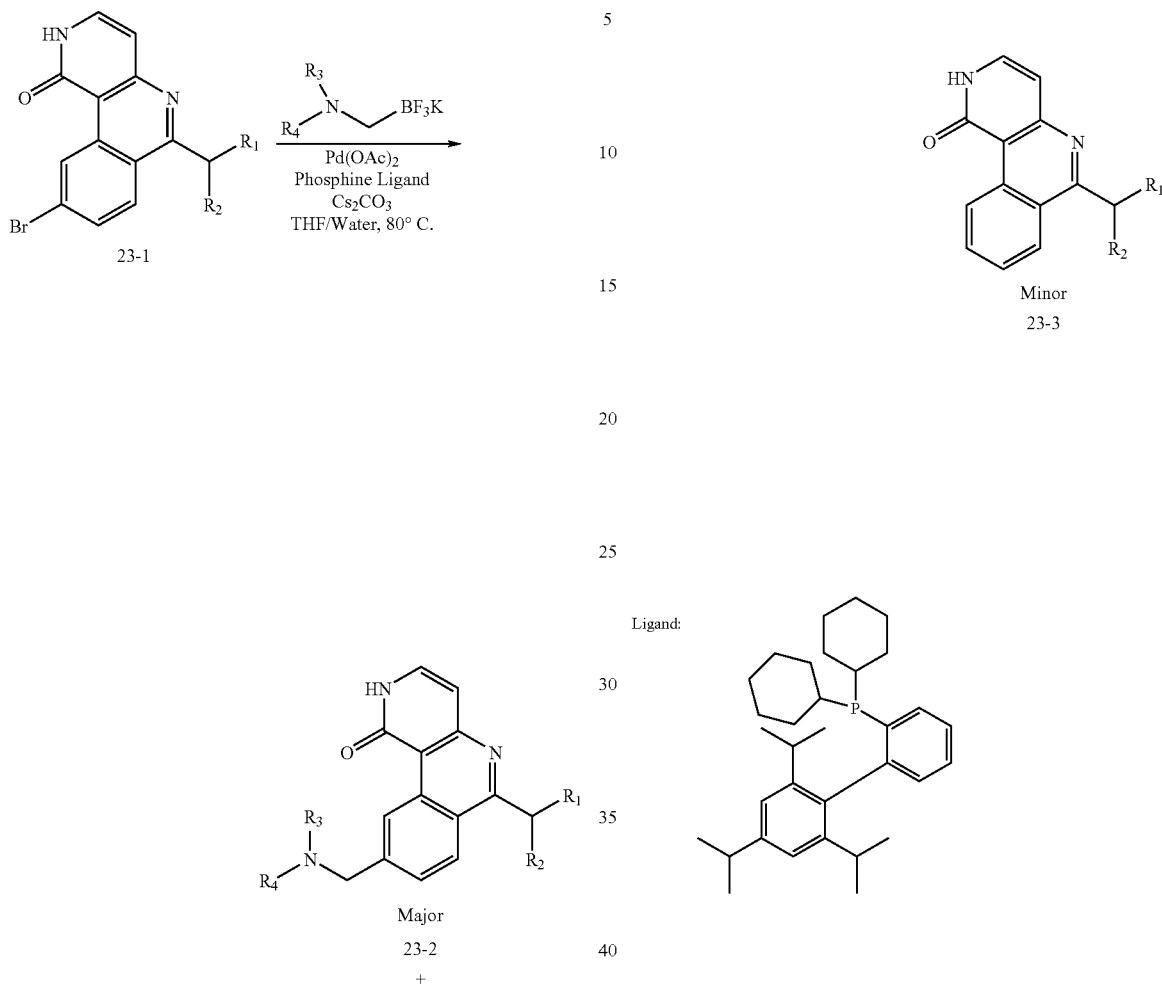
Scheme 23 shows a general method for derivatizing the tricyclic core. Bromide 23-1 was subjected to Suzuki cross-coupling conditions with a potassium trifluoroborate salt to afford 23-2 as well as a minor amount of 23-3.
SCHEME 24
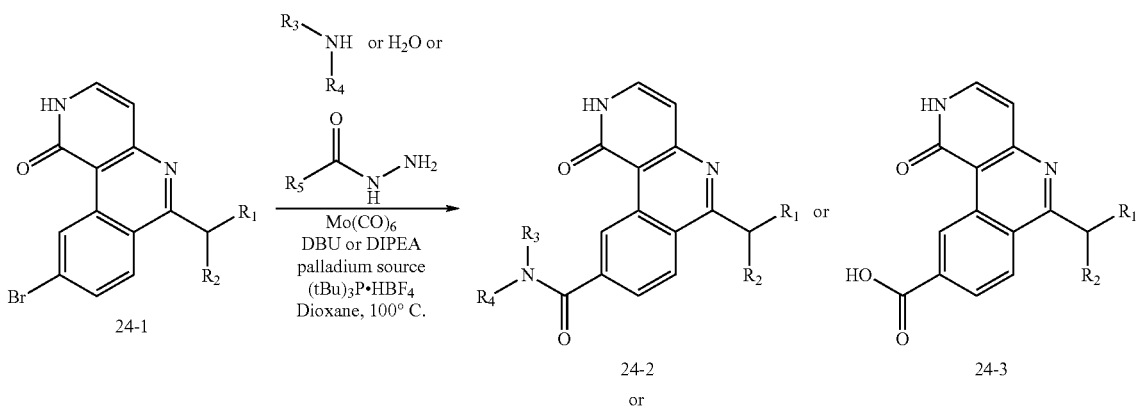

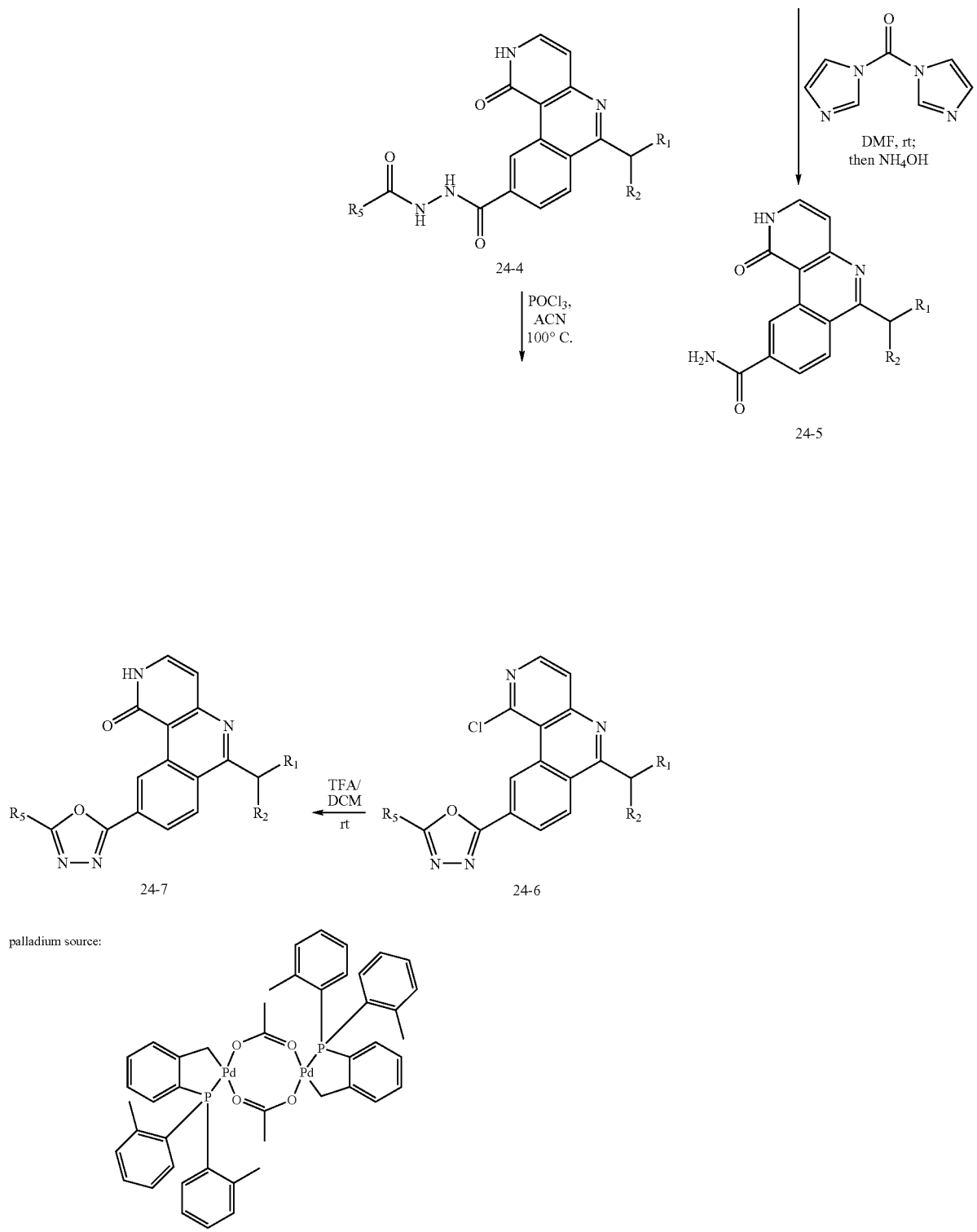

Scheme 24 shows a general method for derivatizing the tricyclic core. Bromide 24-1 was subjected to aminocarbonylation conditions using a CO source, a base, an amine or water, a ligand, and a suitable palladium source to afford 24-2 or 24-3. Acid 24-3 could then be converted to amide 24-5 via an amide coupling protocol with carbonyldiimidazole. 24-4 was dehydrated and chlorinated by the action of POCl₃ to afford oxadiazole 24-6 that was then transformed into pyridone 24-7 under acidic conditions.

SCHEME 25

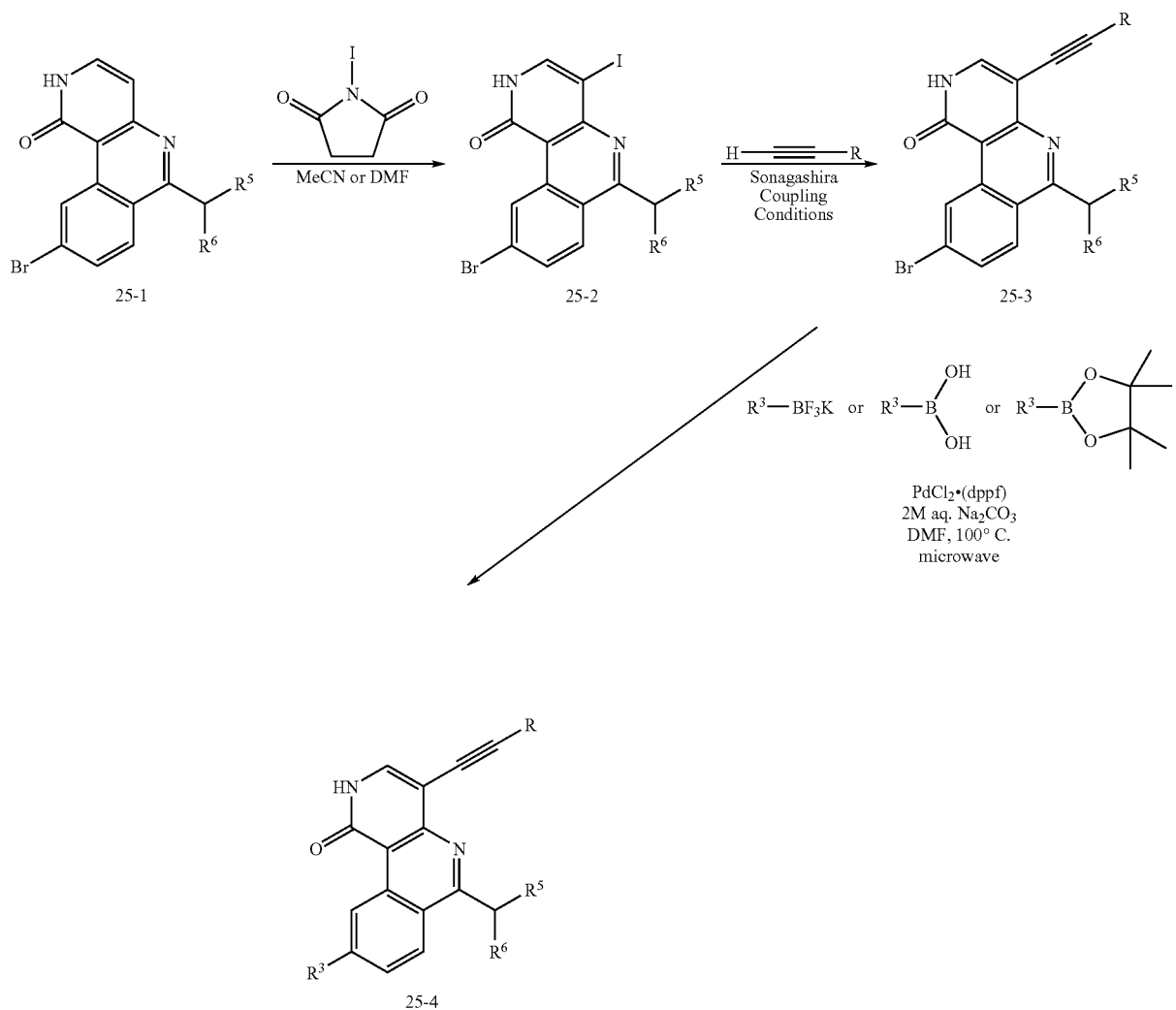

Scheme 25 shows a general method for derivatizing the tricyclic core. Bromide 25-1 was iodinated using NIS in a suitable solvent to afford 25-2. Iodide 25-2 was then subjected to Sonogashira coupling conditions with an alkyne, a base, copper (I) iodide, a ligand, and a suitable palladium source to afford 25-3. Alkynylbromide 25-3 was then subjected to Suzuki cross-coupling conditions to afford 25-4.

SCHEME 26

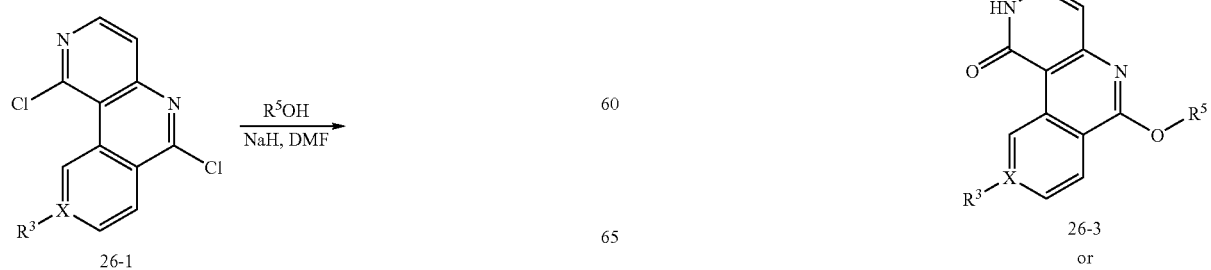

-continued

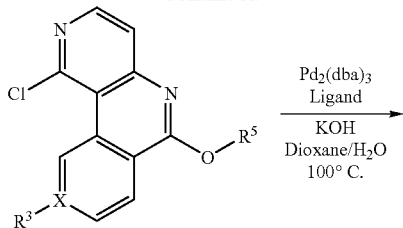

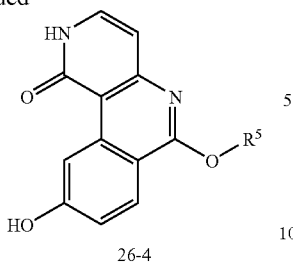
26-4
Ligand:
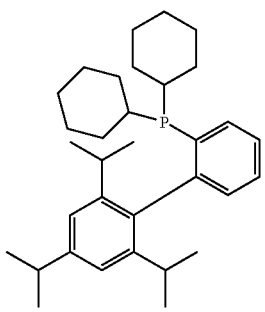
Scheme 26 shows a general method for derivatizing the tricyclic core wherein X—R³═N, C—R³. Dichloride 26-1 was treated with an alcohol and base to afford ether 26-2. Ether 26-2 was then transformed into pyridone 26-3 using a palladium catalyzed coupling of hydroxide to the pyridyl chloride 26-2. When X—R³═C—Br, 26-4 was isolated along with 26-3 from the hydrolysis of 26-2.
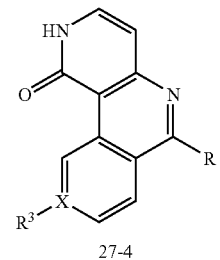
27-4
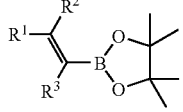
or
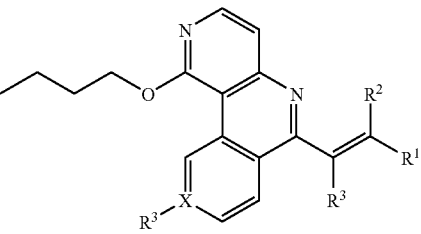
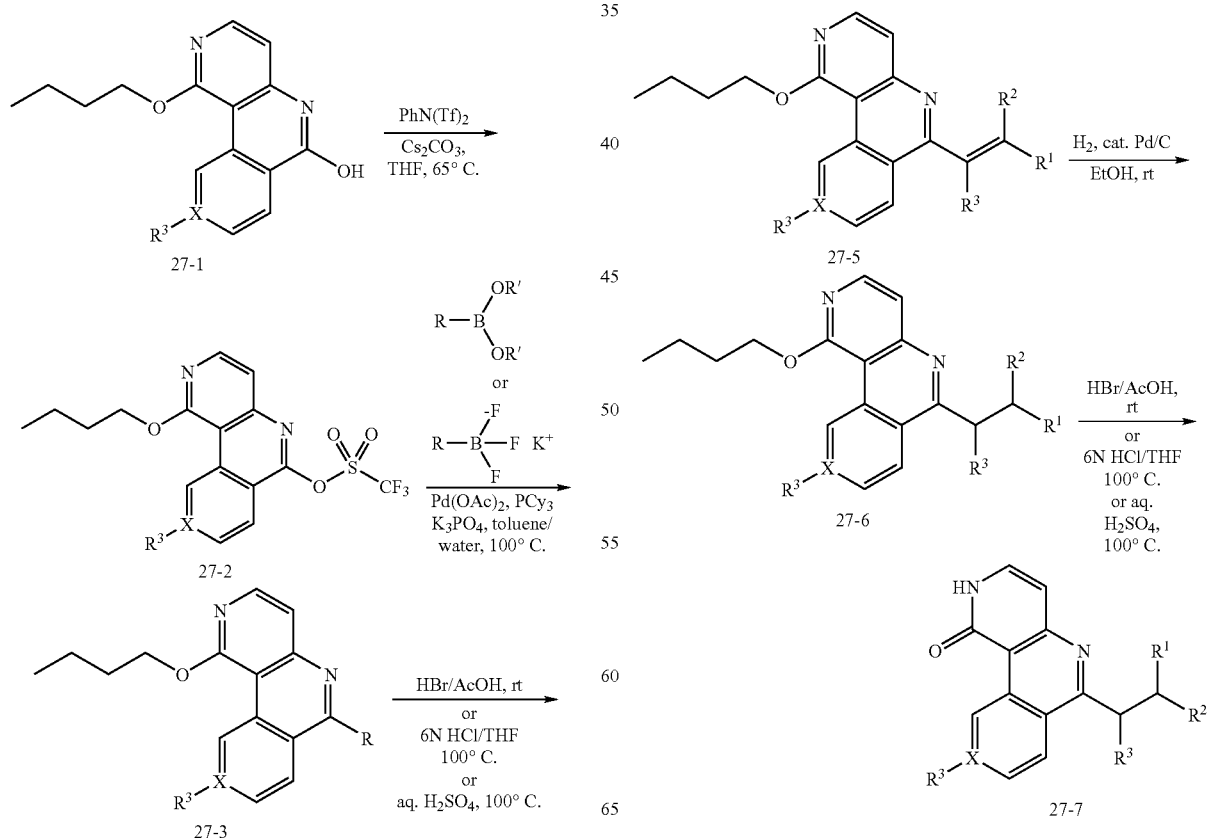
SCHEME 27

Scheme 27 shows several general methods for derivatizing the tricyclic core wherein X—R³═N, C—R³. Hydroxypyridine 27-1 was triflated to afford 27-2 that was then subjected to Suzuki cross-coupling conditions to afford 27-3. 27-3 was then hydrolyzed under acidic conditions to provide pyridone 27-4. 27-2 is also used with vinylboronic acids and vinyltrifluoroborate salts in Suzuki coupling conditions to provide alkenylated tricycle 27-5 that is then hydrogenated using a palladium catalyst to provide 27-6. Butoxy-protected tricycle 27-6 is then deprotected under acidic conditions to afford pyridone 27-7.

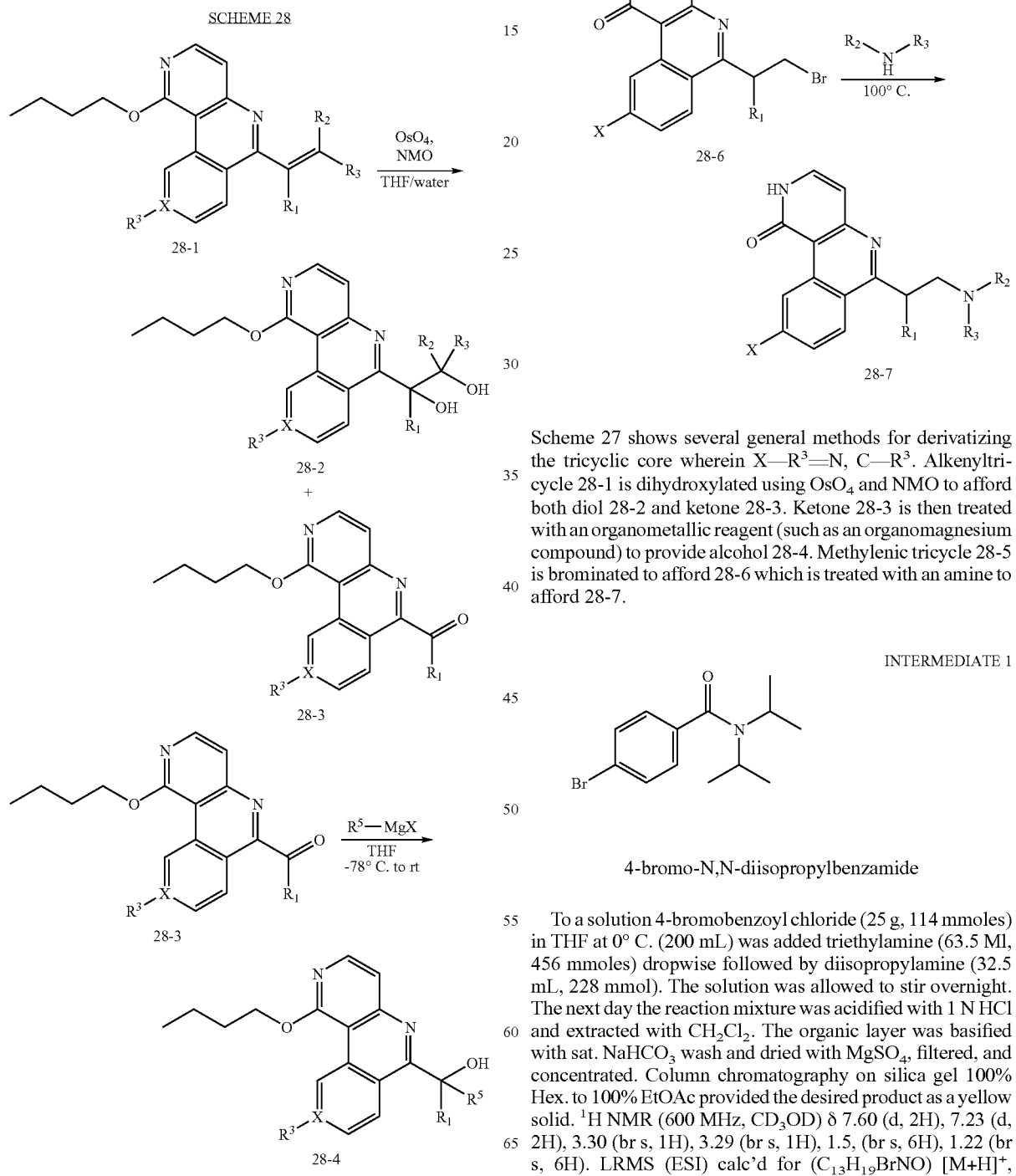

Scheme 27 shows several general methods for derivatizing the tricyclic core wherein X—R³═N, C—R³. Alkenyltricycle 28-1 is dihydroxylated using OsO₄ and NMO to afford both diol 28-2 and ketone 28-3. Ketone 28-3 is then treated with an organometallic reagent (such as an organomagnesium compound) to provide alcohol 28-4. Methylenic tricycle 28-5 is brominated to afford 28-6 which is treated with an amine to afford 28-7.

INTERMEDIATE 1

4-bromo-N,N-diisopropylbenzamide

To a solution 4-bromobenzoyl chloride (25 g, 114 mmoles) in THF at 0° C. (200 mL) was added triethylamine (63.5 Ml, 456 mmoles) dropwise followed by diisopropylamine (32.5 mL, 228 mmol). The solution was allowed to stir overnight. The next day the reaction mixture was acidified with 1 N HCl and extracted with $CH_2Cl_2$. The organic layer was basified with sat. $NaHCO_3$ wash and dried with $MgSO_4$, filtered, and concentrated. Column chromatography on silica gel 100% Hex. to 100% EtOAc provided the desired product as a yellow solid. ¹H NMR (600 MHz, $CD_3OD$) δ 7.60 (d, 2H), 7.23 (d, 2H), 3.30 (br s, 1H), 3.29 (br s, 1H), 1.5, (br s, 6H), 1.22 (br s, 6H). LRMS (ESI) calc'd for ($C_{13}H_{19}BrNO$) [M+H]⁺, 284.1; found 284.1.

INTERMEDIATE 2

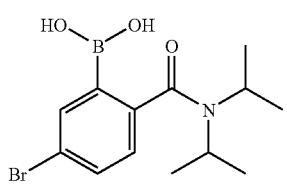

{5-bromo-2-[(diisopropylamino)carbonyl]phenyl}boronic acid

To a solution of 4-bromo-N,N-diisopropylbenzamide (27 g, 95 mmoles) and triisopropyl borate ester (48 g, 55 mL) in THF (190 mL) at −78° C. was added LDA (2.0 M from Acros in Heptanes, THF, ethylbenzene, 71 mL) dropwise by addition funnel. After the addition, the reaction was allowed to warm to room temperature over a period of 1.5 hr. The reaction was complete by TLC and quenched with 1 N HCl and stirred for 30 min. The resulting solution was extracted with EtOAc. The organic layers were combined and washed with sat. NaHCO$_3$ followed by brine. The organic layers were dried with MgSO$_4$, filtered, and concentrated to afford a yellow solid. The solid was treated with Et$_2$O and aged for 2 hr and filtered to produce the desired product. The mother liquor upon sitting for several hours was filtered again to produce more product. This process was repeated 2 more times. LRMS (ESI) calc'd for ($C_{13}H_{20}BBrNO_3$) [M+H]$^+$, 328.1; found 328.0.

INTERMEDIATE 3

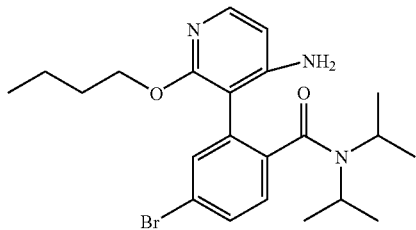

2-(4-amino-2-butoxypyridin-3-yl)-4-bromo-N,N-diisopropylbenzamide

To a solution of {5-bromo-2-[(diisopropylamino)carbonyl]phenyl}boronic acid (9.78 g, 26.7 mmol) and 2-butoxy-3-iodo-4-aminipyridine (5.2 g, 17.8 mmol) (see International Publication WO2005105814, which published on Nov. 10, 2005, to Incyte) in THF (150 mL) and 2.0 M NaHCO$_3$ (40 mL) was added tetrakis(triphenylphosphine) palladium (3.56 mmol, 4.11 g). The solution was degassed by bubbling N$_2$ to the solution for 10 min then heated to 100° C. for 2.5 hr. The reaction was cooled and extracted with EtOAc and washed with H$_2$O. Column chromatography on silica gel 100% Hex. to 100% EtOAc provided 2-(4-amino-2-butoxypyridin-3-yl)-4-bromo-N,N-diisopropylbenzamide. LRMS (ESI) calc'd for ($C_{22}H_{31}BrN_3O_2$) [M+H]$^+$, 448.2; found 448.1.

INTERMEDIATE 4

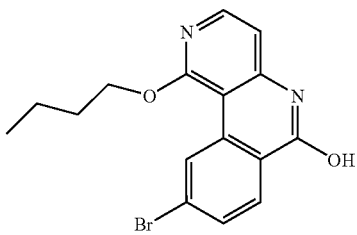

9-bromo-1-butoxybenzo[c]-1,6-naphthyridin-6-ol

To a solution of 2-(4-amino-2-butoxypyridin-3-yl)-4-bromo-N,N-diisopropylbenzamide (8.5 g, 19.0 mmol) in THF (135 mL) was added sodium bis(trimethylsilyl)amide (38 mL, 38 mmol, 1.0 M in THF) dropwise at 0° C. under nitrogen. The solution was allowed to stir for 2 hr then quenched with water. The solid precipitate was filtered, collected, and dried under vacuum to afford 9-bromo-1-butoxybenzo[c]-1,6-naphthyridin-6-ol as a white solid. $^1$H NMR (600 MHz, CD$_6$SO) δ 9.22 (s, 1H), 8.2 (d, 1H), 8.05 (d, 1H), 7.78 (d, 1H), 6.92, (d, 1H), 4.45 (t, 2H), 1.86 (m, 2H), 1.59 (m, 21-1), 1.0 (t, 3H). LRMS (ESI) calc'd for ($C_{16}H_{15}BrN_2O_2$) [M+H]$^+$, 347.0; found 347.0.

INTERMEDIATE 5

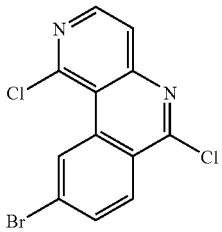

9-bromo-1,6-dichlorobenzo[c]-1,6-naphthyridine 9-bromo-1-butoxybenzo[c]-1,6-naphthyridin-6-ol (2.0 g, 5.76 mmol) in acetonitrile (15 mL) and phosphorous oxychloride (5.37 mL, 57.6 mmol) was heated to 100° C. overnight. The reaction was cooled and quenched with triethylamine (10 mL) at −15° C. followed by the addition of EtOAc and sat. NaHCO$_3$ at −15° C. The organic layers were separated, dried with MgSO$_4$, filtered, and concentrated to produce a solid. The solid was triturated with MeOH and filtered to afford 9-bromo-1,6-dichlorobenzo[c]-1,6-naphthyridine as a pale solid. $^1$H NMR (600 MHz, CD$_6$SO)S 9.88 (s, 1H), 8.66 (d, 1H), 8.55 (d, 1H), 8.22 (dd, 1H), 8.0 (d, 1H). LRMS (ESI) calc'd for ($C_{12}H_6BrCl_2N_2$) [M+H]$^+$, 326.9; found 326.9.

Example 1

Method A for Amine Addition

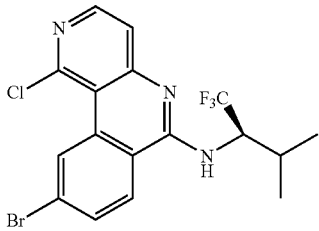

Method A, Step 1: 9-bromo-1-chloro-N-[(1R)-2-methyl-1-(trifluoromethyl)propyl]benzo[c]-1,6-naphthyridin-6-amine

To a solution of dried 9-bromo-1,6-dichlorobenzo[c]-1,6-naphthyridine (0.80 g, 2.46 mmol) in dioxane (16 mL) was added (2R)-1,1,1-trifluoro-3-methylbutan-2-amine (2.4 g, 17.2 mmol) and heated to 150° C. for 24-48 hrs. The reaction was concentrated to dryness to give 9-bromo-1-chloro-N-[(1R)-2-methyl-1-(trifluoromethyl)propyl]benzo[c]-1,6-naphthyridin-6-amine. LRMS (ESI) calc'd for ($C_{17}H_{15}BrClF_3N_3$) [M+H]$^+$, 432.0; found 432.0.

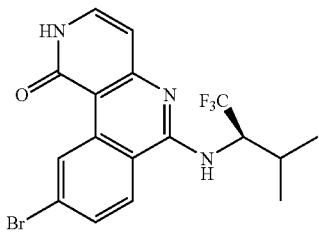

Method A, Step 2: 9-bromo-6-{[(1R)-2-methyl-1-(trifluoromethyl)propyl]amino}benzo[c]-1,6-naphthyridin-1(2H)-one

9-bromo-1-chloro-N-[(1R)-2-methyl-1-(trifluoromethyl)propyl]benzo[c]-1,6-naphthyridin-6-amine (1.0 g, 2.31 mmol) in 6 N HCl (4 mL) and THF (4 mL) was heated to 90° C. for 2 hr. The reaction was cooled and diluted with EtOAc and quenched with sat. NaHCO$_3$. The mixture was extracted and the organic layers were separated, dried with MgSO$_4$, filtered, and concentrated to give the crude product. Column chromatography on silica gel 100% Hex. to 100% EtOAc afforded 9-bromo-6-{[(1R)-2-methyl-1-(trifluoromethyl)propyl]amino}benzo[c]-1,6-naphthyridin-1(2H)-one. $^1$H NMR (600 MHz, CD$_3$OD) δ 10.1 (d, 1H), 8.31 (d, 1H), 7.75 (d, 1H), 7.40 (d, 1H), 6.65, (d, 1H), 5.46 (m, 1H), 2.35 (m, 1H), 1.12 (d, 3H), 1.06 (d, 3H). LRMS (ESI) calc'd for ($C_{17}H_{16}BrF_3N_3O$) [M+H]$^+$, 414.0; found 414.0.

Example 2

Method B for Amine Addition

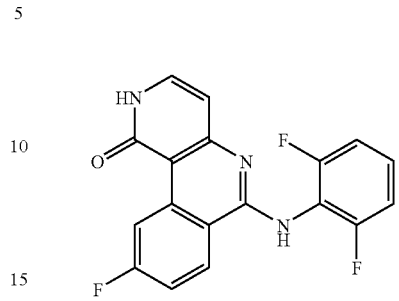

6-[(2,6-difluorophenyl)amino]-9-fluorobenzo[c]-1,6-naphthyridin-1(2H)-one

To a solution of 1,6-dichloro-9-fluorobenzo[c]-1,6-naphthyridine (70 mg, 0.26 mmol) in dioxane (2 mL) were added HCl (0.131 mL, 4 N in dioxane) and 2,6 difluoroaniline (67.7 mg, 0.524 mmol) and heated to 150° C. for 3 hr. The reaction was cooled and purified by reverse phase HPLC. $^1$H NMR (600 MHz, CD$_3$OD) δ 9.66 (dd, 1H), 8.56 (s, 1H) 7.50 (m, 1H), 7.48 (m, 2H), 7.13 (m, 2H), 6.45 (dd, 1H). LRMS (ESI) calc'd for ($C_{18}H_{11}F_3N_3O$) [M+H]$^+$, 342.1; found 342.0.

Example 3

Method C for Amine Addition

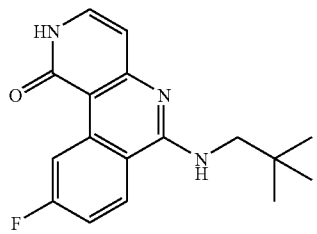

6-[(2,2-dimethylpropyl)amino]-9-fluorobenzo[c]-1,6-naphthyridin-1(2H)-one

To a solution of 1,6-dichloro-9-fluorobenzo[c]-1,6-naphthyridine (20 mg, 0.075 mmol) in dioxane (1.5 mL) was added 2,2-dimethylpropan-1-amine (39 mg, 0.45 mmol) and heated in a microwave reactor at 100° C. for 30 to 50 min. The solution was concentrated and converted to 6-[(2,2-dimethylpropyl)amino]-9-fluorobenzo[c]-1,6-naphthyridin-1(2H)-one in a similar manner exemplified in the synthesis of 9-bromo-6-{[(1R)-2-methyl-1-(trifluoromethyl)propyl]amino}benzo[c]-1,6-naphthyridin-1(2H)-one (Method A, Step 2). $^1$H NMR (600 MHz, CD$_3$OD) δ 9.65 (dd, 1H), 8.60 (dd, 1H), 7.60 (d, 1H), 7.58 (m, 1H), 6.95 (d, 1H), 3.70 (s, 2H), 1.10 (s, 9H). LRMS (ESI) calc'd for ($C_{17}H_{19}FN_3O$) [M+H]$^+$, 300.15; found 300.1.

Example 4

Method D for Amine Addition

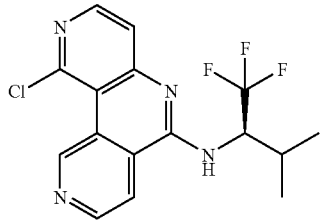

Method D, Step 1: 1-chloro-N-[(1R)-2-methyl-1-(trifluoromethyl)propyl]pyrido[4,3-c]-1,6-naphthyridin-6-amine To a solution of 1,6-dichloropyrido[4,3-c]-1,6-naphthyridine (758 mg, 3.03 mmol) and (2R)-1,1,1-trifluoro-3-methylbutan-2-amine (428 mg, 3.03) in THF (20 mL) was added LiHMDs (9.09 mL, 0.09 mmol) and heated to 85° C. for 1 hr. The reaction was cooled and purified on silica gel column chromatography Hex. to 100% EtOAc to afford. 1-chloro-N-[(1R)-2-methyl-1-(trifluoromethyl)propyl]pyrido[4,3-c]-1,6-naphthyridin-6-amine. LRMS (ESI) calc'd for $(C_{16}H_{15}C1_1F_3N_4)$ $[M+H]^+$, 355.1; found 355.1.

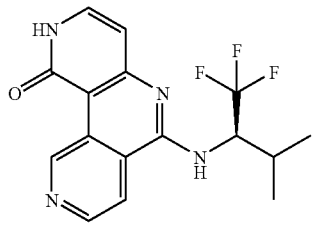

Method D, Step 2: 6-{[(1R)-2-methyl-1-(trifluoromethyl)propyl]amino}pyrido[4,3-c]-1,6-naphthyridin-1(2H)-one The 2-chloro pyridine was converted the pyridone following the procedure of *J. Am. Chem. Soc.* 2006, 128, 1094-10695. To a solution of 1-chloro-N-[(1R)-2-methyl-1-(trifluoromethyl)propyl]pyrido[4,3-c]-1,6-naphthyridin-6-amine (1100 mg, 3.10 mmol) in dioxane (10 mL) and water (10 mL) was added KOH (696 mg, 12.4 mmol), 1-[2'-(di-tert-butylphosphino)-2,6-diisopropylbiphenyl-4-yl]ethyl (263 mg, 0.62 mmol) and $Pd_2$ (dba)$_3$ (284 mg, 0.31 mmol). The stirring solution was heated to 100° C. overnight. The reaction mixture was cooled and worked up with EtOAc and water. The organic layers were separated, dried with $MgSO_4$, filtered, and concentrated by rotary evaporation. The oily residue was purified by silica gel column chromatography $CH_2Cl_2$ to MeOH 30% provided the 6-{[(1R)-2-methyl-1-(trifluoromethyl)propyl]amino}pyrido[4,3-c]-1,6-naphthyridin-1(2H)-one. $^1$H NMR (600 MHz, $CD_3OD$) δ 11.30 (s, 1H), 9.05 (d, 1H), 8.95 (d, 1H), 7.62 (d, 1H), 6.80 (d, 1H), 5.48 (m, 1H), 2.40 (m, 1H), 1.17 (d, 3H), 1.10 (d, 3H). LRMS (ESI) calc'd for $(C_{16}H_{16}F_3N_4O)$ $[M+H]^+$, 337.1; found 337.1.

INTERMEDIATE 6

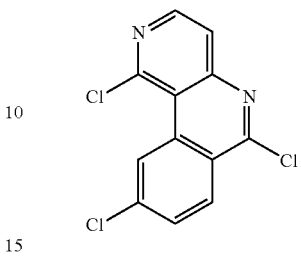

1,6,9-trichlorobenzo[c]-1,6-naphthyridine 1-butoxy-9-chlorobenzo[c]-1,6-naphthyridin-6-ol (see International Publication WO2005105814, which published on Nov. 10, 2005, to Incyte) was converted to 1,6,9-trichlorobenzo[c]-1,6-naphthyridine using the same procedure as shown in 9-bromo-1,6-dichlorobenzo[c]-1,6-naphthyridine. $^1$H NMR (600 MHz, $CDCl_3$) δ 9.90 (s, 1H), 8.62 (d, 1H), 8.56 (s, 1H), 7.89 (s, 1H). 7.84 (d, 1H). LRMS (ESI) calc'd for $(C_{12}H_6Cl_3N_2)$ $[M+H]^+$, 283.0; found 283.0.

INTERMEDIATE 7

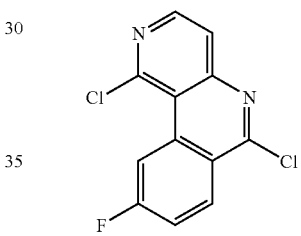

1,6-dichloro-9-fluorobenzo[c]-1,6-naphthyridine 1-butoxy-9-fluorobenzo[c]-1,6-naphthyridin-6-ol (see International Publication WO2005105814, which published on Nov. 10, 2005, to Incyte) was converted to 1,6-dichloro-9-fluorobenzo[c]-1,6-naphthyridine using the same procedure as shown in 9-bromo-1,6-dichlorobenzo[c]-1,6-naphthyridine $^1$H NMR (600 MHz, $CD_3OD$) δ 9.60 (dd, 1H), 8.67 (dd, 1H), 8.62 (d, 1H), 7.90 (d, 1H), 7.62 (m, 1H). LRMS (ESI) calc'd for $(C_{12}H_6Cl_2FN_2)$ $[M+H]^+$, 267.0; found 267.0.

INTERMEDIATE 8

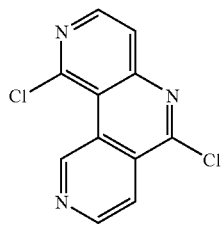

1,6-dichloropyrido[4,3-c]-1,6-naphthyridine 1-butoxypyrido[4,3-c]-1,6-naphthyridin-6-ol (500 mg, 1.9 mmol) (see International Publication WO2005105814, which published on Nov. 10, 2005, to Incyte) and diethylaniline (554 mg, 3.71 mmol) were heated in MeCN (5 mL) and phosphorous oxychloride (1.7 mL) overnight. The reaction was cooled and quenched with triethylamine (10 mL) at −15° C. followed by the addition of EtOAc and sat. NaHCO$_3$ at −15° C. The organic layers were separated, dried with MgSO$_4$, filtered, and concentrated to produce a solid. The solid was purified by silica gel chromatography Hex. to 100% EtOAc to afford 1,6-dichloropyrido[4,3-c]-1,6-naphthyridine. LRMS (ESI) calc'd for (C$_{11}$H$_6$Cl$_2$N$_3$) [M+H]$^+$, 250.0; found 250.0.

INTERMEDIATE 9

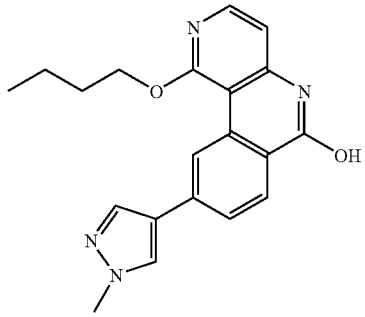

1-butoxy-9-(1-methyl-1H-pyrazol-4-yl)benzo[c]-1,6-naphthyridin-6-ol

To a mixture of 9-bromo-1-butoxybenzo[c]-1,6-naphthyridin-6-ol (251 mg, 0.723 mmol), 1-methyl-4-(4,4,5,5-tetramethyl-1,3,2-dioxaborolan-2-yl)-1H-pyrazole (256 mg, 1.229 mmol), lithium chloride (184 mg, 4.34 mmol), and tetrakis(triphenylphosphine)palladium (251 mg, 0.217 mmol) in DMF (7229 µl) in a sealed tube, sodium carbonate (3615 µl, 7.23 mmol, 2 M) was added, and the reaction mixture was heated to 135° C. After 2 h, the reaction mixture was allowed to cool to room temperature and poured into water. This mixture was then filtered through a frit. The filter cake was washed with dichloromethane. The filter cake was then collected and dried under high vacuum to afford 1-butoxy-9-(1-methyl-1H-pyrazol-4-yl)benzo[c]-1,6-naphthyridin-6-ol as a white solid. LRMS (APCI) calc'd for (C$_{20}$H$_{21}$N$_4$O$_2$) [M+H]+, 349.2; found 349.1.

INTERMEDIATE 10

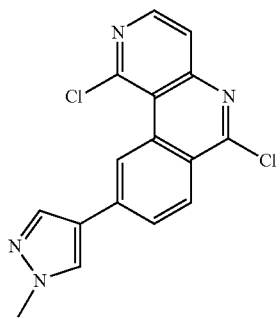

1,6-dichloro-9-(1-methyl-1H-pyrazol-4-yl)benzo[c]-1,6-naphthyridine

A mixture of 1-butoxy-9-(1-methyl-1H-pyrazol-4-yl)benzo[c]-1,6-naphthyridin-6-ol (2.1 g, 6.03 mmol) and phosphorus oxychloride (14.05 ml, 151 mmol) in a sealed tube was heated to 140° C. for 2 h. After cooling to room temperature, the reaction mixture was concentrated under reduced pressure. To the residue, isopropanol was added. The mixture was cooled to 0° C., and triethylamine was added until gas no longer evolved. The mixture was filtered through a frit, and the filter cake was washed with hexane. The filter cake was then triturated with water and dried under reduced pressure to afford 1,6-dichloro-9-(1-methyl-1H-pyrazol-4-yl)benzo[c]-1,6-naphthyridine as a yellow solid. LRMS (APCI) calc'd for (C$_{16}$H$_{11}$Cl$_2$N$_4$) [M+H]+, 329.0; found 329.0.

Example 5

Method E for Amine Addition

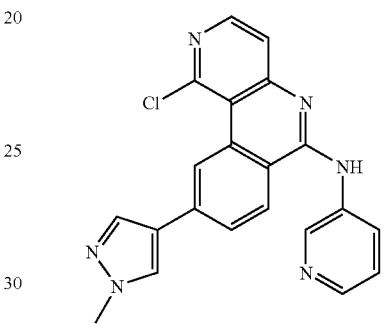

Method E, Step 1: 1-chloro-9-(1-methyl-1H-pyrazol-4-yl)-N-pyridin-3-ylbenzo[c]-1,6-naphthyridin-6-amine To a solution of 1,6-dichloro-9-(1-methyl-1H-pyrazol-4-yl)benzo[c]-1,6-naphthyridine (50 mg, 0.152 mmol) and 3-aminopyridine (14.30 mg, 0.152 mmol) in THF (1.5 mL), sodium tert-butoxide (43.8 mg, 0.456 mmol) was added. The reaction mixture was heated to 85° C. for 1 h. After cooling to room temperature, aqueous ammonium chloride (saturated) and ethyl acetate were added. The mixture was extracted with ethyl acetate. The combined organic extracts were dried over sodium sulfate and concentrated under reduced pressure to afford 1-chloro-9-(1-methyl-1H-pyrazol-4-yl)-N-pyridin-3-ylbenzo[c]-1,6-naphthyridin-6-amine as a yellow solid. LRMS (APCI) calc'd for (C$_{21}$H$_{15}$ClN$_6$) [M+H]+, 387.1; found 387.1.

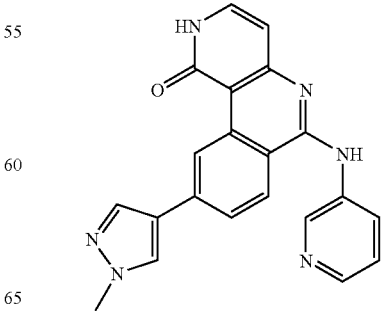

Method E, Step 2: 9-(1-methyl-1H-pyrazol-4-yl)-6-(pyridin-3-ylamino)benzo[c]-1,6-naphthyridin-1(2H)-one 1-chloro-9-(1-methyl-1H-pyrazol-4-yl)-N-pyridin-3-yl-benzo[c]-1,6-naphthyridin-6-amine was converted to 9-(1-methyl-1H-pyrazol-4-yl)-6-(pyridin-3-ylamino)benzo[c]-1,6-naphthyridin-1(2H)-one by the procedure used to make 6-{[(1R)-2-methyl-1-(trifluoromethyl)propyl]amino}pyrido[4,3-c]-1,6-naphthyridin-1(2H)-one. $^1$H NMR (600 MHz, $C_2D_6SO$) δ 11.38 (d, 1H), 10.12 (d, 1H), 9.72 (s, 1H), 9.12 (s, 1H), 8.59 (d, 1H), 8.42 (d, 1H), 8.29 (s, 1H), 8.27 (d, 1H), 7.96 (s, 1H), 7.92 (dd, 1H), 7.41 (m, 2H), 6.44 (d, 1H), 3.90 (s, 3H). LRMS (APCI) calc'd for ($C_{21}H_{17}N_6O$) [M+H]+, 369.1; found 369.1.

Example 6

Method F for Amine Addition

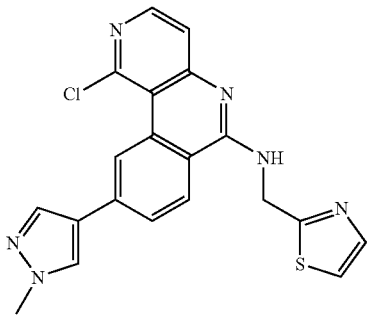

Method F, Step 1: 1-chloro-9-(1-methyl-1H-pyrazol-4-yl)-N-(1,3-thiazol-2-ylmethyl)benzo[c]-1,6-naphthyridin-6-amine To a solution of 1,6-dichloro-9-(1-methyl-1H-pyrazol-4-yl)benzo[c]-1,6-naphthyridine (50 mg, 0.152 mmol) and 2-aminomethylthiazole hydrochloride (92 mg, 0.608 mmol) in DMA (1.5 mL), triethylamine (85 μl, 0.608 mmol) was added. The reaction mixture was heated to 130° C. for 1 h via microwave irradiation. After cooling to room temperature, aqueous sodium hydrogen carbonate (saturated) was added. The aqueous layer was extracted with ethyl acetate. The combined organic extracts were dried over sodium sulfate and concentrated under reduced pressure to afford 1-chloro-9-(1-methyl-1H-pyrazol-4-yl)-N-(1,3-thiazol-2-ylmethyl)benzo[c]-1,6-naphthyridin-6-amine as a yellow solid. LRMS (APCI) calc'd for ($C_{20}H_{16}ClN_6S$) [M+H]+, 407.1; found 407.0.

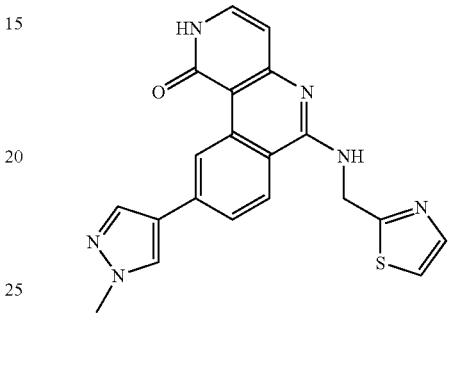

Method F, Step 2: 9-(1-methyl-1H-pyrazol-4-yl)-6-[(1,3-thiazol-2-ylmethyl)amino]benzo[c]-1,6-naphthyridin-1(2H)-one 1-chloro-9-(1-methyl-1H-pyrazol-4-yl)-N-(1,3-thiazol-2-ylmethyl)benzo[c]-1,6-naphthyridin-6-amine was converted to 9-(1-methyl-1H-pyrazol-4-yl)-6-[(1,3-thiazol-2-ylmethyl)amino]benzo[c]-1,6-naphthyridin-1(2H)-one by the procedure used to make 6-{[(1R)-2-methyl-1-(trifluoromethyl)propyl]amino}pyrido[4,3-c]-1,6-naphthyridin-1(2H)-one. $^1$H NMR (600 MHz, $C_2D_6SO$) δ 11.22 (d, 1H), 10.05 (d, 1H), 8.89 (t, 1H), 8.29 (d, 1H), 8.24 (s, 1H), 7.92 (s, 1H), 7.81 (dd, 1H), 7.69 (d, 1H), 7.53 (d, 1H), 7.32 (t, 1H), 6.37 (d, 1H), 5.05 (d, 2H), 3.89 (s, 3H). LRMS (APCI) calc'd for ($C_{20}H_{17}N_6OS$) [M+H]+, 389.1; found 389.1.

The following compounds in Table 1 were prepared according to generic schemes 1-5 above, intermediates and methods A through F described above.

TABLE 1

| Ex. | Structure | Name | Method | LRMS [M + H]+ |
|---|---|---|---|---|
| 7 | 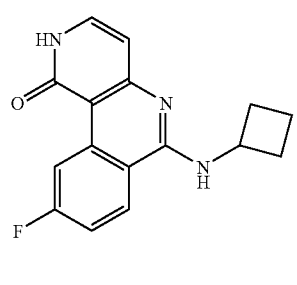 | 6-(cyclobutylamino)-9-fluorobenzo[c]-1,6-naphthyridin-1(2H)-one | C | Calc'd 284.1, found 284.1 |

TABLE 1-continued

| Ex. | Structure | Name | Method | LRMS [M + H]+ |
|---|---|---|---|---|
| 8 | 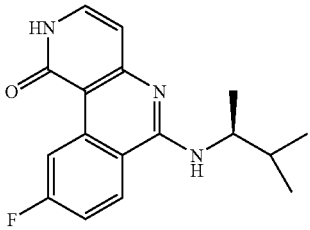 | 6-{[(1S)-1,2-dimethylpropyl]amino}-9-fluorobenzo[c]-1,6-naphthyridin-1(2H)-one | C | Calc'd 300.1, found 300.1 |
| 9 | 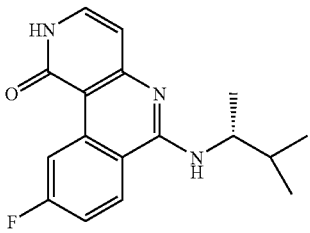 | 6-{[(1R)-1,2-dimethylpropyl]amino}-9-fluorobenzo[c]-1,6-naphthyridin-1(2H)-one | C | Calc'd 300.1, found 300.1 |
| 10 | 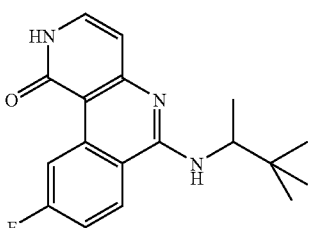 | 9-fluoro-6-[(1,2,2-trimethylpropyl)amino]benzo[c]-1,6-naphthyridin-1(2H)-one | C | Calc'd 314.2, found 314.2 |
| 11 | 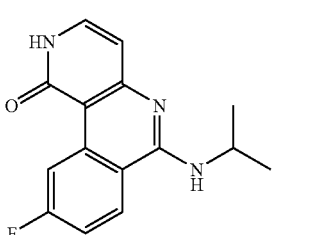 | 9-fluoro-6-(isopropylamino)benzo[c]-1,6-naphthyridin-1(2H)-one | C | Calc'd 272.1, found 272.1 |
| 12 | 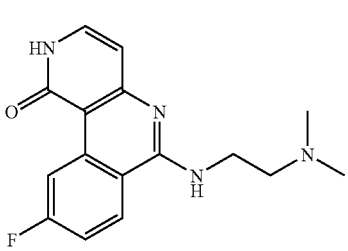 | 6-{[2-(dimethylamino)ethyl]amino}-9-fluorobenzo[c]-1,6-naphthyridin-1(2H)-one | C | Calc'd 301.2, found 301.1 |
| 13 | 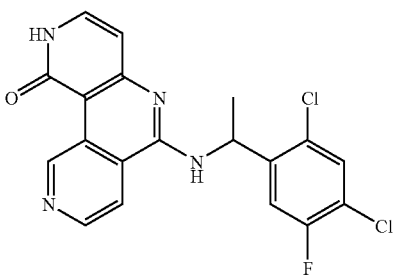 | 6-{[1-(2,4-dichloro-5-fluorophenyl)ethyl]amino}pyrido[4,3-c]-1,6-naphthyridin-1(2H)-one | B | Calc'd 403.1, found 403.0 |

TABLE 1-continued

| Ex. | Structure | Name | Method | LRMS [M + H]+ |
|---|---|---|---|---|
| 14 | 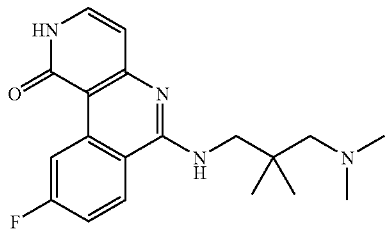 | 6-{[3-(dimethylamino)-2,2-dimethylpropyl]amino}-9-fluorobenzo[c]-1,6-naphthyridin-1(2H)-one | C | Calc'd 343.2, found 343.3 |
| 15 | 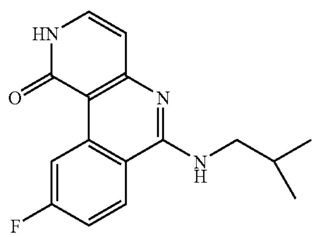 | 9-fluoro-6-(isobutylamino)benzo[c]-1,6-naphthyridin-1(2H)-one | C | Calc'd 286.1, found 286.1 |
| 16 | 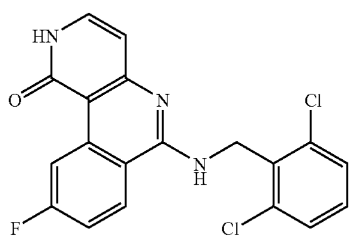 | 6-[(2,6-dichlorobenzyl)amino]-9-fluorobenzo[c]-1,6-naphthyridin-1(2H)-one | C | Calc'd 388.0, found 388.0 |
| 17 | 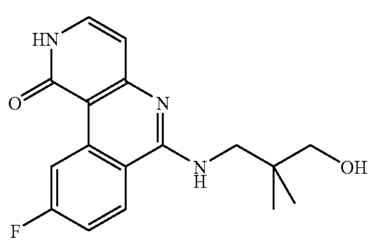 | 9-fluoro-6-[(3-hydroxy-2,2-dimethylpropyl)amino]benzo[c]-1,6-naphthyridin-1(2H)-one | C | Calc'd 316.2, found 316.1 |
| 18 | 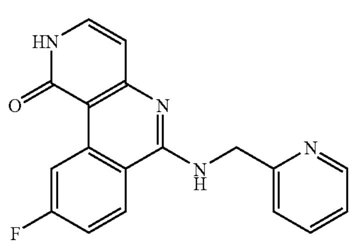 | 9-fluoro-6-[(pyridin-2-ylmethyl)amino]benzo[c]-1,6-naphthyridin-1(2H)-one | C | Calc'd 321.1, found 321.1 |
| 19 | 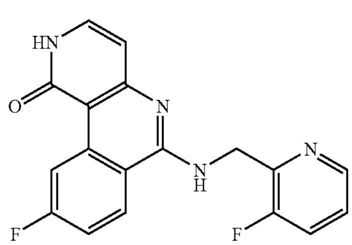 | 9-fluoro-6-{[(3-fluoropyridin-2-yl)methyl]amino}benzo[c]-1,6-naphthyridin-1(2H)-one | C | Calc'd 339.1, found 339.1 |

TABLE 1-continued

| Ex. | Structure | Name | Method | LRMS [M + H]+ |
|---|---|---|---|---|
| 20 | 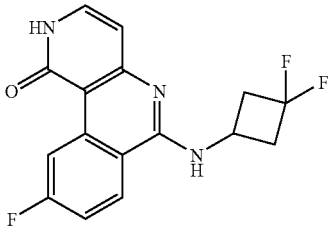 | 6-[(3,3-difluorocyclobutyl)amino]-9-fluorobenzo[c]-1,6-naphthyridin-1(2H)-one | C | Calc'd 320.1, found 320.1 |
| 21 | 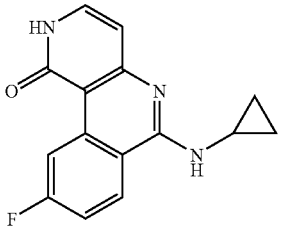 | 6-(cyclopropylamino)-9-fluorobenzo[c]-1,6-naphthyridin-1(2H)-one | C | Calc'd 270.1, found 270.1 |
| 22 | 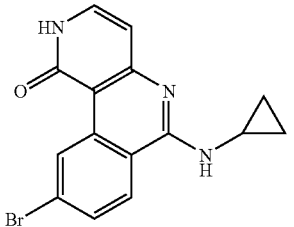 | 6-(cyclopropylamino)-9-bromobenzo[c]-1,6-naphthyridin-1(2H)-one | C | Calc'd 330.0, found 330.0 |
| 23 | 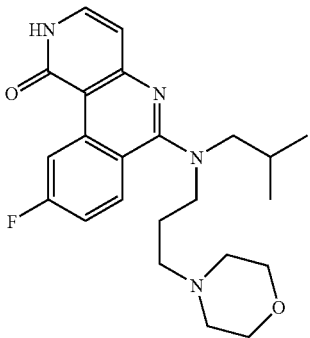 | 9-fluoro-6-[isobutyl(3-morpholin-4-ylpropyl)amino]benzo[c]-1,6-naphthyridin-1(2H)-one | C | Calc'd 413.2, found 413.2 |
| 24 | 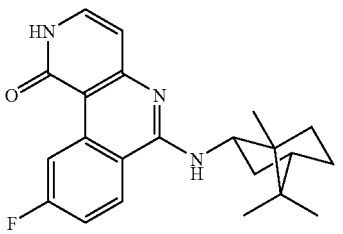 | 9-fluoro-6-[(1,7,7-trimethylcyclo[2.2.1]hept-2-yl)amino]benzo[c]-1,6-naphthyridin-1(2H)-one | C | Calc'd 366.2, found 366.2 |
| 25 | 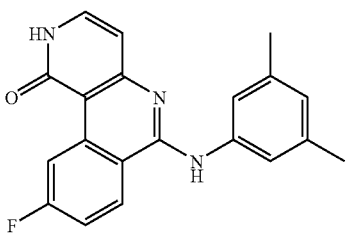 | 6-[(3,5-dimethylphenyl)amino]-9-fluorobenzo[c]-1,6-naphthyridin-1(2H)-one | B | Calc'd 334.1, found 334.1 |

TABLE 1-continued

| Ex. | Structure | Name | Method | LRMS [M + H]+ |
|---|---|---|---|---|
| 26 | 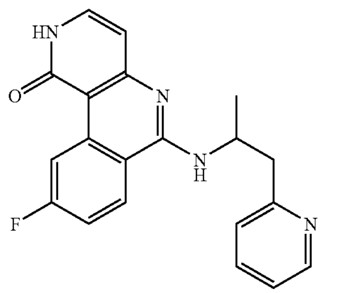 | 9-fluoro-6-[(1-methyl-2-pyridin-2-ylethyl)amino]benzo[c]-1,6-naphthyridin-1(2H)-one | C | Calc'd 349.2. found 349.1 |
| 27 | 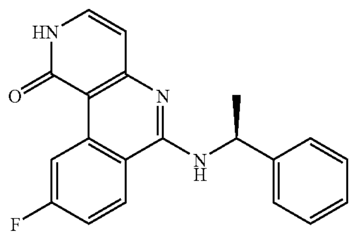 | 9-fluoro-6-{[(1S)-1-phenylethyl]amino}benzo[c]-1,6-naphthyridin-1(2H)-one | A | Calc'd 334.1, found 334.1 |
| 28 | 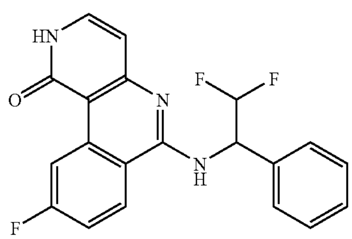 | 6-[(2,2-difluoro-1-phenylethyl)amino]-9-fluorobenzo[c]-1,6-naphthyridin-1(2H)-one | A | Calc'd 370.1, found 370.1 |
| 29 | 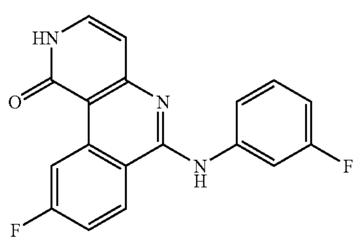 | 9-fluoro-6-[(3-fluorophenyl)amino]benzo[c]-1,6-naphthyridin-1(2H)-one | B | Calc'd 324.1, found 324.1 |
| 30 | 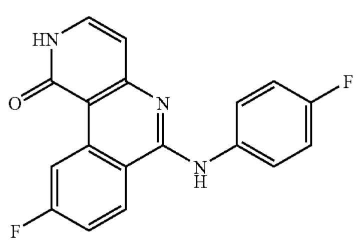 | 9-fluoro-6-[(4-fluorophenyl)amino]benzo[c]-1,6-naphthyridin-1(2H)-one | B | Calc'd 324.1, found 324.1 |
| 31 | 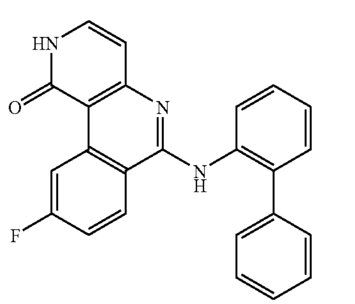 | 6-(biphenyl-2-ylamino)-9-fluorobenzo[c]-1,6-naphthyridin-1(2H)-one | B | Calc'd 382.1, found 382.1 |

TABLE 1-continued

| Ex. | Structure | Name | Method | LRMS [M + H]+ |
|---|---|---|---|---|
| 32 | 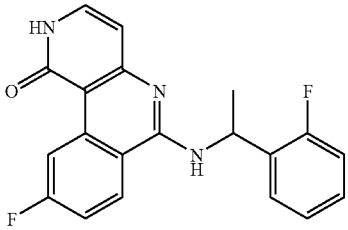 | 9-fluoro-6-{[1-(2-fluorophenyl)ethyl]amino}-benzo[c]-1,6-naphthyridin-1(2H)-one | A | Calc'd 352.1, found 352.1 |
| 33 | 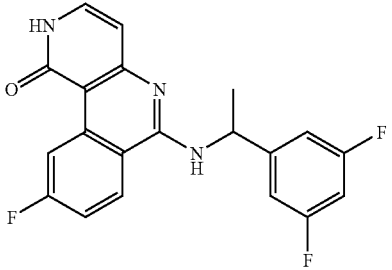 | 6-{[1-(3,5-difluorophenyol)ethyl]amino}-9-fluorobenzo[c]-1,6-naphthyridin-1(2H)-one | A | Calc'd 370.1, found 370.1 |
| 34 | 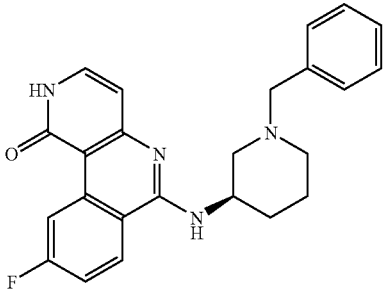 | 6-{[(3R)-1-benzylpiperidin-3-yl]amino}-9-fluorobenzo[c]-1,6-naphthyridin-1(2H)-one | C | Calc'd 403.2, found 403.2 |
| 35 | 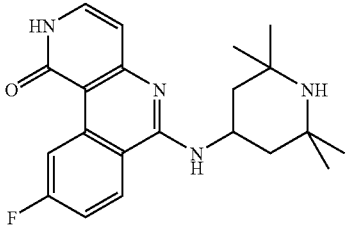 | 9-fluoro-6-[(2,2,6,6-tetramethylpiperidin-4-yl)amino]benzo[c]-1,6-naphthyridin-1(2H)-one | C | Calc'd 369.2, found 369.2 |
| 36 | 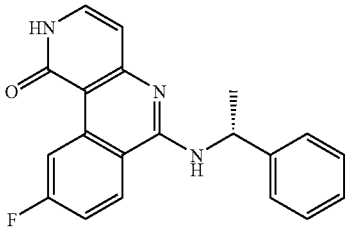 | 9-fluoro-6-{[(1R)-1-phenylethyl]amino}benzo[c]-1,6-naphthyridin-1(2H)-one | A | Calc'd 334.1, found 334.1 |
| 37 | 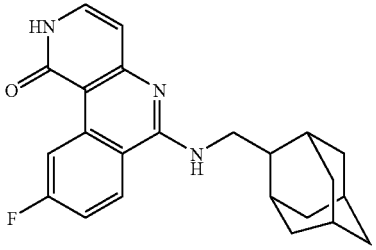 | 6-[(2-adamantylmethyl)amino]-9-fluorobenzo[c]-1,6-naphthyridin-1(2H)-one | C | Calc'd 378.2, found 378.2 |

TABLE 1-continued

| Ex. | Structure | Name | Method | LRMS [M + H]+ |
|---|---|---|---|---|
| 38 | 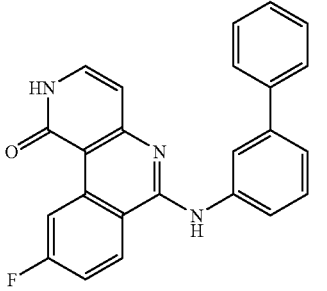 | 6-(biphenyl-4-ylamino)-9-fluorobenzo[c]-1,6-naphthyridin-1(2H)-one | B | Calc'd 382.1, found 382.1 |
| 39 | 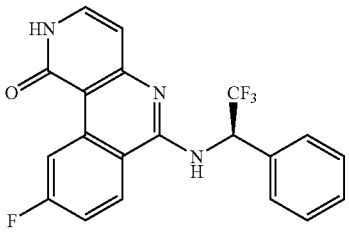 | 9-fluoro-6-{[(1R)-2,2,2-trifluoro-1-phenylethyl]amino}benzo[c]-1,6-naphthyridin-1(2H)-one | A | Calc'd 388.1, found 388.1 |
| 40 | 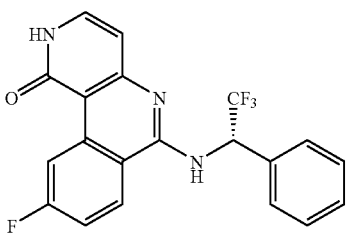 | 9-fluoro-6-{[(1S)-2,2,2-trifluoro-1-phenylethyl]amino}benzo[c]-1,6-naphthyridin-1(2H)-one | A | Calc'd 388.1, found 388.1 |
| 41 | 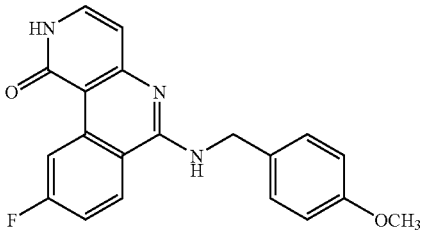 | 9-fluoro-6-[(4-methoxybenzyl)amino]benzo[c]-1,6-naphthyridin-1(2H)-one | A | Calc'd 350.1, found 350.1 |
| 42 | 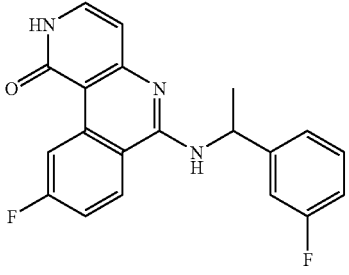 | 9-fluoro-6-{[1-(3-fluorophenyl)ethyl]amino}-benzo[c]-1,6-naphthyridin-1(2H)-one | A | Calc'd 352.1, found 352.1 |
| 43 | 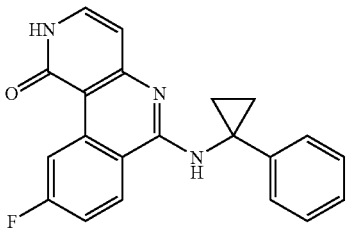 | 9-fluoro-6-[(1-phenylcyclopropyl)amino]-benzo[c]-1,6-naphthyridin-1(2H)-one | C | Calc'd 346.1, found 346.1 |

TABLE 1-continued

| Ex. | Structure | Name | Method | LRMS [M + H]+ |
|---|---|---|---|---|
| 44 | 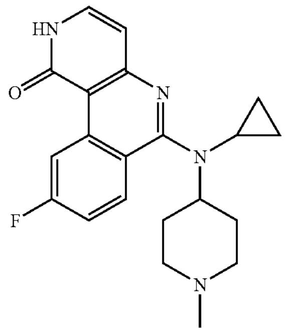 | 6-[cyclopropyl(1-methylpiperidin-4-yl)amino]-9-fluorobenzo[c]-1,6-naphthyridin-1(2H)-one | C | Calc'd 367.2, found 367.2 |
| 45 | 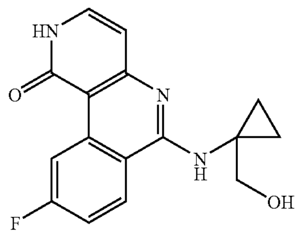 | 9-fluoro-6-{[1-(hydroxymethyl)cyclopropyl]-amino}benzo[c]-1,6-naphthyridin-1(2H)-one | C | Calc'd 300.1, found 300.1 |
| 46 | 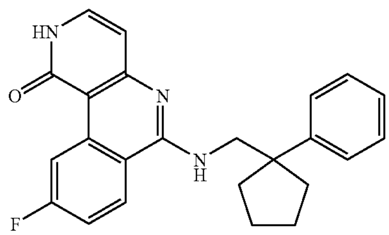 | 9-fluoro-6-{[(1-phenylcyclopentyl)methyl]amino}benzo[c]-1,6-naphthyridin-1(2H)-one | C | Calc'd 388.2, found 388.2 |
| 47 | 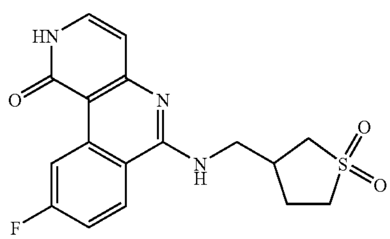 | 6-{[(1,1-dioxidotetrahydro-3-thienyl)methyl]amino}-9-fluorobenzo[c]-1,6-naphthyridin-1(2H)-one | C | Calc'd 362.1, found 362.1 |
| 48 | 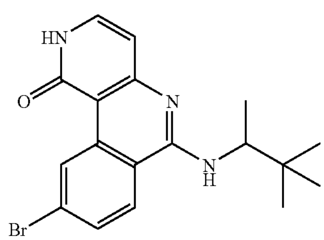 | 9-bromo-6-[(1,2,2-trimethylpropyl)amino]benzo[c]-1,6-naphthyridin-1(2H)-one | C | Calc'd 374.1, found 374.1 |
| 49 | 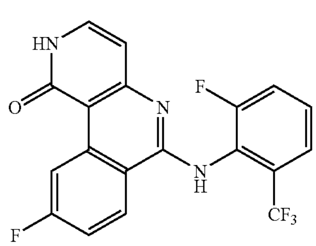 | 9-fluoro-6-{[2-fluoro-6-(trifluoromethyl)phenyl]amino}benzo[c]-1,6-naphthyridin-1(2H)-one | B | Calc'd 392.1, found 392.0 |

TABLE 1-continued

| Ex. | Structure | Name | Method | LRMS [M + H]+ |
|---|---|---|---|---|
| 50 | 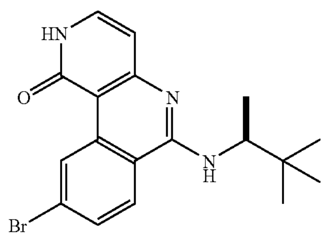 | 9-bromo-6-{[(1S)-1,2,2-trimethylpropyl]amino}benzo[c]-1,6-naphthyridin-1(2H)-one | C | Calc'd 374.1, found 374.1 |
| 51 | 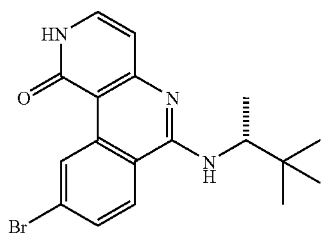 | 9-bromo-6-{[(1R)-1,2,2-trimethylpropyl]amino}benzo[c]-1,6-naphthyridin-1(2H)-one | C | Calc'd 374.1, found 374.1 |
| 52 | 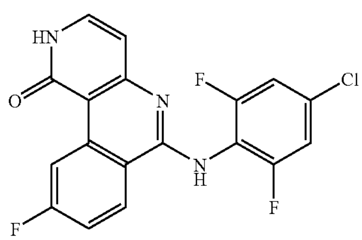 | 6-[(4-chloro-2,6-difluorophenyl)amino]-9-fluorobenzo[c]-1,6-naphthyridin-1(2H)-one | B | Calc'd 376.1, found 376.0 |
| 53 | 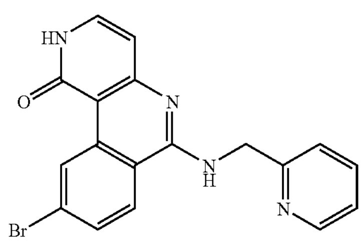 | 9-bromo-6-[(pyridin-2-ylmethyl)amino]benzo[c]-1,6-naphthyridin-1(2H)-one | C | Calc'd 383.0, found 383.0 |
| 54 | 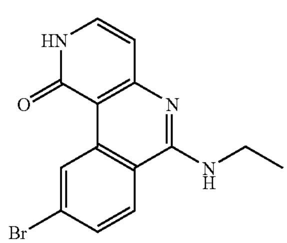 | 9-bromo-6-(ethylamino)benzo[c]-1,6-naphthyridin-1(2H)-one | C | Calc'd 320.0, found 320.0 |
| 55 | 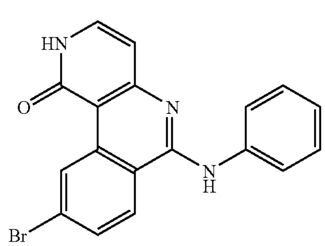 | 6-anilino-9-bromobenzo[c]-1,6-naphthyridin-1(2H)-one | C | Calc'd 368.0, found 368.0 |

TABLE 1-continued

| Ex. | Structure | Name | Method | LRMS [M + H]+ |
|---|---|---|---|---|
| 56 | 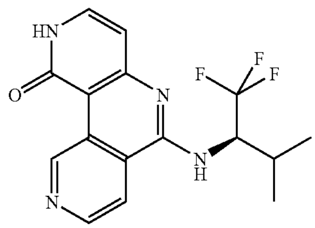 | 6-{[(1R)-2-methyl-1-(trifluoromethyl)propyl]amino}pyrido[4,3-c]-1,6-naphthyridin-1(2H)-one | A | Calc'd 337.1, found 337.1 |
| 57 | 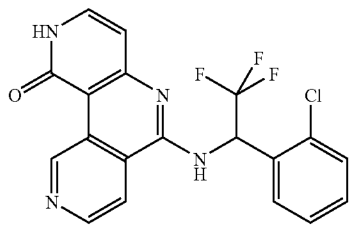 | 6-{[1-(2-chlorophenyl)-2,2,2-trifluoroethyl]amino}pyrido[4,3-c]-1,6-naphthyridin-1(2H)-one | B | Calc'd 405.1, found 405.1 |
| 58 | 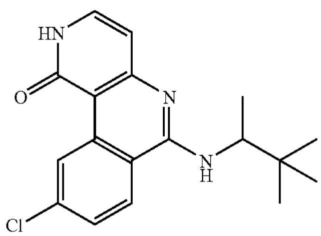 | 9-chloro-6-[(1,2,2-trimethylpropyl)amino]benzo[c]-1,6-naphthyridin-1(2H)-one | C | Calc'd 330.1, found 330.1 |
| 59 | 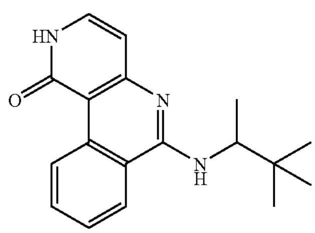 | 6-[(1,2,2-trimethylpropyl)amino]benzo[c]-1,6-naphthyridin-1(2H)-one | C | Calc'd 296.2, found 296.1 |
| 60 | 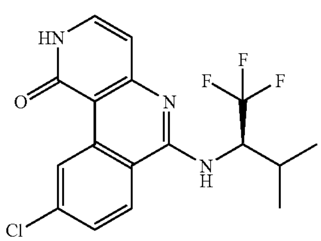 | 9-chloro-6-{[(1R)-2-methyl-1-(trifluoromethyl)propyl]amino}benzo[c]-1,6-naphthyridin-1(2H)-one | A | Calc'd 370.1, found 370.1 |
| 61 | 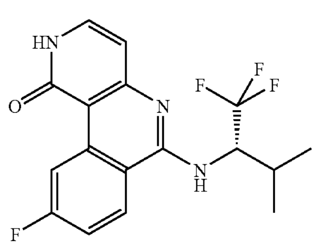 | 9-fluoro-6-{[(1S)-2-methyl-1-(trifluoromethyl)propyl]amino}benzo[c]-1,6-naphthyridin-1(2H)-one | A | Calc'd 354.1, found 354.1 |

TABLE 1-continued

| Ex. | Structure | Name | Method | LRMS [M + H]+ |
|---|---|---|---|---|
| 62 | 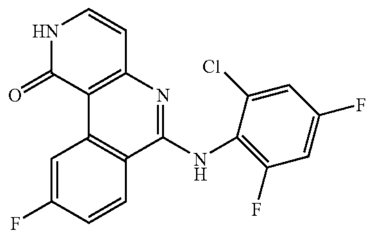 | 6-[(2-chloro-4,6-difluorophenyl)amino]-9-fluorobenzo[c]-1,6-naphthyridin-1(2H)-one | A | Calc'd 376.1, found 376.0 |
| 63 | 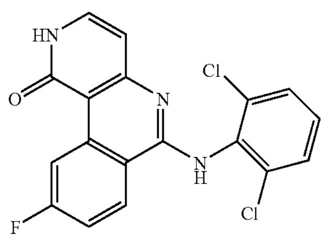 | 6-[(2,6-dichlorophenyl)amino]-9-fluorobenzo[c]-1,6-naphthyridin-1(2H)-one | B | Calc'd 374.0, found 374.0 |
| 64 | 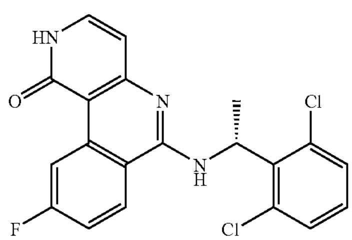 | 6-{[(1R)-1-(2,6-dichlorophenyl)ethyl]amino}-9-fluorobenzo[c]-1,6-naphthyridin-1(2H)-one | A | Calc'd 402.1, found 402.0 |
| 65 | 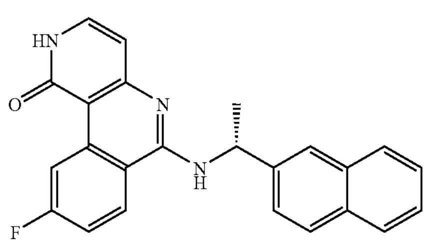 | 9-fluoro-6-{[(1R)-1-(2-naphthyl)ethyl]amino}benzo[c]-1,6-naphthyridin-1(2H)-one | A | Calc'd 384.2, found 384.1 |
| 66 | 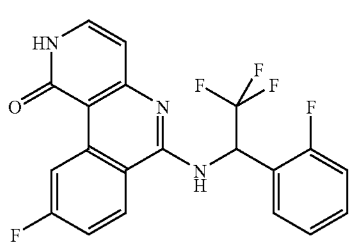 | 9-fluoro-6-{[2,2,2-trifluoro-1-(2-fluorophenyl)ethyl]amino}benzo[c]-1,6-naphthyridin-1(2H)-one | A | Calc'd 406.1, found 406.1 |
| 67 | 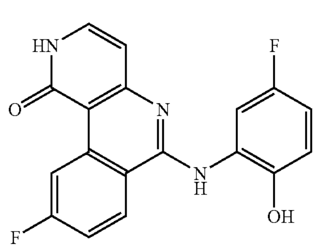 | 9-fluoro-6-[(5-fluoro-2-hydroxyphenyl)amino]benzo[c]-1,6-naphthyridin-1(2H)-one | B | Calc'd 340.1, found 340.1 |

TABLE 1-continued

| Ex. | Structure | Name | Method | LRMS [M + H]+ |
|---|---|---|---|---|
| 68 | 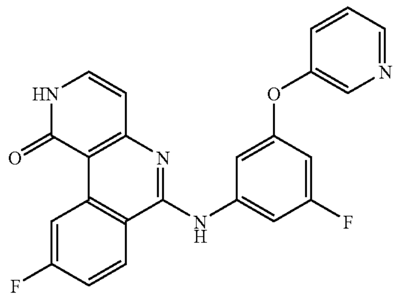 | 9-fluoro-6-{[3-fluoro-5-(pyridin-3-yloxy)phenyl]amino}benzo[c]-1,6-naphthyridin-1(2H)-one | B | Calc'd 417.1, found 417.1 |
| 69 | 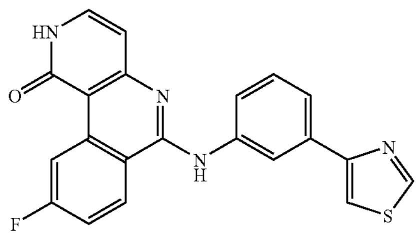 | 9-fluoro-6-{[3-(1,3-thiazol-4-yl)phenyl]amino}benzo[c]-1,6-naphthyridin-1(2H)-one | B | Calc'd 389.1, found 389.0 |
| 70 | 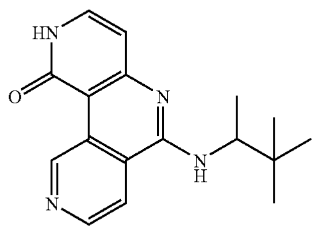 | 6-[(1,2,2-trimethylpropyl)amino]pyrido[4,3-c]-1,6-naphthyridin-1(2H)-one | C | Calc'd 297.2, found 297.2 |
| 71 | 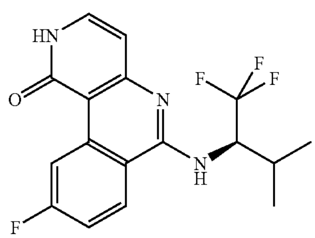 | 9-fluoro-6-{[(1R)-2-methyl-1-(trifluoromethyl)propyl]amino}benzo[c]-1,6-naphthyridin-1(2H)-one | A | Calc'd 354.1, found 354.1 |
| 72 | 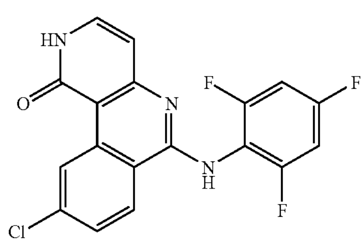 | 9-chloro-6-[(2,4,6-trifluorophenyl)amino]benzo[c]-1,6-naphthyridin-1(2H)-one | B | Calc'd 376.1, found 376.0 |
| 73 | 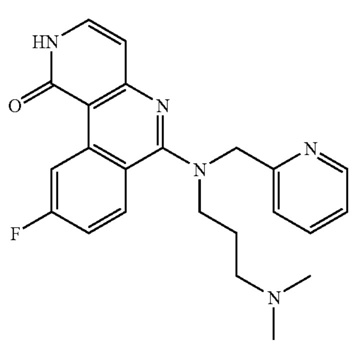 | 6-[[3-(dimethylamino)propyl](pyridin-2-ylmethyl)amino]-9-fluorobenzo[c]-1,6-naphthyridin-1(2H)-one | C | Calc'd 406.2, found 406.1 |

TABLE 1-continued

| Ex. | Structure | Name | Method | LRMS [M + H]+ |
|---|---|---|---|---|
| 74 | 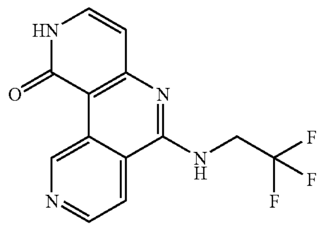 | 6-[(2,2,2-trifluoroethyl)amino]pyrido[4,3-c]-1,6-naphthyridin-1(2H)-one | D | Calc'd 295.1, found 295.1 |
| 75 | 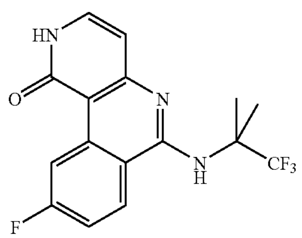 | 9-fluoro-6-[(2,2,2-trifluoro-1,1-dimethylethyl)amino]benzo[c]-1,6-naphthyridin-1(2H)-one | A | Calc'd 340.1 found 340.1 |
| 76 | 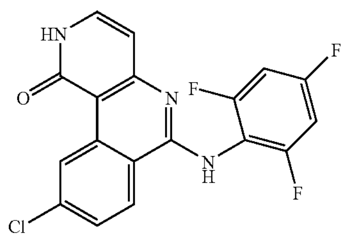 | 9-chloro-6-[(2,4,6-trifluorophenyl)amino]benzo[c]-1,6-naphthyridin-1(2H)-one | B | Calc'd 376.0, found 376.0 |
| 77 | 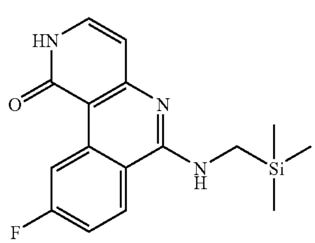 | 9-fluoro-6-{[(trimethylsilyl)methyl]amino}benzo[c]-1,6-naphthyridin-1(2H)-one | C | Calc'd 316.1, found 316.1 |
| 78 | 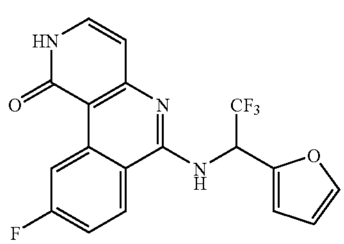 | 9-fluoro-6-{[2,2,2-trifluoro-1-(2-furyl)ethyl]amino}benzo[c]-1,6-naphthyridin-1(2H)-one | A | Calc'd 378.1, found 378.0 |
| 79 | 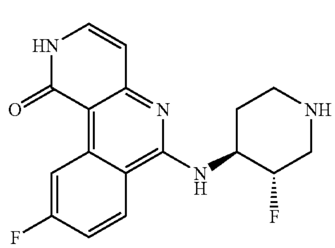 | trans-9-fluoro-6-[(3-methylpiperidin-4-yl)amino]benzo[c]-1,6-naphthyridin-1(2H)-one | A | Calc'd 331.1, found 331.1 |

TABLE 1-continued

| Ex. | Structure | Name | Method | LRMS [M + H]+ |
|---|---|---|---|---|
| 80 | 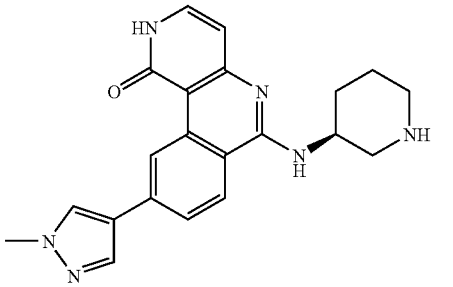 | 9-(1-methyl-1H-pyrazol-4-yl)-6-[(3S)-piperidin-3-ylamino]benzo[c]-1,6-naphthyridin-1(2H)-one | C[1] | Calc'd 375.2, found 375.1 |
| 81 | 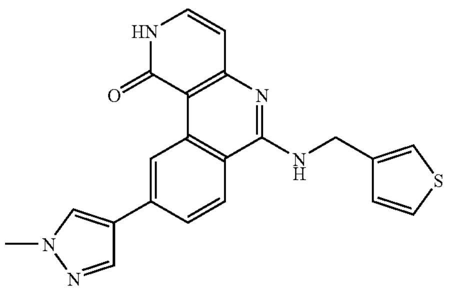 | 9-(1-methyl-1H-pyrazol-4-yl)-6-[(3-thienylmethyl)amino]benzo[c]-1,6-naphthyridin-1(2H)-one | C | Calc'd 388.1, found 388.1 |
| 82 | 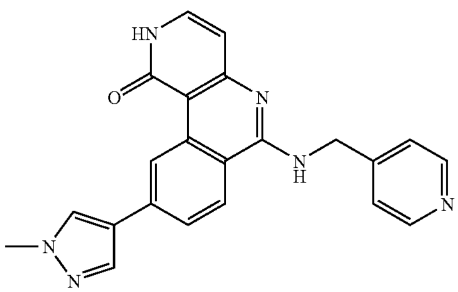 | 9-(1-methyl-1H-pyrazol-4-yl)-6-[(pyridin-4-ylmethyl)amino]benzo[c]-1,6-naphthyridin-1(2H)-one | Method A-Step 1; method D-Step 2 | Calc'd 383.2, found 383.1 |
| 83 | 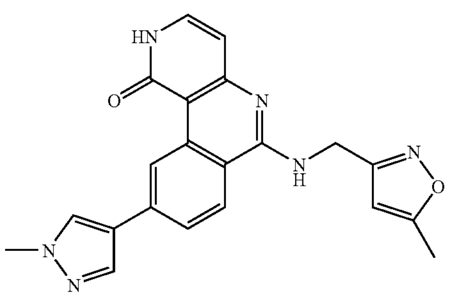 | 6-{[(5-methylisoxazol-3-yl)methyl]amino}-9-(1-methyl-1H-pyrazol-4-yl)benzo[c]-1,6-naphthyridin-1(2H)-one | Method A-Step 1; method D-Step 2 | Calc'd 387.2, found 387.1 |
| 84 | 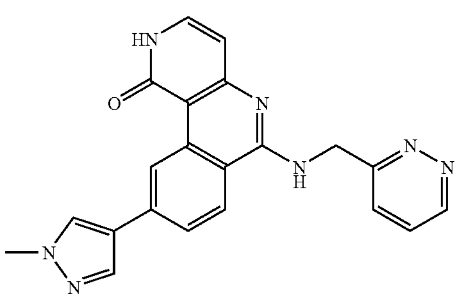 | 9-(1-methyl-1H-pyrazol-4-yl)-6-[(pyridazin-3-ylmethyl)amino]benzo[c]-1,6-naphthyridin-1(2H)-one | Method A-Step 1; Method D-Step 2 | Calc'd 384.2, found 384.1 |

TABLE 1-continued

| Ex. | Structure | Name | Method | LRMS [M + H]+ |
|---|---|---|---|---|
| 85 | 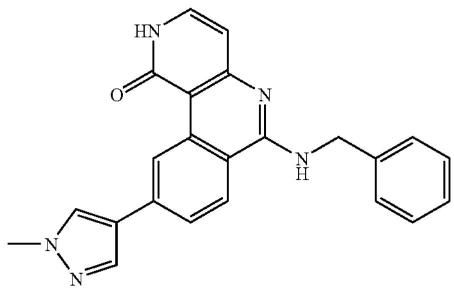 | 6-(benzylamino)-9-(1-methyl-1H-pyrazol-4-yl)benzo[c]-1,6-naphthyridin-1(2H)-one | C | Calc'd 382.2, found 382.1 |
| 86 | 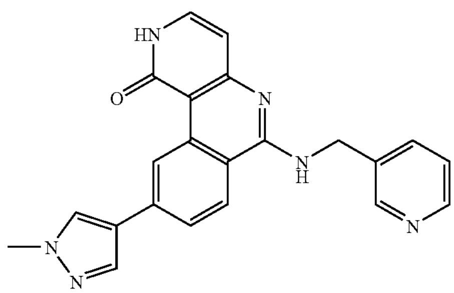 | 9-(1-methyl-1H-pyrazol-4-yl)-6-[(pyridin-3-ylmethyl)amino]benzo[c]-1,6-naphthyridin-1(2H)-one | C | Calc'd 383.2, found 383.1 |
| 87 | 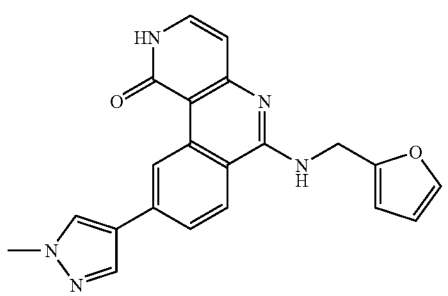 | 6-[(2-furylmethyl)amino]-9-(1-methyl-1H-pyrazol-4-yl)benzo[c]-1,6-naphthyridin-1(2H)-one | C | Calc'd 372.1, found 372.1 |
| 88 | 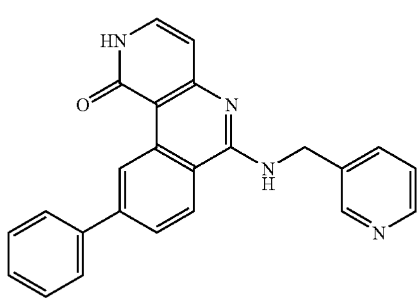 | 9-phenyl-6-[(pyridin-3-ylmethyl)amino]benzo[c]-1,6-naphthyridin-1(2H)-one | C | Calc'd 379.2, found 379.1 |
| 89 | 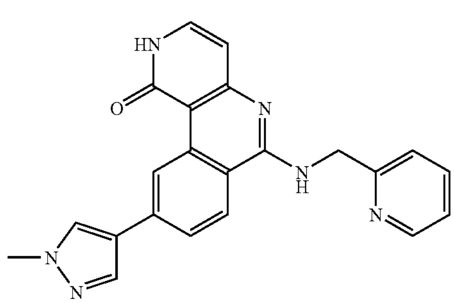 | 9-(1-methyl-1H-pyrazol-4-ul)-6-[(pyridin-2-ylmethyl)amino]benzo[c]-1,6-naphthyridin-1(2H)-one | C | Calc'd 383.2, found 383.1 |

TABLE 1-continued

| Ex. | Structure | Name | Method | LRMS [M + H]+ |
|---|---|---|---|---|
| 90 | 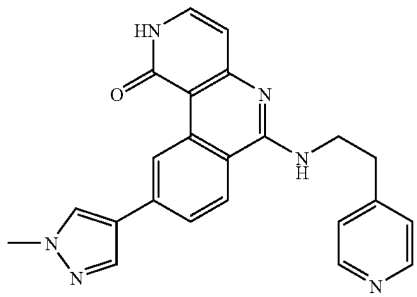 | 9-(1-methyl-1H-pyrazol-4-yl)-6-[(2-pyridin-4-ylethyl)amino]benzo[c]-1,6-naphthyridin-1(2H)-one | C | Calc'd 397.2, found 397.1 |
| 91 | 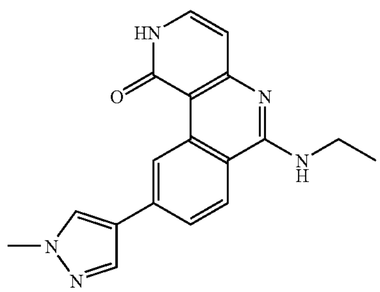 | 6-(ethylamino)-9-(1-methyl-1H-pyrazol-4-yl)benzo[c]-1,6-naphthyridin-1(2H)-one | C | Calc'd 320.2, found 320.1 |
| 92 | 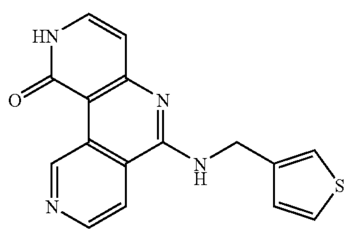 | 6-[(3-thienylmethyl)amino]pyrido[4,3-c]-1,6-naphthyridin-1(2H)-pne | Method A-Step 1; Method D-Step 2 | Calc'd 309.1, found 309.0 |
| 93 | 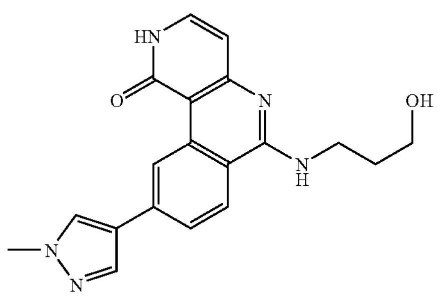 | 6-[(3-hydroxypropyl)amino]-9-(1-methyl-1H-pyrazol-4-yl)benzo[c]-1,6-naphthyridin-1(2H)-one | C | Calc'd 350.2, found 350.1 |
| 94 | 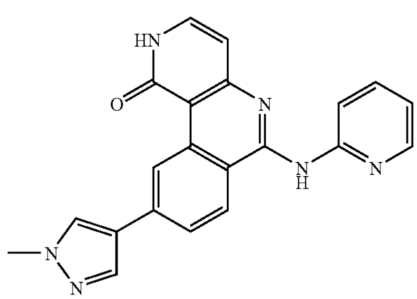 | 9-(1-methyl-1H-pyrazol-4-yl)-6-(pyridin-2-ylamino)benzo[c]-1,6-naphthyridin-1(2H)-one | E | Calc'd 369.1, found 369.1 |

TABLE 1-continued

| Ex. | Structure | Name | Method | LRMS [M + H]+ |
|---|---|---|---|---|
| 95 | 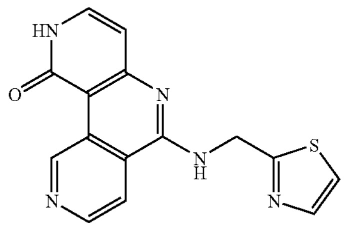 | 6-[(1,3-thiazol-2-ylmethyl)amino]pyrido[4,3-c]-1,6-naphthyridin-1(2H)-one | F | Calc'd 310.1, found 310.0 |
| 96 | 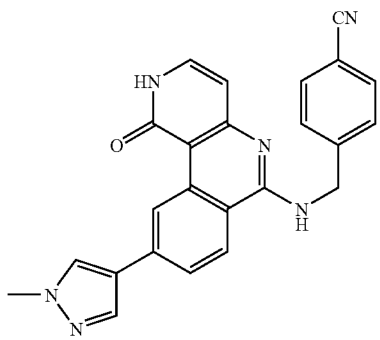 | 4-({[9-(1-methyl-1H-pyrazol-4-yl)-1-oxo-1,2-dihydrobenzo[c]-1,6-naphthyridin-6-yl]amino}methyl)benzonitrile | C | Calc'd 407.2, found 407.1 |
| 97 | 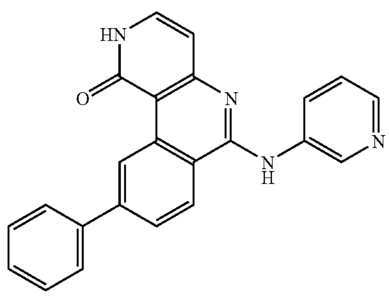 | 9-phenyl-6-(pyridin-3-ylamino)benzo[c]-1,6-naphthyridin-1(2H)-one | E | Calc'd 365.1, found 365.1 |
| 98 | 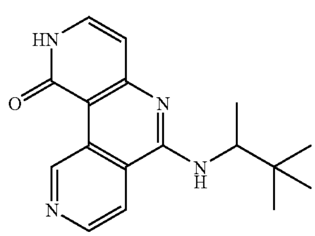 | 6-[(1,2,2-trimethylpropyl)amino]pyrido[4,3-c]-1,6-naphthyridin-1(2H)-one | Method A-Step 1; Method D-Step 2 | Calc'd 297.2, found 297.1 |
| 99 | 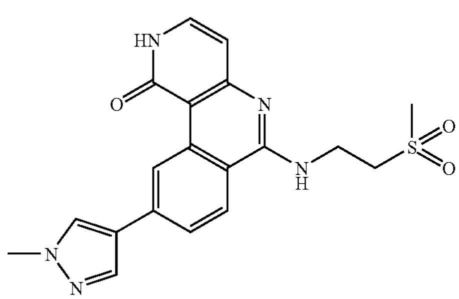 | 9-(1-methyl-1H-pyrazol-4-yl)-6-{[2-(methylsulfonyl)ethyl]amino}benzo[c]-1,6-naphthyridin-1(2H)-one | Method F-Step 1, Method A-Step 2 | Calc'd 398.1, found 398.1 |

TABLE 1-continued

| Ex. | Structure | Name | Method | LRMS [M + H]+ |
|---|---|---|---|---|
| 100 | 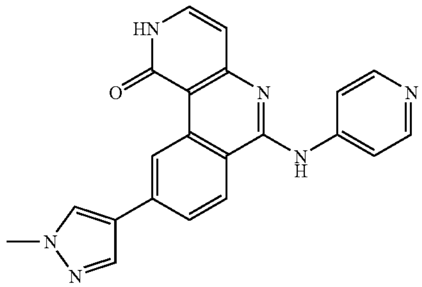 | 9-(1-methyl-1H-pyrazol-4-yl)-6-(pyridin-4-ylamino)benzo[c]-1,6-naphthyridin-1(2H)-one | E | Calc'd 369.1, found 369.1 |
| 101 | 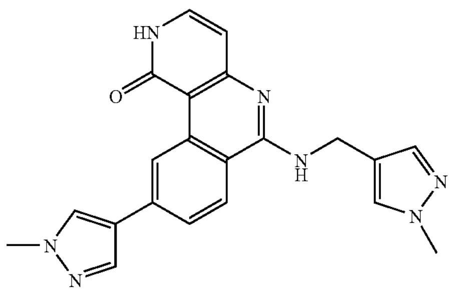 | 9-(1-methyl-1H-pyrazol-4-yl)-6-{[(1-methyl-1H-pyrazol-4-yl)methyl]amino}benzo[c]-1,6-naphthyridin-1(2H)-one | C | Calc'd 386.2, found 386.1 |
| 102 | 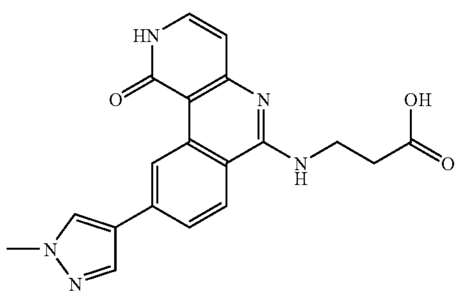 | N-[9-(1-methyl-1H-pyrazol-4-yl)-1-oxo-1,2-dihydrobenzo[c]-1,6-naphthyridin-6-yl]-beta-alanine | Method F-Step 1, Method A-Step 2[2] | Calc'd 364.1, found 364.0 |
| 103 | 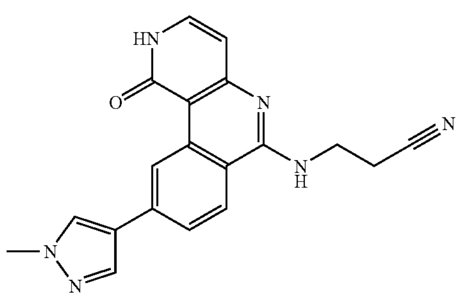 | 3-{[9-(1-methyl-1-pyrazol-4-yl)-1-oxo-1,2-dihydrobenzo[c]-1,6-naphthyridin-6-yl]amino}propanenitrile | C | Calc'd 345.1, found 345.1 |
| 104 | 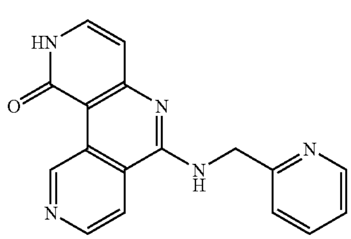 | 6-[(pyridin-2-ylmethyl)amino]pyrido[4,3-c]-1,6-naphthyridin-1(2H)-one | Method A-Step 11 Method D-Step 2 | Calc'd 304.1, found 304.1 |

TABLE 1-continued

| Ex. | Structure | Name | Method | LRMS [M + H]+ |
|---|---|---|---|---|
| 105 | 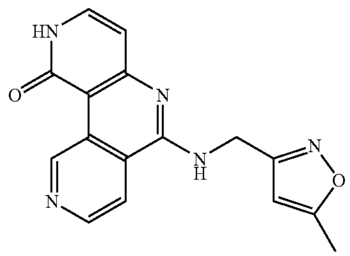 | 6-{[(5-methylisoxazol-3-yl)methyl]amino}pyrido[4,3-c]-1,6-naphthyridin-1(2H)-one | Method A-Step 1; Method D-Step 2 | Calc'd 308.1, found 308.0 |
| 106 | 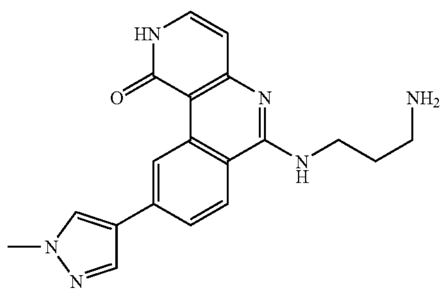 | 6-[(3-aminopropyl)amino]-9-(1-methyl-1H-pyrazol-4-yl)benzo[c]-1,6-naphthyridin-1(2H)-one | C | Calc'd 349.2, found 349.1 |
| 107 | 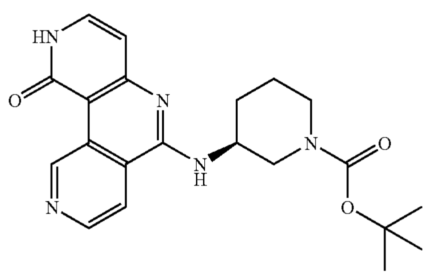 | tert-butyl (3S)-3-[(1-oxo-1,2-dihydropyrido[4,3-c]-1,6-naphthyridin-6-yl)amino]piperidine-1-carboxylate | Method A-Step 1; method D-Step 2 | Calc'd 396.2, found 396.1 |
| 108 | 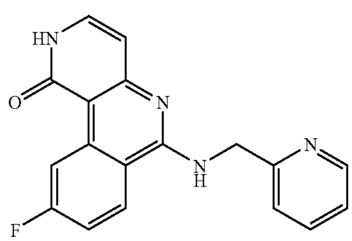 | 9-fluoro-6-[(pyridin-2-ylmethyl)amino]benzo[c]-1,6-naphthyridin-1(2H)-one | Method A Step 1, Method D Step 2 | Calc'd 321.1, found 321.1 |
| 109 | 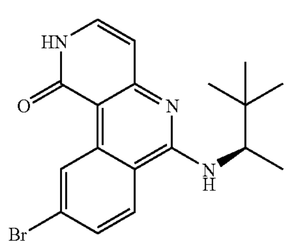 | 9-bromo-6-{[(1R)-1,2,2-trimethylpropyl]amino}benzo[c]-1,6-naphthyridin-1(2H)-one | A | Calc'd 374.1, found 374.0 |
| 110 | 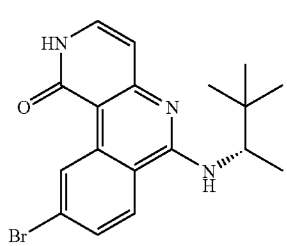 | 9-bromo-6-{[(1S)-1,2,2-trimethylpropyl]amino}benzo[c]-1,6-naphthyridin-1(2H)-one | A | Calc'd 374.1, found 374.0 |

TABLE 1-continued

| Ex. | Structure | Name | Method | LRMS [M + H]+ |
|---|---|---|---|---|
| 111 | 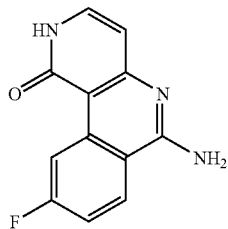 | 6-[(2,4-dimethoxybenzyl)amino]-9-fluorobenzo[c]-1,6-naphthyridin-1(2H)-one | Method A Step 1, Method D Step 2 | Calc'd 380.1, found 380.1 |

[1]This compound was made by adding tert-butyl (3S)-3-aminopiperidine-1-carboxylate to the dichloride, and the Boc-piperidine was deprotected under the acidic hydrolysis conditions.
[2]This compound was made adding beta-alanamide to the dichloride, and the amide was converted to the acid under the acidic hydrolysis conditions.

Example 112

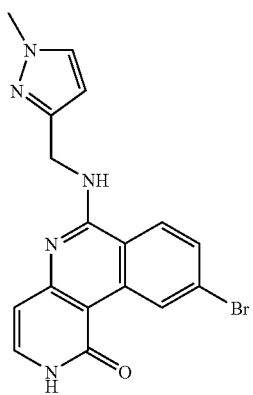

tert-butyl trans-3-fluoro-4-[(9-fluoro-1-oxo-1,2-dihydrobenzo[c]-1,6-naphthyridin-6-yl)amino]piperidine-1-carboxylate ditrifluoroacetic acid salt To a suspension of 6-[(2,4-dimethoxybenzyl)amino]-9-fluorobenzo[c]-1,6-naphthyridin-1(2H)-one (59 mg, 0.148 mmol) in THF (2 mL) was added 6N HCl (2 mL, 12.0 mmol), immediately producing a yellow solution. The reaction was placed in an oil bath preheated to 95° C., and the reaction was stirred at this temperature for three hours. The reaction was cooled to room temperature, then added dropwise to a rapidly stirring dilute aqueous NaHCO$_3$ solution. The resultant crude product was collected by filtration, and purified by reverse-phase HPLC to afford the title compound as the di-TFA salt. LRMS (APCI) calc'd (C$_{12}$H$_8$FN$_3$O) [M+H]$^+$, 230.1; found 230.0. $^1$H NMR (500 MHz, DMSO-d$_6$) δ 11.92 (broad s, 1H), 9.60 (dd, 1H), 8.95 (broad s, 2H), 8.61 (t, 1H), 7.66 (t, 1H), 7.61 (t, 1H), 6.50 (d, 1H).

Example 113

9-bromo-6-{[(1-methyl-1H-pyrazol-3-yl)methyl]amino}benzo[c]-1,6-naphthyridin-1(2H)-one Step 1: 9-bromo-1-chloro-N-[(1-methyl-1H-pyrazol-3-yl)methyl]benzo[c]-1,6-naphthyridin-6-amine

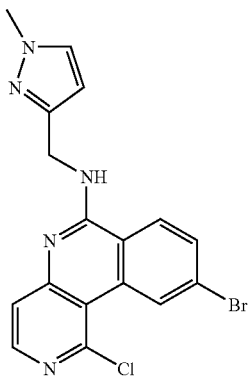

To a solution of 9-bromo-1,6-dichloro-benzo[c][1,6]naphthyridine (0.10 g, 0.31 mMol) in anhydrous CH$_3$CN (4.0 mL) was added C-(1-methyl-1H-pyrazol-3-yl)-methylamine (0.040 g 0.36 mMol) and anhydrous Et$_3$N (0.22 mL, 1.6 mMol). The reaction mixture was heated in a sealed tube at 120° C. After 3 hours the solvent was removed and the solid obtained was re-dissolved in EtOAc (10 mL). The EtOAc layer was washed with water (2×5 mL), brine (1×10 mL), and dried over MgSO$_4$. The filtrate was concentrated and the resulting residue was purified using preparative HPLC to afford 9-bromo-1-chloro-N-[(1-methyl-1H-pyrazol-3-yl)methyl]benzo[c]-1,6-naphthyridin-6-amine. $^1$H NMR (400 MHz, DMSO-d$_6$) δ 11.34 (br d, 1H), 10.11 (d, 1H), 8.61 (t, 1H), 8.32 (d, 1H), 7.75-7.73 (dd, 1H), 7.55 (d, 1H), 7.37 (t, 1H), 6.40 (d, 1H), 6.18 (d, 1H), 4.74 (d, 2H), 3.77 (s, 3H). LRMS calculated for C$_{17}$H$_{14}$BrClN$_5$ [M+H]+, 404.0; found 403.9.

Step 2: 9-Bromo-6-[(1-methyl-1H-pyrazol-3-ylmethyl)-amino]-2H-benzo[c][1,6]naphthyridin-1-one Water (0.5 mL) and NaOAc (0.015 g, 0.18 mMol) were added to a solution of (9-Bromo-1-chloro-benzo[c][1,6]naphthyridin-6-yl)-(1-methyl-1H-pyrazol-3-ylmethyl)- amine (0.05 g, 0.12 mMol) in acetic acid (1 mL) and the resulting reaction mixture was heated to 120° C. After 2.5 hours the flask was then cooled in an ice bath and made slightly alkaline by the dropwise addition of 10% NaHCO$_3$ solution. It was then extracted with EtOAc (4×6 mL), and the EtOAc layer was washed with brine (1×10 mL). The organic layer was dried with MgSO$_4$, filtered and concentrated. The crude residue was purified by preparative HPLC(C18-reverse phase column, 50×250 mm) using a water/acetonitrile (with 0.1% formic acid modifier) gradient to afford 9-bromo-6-[(1-methyl-1H-pyrazol-3-ylmethyl)-amino]-2H-benzo[c][1,6]naphthyridin-1-one. $^1$H NMR (400 MHz, DMSO-d$_6$) δ 11.34 (d, 1H), 10.11 (d, 1H), 8.61 (t, 1H), 8.32 (d, 1H), 7.75-7.73 (dd, 1H), 7.55 (d, 1H), 7.37 (t, 1H), 6.40 (d, 1H), 6.18 (d, 1H), 4.74 (d, 2H), 3.33 (s, 3H). LRMS calculated for C$_{17}$H$_{14}$BrN$_5$O [M+H]+, 386.0; found 386.0

The compounds listed in Table 2 below were prepared according to Scheme 6, substituting the appropriate amine in step 1. Unless, otherwise indicated, the compounds were isolated as the free base.

TABLE 2

| Ex. | Structure | Name | LRMS [M + H]+ |
|---|---|---|---|
| 114 | 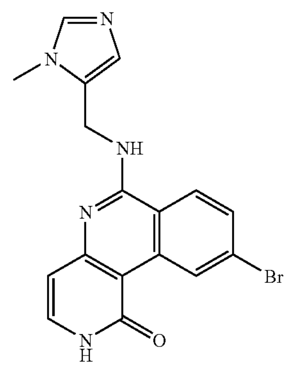 | 9-Bromo-6-[(3-methyl-3H-imidazol-4-ylmethyl)-amino]-2H-benzo[c][1,6]naphthyridin-1-one | Calc'd 386.0 Found 387.0 |
| 115 | 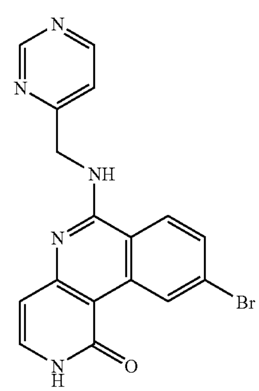 | 9-Bromo-6-[(pyrimidin-2-ylmethyl)-amino]-2H-benzo[c][1,6]naphthyridin-1-one | Calc'd 382.0 Found 382.2 |
| 116 | 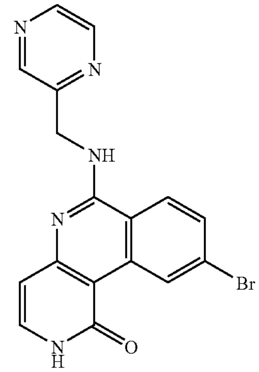 | 9-Bromo-6-[(pyrazin-2-ylmethyl)-amino]-2H-benzo[c][1,6]naphthyridin-1-one | Calc'd 384.0 Found 384.0 |

TABLE 2-continued

| Ex. | Structure | Name | LRMS [M + H]+ |
|---|---|---|---|
| 117 | 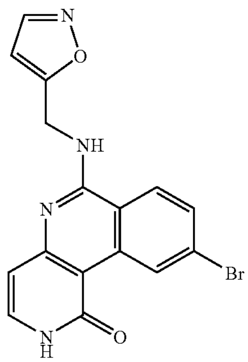 | 9-Bromo-6-[(isoxazol-5-ylmethyl)-amino]-2H-benzo[c][1,6]naphthyridin-1-one | Calc'd 373.0<br>Found 373.1 |
| 118 | 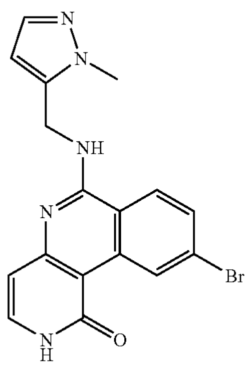 | 9-Bromo-6-[(2-methyl-2H-pyrazol-3-ylmethyl)-amino]-2H-benzo[c][1,6]naphthyridin-1-one | Calc'd 385.0<br>Found 384.9 |
| 119 | 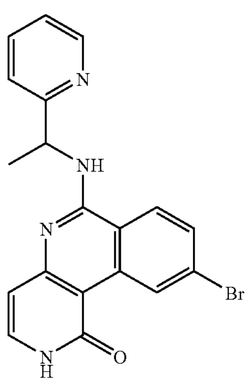 | 9-Bromo-6-(1-pyridin-2-yl-ethylamino)-2H-benzo[c][1,6]naphthyridin-1-one | Calc'd 397.0<br>Found 397.1 |
| 120 | 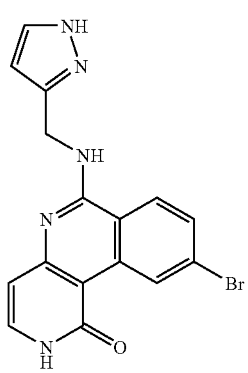 | 9-Bromo-6-[(1H-pyrazol-3-ylmethyl)-amino]-2H-benzo[c][1,6]naphthyridin-1-one | Calc'd 371.0<br>Found 373.1 |

TABLE 2-continued

| Ex. | Structure | Name | LRMS [M + H]+ |
|---|---|---|---|
| 121 | 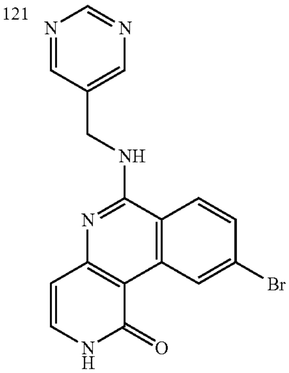 | 9-Bromo-6-[(pyrimidin-5-ylmethyl)-amino]-2H-benzo[c][1,6]naphthyridin-1-one | Calc'd 383.0 Found 383.8 |
| 122 | 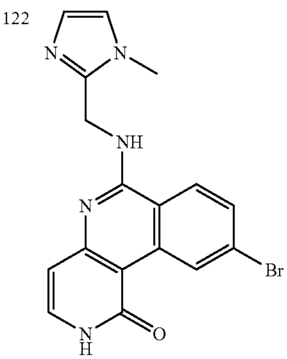 | 9-bromo-6-[(1-methyl-1H-imidazol-2-ylmethyl)-amino]-2H-benzo[c][1,6]naphthyridin-1-one | Calc'd 385.0 Found 386.0 |

Example 123

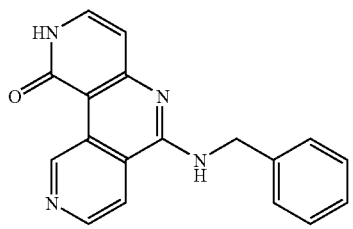

6-(benzylamino)pyrido[4,3-c]-1,6-naphthyridin-1(2H)-one

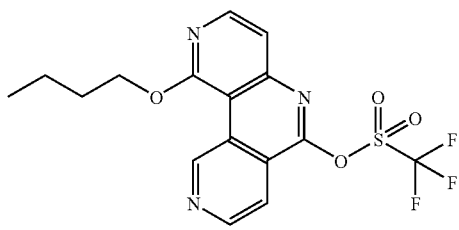

Step 1: 1-butoxypyrido[4,3-c]-1,6-naphthyridin-6-yl trifluoromethanesulfonate

To a mixture of 1-butoxypyrido[4,3-c]-1,6-naphthyridin-6-ol (2 g, 7.43 mmol) and cesium carbonate (4.84 g, 14.85 mmol) in DMA (75 ml), N-phenyltrifluoromethanesulfonamide (5.31 g, 14.85 mmol) was added. The reaction mixture was heated to 80° C. and stirred for 7 min. The reaction was then cooled to room temperature and added to ethyl acetate. The organic mixture was washed with aqueous sodium hydrogen carbonate (saturated), aqueous sodium carbonate (saturated), and brine. The organic extracts were combined, dried over sodium sulfate, and concentrated under reduced pressure. The residue was purified by column chromatography on silica gel, eluting with ethyl acetate/hexanes, to afford 1-butoxypyrido[4,3-c]-1,6-naphthyridin-6-yl trifluoromethanesulfonate as a yellow solid. $^1$H NMR (500 MHz, $C_2D_6SO$) δ 10.68 (s, 1H), 9.08 (d, 1H), 8.52 (d, 1H), 8.14 (d, 1H), 7.62 (d, 1H), 4.70 (t, 2H), 1.96 (m, 2H), 1.57 (m, 2H), 1.00 (t, 3H). LRMS (APCI) calc'd for ($C_{16}H_{15}F_3N_3O_4S$) [M+H]+, 402.1; found 402.0.

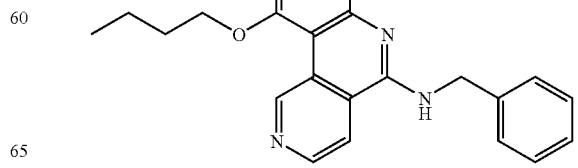

Step 2: N-benzyl-1-butoxypyrido[4,3-c]-1,6-naphthyridin-6-amine

To a solution of 1-butoxypyrido[4,3-c]-1,6-naphthyridin-6-yl trifluoromethanesulfonate (127 mg, 0.253 mmol) in THF (2531 µl), benzylamine (111 µl, 1.013 mmol) was added. The reaction mixture was heated at 80° C. for 1 h. After cooling to room temperature, the reaction mixture was diluted with ethyl acetate. Aqueous sodium hydrogen carbonate (saturated) was added, and the mixture was extracted with ethyl acetate. The combined organic extracts were dried over sodium sulfate and concentrated under reduced pressure to afford N-benzyl-1-butoxypyrido[4,3-c]-1,6-naphthyridin-6-amine as a brown oil. LRMS (APCI) calc'd for ($C_{22}H_{23}N_4O$) [M+H]+, 359.2; found 359.1.

Step 3: 6-(benzylamino)pyrido[4,3-c]-1,6-naphthyridin-1(2H)-one

N-benzyl-1-butoxypyrido[4,3-c]-1,6-naphthyridin-6-amine (90 mg, 0.251 mmol) was dissolved in hydrobromic acid (2.5 mL, 33% in acetic acid). The reaction mixture was left to stir overnight at room temperature. The reaction mixture was quenched with aqueous sodium hydrogen carbonate. The aqueous mixture was extracted with ethyl acetate. The combined organic extracts were dried over sodium sulfate and concentrated under reduced pressure. The residue was purified by preparative HPLC Reverse phase (C-18), eluting with Acetonitrile/Water+0.05% TFA, to afford 6-(benzylamino)pyrido[4,3-c]-1,6-naphthyridin-1(2H)-one as a red solid. $^1$H NMR (500 MHz, $C_2D_6SO$) δ 11.39 (d, 1H), 11.00 (s, 1H), 8.94 (t, 1H), 8.72 (d, 1H), 8.24 (d, 1H), 7.40 (t, 3H), 7.30 (t, 2H), 7.22 (t, 1H), 6.39 (d, 1H), 4.82 (d, 2H). LRMS (APCI) calc'd for ($C_{18}H_{15}N_4O$) [M+H]+, 303.1; found 303.1.

The compounds listed in Table 3 below were prepared according to Scheme 7, following analogous procedures to those used to prepare Example 123.

TABLE 3

| Ex. | Structure | Name | LRMS |
|---|---|---|---|
| 124 | 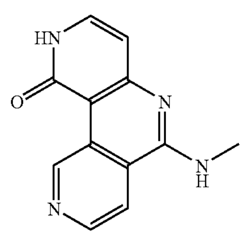 | 6-(methylamino)pyrido[4,3-c]-1,6-naphthyridin-1(2H)-one | Calc'd 227.1, found 227.0 |
| 125 | 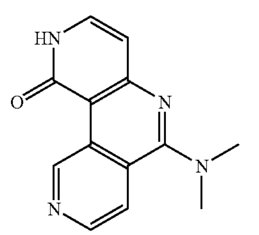 | 6-(dimethylamino)pyrido[4,3-c]-1,6-naphthyridin-1(2H)-one | Calc'd 241.1, found 241.0 |
| 126 | 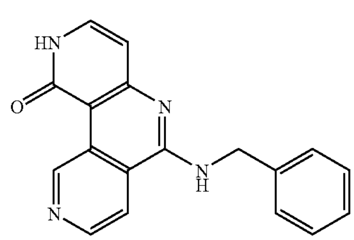 | 6-(benzylamino)pyrido[4,3-c]-1,6-naphthyridin-1(2H)-one | Calc'd 303.1, found 303.1 |
| 127 | 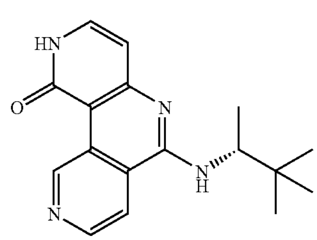 | 6-{[91R)-1,2,2-trimethylpropyl]amino}pyrido[4,3-c]-1,6-naphthyridin-1(2H)-one | Calc'd 297.2, found 297.1 |

TABLE 3-continued

| Ex. | Structure | Name | LRMS |
|---|---|---|---|
| 128 | 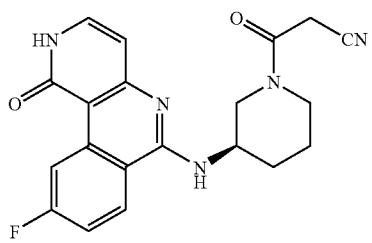 | 6-{[(1S)-1,2,2-trimethylpropyl]amino}pyrido[4,3-c]-1,6-naphthyridin-1(2H)-one | Calc'd 297.2, found 297.1 |

Example 129

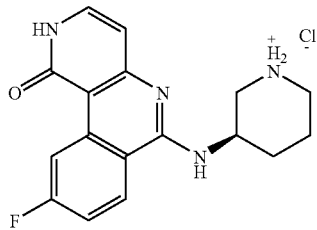

3-{(3R)-3-[(9-fluoro-1-oxo-1,2-dihydrobenzo[c]-1,6-naphthyridin-6-yl)amino]piperidin-1-yl}-3-oxo-propanenitrile Step 1: (3R)-3-[(9-fluoro-1-oxo-1,2-dihydrobenzo[c]-1,6-naphthyridin-6-yl)amino]piperidinium chloride To a solution of 1,6-dichloro-9-fluorobenzo[c]-1,6-naphthyridine (320 mg, 1.2 mmol) in dioxane (8 mL) was added tert-butyl (3R)-3-aminopiperidine-1-carboxylate (960 mg, 4.79 mmol) and heated in a microwave reactor for 1 hr at 125° C. The solution was concentrated to provide the crude solid. The crude material was dissolved in THF (5 mL) and 6 N HCl 5 mL) and heated to 85° C. for 2 hr. Upon cooling the solution solidifies and the reaction mixture was triturated with $Et_2O$ and filtered to afford (3R)-3-[(9-fluoro-1-oxo-1,2-dihydrobenzo[c]-1,6-naphthyridin-6-yl)amino]piperidinium chloride. LRMS (ESI) calc'd for ($C_{17}H_{18}FN_4O$) $[M+H]^+$, 313.2; found 313.1.

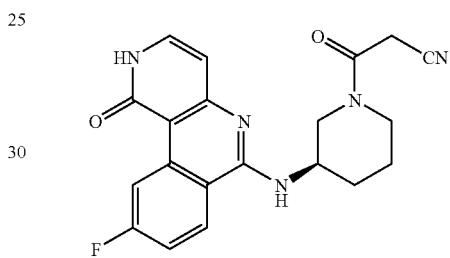

Step 2: 3-{(3R)-3-[(9-fluoro-1-oxo-1,2-dihydrobenzo[c]-1,6-naphthyridin-6-yl)amino]piperidin-1-yl}-3-oxopropanenitrile To a solution of (3R)-3-[(9-fluoro-1-oxo-1,2-dihydrobenzo[c]-1,6-naphthyridin-6-yl)amino]piperidinium chloride (40 mg, 0.09 mmol) in DMF (2 mL) were added triethylamine (0.13 mL, 0.94 mmol), HATU (0-(7-Azabenzotriazol-1-yl)-N,N,N,N-tetramethyluronium hexafluorophosphate) (36 mg, 0.094 mmol), and cyanoacetic acid (40 mg, 0.47 mmol). The solution was stirred at room temperature overnight. The crude solution was filtered and purified by reverse phase HPLC. LRMS (ESI) calc'd for ($C_{20}H_{19}FN_5O_2$) $[M+H]^+$, 380.2; found 380.1.

The compounds listed in Table 4 below were prepared according to Scheme 2, following analogous procedures to those used to prepare Example 129.

TABLE 4

| | Structure | Name | LRMS |
|---|---|---|---|
| 130 | 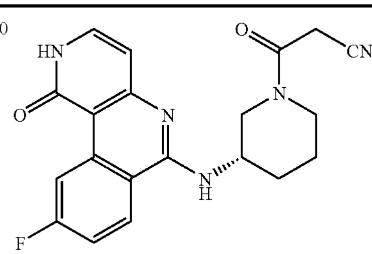 | 3-{(3S)-3-[(9-fluoro-1-oxo-1,2-dihydrobenzo[c]-1,6-naphthyridin-6-yl)amino]piperidin-1-yl}-3-oxopropanenitrile | Calc'd 380.2, found 380.1 |

TABLE 4-continued

| | Structure | Name | LRMS |
|---|---|---|---|
| 131 | | 9-fluoro-6-(piperidin-4-ylamino)benzo[c]-1,6-naphthyridin-1(2H)-one | Calc'd 313.2, found 313.1 |
| 132 | | 3-{4-[(9-fluoro-1-oxo-1,2-dihydrobenzo[c]-1,6-naphthyridin-6-yl)amino]piperidin-1-yl}-3-oxopropanenitrile | Calc'd 380.2, found 380.1 |
| 133 | | 3-{(3S,4S)-3-fluoro-4-[(9-fluoro-1-oxo-1,2-dihydrobenzo[c]-1,6-naphthyridin-6-yl)amino]piperidin-1-yl}-3-oxopropanenitrile | Calc'd 398.1, found 398.1 |
| 134 | | 9-fluoro-6-{[(3R,4S)-3-fluoropiperidin-4-yl]amino}benzo[c]-1,6-naphthyridin-1(2H)-one | Calc'd 331.1, found 331.1 |
| 135 | | 3-{(3R,4S)-3-fluoro-4-[(9-fluoro-1-oxo-1,2-dihydrobenzo[c]-1,6-naphthyridin-6-yl)amino]piperidin-1-yl}-3-oxopropanenitrile | Calc'd 398.1, found 398.1 |
| 136 | | 3-{(1R,5S)-6-[(9-fluoro-1-oxo-1,2-dihydrobenzo[c]-1,6-naphthyridin-6-yl)amino]-3-azabicyclo[3.1.0]hex-3-yl}-3-oxopropanenitrile | Calc'd 378.1, found 378.1 |

TABLE 4-continued

| Structure | Name | LRMS |
|---|---|---|
| 137 | 6-({(3R)-1-[(2,4-difluorophenyl)acetyl]piperidin-3-yl}amino)-9-fluorobenzo[c]-1,6-naphthyridin-1(2H)-one | Calc'd 467.2, found 467.1 |
| 138 | 6-(8-azabicyclo[3.2.1]oct-3-ylamino)-9-fluorobenzo[c]-1,6-naphthyridin-1(2H)-one | Calc'd 339.2, found 339.1 |
| 139 | 9-fluoro-6-({(3R)-1-[(4-methylmorpholin-2-yl)carbonyl]piperidin-3-yl}amino)benzo[c]-1,6-naphthyridin-1(2H)-one | Calc'd 440.2, found 44.2 |
| 140 | 4-{(3R)-3-[(9-fluoro-1-oxo-1,2-dihydrobenzo[c]-1,6-naphthyridin-6-yl)amino]piperidin-1-yl}-4-oxobutane-1-sulfonamide | Calc'd 462.2, found 462.1 |
| 141 | 6-{[(3R)-1-(N,N-dimethyl-b-alanyl)piperidin-3-yl]amino}-9-fluorobenzo[c]-1,6-naphthyridin-1(2H)-one | Calc'd 412.2, found 412.2 |

TABLE 4-continued

| | Structure | Name | LRMS |
|---|---|---|---|
| 142 | | 9-fluoro-6-({(3R)-1-[3-(2-oxopyrrolidin-1-yl)propanoyl]piperidin-3-yl}amino)benzo[c]-1,6-naphthyridin-1(2H)-one | Calc'd 452.2, found 452.2 |
| 143 | | 6-({(3R)-1-[(1,1-dioxidotetrahydro-3-thienyl)carbonyl]piperidin-3-yl}amino)-9-fluorobenzo[c]-1,6-naphthyridin-1(2H)-one | Calc'd 459.2, found 459.1 |
| 144 | | 3-{3-[(9-fluoro-1-oxo-1,2-dihydrobenzo[c]-1,6-naphthyridin-6-yl)amino]-8-azabicyclo[3.2.1]oct-8-yl}-3-oxopropanenitrile | Calc'd 406.2, found 406.1 |
| 145 | | 9-fluoro-6-{[(3R)-1-(2-thienylcarbonyl)piperidin-3-yl]amino}benzo[c]-1,6-naphthyridin-1(2H)-one | Calc'd 423.1, found 423.1 |
| 146 | | 6-{[(3R)-1-(2,6-dichlorobenzoyl)piperidin-3-yl]amino}-9-fluorobenzo[c]-1,6-naphthyridin-1(2H)-one | Calc'd 485.1, found 485.0 |

TABLE 4-continued

| | Structure | Name | LRMS |
|---|---|---|---|
| 147 | | 9-fluoro-6-({(3R)-1-[(1-hydroxycyclopropyl)carbonyl]piperidin-3-yl}amino)benzo[c]-1,6-naphthyridin-1(2H)-one | Calc'd 397.2, found 397.1 |
| 148 | | 9-fluoro-6-({(3R)-1-[(1-methylpiperidin-4-yl)carbonyl]piperidin-3-yl}amino)benzo[c]-1,6-naphthyridin-1(2H)-one | Calc'd 438.2, found 438.2 |
| 149 | | 6-({(3R)-1-[(5-amino-4H-1,2,4-triazol-3-yl)carbonyl]piperidin-3-yl}amino)-9-fluorobenzo[c]-1,6-naphthyridin-1(2H)-one | Calc'd 423.2, found 423.1 |
| 150 | | 6-({(3R)-1-[(4,4-difluorocyclohexyl)carbonyl]piperidin-3-yl}amino)-9-fluorobenzo[c]-1,6-naphthyridin-1(2H)-one | Calc'd 459.2, found 459.2 |
| 151 | | 9-fluoro-6-{[(3R)-1-(pyrimidin-4-ylcarbonyl)piperidin-3-yl]amino}benzo[c]-1,6-naphthyridin-1(2H)-one | Calc'd 419.2, found 419.1 |

TABLE 4-continued

| | Structure | Name | LRMS |
|---|---|---|---|
| 152 | | 9-fluoro-6-[((3R)-1-{[1-(trifluoromethyl)cyclobutyl]carbonyl}piperidin-3-yl)amino]benzo[c]-1,6-naphthyridin-1(2H)-one | Calc'd 463.2, found 463.1 |
| 153 | | 9-fluoro-6-{[(3R)-1-(isoquinolin-8-ylcarbonyl)piperidin-3-yl]amino}benzo[c]-1,6-naphthyridin-1(2H)-one | Calc'd 468.2, found 468.1 |
| 154 | | N-(3-{(3R)-3-[(9-fluoro-1-oxo-1,2-dihydrobenzo[c]-1,6-naphthyridin-6-yl)amino]piperidin-1-yl}-3-oxopropyl)acetamide | Calc'd 426.2, found 426.2 |
| 155 | | 9-fluoro-6-({(3R)-1-[(1-methyl-1H-pyrazol-4-yl)carbonyl]piperidin-3-yl}amino)benzo[c]-1,6-naphthyridin-1(2H)-one | Calc'd 421.2, found 421.1 |
| 156 | | 6-({(3R)-1-[(3,3-difluorocyclobutyl)carbonyl]piperidin-3-yl}amino)-9-fluorobenzo[c]-1,6-naphthyridin-1(2H)-one | Calc'd 431.2, found 431.1 |

TABLE 4-continued

| Structure | Name | LRMS |
|---|---|---|
| 157 | 9-fluoro-6-{[(3R)-1-(tetrahydro-2H-pyran-4-ylcarbonyl)piperidin-3-yl]amino}benzo[c]-1,6-naphthyridin-1(2H)-one | Calc'd 425.2, found 425.2 |
| 158 | 9-fluoro-6-({(3R)-1-[(5-oxopyrrolidin-3-yl)carbonyl]piperidin-3-yl}amino)benzo[c]-1,6-naphthyridin-1(2H)-one | Calc'd 424.2, found 424.1 |
| 159 | 3-{(3R)-3-[(9-fluoro-1-oxo-1,2-dihydrobenzo[c]-1,6-naphthyridin-6-yl)amino]pyrrolidin-1-yl}-3-oxopropanenitrile | Calc'd 366.1, found 366.1 |

Example 160

6-{[(1R)-1,2-dimethylpropyl]amino}-9-fluoro-4-(3-thienyl)benzo[c]-1,6-naphthyridin-1(2H)-one

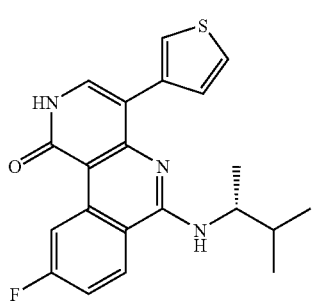

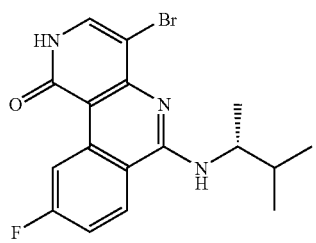

Step 1: 4-bromo-6-{[(1R)-1,2-dimethylpropyl]amino}-9-fluorobenzo[c]-1,6-naphthyridin-1(2H)-one To a solution of 6-{[(1R)-1,2-dimethylpropyl]amino}-9-fluoro-1-oxo-1,2-dihydrobenzo[c]-1,6-naphthyridin-5-ium trifluoroacetate (53 mg, 0.13 mmol) in DMF (3 mL) were added triethylamine (18 uL, 0.13 mmol) and N-bromosuccinamide (27 mg, 0.15 mmol). The solution was stirred for 2 hr then diluted with EtOAc and sat. NaHCO$_3$. The organic layers were separated, dried with MgSO$_4$, filtered, and concentrated. The resulting crude mixture was purified by silica column chromatography 100% Hex. to 100% EtOAC to afford 4-bromo-6-{[(1R)-1,2-dimethylpropyl]amino}-9-fluorobenzo[c]-1,6-naphthyridin-1(2H)-one. $^1$H NMR (600 MHz, CD$_3$OD) δ 9.55 (d, 1H), 8.37 (m, 1H), 7.66 (s, 1H), 7.36 (m, 1H), 4.65 (m, 1H), 2.1 (m, 1H) 1.30 (d, 3H), 1.0 (m, 6H). LRMS (ESI) calc'd for (C$_{17}$H$_{18}$Br$_2$FN$_3$O) [M+H]$^+$, 378.1; found 378.0.

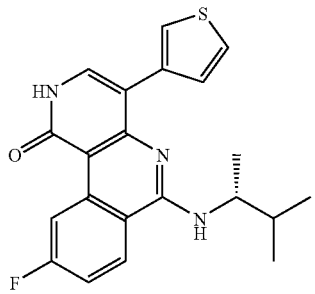

Step 2: 6-{[(1R)-1,2-dimethylpropyl]amino}-9-fluoro-4-(3-thienyl)benzo[c]-1,6-naphthyridin-1(2H)-one To a solution of 4-bromo-6-{[(1R)-1,2-dimethylpropyl]amino}-9-fluorobenzo[c]-1,6-naphthyridin-1(2H)-one (32 mg, 0.085 mmol) in dioxane (2 mL) and Na$_2$CO$_3$ (1 mL, 2.0 M) were added 3-thienylboronic acid (13 mg, 0.10 mmol) and palladium tetrakistriphenylphosphine (24 mg, 0.021 mmol). The solution was degassed by bubbling nitrogen gas and heated in a microwave reactor at 150° C. for 1 hr. The resulting solution was filtered and purified by reverse phase HPLC to produce 6-{[(1R)-1,2-dimethylpropyl]amino}-9-fluoro-4-(3-thienyl)benzo[c]-1,6-naphthyridin-1(2H)-one. $^1$H NMR (600 MHz, CD$_3$OD) δ 9.63 (dd, 1H), 8.40 (m, 1H), 7.68 (m, 1H), 7.57 (s, 1H), 7.50 (m, 1H), 7.46 (d, 1H), 7.40 (m, 1H), 4.20 (br s, 1H), 1.98 (m, 1H), 1.24 (d, 3H), 0.93 (m, 6H). LRMS (ESI) calc'd for (C$_{21}$H$_{21}$FN$_3$OS) [M+H]$^+$, 382.1; found 382.1.

The compounds listed in Table 5 below were prepared according to Scheme 3, following analogous procedures to those used to prepare Example 160.

TABLE 5

| | Structure | Name | LRMS |
|---|---|---|---|
| 161 | 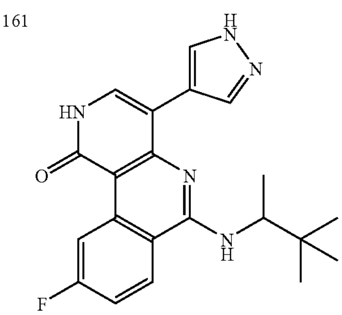 | 9-fluoro-4-(1H-pyrazol-4-yl)-6-[(1,2,2-trimethylpropyl)amino]benzo[c]-1,6-naphthyridin-1(2H)-one | Calc'd 380.2, found 380.2 |
| 162 | 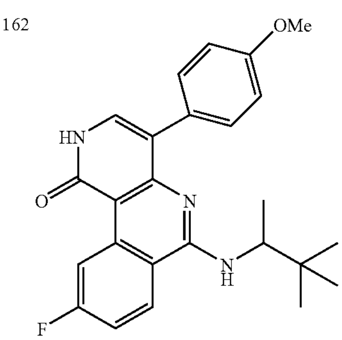 | 9-fluoro-4-(4-methoxyphenyl)-6-[(1,2,2-trimethylpropyl)amino]benzo[c]-1,6-naphthyridin-1(2H)-one | Calc'd 420.2, found 420.2 |

TABLE 5-continued

| Structure | Name | LRMS |
|---|---|---|
| 163 | 9-chloro-4-(1H-pyrazol-4-yl)-6-[(1,2,2-trimethylpropyl)amino]benzo[c]-1,6-naphthyridin-1(2H)-one | Calc'd 396.2, found 396.1 |
| 164 | 9-chloro-4-(1H-indol-3-yl)-6-[(1,2,2-trimethylpropyl)amino]benzo[c]-1,6-naphthyridin-1(2H)-one | Calc'd 445.2, found 445.1 |
| 165 | 9-chloro-4-(1-methyl-1H-pyrazol-4-yl)-6-[(1,2,2-trimethylpropyl)amino]benzo[c]-1,6-naphthyridin-1(2H)-one | Calc'd 410.2, found 410.0 |
| 166 | 9-chloro-6-{[(1R)-2-methyl-1-(trifluoromethyl)propyl]amino}-4-(1H-pyrazol-4-yl)benzo[c]-1,6-naphthyridin-1(2H)-one | Calc'd 436.1, found 436.1 |
| 167 | 6-[(1-cyclopropylethyl)amino]-9-fluoro-4-(1H-pyrazol-4-yl)benzo[c]-1,6-naphthyridin-1(2H)-one | Calc'd 364.1, found 364.1 |

Example 168

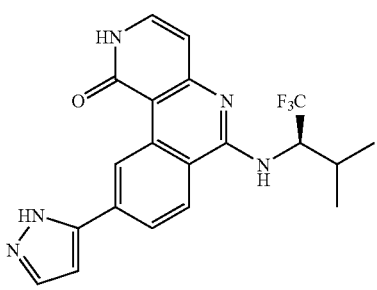

6-{[(1R)-2-methyl-1-(trifluoromethyl)propyl]amino}-9-(1H-pyrazol-5-yl)benzo[c]-1,6-naphthyridin-1(2H)-one To a solution of 9-bromo-6-{[(1R)-2-methyl-1-(trifluoromethyl)propyl]amino}benzo[c]-1,6-naphthyridin-1(2H)-one (33 mg, 0.08 mmol) in DMF (1 mL) and sodium carbonate (0.5 mL, 2.0 M), were added lithium chloride (19.7 mg, 0.464 mg), 1H-pyrazol-5-ylboronic acid (17 mg, 0.16 mmol), and palladium tetrakis triphenylphosphine (27 mg). The mixture was degassed with nitrogen and heated in the microwave at 130° C. for 1 hr. The resulting black solution was filtered and purified by reverse phase HPLC to afford 6-{[(1R)-2-methyl-1-(trifluoromethyl)propyl]amino}-9-(1H-pyrazol-5-yl)benzo[c]-1,6-naphthyridin-1(2H)-one. $^1$H NMR (600 MHz, CD$_3$OD) δ 10.3 (s, 1H), 8.53 (d, 1H), 8.16 (d, 1H), 7.77 (s, 1H), 7.50 (d, 1H), 6.95 (s, 1H), 6.74 (d, 1H), 5.34 (m, 1H), 2.43 (m, 1H), 1.19 (d, 3H), 1.11 (d, 3H). LRMS (ESI) calc'd for (C$_{20}$H$_{19}$F$_3$N$_5$O) [M+H]$^+$, 402.2; found 402.1.

The compounds listed in Table 6 below were prepared according to Scheme 4, following analogous procedures to those used to prepare Example 168.

TABLE 6

| Ex. | Structure | Name | LRMS [M + H]$^+$ |
|---|---|---|---|
| 169 | 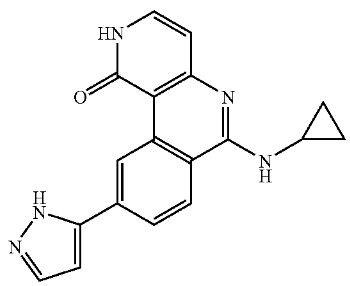 | 6-(cyclopropylamino)-9-(1H-pyrazol-5-yl)benzo[c]-1,6-naphthyridin-1(2H)-one | Calc'd 318.3, found 318.0 |
| 170 | 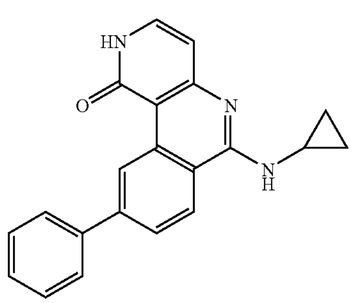 | 6-(cyclopropylamino)-9-phenylbenzo[c]-1,6-naphthyridin-1(2H)-one | Calc'd 328.1, found 328.1 |
| 171 | 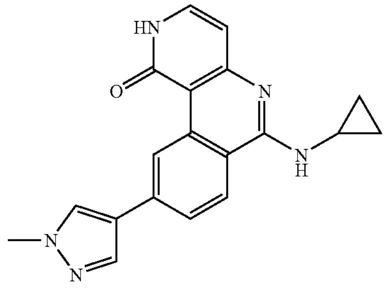 | 6-(cyclopropylamino)-9-(1-methyl-1H-pyrazol-4-yl)benzo[c]-1,6-naphthyridin-1(2H)-one | Calc'd 332.2, found 332.1 |

TABLE 6-continued

| Ex. | Structure | Name | LRMS [M + H]+ |
|---|---|---|---|
| 172 | 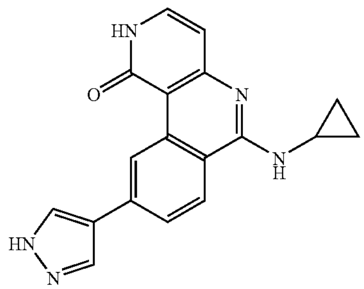 | 6-(cyclopropylamino)-9-(1H-pyrazol-4-yl)benzo[c]-1,6-naphthyridin-1(2H)-one | Calc'd 318.1, found 318.1 |
| 173 | 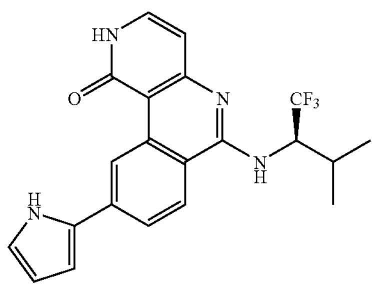 | 6-{[(1R)-2-methyl-1-(trifluoromethyl)propyl]amino}-9-(1H-pyrrol-2-yl)benzo[c]-1,6-naphthyridin-1(2H)-one | Calc'd 401.1, found 401.1 |
| 174 | 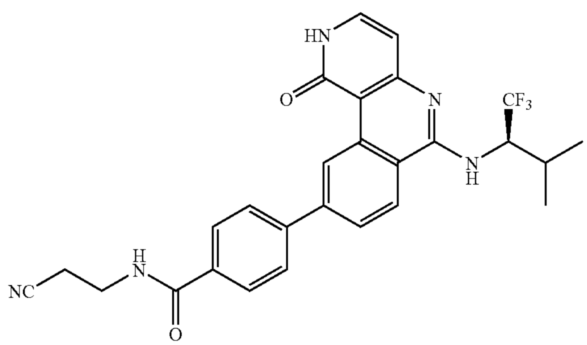 | N-(2-cyanoethyl)-4-(6-{[(1R)-2-methyl-1-(trifluoromethyl)propyl]amino}-1-oxo-1,2-dihydrobenzo[c]-1,6-naphthyridin-9-yl)benzamide | Calc'd 508.2, found 508.2 |
| 175 | 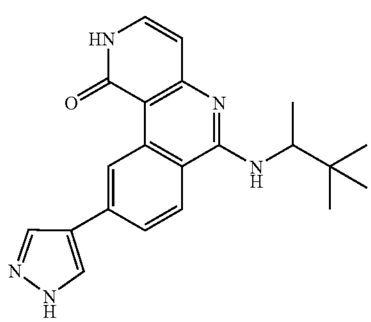 | 9-(1H-pyrazol-4-yl)-6-[(1,2,2-trimethylpropyl)amino]benzo[c]-1,6-naphthyridin-1(2H)-one | Calc'd 362.2, found 362.2 |
| 176 | 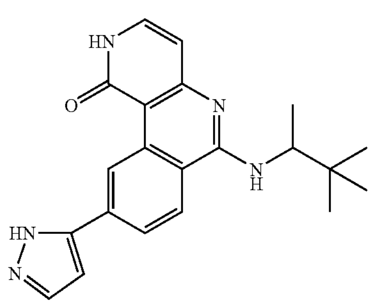 | 9-(1H-pyrazol-5-yl)-6-[(1,2,2-trimethylpropyl)amino]benzo[c]-1,6-naphthyridin-1(2H)-one | Calc'd 362.2, found 362.2 |

TABLE 6-continued

| Ex. | Structure | Name | LRMS [M + H]+ |
|---|---|---|---|
| 177 | 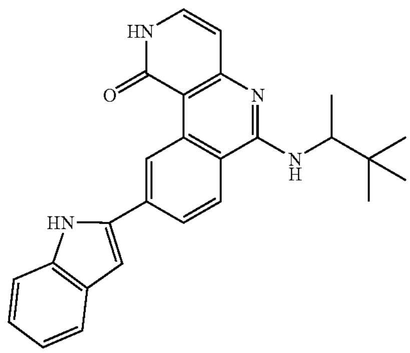 | 9-(1H-indol-2-yl)-6-[(1,2,2-trimethylpropyl)amino]benzo[c]-1,6-naphthyridin-1(2H)-one | Calc'd 411.2, found 411.2 |
| 178 | 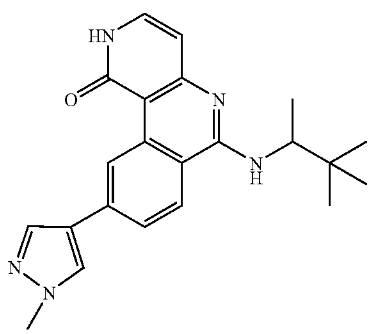 | 9-(1-methyl-1H-pyrazol-4-yl)-6-[(1,2,2-trimethylpropyl)amino]benzo[c]-1,6-naphthyridin-1(2H)-one | Calc'd 376.2, found 376.2 |
| 179 | 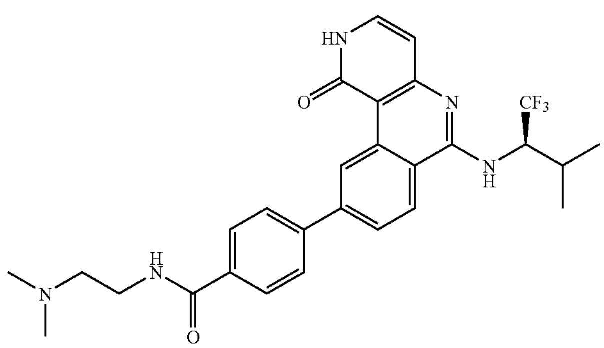 | N-[2-(dimethylamino)ethyl]-4-(6-{[(1R)-2-methyl-1-(trifluoromethyl)propyl]amino}-1-oxo-1,2-dihydrobenzo[c]-1,6-naphthyridin-9-yl)benzamide | Calc'd 526.2, found 526.2 |
| 180 | 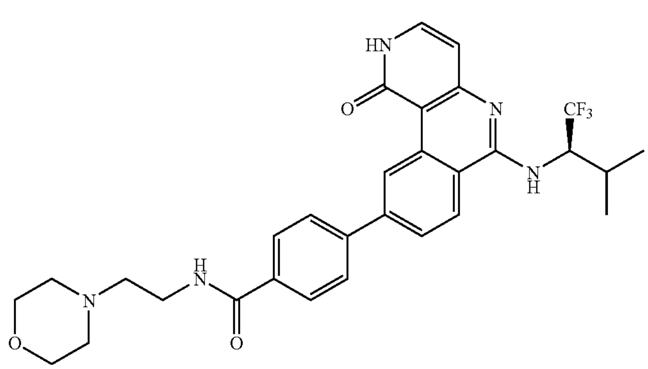 | 4-(6-{[(1R)-2-methyl-1-(trifluoromethyl)propyl]amino}-1-oxo-1,2-dihydrobenzo[c]-1,6-naphthyridin-9-yl)-N-(2-morpholin-4-ylethyl)benzamide | Calc'd 568.2, found 568.2 |

TABLE 6-continued

| Ex. | Structure | Name | LRMS [M + H]+ |
|---|---|---|---|
| 181 | 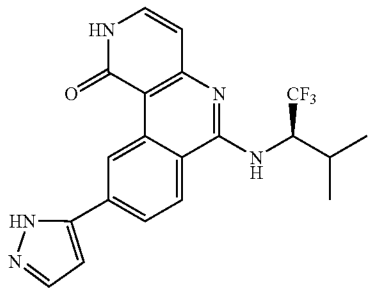 | 6-{[(1R)-2-methyl-1-(trifluoromethyl)propyl]amino}-9-(1H-pyrazol-5-yl)benzo[c]-1,6-naphthyridin-1(2H)-one | Calc'd 402.2, found 402.1 |
| 182 | 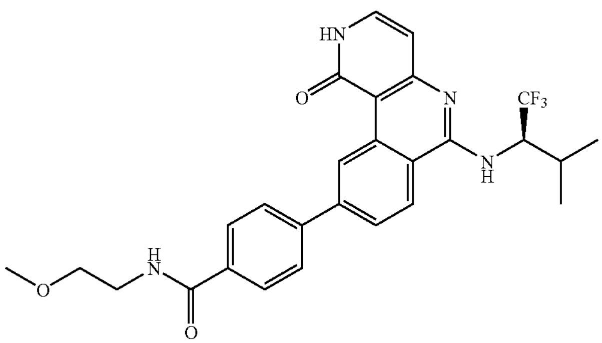 | N-(2-methoxyethyl)-4-(6-{[(1R)-2-methyl-1-(trifluoromethyl)propyl]amino}-1-oxo-1,2-dihydrobenzo[c]-1,6-naphthyridin-9-yl)benzamide | Calc'd 513.2, found 513.2 |
| 183 | 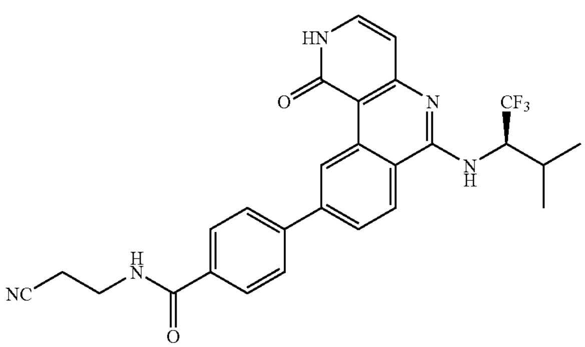 | N-(2-cyanoethyl)-4-(6-{[(1R)-2-methyl-1-(trifluoromethyl)propyl]amino}-1-oxo-1,2-dihydrobenzo[c]-1,6-naphthyridin-9-yl)benzamide | Calc'd 508.2, found 508.2 |
| 184 | 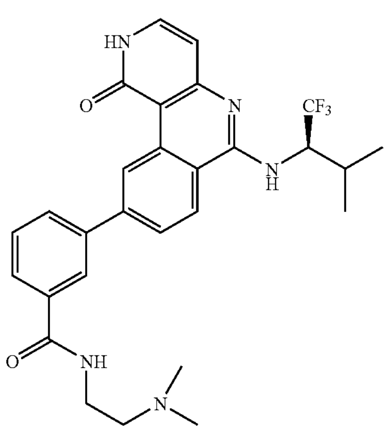 | N-[2-(dimethylamino)ethyl]-3-(6-{[(1R)-2-methyl-1-(trifluoromethyl)propyl]amino}-1-oxo-1,2-dihydrobenzo[c]-1,6-naphthyridin-9-yl)benzamide | Calc'd 526.2, found 526.2 |

TABLE 6-continued

| Ex. | Structure | Name | LRMS [M + H]+ |
|---|---|---|---|
| 185 | 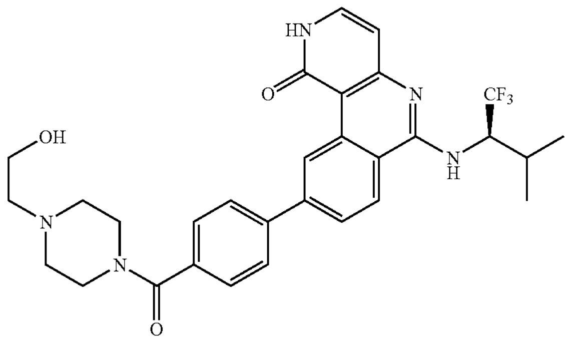 | 9-(4-{[4-(2-hydroxyethyl)piperazin-1-yl]carbonyl}phenyl)-6-{[(1R)-2-methyl-1-(trifluoromethyl)propyl]amino}benzo[c]-1,6-naphthyridin-1(2H)-one | Calc'd 568.3, found 568.2 |
| 186 | 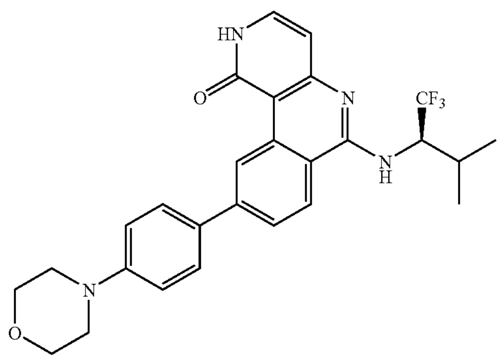 | 6-{[(1R)-2-methyl-1-(trifluoromethyl)propyl]amino}-9-(4-morpholin-4-ylphenyl)benzo[c]-1,6-naphthyridin-1(2H)-one | Calc'd 497.21, found 497.2 |
| 187 | 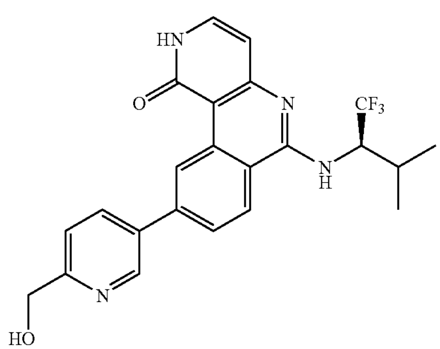 | 9-[6-(hydroxymethyl)pyridin-3-yl]-6-{[(1R)-2-methyl-1-(trifluoromethyl)propyl]amino}benzo[c]-1,6-naphthyridin-1(2H)-one | Calc'd 443.2, found 443.1 |
| 188 | 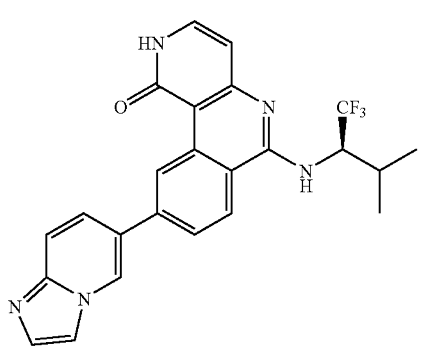 | 9-imidazo[1,2-a]pyridin-6-yl-6-{[(1R)-2-methyl-1-(trifluoromethyl)propyl]amino}benzo[c]-1,6-naphthyridin-1(2H)-one | Calc'd 452.1, found 452.1 |

TABLE 6-continued

| Ex. | Structure | Name | LRMS [M + H]+ |
|---|---|---|---|
| 189 | 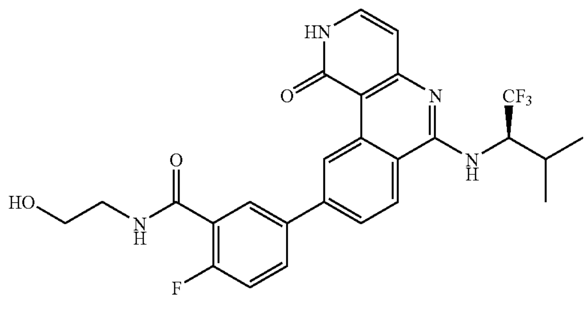 | 2-fluoro-N-(2-hydroxyethyl)-5-(6-{[(1R)-2-methyl-1-(trifluoromethyl)propyl]amino}-1-oxo-1,2-dihydrobenzo[c]-1,6-naphthyridin-9-yl)benzamide | Calc'd 517.1, found 517.1 |
| 190 | 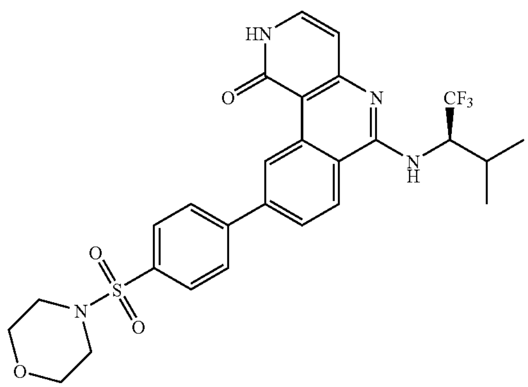 | 6-{[(1R)-2-methyl-1-(trifluoromethyl)propyl]amino}-9-[4-(morpholin-4-ylsulfonyl)phenyl]benzo[c]-1,6-naphthyridin-1(2H)-one | Calc'd 561.1, found 561.1 |
| 191 | 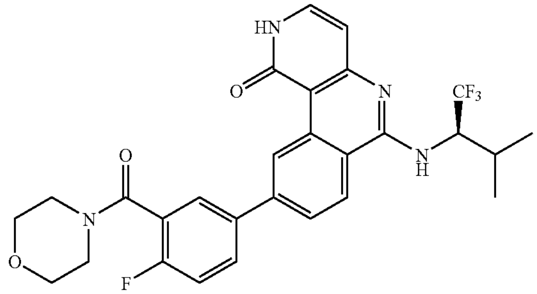 | 9-[4-fluoro-3-(morpholin-4-ylcarbonyl)phenyl]-6-{[(1R)-2-methyl-1-(trifluoromethyl)propyl]amino}benzo[c]-1,6-naphthyridin-1(2H)-one | Calc'd 543.2, found 543.1 |
| 192 | 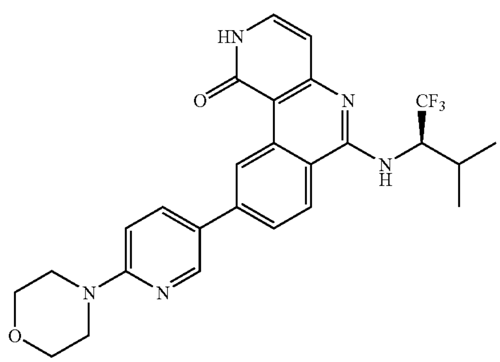 | 6-{[(1R)-2-methyl-1-(trifluoromethyl)propyl]amino}-9-(6-morpholin-4-ylpyridin-3-yl)benzo[c]-1,6-naphthyridin-1(2H)-one | Calc'd 498.2, found 498.2 |

TABLE 6-continued

| Ex. | Structure | Name | LRMS [M + H]+ |
|---|---|---|---|
| 193 | 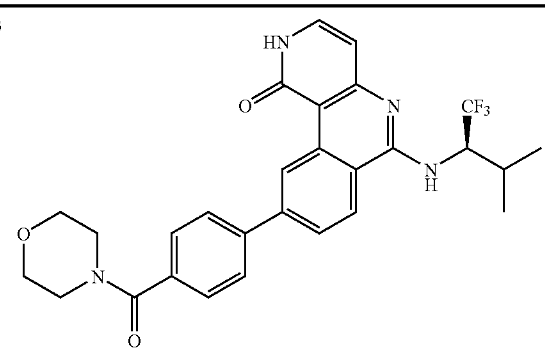 | 6-{[(1R)-2-methyl-1-(trifluoromethyl)propyl]amino}-9-[4-(morpholin-4-ylcarbonyl)phenyl]benzo[c]-1,6-naphthyridin-1(2H)-one | Calc'd 525.2, found 525.2 |

Example 194

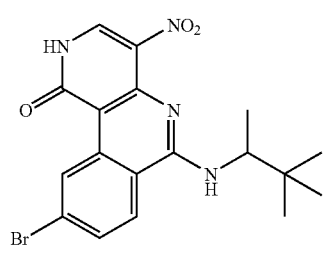

9-bromo-4-nitro-6-[(1,2,2-trimethylpropyl)amino]benzo[c]-1,6-naphthyridin-1(2H)-one Nitric acid (0.271 mL, 4.24 mmol) was added to 9-bromo-6-[(1,2,2-trimethylpropyl)amino]benzo[c]-1,6-naphthyridin-1(2H)-one (397 mg, 1.061 mmol) in TFA (10.600 mL) at room temperature. Reaction was then heated to 40° C. and stirred for 1.5 h. The reaction was then diluted with dichloromethane (150 mL) and quenched by pouring cautiously into saturated NaHCO$_3$. The layers were separated and the aqueous phase was further extracted with a 75 mL portion of dichloromethane. The combined organic layers were then dried over anhydrous sodium sulfate, filtered and concentrated under reduced pressure. The residue was purified by column chromatography on silica gel, loading with THF/hexanes and eluting with EtOAc/Hexanes to give the title compound as an orange solid. $^1$H NMR (500 MHz, C$_2$D$_6$SO) δ 12.11 (s, 1H), 9.98 (d, 1H, J=2.0 Hz), 8.55 (d, 11-1, J=9.0 Hz), 8.44 (s, 1H), 7.95 (d, 1H, J=9.0 Hz), 7.85 (dd, 1H, J=8.5, 2.0 Hz), 4.69 (m, 1H), 1.17 (d, 3H, J=7.0 Hz), 0.94 (s, 9H). LRMS (ESI) calc'd for (C$_{18}$H$_{20}$BrN$_4$O$_3$) [M+H]$^+$ 419.1; found 419.0.

Example 195

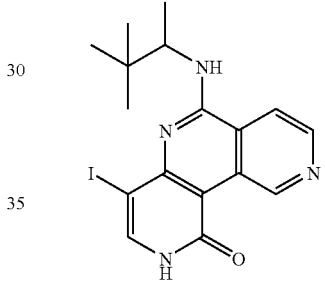

4-iodo-6-[(1,2,2-trimethylpropyl)amino]pyrido[4,3-c]-1,6-naphthyridin-1(2H)-one

To a solution of 6-[(1,2,2-trimethylpropyl)amino]pyrido[4,3-c]-1,6-naphthyridin-1(2H)-one (221 mg, 0.746 mmol) in acetic acid (7.5 mL), NIS (336 mg, 1.491 mmol) was added. After stirring for 2 h at room temperature, aqueous sodium hydrogen carbonate was added, and then aqueous sodium thiosulfate pentahydrate (5%) was added. The aqueous mixture was extracted with dichloromethane. The combined organic extracts were dried over sodium sulfate and concentrated under reduced pressure. The residue was purified by preparative HPLC Reverse phase (C-18), eluting with Acetonitrile/Water+0.05% TFA, to afford 4-iodo-6-[(1,2,2-trimethylpropyl)amino]pyrido[4,3-c]-1,6-naphthyridin-1(2H)-one as an orange solid. $^1$H NMR (500 MHz, C$_2$D$_6$SO) δ 11.58 (d, 1H), 11.00 (s, 1H), 8.74 (s, 1H), 8.47 (d, 1H), 7.94 (d, 1H), 7.84 (d, 1H), 4.93 (m, 1H), 1.23 (d, 3H), 0.99 (s, 9H). LRMS (ESI) calc'd for (C$_{17}$H$_{19}$IN$_4$O) [M+H]+, 423.1; found 423.0.

The compounds listed in Table 7 below were prepared according to Scheme 8, following analogous procedures to those used to prepare Example 195.

TABLE 7

| Ex. | Structure | Name | LRMS [M + H]+ |
|---|---|---|---|
| 196 | 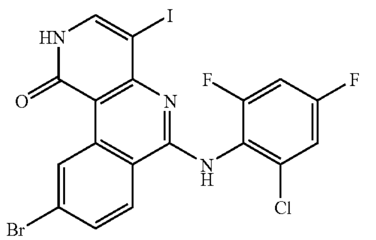 | 9-bromo-6-[(2-chloro-4,6-difluorophenyl)amino]-4-iodobenzo[c]-1,6-naphthyridin-1(2H)-one | Calc'd 563.9, found 563.8 |
| 197 | 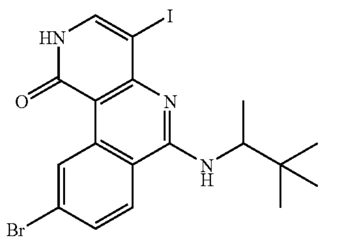 | 9-bromo-4-iodo-6-[(1,2,2-trimethylpropyl)amino]benzo[c]-1,6-naphthyridin-1(2H)-one | Calc'd 500.0, found 499.9 |
| 198 | 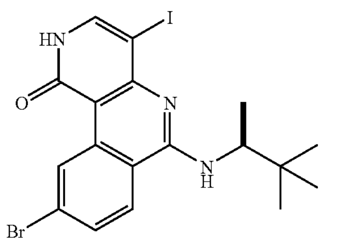 | 9-bromo-4-iodo-6-{[(1S)-1,2,2-trimethylpropyl]amino}benzo[c]-1,6-naphthyridin-1(2H)-one | Calc'd 500.0, found 499.9 |
| 199 | 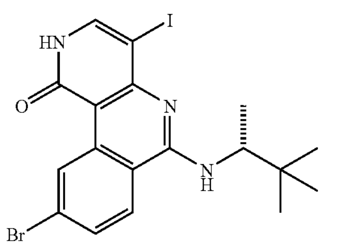 | 9-bromo-4-iodo-6-{[(1R)-1,2,2-trimethylpropyl]amino}benzo[c]-1,6-naphthyridin-1(2H)-one | Calc'd 500.0, found 499.9 |
| 200 | 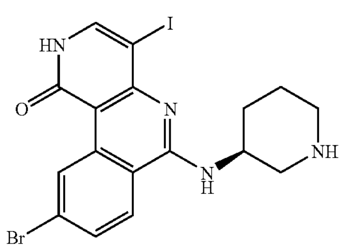 | 9-bromo-4-iodo-6-[(3S)-piperidin-3-ylamino]benzo[c]-1,6-naphthyridin-1(2H)-one | Calc'd 501.0, found 500.9 |
| 201 | 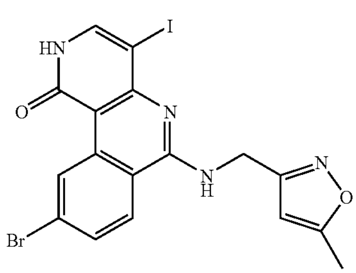 | 9-bromo-4-iodo-6-{[(5-methylisoxazol-3-yl)methyl]amino}benzo[c]-1,6-naphthyridin-1(2H)-one | Calc'd 510.9, found 510.9 |

TABLE 7-continued

| Ex. | Structure | Name | LRMS [M + H]+ |
|---|---|---|---|
| 202 | 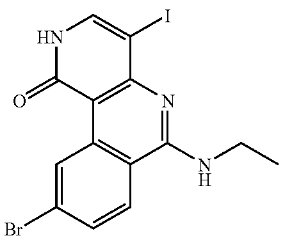 | 9-bromo-6-(ethylamino)-4-iodobenzo[c]-1,6-naphthyridin-1(2H)-one | Calc'd 443.9, found 443.9 |
| 203 | 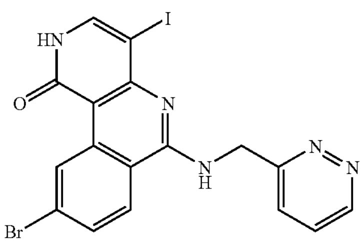 | 9-bromo-4-iodo-6-[(pyridazin-3-ylmethyl)amino]benzo[c]-1,6-naphthyridin-1(2H)-one | Calc'd 509.9, found 509.9 |
| 204 | 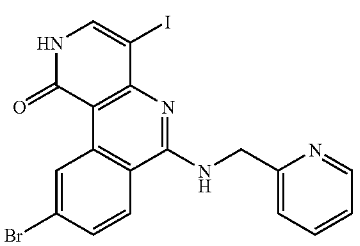 | 9-bromo-4-iodo-6-[(pyridin-2-ylmethyl)amino]benzo[c]-1,6-naphthyridin-1(2H)-one | Calc'd 506.9, found 506.9 |
| 205 | 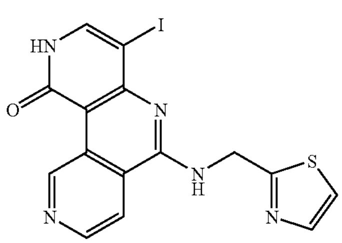 | 4-iodo-6-[(1,3-thiazol-2-ylmethyl)amino]pyrido[4,3-c]-1,6-naphthyridin-1(2H)-one | Calc'd 436.0, found 435.9 |
| 206 | 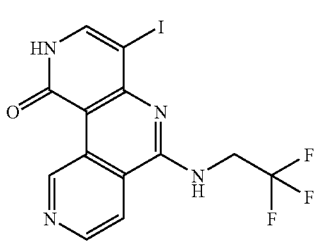 | 4-iodo-6-[(2,2,2-trifluoroethyl)amino]pyrido[4,3-c]-1,6-naphthyridin-1(2H)-one | Calc'd 421.0, found 420.9 |
| 207 | 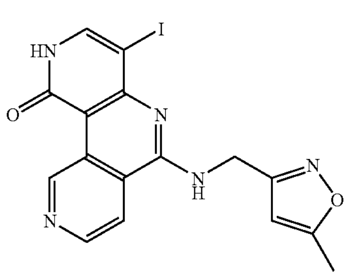 | 4-iodo-6-{[(5-methylisoxazol-3-yl)methyl]amino}pyrido[4,3-c]-1,6-naphthyridin-1(2H)-one | Calc'd 434.0, found 433.9 |

TABLE 7-continued

| Ex. | Structure | Name | LRMS [M + H]+ |
|---|---|---|---|
| 208 | 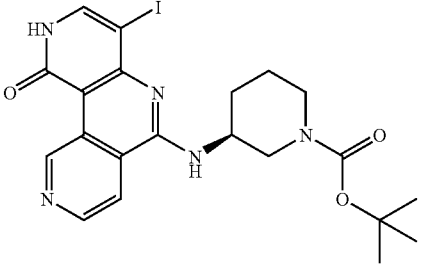 | tert-butyl (3S)-3-[(4-iodo-1-oxo-1,2-dihydropyrido[4,3-c]-1,6-naphthyridin-6-yl)amino]piperidine-1-carboxylate | Calc'd 522.1, found 522.0 |
| 209 | 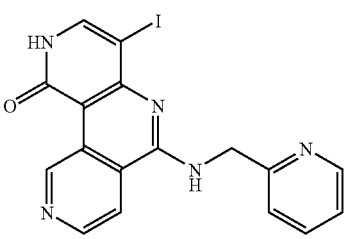 | 4-iodo-6-[(pyridin-2-ylmethyl)amino]pyrido[4,3-c]-1,6-naphthyridin-1(2H)-one | Calc'd 430.0, found 429.9 |
| 210 | 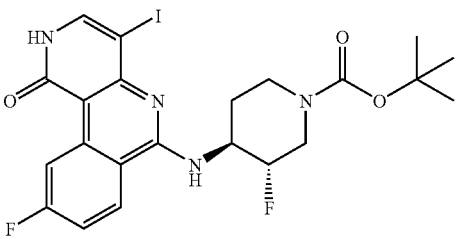 | tert-butyl trans-3-fluoro-4-[(9-fluoro-4-iodo-1-oxo-1,2-dihydrobenzo[c]-1,6-naphthyridin-6-yl)amino]piperidine-1-carboxylate | Calc'd 557.1, found 557.0 |

Example 211

9-bromo-4-iodo-6-{[(3S)-1-(4-(dimethylamino)benzyl)piperidin-3-yl]amino}-benzo[c]-1,6-naphthyridin-1(2H)-one

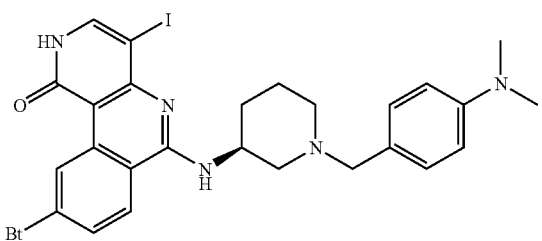

To a solution of 9-bromo-4-iodo-6-{[(3S)-1-piperidin-3-yl]amino}-benzo[c]-1,6-naphthyridin-1(2H)-one (40 mg, 0.080 mmol) in acetic acid (5% in THF) was added 4-(dimethylamino)benzaldehyde (13 mg, 0.088 mmol) and shaken overnight. (Polystyrylmethyl)trimethylammonium cyanoborohydride (211 mg, 0.200 mmol) was added and allowed to shake overnight. Reaction mixture was filtered, washed with THF (2 mL), and dried in vacuo. LRMS (ESI) calc'd for ($C_{26}H_{27}BrIN_5O$) [M+H]+, 634.04; found 634.1.

The compounds listed in Table 8 below were prepared according to Scheme 9, following analogous procedures to those used to prepare Example 211.

TABLE 8

| Ex. | Structure | Name | LRMS [M + H]+ |
|---|---|---|---|
| 212 | 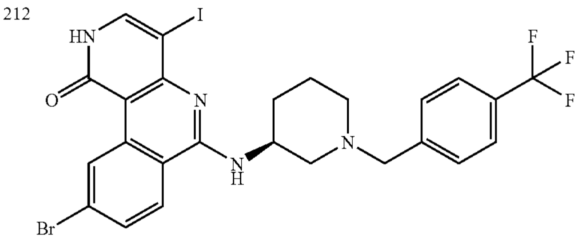 | 9-bromo-4-iodo-6-{[(3S)-1-(4-(trifluoromethyl)benzyl)piperidin-3-yl]amino}-benzo[c]-1,6-naphthyridin-1(2H)-one | Calc'd 659.0, found 658.9 |
| 213 | 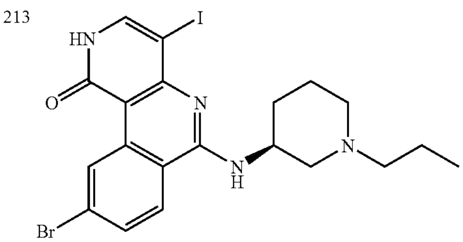 | 9-bromo-4-iodo-6-{[(3S)-1-(propyl)piperidin-3-yl]amino}-benzo[c]-1,6-naphthyridin-1(2H)-one | Calc'd 541.2, found 540.9 |
| 214 | 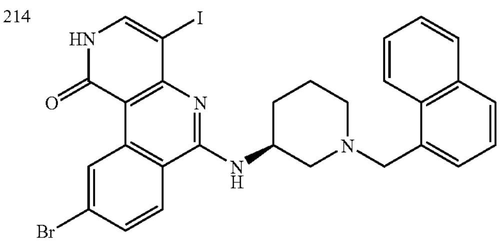 | 9-bromo-4-iodo-6-{[(3S)-1-(methylnaphthyridinyl)piperidin-3-yl]amino}-benzo[c]-1,6-naphthyridin-1(2H)-one | Calc'd 641.0, found 640.9 |
| 215 | 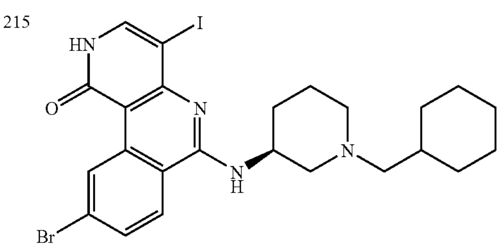 | 9-bromo-4-iodo-6-{[(3S)-1-(methylcyclohexyl)piperidin-3-yl]amino}-benzo[c]-1,6-naphthyridin-1(2H)-one | Calc'd 597.1, found 597.0 |

Example 216

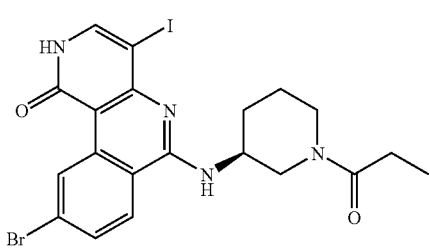

9-bromo-4-iodo-6-{[(3S)-1-(ethyl)piperidin-3-ylcarbonyl]amino}-benzo[c]-1,6-naphthyridin-1(2H)-one To a solution of 9-bromo-4-iodo-6-{[(3R)-1-piperidin-3-yl]amino}-benzo[c]-1,6-naphthyridin-1(2H)-one (50 mg, 0.100 mmol) in DMF (2 mL)) was added propionic acid (0.037 mL, 0.501 mmol), HATU (38.1 mg, 0.100 mmol), and triethylamine (0.140 mL, 1.002 mmol). After shaking overnight, reaction mixture was filtered, washed with DMF (2 mL), and dried in vacuo. LRMS (ESI) calc'd for ($C_{20}H_{20}BrIN_4O_2$) [M+H]+, 555.98; found 556.1.

The compounds listed in Table 9 below were prepared according to Scheme 9, following analogous procedures to those used to prepare Example 216.

TABLE 9

| Ex. | Structure | Name | LRMS [M + H]+ |
|---|---|---|---|
| 217 | 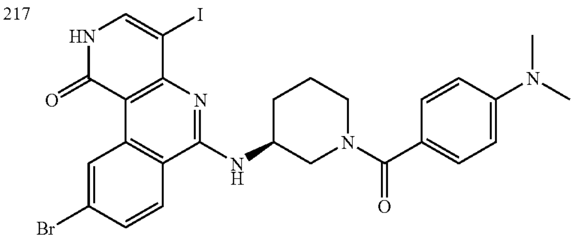 | 9-bromo-4-iodo-6-{[(3S)-1-(4-(dimethylamino)phenyl)piperidin-3-ylcarbonyl]amino}-benzo[c]-1,6-naphthyridin-1(2H)-one | Calc'd 648.0, found 647.9 |
| 218 | 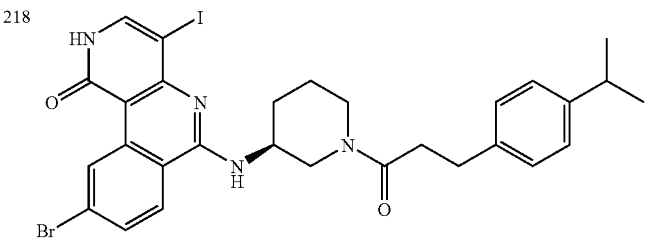 | 9-bromo-4-iodo-6-{[(3S)-1-(3-(4-isopropylphenyl)ethyl)piperidin-3-ylcarbonyl]amino}-benzo[c]-1,6-naphthyridin-1(2H)-one | Calc'd 675.1, found 675.1 |
| 219 | 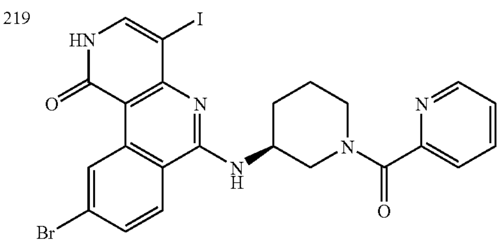 | 9-bromo-4-iodo-6-{[(3S)-1-(2-pyridyl)piperidin-3-ylcarbonyl]amino}-benzo[c]-1,6-naphthyridin-1(2H)-one | Calc'd 606.0, found 605.9 |
| 220 | 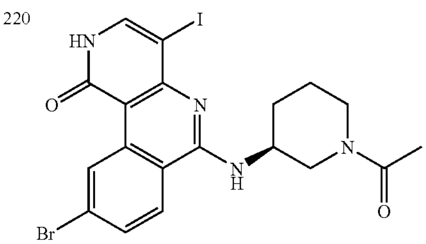 | 9-bromo-4-iodo-6-{[(3S)-1-(methyl)piperidin-3-ylcarbonyl]amino}-benzo[c]-1,6-naphthyridin-1(2H)-one | Calc'd 643.0, found 642.9 |

Example 221

9-bromo-4-iodo-6-{[(3S)-1-(methanesulfonyl)piperidin-3-yl]amino}-benzo[c]-1,6-naphthyridin-1(2H)-one

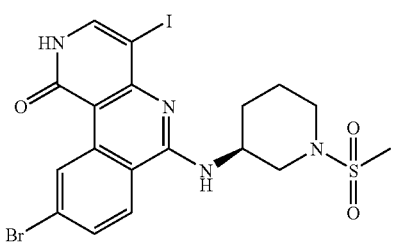

To a solution of 9-bromo-4-iodo-6-{[(3S)-1-piperidin-3-yl]amino}-benzo[c]-1,6-naphthyridin-1(2H)-one (30 mg, 0.060 mmol) in dichloromethane (1.2 mL)/DMF (0.2 mL) was added methanesulfonyl chloride (7.41 mg, 0.066 mmol) and pyridine (0.140 mL, 1.002 mmol). After shaking overnight, reaction mixture was filtered, washed with DMF (2 mL), and dried in vacuo. LRMS (ESI) calc'd for ($C_{20}H_{20}BrIN_4O_2$) [M+H]+, 578.93; found 578.9.

The compounds listed in Table 10 below were prepared according to Scheme 9, following analogous procedures to those used to prepare Example 221.

TABLE 10

| Ex. | Structure | Name | LRMS [M + H]+ |
|---|---|---|---|
| 222 | 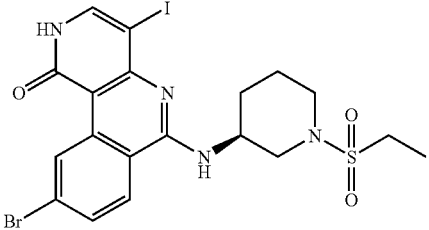 | 9-bromo-4-iodo-6-{[(3S)-1-(ethanesulfonyl)piperidin-3-yl]amino}-benzo[c]-1,6-naphthyridin-1(2H)-one | Calc'd 593.0, found 592.9 |
| 223 | 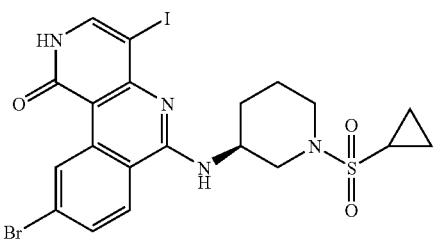 | 9-bromo-4-iodo-6-{[(3S)-1-(cyclopropylsulfonyl)piperidin-3-yl]amino}-benzo[c]-1,6-naphthyridin-1(2H)-one | Calc'd 605.0, found 604.9 |
| 224 | 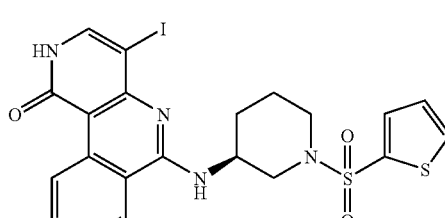 | 9-bromo-4-iodo-6-{[(3S)-1-(2-(thiophenylsulfonyl))piperidin-3-yl]amino}-benzo[c]-1,6-naphthyridin-1(2H)-one | Calc'd 646.9, found 646.9 |

Example 225

9-bromo-4-iodo-6-{[(3S)-1-(propylamino)piperidin-3-ylcarbonyl]amino}-benzo[c]-1,6-naphthyridin-1(2H)-one

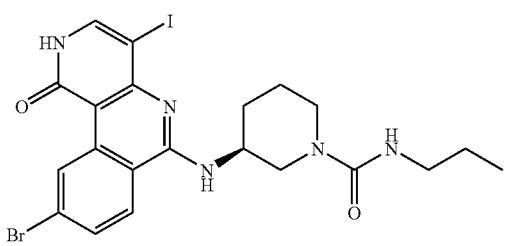

To a solution of 9-bromo-4-iodo-6-{[(3S)-1-piperidin-3-yl]amino}-benzo[c]-1,6-naphthyridin-1(2H)-one (30 mg, 0.060 mmol) in dichloromethane (0.2 mL)/DMF (1.2 mL) was added propyl isocyanate (5.12 mg, 0.060 mmol). After shaking overnight, reaction mixture was dried in vacuo. LRMS (ESI) calc'd for ($C_{20}H_{20}BrIN_4O_2$) [M+H]+, 586.01; found 585.9.

The compounds listed in Table 11 below were prepared according to Scheme 9, following analogous procedures to those used to prepare Example 225.

TABLE 11

| Ex. | Structure | Name | LRMS [M + H]+ |
|---|---|---|---|
| 226 | 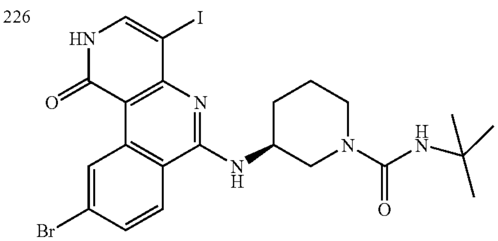 | 9-bromo-4-iodo-6-{[(3S)-1-(tert-butylamino)piperidin-3-ylcarbonyl]amino}-benzo[c]-1,6-naphthyridin-1(2H)-one | Calc'd 600.0, found 00.0 |
| 227 | 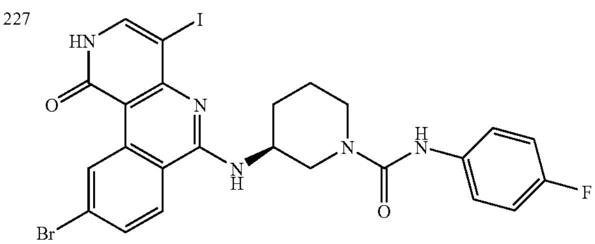 | 9-bromo-4-iodo-6-{[(3S)-1-(4-fluorophenyl)piperidin-3-ylcarbonyl]amino}-benzo[c]-1,6-naphthyridin-1(2H)-one | Calc'd 639.0, found 638.9 |
| 228 | 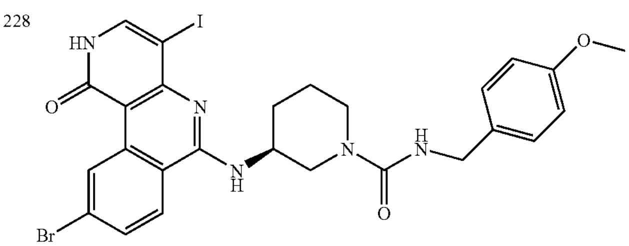 | 9-bromo-4-iodo-6-{[(3S)-1-(4-methoxybenzyl)pipendin-3-ylcarbonyl]amino}-benzo[c]-1,6-naphthyridin-1(2H)-one | Calc'd 664.0, found 664.0 |

Example 229

9-bromo-4-iodo-6-{[(3S)-1-(methyl)piperidin-3-ylcarboxylate]amino}-benzo[c]-1,6-naphthyridin-1(2H)-one

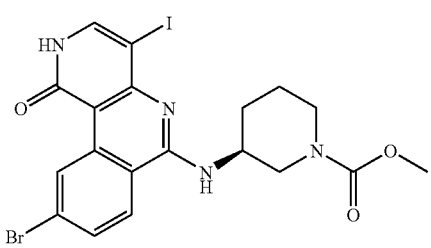

To a solution of 9-bromo-4-iodo-6-{[(3R)-1-piperidin-3-yl]amino}-benzo[c]-1,6-naphthyridin-1(2H)-one (50 mg, 0.100 mmol) in water (0.30 mL) cooled to 0° C. was added solid sodium bicarbonate (43.8 mg, 0.521 mmol). Methyl chloroformate (7.76 μL, 0.100 mmol) was added and allowed to warm to room temperature. After shaking overnight, reaction mixture was filtered, washed with acetonitrile (1 mL), and dried in vacuo. LRMS (ESI) calc'd for ($C_{20}H_{20}BrIN_4O_2$) [M+H]+, 558.96; found 558.9.

The compounds listed in Table 12 below were prepared according to Scheme 8, following analogous procedures to those used to prepare Example 229.

TABLE 12

| Ex. | Structure | Name | LRMS [M + H]+ |
|---|---|---|---|
| 230 | 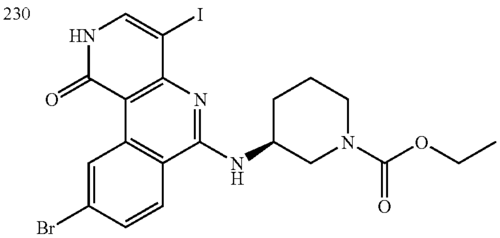 | 9-bromo-4-iodo-6-{[(3S)-1-(ethyl)piperidin-3-ylcarboxylate]amino}-benzo[c]-1,6-naphthyridin-1(2H)-one | Calc'd 573.0, found 572.9 |
| 231 | 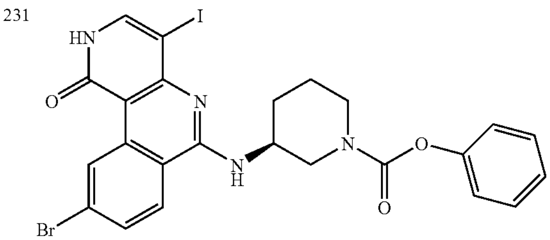 | 9-bromo-4-iodo-6-{[(3S)-1-(phenyl)piperidin-3-ylcarboxylate]amino}-benzo[c]-1,6-naphthyridin-1(2H)-one | Calc'd 521.0, found 520.9 |
| 232 | 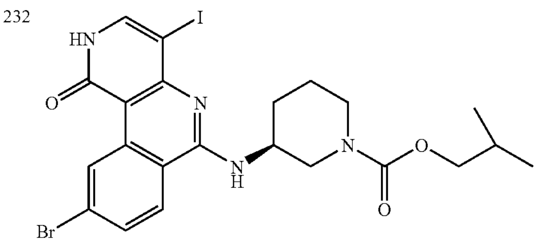 | 9-bromo-4-iodo-6-{[(3S)-1-(isobutyl)piperidin-3-ylcarboxylate]amino}-benzo[c]-1,6-naphthyridin-1(2H)-one | Calc'd 601.0, found 601.0 |

Example 233

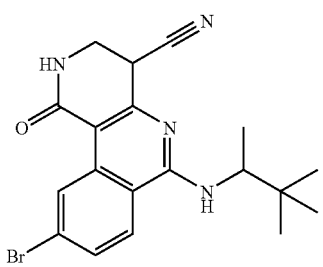

9-bromo-1-oxo-6-[(1,2,2-trimethylpropyl)amino]-1,2-dihydrobenzo[c]-1,6-naphthyridine-4-carbonitrile 9-bromo-4-iodo-6-[(1,2,2-trimethylpropyl)amino]benzo[c]-1,6-naphthyridin-1(2H)-one (50 mg, 0.10 mmol), Zinc Cyanide (7.04 mg, 0.060 mmol), and Pd(Ph$_3$P)$_4$ (11.55 mg, 10.00 μmol) were combined in a 2-dram vial that was then flushed with nitrogen and kept under a nitrogen atmosphere. DMF (500 μl) was then added and the reaction was heated to 90° C. and stirred for 3 h. Then, the reaction was purified by preparative HPLC Reverse phase (C-18), eluting with Acetonitrile/Water+0.05% TFA, to give the title compound as a pale yellow solid. LRMS (ESI) calc'd for (C$_{19}$H$_{20}$BrN$_4$O) [M+H]+ 399.1; found 399.0.

Example 234

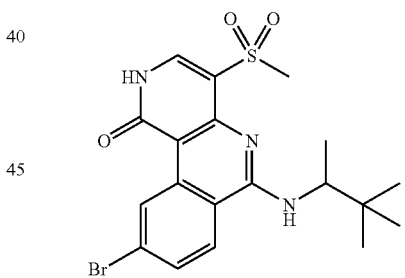

9-bromo-4-(methylsulfonyl)-6-[(1,2,2-trimethylpropyl)amino]benzo[c]-1,6-naphthyridin-1(2H)-one 9-bromo-4-iodo-6-[(1,2,2-trimethylpropyl)amino]benzo[c]-1,6-naphthyridin-1(2H)-one (50 mg, 0.10 mmol), sodium methanesulfinate (13.27 mg, 0.130 mmol), DL-proline (2.302 mg, 0.020 mmol), copper(I) iodide (1.904 mg, 10.00=01) and NaOH (0.800 mg, 0.020 mmol) were combined in a 2-dram vial that was then flushed with nitrogen and kept under a nitrogen atmosphere. DMSO (500 μl) was then added and the reaction was heated to 90° C. and stirred for 72 h. Then, the reaction was purified by preparative HPLC reverse phase (C-18), eluting with Acetonitrile/Water+0.05% TFA, to give the title compound as a pale yellow solid. LRMS (ESI) calc'd for (C$_{19}$H$_{23}$BrN$_3$O$_3$S) [M+H]+ 452.1; found 452.0.

Example 235

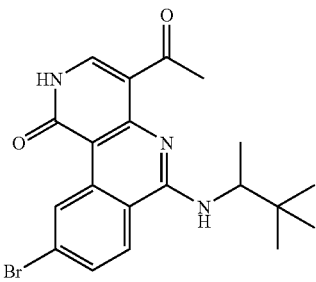

9-bromo-4-nitro-6-[(1,2,2-trimethylpropyl)amino]benzo[c]-1,6-naphthyridin-1(2H)-one 9-bromo-4-iodo-6-[(1,2,2-trimethylpropyl)amino]benzo[c]-1,6-naphthyridin-1(2H)-one (50 mg, 0.100 mmol), Pd$_2$(dba)$_3$ (4.58 mg, 5.00 µmol) and t-butylphosphine HBF$_4$ salt (2.90 mg, 10.00 µmol) were combined in a 2-dram vial and flushed with nitrogen. Dioxane (1000 µl) was then added followed by dicyclohexylmethylamine (24.38 µl, 0.115 mmol) and butyl vinyl ether (19.50 µl, 0.150 mmol). The suspension was degassed by subsurface bubbling of nitrogen for 5 minutes. The reaction was then heated to 60° C. under nitrogen for 24 h. The reaction was then diluted with ethyl acetate (150 mL) and washed with 0.1N HCl and the brine. The organics were dried over anhydrous sodium sulfate, filtered and concentrated under reduced pressure. The residue was purified by column chromatography on silica gel eluting with EtOAc/Hexanes to afford the title compound as a white solid. $^1$H NMR (500 MHz, C$_2$D$_6$SO) δ 11.85 (d, 1H, J=6.5 Hz), 10.07 (d, 1H, J=2.0 Hz), 8.51 (d, 1H, J=9.0 Hz), 7.80 (m, 2H), 7.74 (dd, 1H, J=8.5, 4.0 Hz), 4.66 (m, 1H), 2.75 (s, 3H), 1.20 (d, 3H, J=7.0 Hz), 0.95 (s, 9H). LRMS (ESI) calc'd for (C$_{20}$H$_{23}$BrN$_3$O$_2$) [M+H]$^+$ 418.1; found 418.0.

Example 236

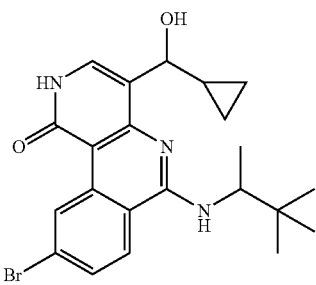

9-bromo-4-[cyclopropyl(hydroxy)methyl]-6-[(1,2,2-trimethylpropyl)amino]benzo[c]-1,6-naphthyridin-1(2H)-one 9-bromo-4-iodo-6-[(1,2,2-trimethylpropyl)amino]benzo[c]-1,6-naphthyridin-1(2H)-one (50 mg, 0.100 mmol) was dissolved in THF and cooled to −30° C. Phenylmagnesium chloride (2M in THF) (105 µl, 0.210 mmol) was added dropwise, then stirred for 30 minutes before allowing to warm to room temperature by removing cooling baths and stirring an additional 30 minutes. Then, isopropylmagnesium chloride (2M in ether) (60.0 µl, 0.120 mmol) was added dropwise and stirred for 1 h. Then, cyclopropanecarboxaldehyde (29.9 µl, 0.400 mmol) was added and the reaction mixture was stirred for 30 minutes before quenching with saturated NH$_4$Cl (10 mL). The reaction was then diluted with brine and extracted with ethyl acetate. The organic extract was then dried over anhydrous sodium sulfate, filtered and concentrated under reduced pressure. Then, the residue was purified by preparative HPLC reverse phase (C-18), eluting with Acetonitrile/Water+0.05% TFA, to give the title compound as a pale yellow solid as an approximate 1:1 mixture of diastereomers. LRMS (ESI) calc'd for (C$_{22}$H$_{27}$BrN$_3$O$_2$) [M+H]$^+$ 444.1; found 444.1.

Example 237

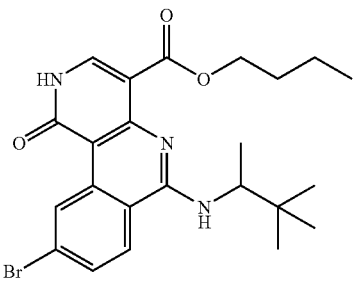

9-bromo-4-[cyclopropyl(hydroxy)methyl]-6-[(1,2,2-trimethylpropyl)amino]benzo[c]-1,6-naphthyridin-1(2H)-one 9-bromo-4-iodo-6-[(1,2,2-trimethylpropyl)amino]benzo[c]-1,6-naphthyridin-1(2H)-one (50 mg, 0.100 mmol), palladium(II) chloride (0.355 mg, 1.999 µmol), (9,9-dimethyl-9H-xanthene-4,5-diyl)bis(diphenylphosphine) (1.157 mg, 1.999 µmol), triethylamine (18.11 µl, 0.130 mmol) and 1-butanol (1000 µl) were combined in a 40 mL vial and sparged with nitrogen for 5 minutes. The cap on the vial was removed and the atmosphere changed to carbon monoxide by pressurizing to 30 psi and releasing the pressure 3 times inside a stainless steel pressure vessel. Then, the pressure of CO was adjusted to 100 psi and heated to 100° C. for 5 h. Then, the reaction was cooled to room temperature, the reaction was then poured into ethyl acetate, washed with saturated NaHCO$_3$, brine, dried over anhydrous sodium sulfate, filtered and concentrated under reduced pressure. The residue was purified by preparative HPLC Reverse phase (C-18), eluting with Acetonitrile/Water+0.05% TFA, to afford the title compound as a white solid. $^1$H NMR (500 MHz, C$_2$D$_6$SO) δ 11.68 (d, 1H, J=6.0 Hz), 10.04 (d, 1H, J=2.0 Hz), 8.50 (d, 1H, J=9.0 Hz), 7.83 (d, 1H, J=7.0 Hz), 7.78 (d, 1H, J=7.5 Hz), 7.68 (d, 1H, J=8.5 Hz), 4.81 (m, 1H), 4.22 (m, 2H), 1.68 (m, 2H), 1.37 (m, 2H), 1.17

(m, 6H), 0.93 (s, 9H). LRMS (ESI) calc'd for (C$_{23}$H$_{29}$BrN$_3$O$_3$) [M+H]$^+$ 476.1; found 476.1.

Example 238

Method G for Sonogashira Coupling

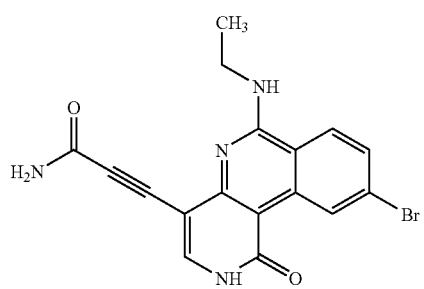

3-[9-bromo-6-(ethylamino)-1-oxo-1,2-dihydrobenzo[c]-1,6-naphthyridin-4-yl]prop-2-ynamide To a solution of 9-bromo-6-(ethylamino)-4-iodobenzo[c]-1,6-naphthyridin-1(2H)-one (2.5 g, 5.63 mmol) in DMF at room temperature (49.3 ml) was added propiolamide (583 mg, 8.44 mmol), Copper (I) Iodide (161 mg, 0.844 mmol), triethylamine (1.569 ml, 11.26 mmol), and tetrakis(triphenylphosphine) palladium (651 mg, 0.563 mmol). The flask was put under a blanket of argon, sealed and allowed to stir overnight. The next day the reaction was diluted with 100 ml of DCM, which caused the product to precipitate out of solution. The precipitate was collected by filtration, washed with 50 ml of DCM and dried in vacuo to give the product, 3-[9-bromo-6-(ethylamino)-1-oxo-1,2-dihydrobenzo[c]-1,6-naphthyridin-4-yl]prop-2-ynamide. $^1$H NMR (600 MHz, DMSO-D$_6$) δ 11.76 (br s, 1H), 10.00 (s, 1H), 8.40 (t, 1H), 8.27 (d, 1H), 7.79-7.76, (m, 3H), 7.47 (s, 1H), 3.66 (m, 2H), 1.25 (t, 3H). LRMS (ESI) calc'd for (C$_{17}$H$_{13}$BrN$_4$O$_2$) [M+H]$^+$, 385.0; found 385.0.

Example 239

Method H for Sonogashira Coupling

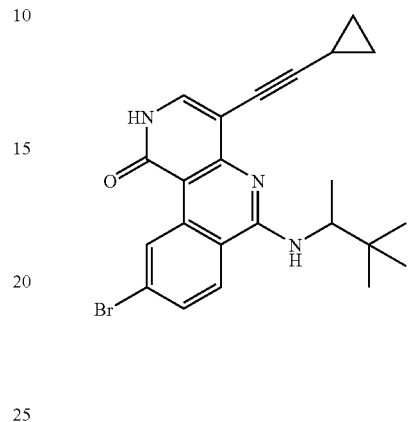

9-bromo-4-(cyclopropylethynyl)-6-[(1,2,2-trimethylpropyl)amino]benzo[c]-1,6-naphthyridin-1(2H)-one 9-bromo-4-iodo-6-[(1,2,2-trimethylpropyl)amino]benzo[c]-1,6-naphthyridin-1(2H)-one (5.03 g, 10.06 mmol), copper(I) iodide (0.230 g, 1.207 mmol), Pd(allyl)Cl dimer (0.221 g, 0.603 mmol) and tri(2-furyl)phosphine (0.280 g, 1.207 mmol) were combined in a 10-dram vial that was then flushed with nitrogen and kept under a nitrogen atmosphere. MeCN (101 ml) was then added followed by diisopropylamine (4.30 ml, 30.2 mmol) and cyclopropylacetylene (2.57 ml, 30.2 mmol). The resulting solution was then heated to 45° C. and stirred in the dark for 30 min. Then, the reaction was poured into ethyl acetate (350 mL) and washed with sat NaHCO$_3$, water, brine, dried over anhydrous sodium sulfate, filtered and concentrated under reduced pressure. The resulting oil was purified by column chromatography on silica gel, eluting with EtOAc/Hexanes to afford the title compound as a pale yellow solid. LRMS (ESI) calc'd for (C$_{23}$H$_{25}$BrN$_3$O) [M+H]$^+$, 438.1; found 438.0.

The compounds listed in Table 13 below were prepared according to Scheme 14, following analogous procedures to Method G or Method H as noted.

TABLE 13

| Ex. | Structure | Name | Method | LRMS |
| --- | --- | --- | --- | --- |
| 240 | 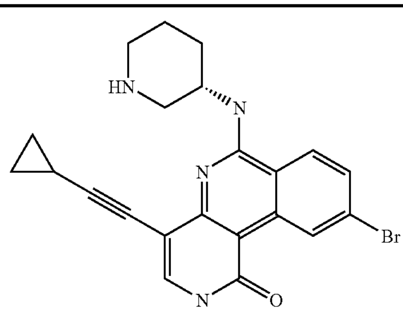 | 9-bromo-4-(cyclopropylethynyl)-6-[(3S)-piperidin-3-ylamino]benzo[c]-1,6-naphthyridin-1(2H)-one | G | Calc'd 435.1, found |

TABLE 13-continued

| Ex. | Structure | Name | Method | LRMS |
|---|---|---|---|---|
| 241 | 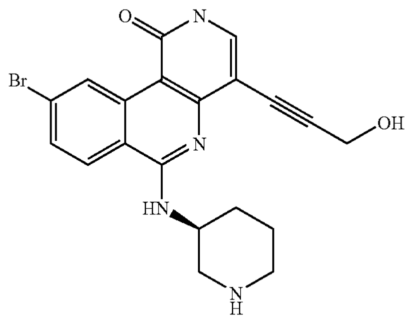 | 9-bromo-4-(3-hydroxyprop-1-yn-1-yl)-6-[(3S)-piperidin-3-ylamino]benzo[c]-1,6-naphthyridin-1(2H)-one | G | Calc'd 437.1, found |
| 242 | 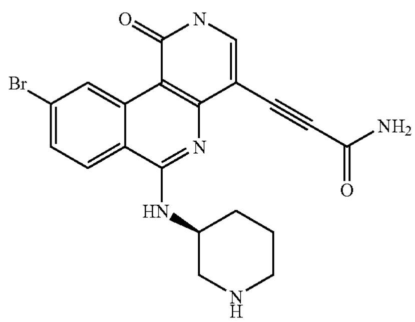 | 3-{9-bromo-1-oxo-6-[(3S)-piperidin-3-ylamino]-1,2-dihydrobenzo[c]-1,6-naphthyridin-4-yl}prop-2-ynamide | G | Calc'd 440.1, found 440.0 |
| 243 | 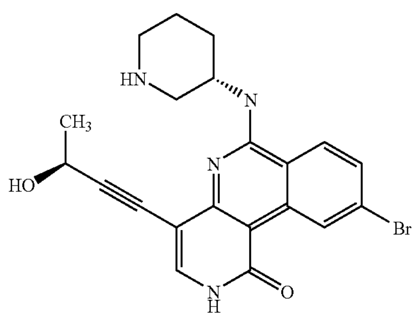 | 9-bromo-4-[(3S)-3-hydroxybut-1-yn-1-yl]-6-[(3S)-piperidin-3-ylamino]benzo[c]-1,6-naphthyridin-1(2H)-one | G | Calc'd 441.1, found 441.0 |
| 244 | 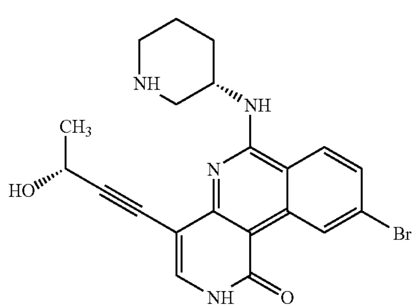 | 9-bromo-4-[(3R)-3-hydroxybut-1-yn-1-yl]-6-[(3S)-piperidin-3-ylamino]benzo[c]-1,6-naphthyridin-1(2H)-one | G | Calc'd 440.1, found 440.0 |
| 245 | 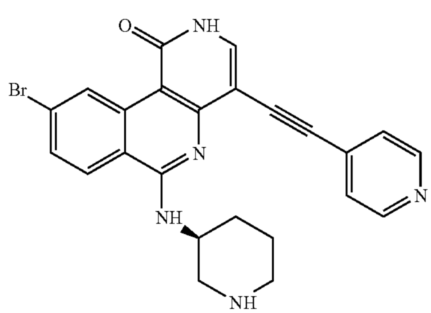 | 9-bromo-6-[(3S)-piperidin-3-ylamino]-4-(pyridin-4-ylethynyl)benzo[c]-1,6-naphthyridin-1(2H)-one | G | Calc'd 474.1, found 474.0 |

TABLE 13-continued

| Ex. | Structure | Name | Method | LRMS |
|---|---|---|---|---|
| 246 | 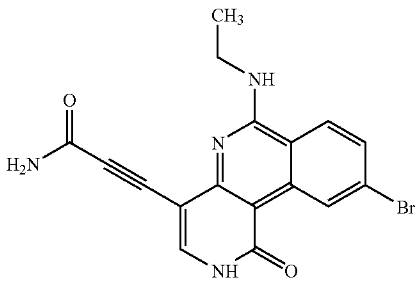 | 3-[9-bromo-6-(ethylamino)-1-oxo-1,2-dihydrobenzo[c]-1,6-naphthyridin-4-yl]prop-2-ynamide | G | Calc'd 385.0, found 385.0 |
| 247 | 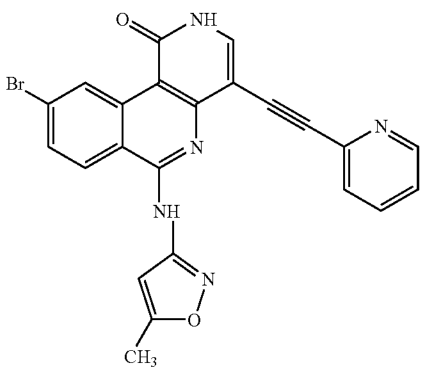 | 9-bromo-6-{[(5-methylisoxazol-3-yl)methyl]amino}-4-(pyridin-2-ylethynyl)benzo[c]-1,6-naphthyridin-1(2H)-one | G | Calc'd 486.1, found 486.0 |
| 248 | 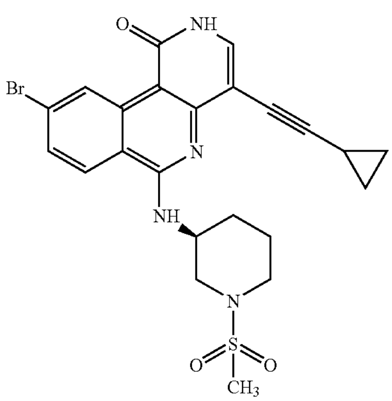 | 9-bromo-4-(cyclopropylethynyl)-6-{[(3S)-1-(methylsulfonyl)piperidin-3-yl]amino}benzo[c]-1,6-naphthyridin-1(2H)-one | G | Calc'd 515.1, found 515.1 |
| 249 | 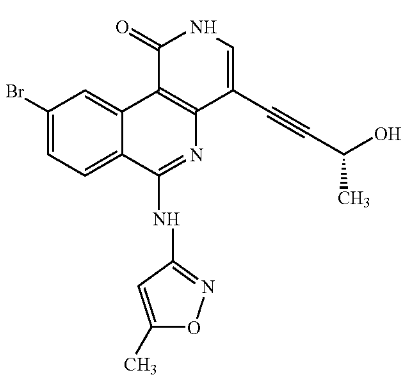 | 9-bromo-4-[(3R)-3-hydroxybut-1-yn-1-yl]-6-{[(5-methylisoxazol-3-yl)methyl]amino}benzo[c]-1,6-naphthyridin-1(2H)-one | G | Calc'd 453.1, found 453.1 |

TABLE 13-continued

| Ex. | Structure | Name | Method | LRMS |
|---|---|---|---|---|
| 250 | 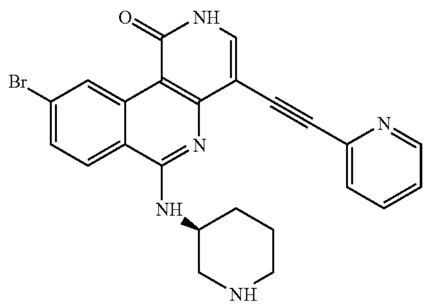 | 9-bromo-6-[(3S)-piperidin-3-ylamino]-4-(pyridin-2-ylethynyl)benzo[c]-1,6-naphthyridin-1(2H)-one | G | Calc'd 474.1, found 474.0 |
| 251 | 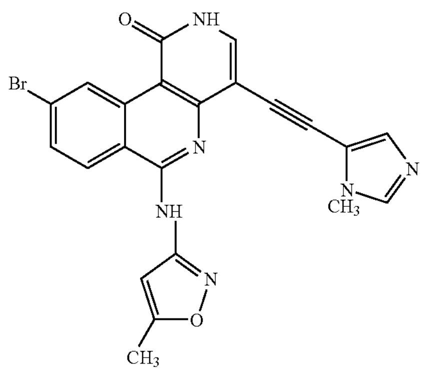 | 9-bromo-4-[(1-methyl-1H-imidazol-5-yl)ethynyl]-6-{[(5-methylisoxazol-3-yl)methyl]amino}benzo[c]-1,6-naphthyridin-1(2H)-one | G | Calc'd 489.1, found 489.0 |
| 252 | 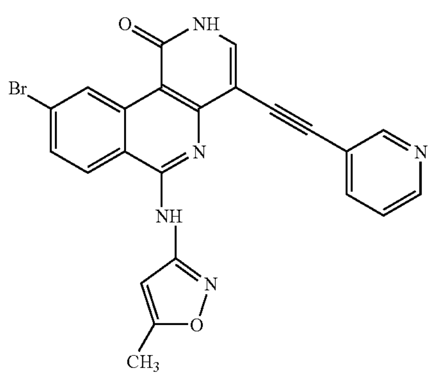 | 9-bromo-6-{[(5-methylisoxazol-3-yl)methyl]amino}-4-(pyridin-3-ylethynyl)benzo[c]-1,6-naphthyridin-1(2H)-one | G | Calc'd 486.1, found 486.0 |
| 253 | 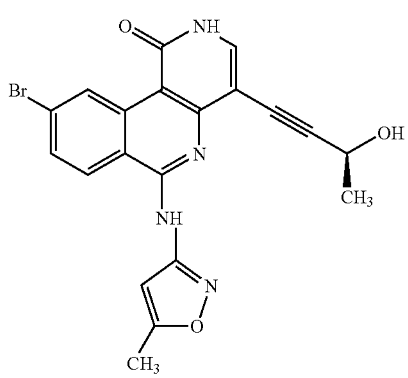 | 9-bromo-4-[(3S)-3-hydroxybut-1-yn-1-yl]-6-{[(5-methylisoxazol-3-yl)methyl]amino}benzo[c]-1,6-naphthyridin-1(2H)-one | G | Calc'd 453.1, found 453.1 |

TABLE 13-continued

| Ex. | Structure | Name | Method | LRMS |
|---|---|---|---|---|
| 254 | 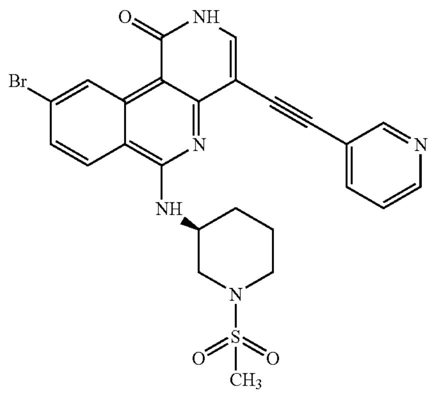 | 9-bromo-6-{[(3S)-1-(methylsulfonyl)piperidin-3-yl]amino}-4-(pyridin-3-ylethynyl)benzo[c]-1,6-naphthyridin-1(2H)-one | G | Calc'd 552.1, found 552.1 |
| 255 | 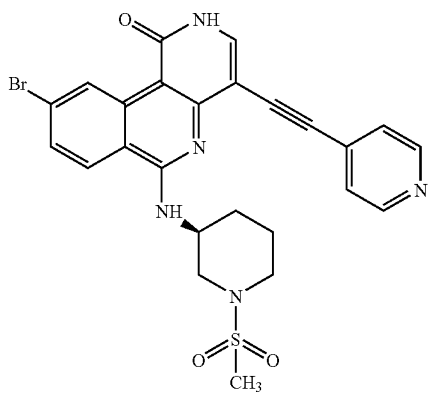 | 9-bromo-6-{[(3S)-1-(methylsulfonyl)piperidin-3-yl]amino}-4-(pyridin-4-ylethynyl)benzo[c]-1,6-naphthyridin-1(2H)-one | G | Calc'd 552.1, found 552.1 |
| 256 | 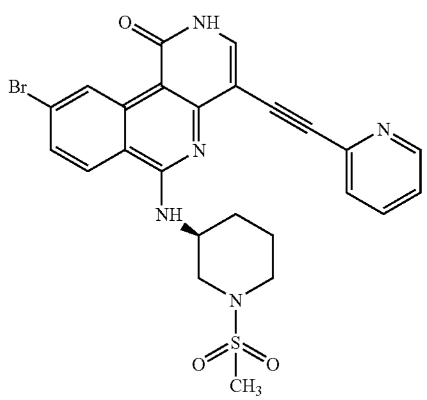 | 9-bromo-6-{[(3S)-1-(methylsulfonyl)piperidin-3-yl]amino}-4-(pyridin-2-ylethynyl)benzo[c]-1,6-naphthyridin-1(2H)-one | G | Calc'd 552.1, found 552.1 |
| 257 | 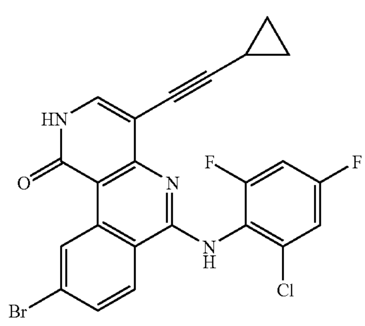 | 9-bromo-6-[(2-chloro-4,6-difluorophenyl)amino]-4-(cyclopropylethynyl)benzo[c]-1,6-naphthyridin-1(2H)-one | G | Calc'd 502.0, found 501.9 |

TABLE 13-continued

| Ex. | Structure | Name | Method | LRMS |
|---|---|---|---|---|
| 258 | 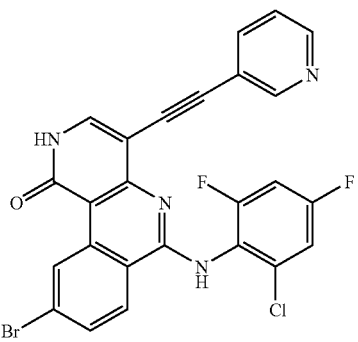 | 9-bromo-6-[(2-chloro-4,6-difluorophenyl)amino]-4-(pyridin-3-ylethynyl)benzo[c]-1,6-naphthyridin-1(2H)-one | G | Calc'd 539.0, found 538.9 |
| 259 | 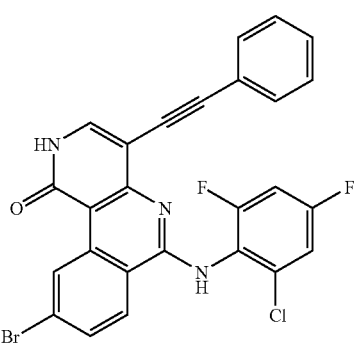 | 9-bromo-6-[(2-chloro-4,6-difluorophenyl)amino]-4-(phenylethynyl)benzo[c]-1,6-naphthyridin-1(2H)-one | G | Calc'd 538.0, found 537.9 |
| 260 | 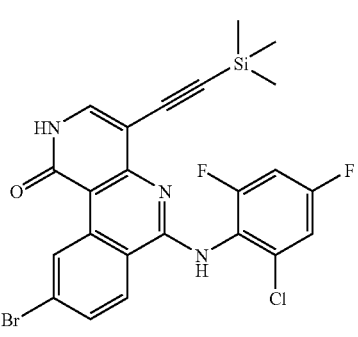 | 9-bromo-6- [(2-chloro-4,6-difluorophenyl)amino]-4-[(trimethylsilyl)ethynyl]benzo[c]-1,6-naphthyridin-1(2H)-one | G | Calc'd 534.0, found 534.0 |
| 261 | 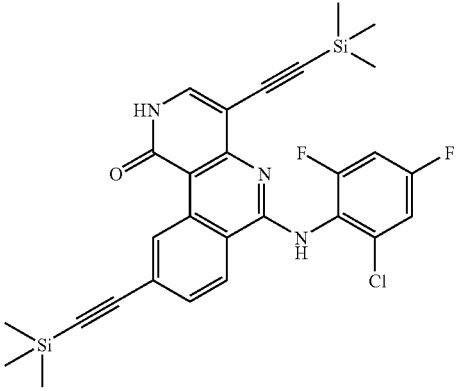 | 6-[(2-chloro-4,6-difluorophenyl)amino]-4,9-bis[(trimethylsilyl)ethynyl]benzo[c]-1,6-naphthyridin-1(2H)-one | G | Calc'd 550.1, found 550.1 |

| Ex. | Structure | Name | Method | LRMS |
|---|---|---|---|---|
| 262 | 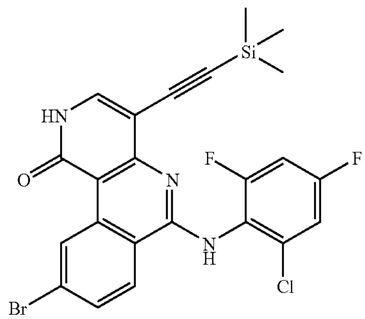 | 9-bromo-6-[(2-chloro-4,6-difluorophenyl)amino]-4-[(trimethylsilyl)ethynyl]benzo[c]-1,6-naphthyridin-1(2H)-one | G | Calc'd 534.0, found 534.0 |
| 263 | 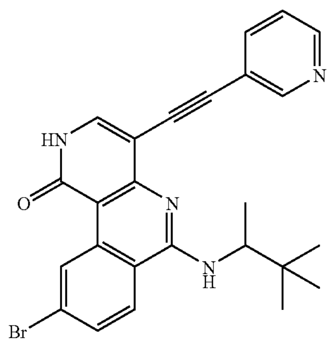 | 9-bromo-4-(pyridin-3-ylethynyl)-6-[(1,2,2-trimethylpropyl)amino]benzo[c]-1,6-naphthyridin-1(2H)-one | G | Calc'd 475.1, found 475.1 |
| 264 | 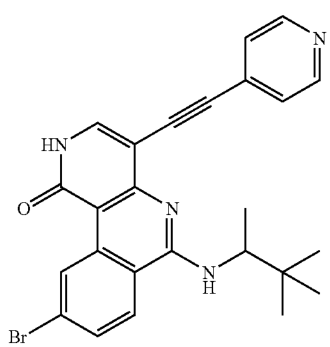 | 9-bromo-4-(pyridin-4-ylethynyl)-6-[(1,2,2-trimethylpropyl)amino]benzo[c]-1,6-naphthyridin-1(2H)-one | G | Calc'd 475.1, found 475.0 |
| 265 | 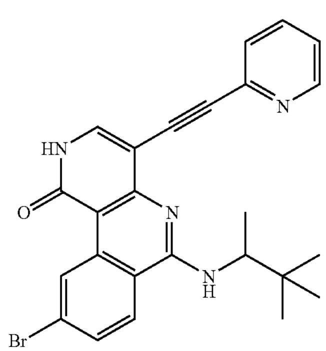 | 9-bromo-4-(pyridin-2-ylethynyl)-6-[(1,2,2-trimethylpropyl)amino]benzo[c]-1,6-naphthyridin-1(2H)-one | G | Calc'd 475.1, found 475.0 |

TABLE 13-continued

| Ex. | Structure | Name | Method | LRMS |
|---|---|---|---|---|
| 266 | 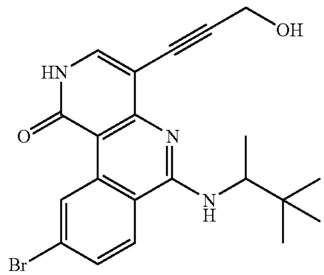 | 9-bromo-4-(3-hydroxyprop-1-yn-l-yl)-6-[(1,2,2-trimethylpropyl)amino]benzo[c]-1,6-naphthyridin-1(2H)-one | G | Calc'd 428.1, found 428.0 |
| 267 | 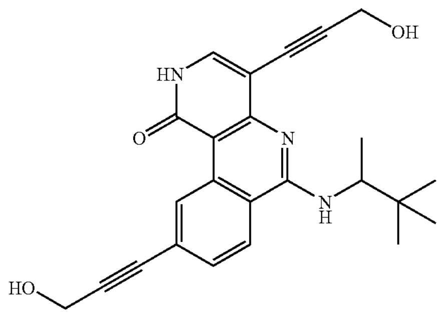 | 4,9-bis(3-hydroxyprop-1-yn-1-yl)-6-[(1,2,2-trimethylpropyl)amino]benzo[c]-1,6-naphthyridin-1(2H)-one | G | Calc'd 404.2, found 404.1 |
| 268 | 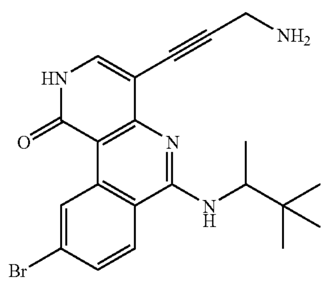 | 4-(3-aminoprop-1-yn-1-yl)-9-bromo-6-[(1,2,2-trimethylpropyl)amino]benzo[c]-1,6-naphthyridin-1(2H)-one | G | Calc'd 427.1, found 427.0 |
| 269 | 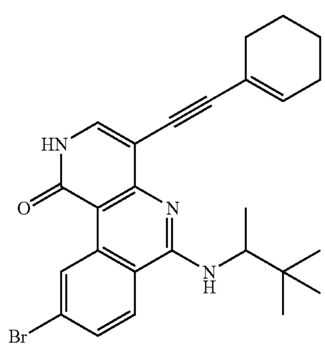 | 9-bromo-4-(cyclohex-1-en-1-ylethynyl)-6-[(1,2,2-trimethylpropyl)amino]benzo[c]-1,6-naphthyridin-1(2H)-one | G | Calc'd 480.2, found 480.1 |
| 270 | 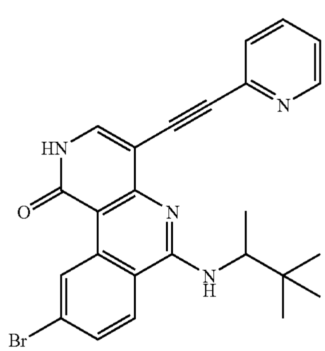 | 9-bromo-4-[(4-methoxyphenyl)ethynyl]-6-[(1,2,2-trimethylpropyl)amino]benzo[c]-1,6-naphthyridin-1(2H)-one | G | Calc'd 504.1, found 504.1 |

TABLE 13-continued

| Ex. | Structure | Name | Method | LRMS |
|---|---|---|---|---|
| 271 | 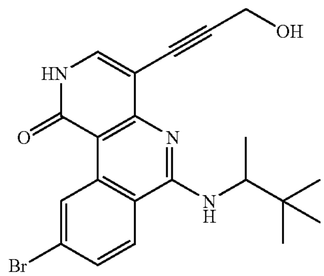 | 9-bromo-4-[(3-methylphenyl)ethynyl]-6-[(1,2,2-trimethylpropyl)amino]benzo[c]-1,6-naphthyridin-1(2H)-one | G | Calc'd 490.1, found 490.1 |
| 272 | 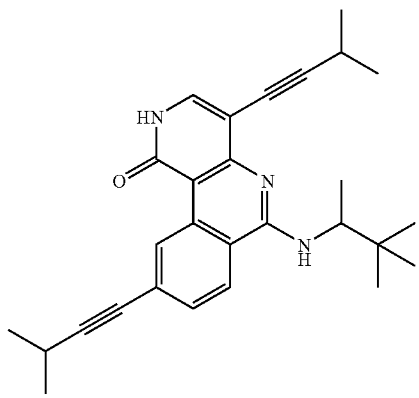 | 4,9-bis(3-methylbut-1-yn-1-yl)-6-[(1,2,2,2-trimethylpropyl)amino]benzo[c]-1,6-naphthyridin-1(2H)-one | G | Calc'd 428.3, found 428.2 |
| 273 | 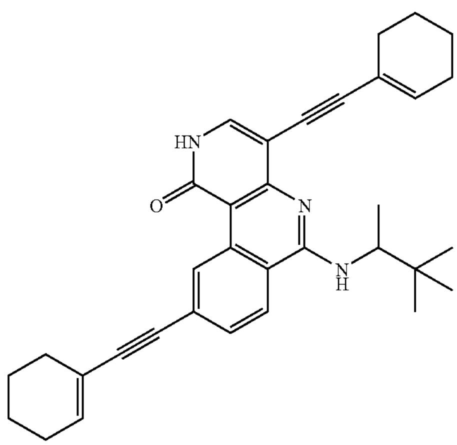 | 4,9-bis(cyclohex-1-en-1-ylethynyl)-6-[(1,2,2-trimethylpropyl)amino]benzo[c]-1,6-naphthyridin-1(2H)-one | G | Calc'd 504.3, found 504.2 |
| 274 | 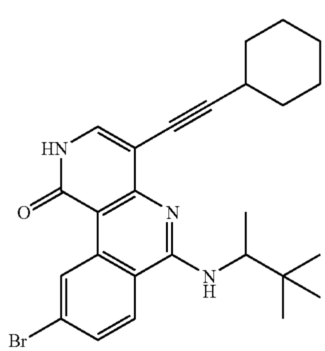 | 9-bromo-4-(cyclohexylethynyl)-6-[(1,2,2-trimethylpropyl)amino]benzo[c]-1,6-naphthyridin-1(2H)-one | G | Calc'd 428.2, found 428.1 |

TABLE 13-continued

| Ex. | Structure | Name | Method | LRMS |
|---|---|---|---|---|
| 275 | 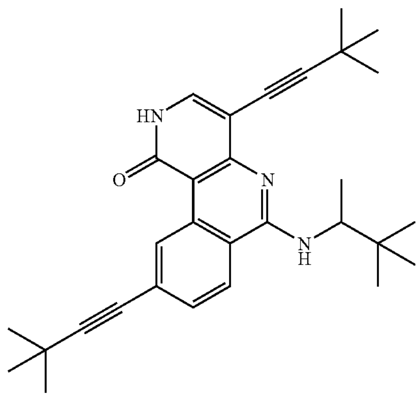 | 4,9-bis(3,3-dimethylbut-1-yn-1-yl)-6-[(1,2,2-trimethylpropyl)amino]benzo[c]-1,6-naphthyridin-1(2H)-one | G | Calc'd 456.3, found 456.2 |
| 276 | 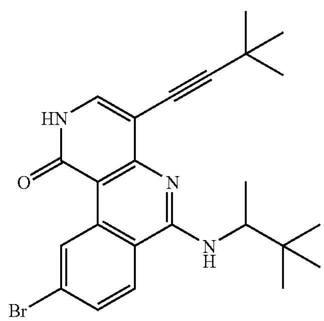 | 9-bromo-4-(3,3-dimethylbut-1-yn-1-yl)-6-[(1,2,2-trimethylpropyl)amino]benzo[c]-1,6-naphthyridin-1(2H)-one | G | Calc'd 456.2, found 456.2 |
| 277 | 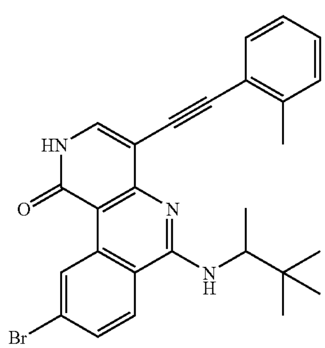 | 9-bromo-4-[(2-methylphenyl)ethynyl]-6-[(1,2,2-trimethylpropyl)amino]benzo[c]-1,6-naphthyridin-1(2H)-one | G | Calc'd 490.1, found 490.1 |
| 278 | 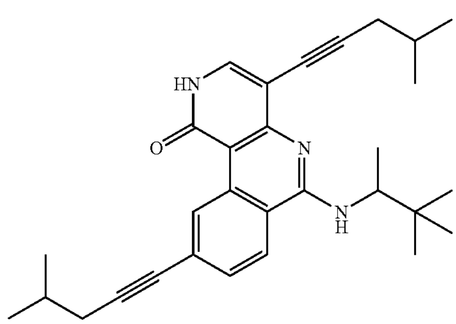 | 4,9-bis(4-methylpent-1-yn-1-yl)-6-[(1,2,2-trimethylpropyl)amino]benzo[c]-1,6-naphthyridin-1(2H)-one | G | Calc'd 456.3, found 456.1 |

TABLE 13-continued

| Ex. | Structure | Name | Method | LRMS |
|---|---|---|---|---|
| 279 | 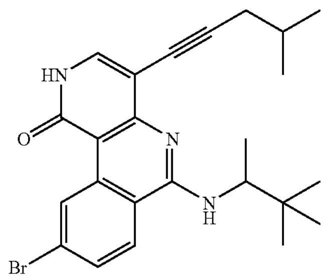 | 9-bromo-4-(3,3-dimethylbut-1-yn-1-yl)-6-[(1,2,2-trimethylpropyl)amino]benzo[c]-1,6-naphthyridin-1(2H)-one | G | Calc'd 456.2, found 456.2 |
| 280 | 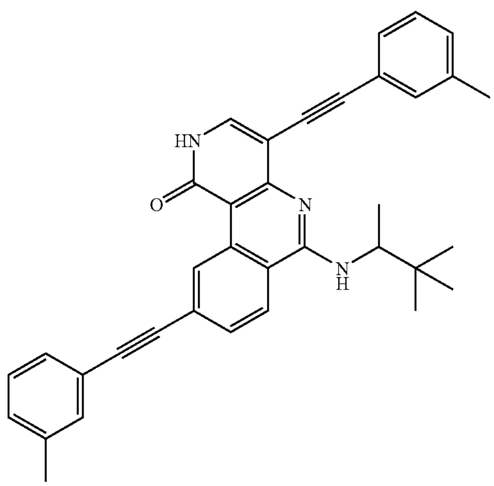 | 4,9-bis[(3-methylphenyl)ethynyl]-6-[(1,2,2-trimethylpropyl)amino]benzo[c]-1,6-naphthyridin-1(2H)-one | G | Calc'd 524.3, found 524.2 |
| 281 | 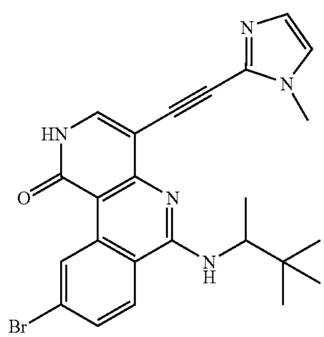 | 9-bromo-4-[(1-methyl-1H-imidazol-2-yl)ethynyl]-6-[(1,2,2-trimethylpropyl)amino]benzo[c]-1,6-naphthyridin-1(2H)-one | G | Calc'd 480.1, found 480.1 |
| 282 | 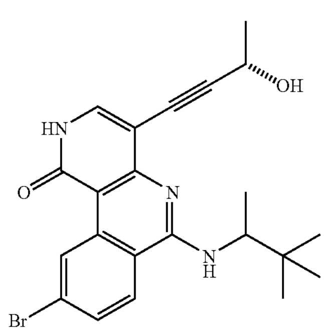 | 9-bromo-4-[(3S)-3-hydroxybut-1-yn-1-yl]-6-[(1,2,2-trimethylpropyl)amino]benzo[c]-1,6-naphthyridin-1(2H)-one | G | Calc'd 444.1, found 441.1 |

TABLE 13-continued

| Ex. | Structure | Name | Method | LRMS |
|---|---|---|---|---|
| 283 | 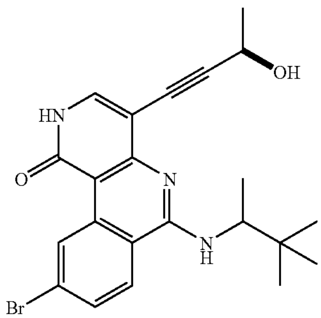 | 9-bromo-4-[(3R)-3-hydroxybut-1-yn-1-yl]-6-[(1,2,2-trimethylpropyl)amino]benzo[c]-1,6-naphthyridin-1(2H)-one | G | Calc'd 444.1, found 441.1 |
| 284 | 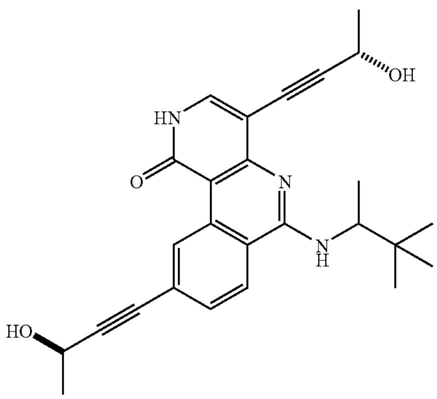 | 9-[(3R)-3-hydroxybut-1-yn-1-yl]-4-[(3S)-3-hydroxybut-1-yn-1-yl]-6-[(1,2,2-trimethylpropyl)amino]benzo[c]-1,6-naphthyridin-1(2H)-one | G | Calc'd 432.2, found 432.2 |
| 285 | 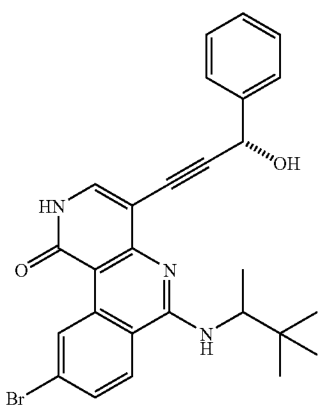 | 9-bromo-4-[(3S)-3-hydroxy-3-phenylprop-1-yn-1-yl]-6-[(1,2,2-trimethylpropyl)amino]benzo[c]-1,6-naphthyridin-1(2H)-one | G | Calc'd 504.1, found 504.1 |
| 286 | 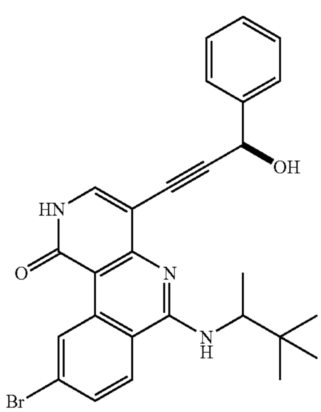 | 9-bromo-4-[(3R)-3-hydroxy-3-phenylprop-1-yn-1-yl]-6-[(1,2,2-trimethylpropyl)amino]benzo[c]-1,6-naphthyridin-1(2H)-one | G | Calc'd 504.1, found 504.1 |

TABLE 13-continued

| Ex. | Structure | Name | Method | LRMS |
|---|---|---|---|---|
| 287 | 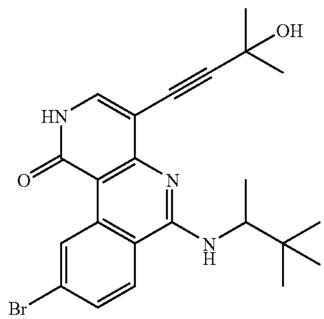 | 9-bromo-4-(3-hydroxy-3-methylbut-1-yn-1-yl)-6-[(1,2,2-trimethylpropyl)amino]benzo[c]-1,6-naphthyridin-1(2H)-one | G | Calc'd 456.1, found 456.1 |
| 288 | 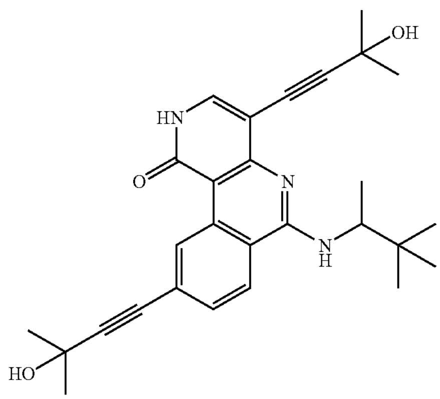 | 4,9-bis(3-hydroxy-3-methylbut-1-yn-1-yl)-6-[(1,2,2-trimethylpropyl)amino]benzo[c]-1,6-naphthyridin-1(2H)-one | G | Calc'd 460.3, found 460.2 |
| 289 | 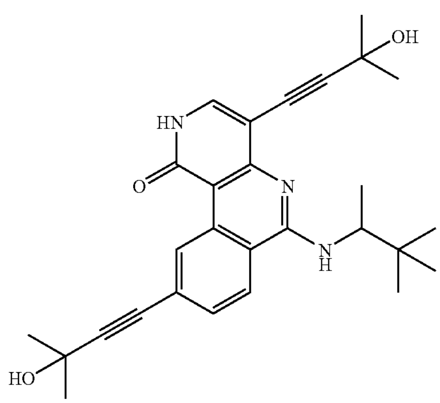 | 3-{9-bromo-1-oxo-6-[(pyridin-2-ylmethyl)amino]-1,2-dihydrobenzo[c]-1,6-naphthyridin-4-yl}prop-2-ynamide | G | Calc'd 448.0, found 448.0 |
| 290 | 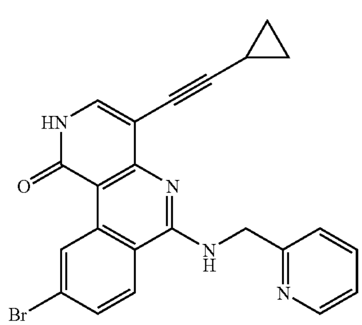 | 9-bromo-4-(cyclopropylethynyl)-6-[(pyridin-2-ylmethyl)amino]benzo[c]-1,6-naphthyridin-1(2H)-one | G | Calc'd 445.1, found 445.0 |

TABLE 13-continued

| Ex. | Structure | Name | Method | LRMS |
|---|---|---|---|---|
| 291 | 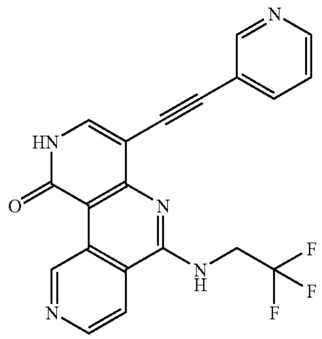 | 4-(pyridin-3-ylethynyl)-6-[(2,2,2-trifluoroethyl)amino]pyrido[4,3-c]-1,6-naphthydin-1(2H)-one | G | Calc'd 396.1, found 396.0 |
| 292 | 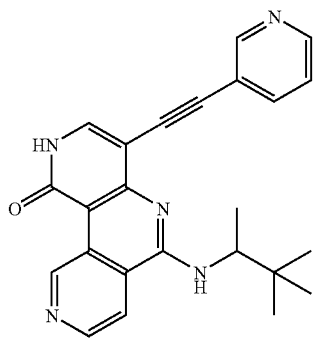 | 4-(pyridin-3-ylethynyl)-6-[(1,2,2-trimethylpropyl)amino]pyrido[4,3-c]-1,6-naphthyridin-1(2H)-one | G | Calc'd 398.2, found 398.1 |
| 293 | 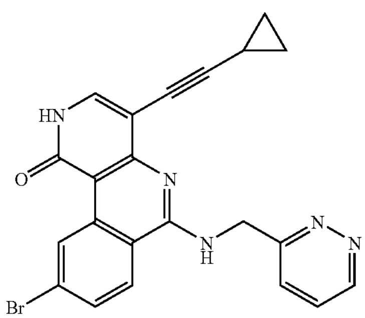 | 9-bromo-4-(cyclopropylethynyl)-6-[(pyridazin-3-ylmethyl)amino]benzo[c]-1,6-naphthyridin-1(2H)-one | G | Calc'd 446.1, found 445.9 |
| 294 | 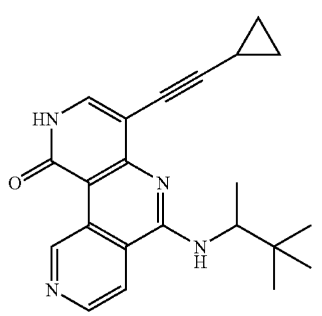 | 4-(cyclopropylethynyl)-6-[(1,2,2-trimethylpropyl)amino]pyrido[4,3-c]-1,6-naphthyridin-1(2H)-one | G | Calc'd 361.2, found |
| 295 | 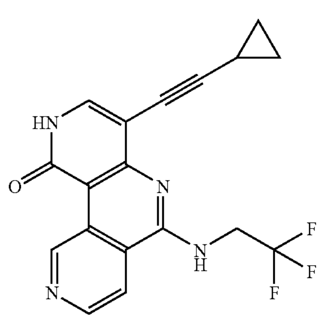 | 4-(cyclopropylethynyl)-6-[(2,2,2-trifluoroethyl)amino]pyrido[4,3-c]-1,6-naphthyridin-1(2H)-one | G | Calc'd 359.1, found 359.1 |

TABLE 13-continued

| Ex. | Structure | Name | Method | LRMS |
|---|---|---|---|---|
| 296 | 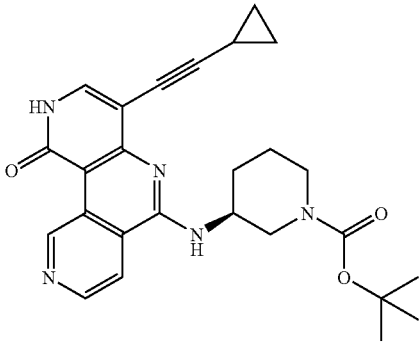 | tert-butyl (3S)-3-{[4-(cyclopropylethynyl)-1-oxo-1,2-dihydropyrido[4,3-c]-1,6-naphthyridin-6-yl]amino}piperidine-1-carboxylate | H | Calc'd 460.2, found 460.2 |
| 297 | 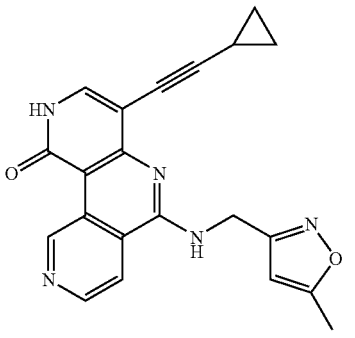 | 4-(cyclopropylethynyl)-6-{[(5-methylisoxazol-3-yl)methyl]amino}pyrido[4,3-c]-1,6-naphthyridin-1(2H)-one | G | Calc'd 372.1, found 372.1 |
| 298 | 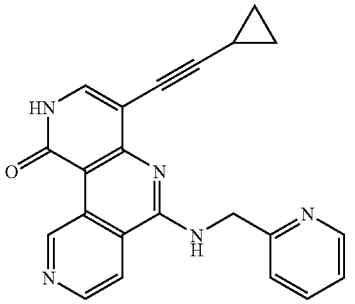 | 4-(cyclopropylethynyl)-6-[(pyridin-2-ylmethyl)amino]pyrido[4,3-c]-1,6-naphthyridin-1(2H)-one | G | Calc'd 368.2, found 368.1 |
| 299 | 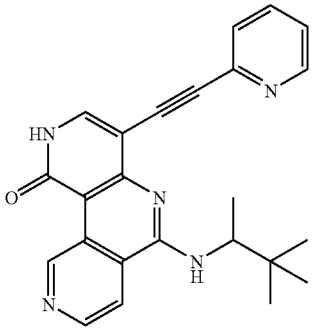 | 4-(pyridin-2-ylethynyl)-6-[(1,2,2-trimethylpropyl)amino]pyrido[4,3-c]-1,6-naphthyridin-1(2H)-one | G | Calc'd 398.2, found 398.1 |

TABLE 13-continued

| Ex. | Structure | Name | Method | LRMS |
|---|---|---|---|---|
| 300 | 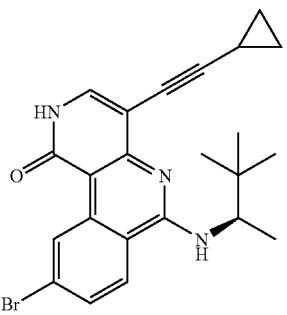 | 9-bromo-4-(cyclopropylethynyl)-6-{[(1R)-1,2,2-trimethylpropyl]amino}benzo[c]-1,6-naphthyridin-1(2H)-one | H | Calc'd 438.1, found 438.1 |
| 301 | 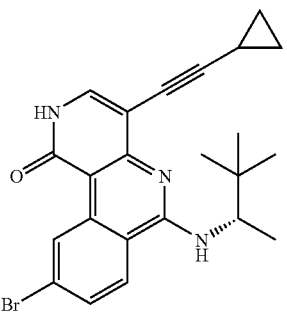 | 9-bromo-4-(cyclopropylethynyl)-6-{[(1S)-1,2,2-trimethylpropyl]amino}benzo[c]-1,6-naphthyridin-1(2H)-one | H | Calc'd 438.1, found 438.1 |
| 302 | 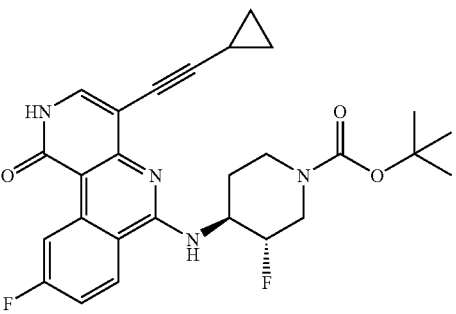 | tert-butyl trans-4-{[4-(cyclopropylethynyl)-9-fluoro-1-oxo-1,2-dihydrobenzo[c]-1,6-naphthyridin-6-yl]amino}-3-fluoropiperidines-1-carboxylate | H | Calc'd 494.2, found 495.2 |

Example 303

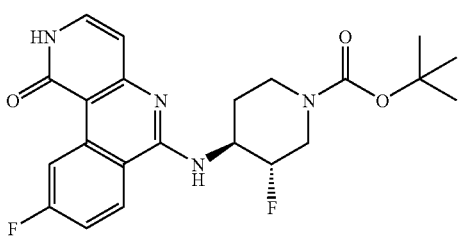

tert-butyl trans-3-fluoro-4-[(9-fluoro-1-oxo-1,2-dihydrobenzo[c]-1,6-naphthyridin-6-yl)amino]piperidine-1-carboxylate To a suspension of trans-9-fluoro-6-[(3-methylpiperidin-4-yl)amino]benzo[c]-1,6-naphthyridin-1(2H)-one (770 mg, 2.33 mmol) in THF (8 mL) under a nitrogen atmosphere was added di-tert-butyl dicarbonate (458 mg, 2.10 mmol) as a liquid, and the reaction was left stirring overnight at room temperature. The reaction mixture was then added to a separatory funnel containing 3:1 CHCl$_3$:2-propanol and saturated aqueous NaHCO$_3$. The phases were separated, and the organic layer was washed with water, then brine, dried over anhydrous MgSO$_4$ and concentrated in vacuo to remove the chloroform, producing a heterogeneous mixture in 2-propanol. The mixture was filtered, and the precipitate was rinsed with 2-propanol. The product was then dried under high vacuum to afford the title compound tert-butyl trans-3-fluoro-4-[(9-fluoro-1-oxo-1,2-dihydrobenzo[c]-1,6-naphthyridin-6-yl)amino]piperidine-1-carboxylate as a stable 2-propanol solvate. LRMS (APCI) calc'd (C$_{22}$H$_{24}$F$_2$N$_4$O$_3$) [M+H]$^+$, 431.2; found 431.1. $^1$H NMR (500 MHz, DMSO-d$_6$) δ 11.30 (d, 1H), 9.60 (dd, 1H), 8.43 (dd, 1H), 7.93 (d, 1H), 7.49 (ddd, 1H), 7.35 (t, 1H), 6.36 (dd, 1H), 4.74 (m, 1H), 4.67 (m, 1H), 4.11 (broad s, 1H), 3.82 (d, 1H), 3.21-2.97 (m, 2H), 2.01 (m, 1H), 1.53 (m, 1H), 1.40 (S, 9H).

Example 304

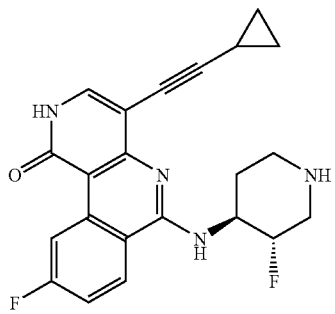

4-(cyclopropylethynyl)-9-fluoro-6-[(trans-3-fluoropiperidin-4-yl)amino]benzo[c]-1,6-naphthyridin-1(2H)-one To a solution of tert-butyl trans-4-{[4-(cyclopropylethynyl)-9-fluoro-1-oxo-1,2-dihydrobenzo[c]-1,6-naphthyridin-6-yl]amino}-3-fluoropiperidine-1-carboxylate (160 mg, 0.324 mmol) in THF (5 mL) under a nitrogen atmosphere was added HCl (4.0 M in 1,4-dioxane) (2 mL, 8.0 mmol), and the reaction was left stirring for two days at room temperature. The reaction mixture was then added to a separatory funnel containing 3:1 CHCl$_3$:2-propanol and saturated aqueous NaHCO$_3$. The phases were separated, and the organic layer was washed with water, then brine, dried over anhydrous Na$_2$SO$_4$ and concentrated in vacuo. The crude product mixture was purified by silica gel chromatography (0-10% CH$_3$OH in CH$_2$Cl$_2$), followed by trituration with methanol afforded the title compound 4-(cyclopropylethynyl)-9-fluoro-6-[(trans-3-fluoropiperidin-4-yl)amino]benzo[c]-1,6-naphthyridin-1(2H)-one. LRMS (APCI) calc'd (C$_{22}$H$_{20}$F$_2$N$_4$O$_3$) [M+H]$^+$, 395.2; found 395.1. $^1$H NMR (500 MHz, DMSO-d$_6$) δ 11.51 (d, 1H), 9.57 (dd, 1H), 8.51 (dd, 1H), 8.19 (d, 1H), 7.57 (d, 1H), 7.53 (dt, 1H), 4.80-4.64 (m, 2H), 3.35 (m [under H$_2$O], 1H), 2.97 (d, 1H), 2.55 (t, 2H), 2.12 (m, 1H), 1.56 (m, 1H), 1.50 (m, 1H), 1.15 (m, 1H), 0.89 (m, 2H), 0.72 (m, 2H).

Example 305

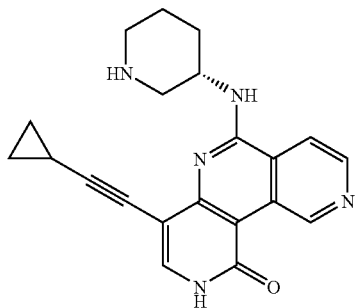

4-(cyclopropylethynyl)-6-[(3S)-piperidin-3-ylamino]pyrido[4,3-c]-1,6-naphthyridin-1(2H)-one To a solution of tert-butyl (3S)-3-{[4-(cyclopropylethynyl)-1-oxo-1,2-dihydropyrido[4,3-c]-1,6-naphthyridin-6-yl]amino}piperidine-1-carboxylate (100 mg, 0.218 mmol) in dichloromethane (2 mL), trifluoroacetic acid (2000 26.0 mmol) was added. After stirring at room temperature for 10 min, the mixture was quenched with aqueous sodium hydrogen carbonate (saturated). The aqueous layer was extracted with ethyl acetate. The combined organic extracts were dried over sodium sulfate and concentrated under reduced pressure. The residue was purified by preparative HPLC Reverse phase (C-18), eluting with Acetonitrile/Water+0.05% TFA, to afford 4-(cyclopropylethynyl)-6-[(3S)-piperidin-3-ylamino]pyrido[4,3-c]-1,6-naphthyridin-1(2H)-one as a yellow solid. $^1$H NMR (500 MHz, C$_2$D$_6$SO) δ 10.97 (s, 1H), 8.74 (d, 1H), 8.29 (d, 1H), 8.06 (d, 1H), 7.61 (s, 1H), 4.42 (m, 1H), 3.03 (m, 2H), 2.74 (m, 1H), 2.16 (t, 2H), 1.66 (m, 2H), 0.84 (m, 6H). LRMS (APCI) calc'd for (C$_{21}$H$_{22}$N$_5$O) [M+H]+, 360.2; found 360.1.

Example 306

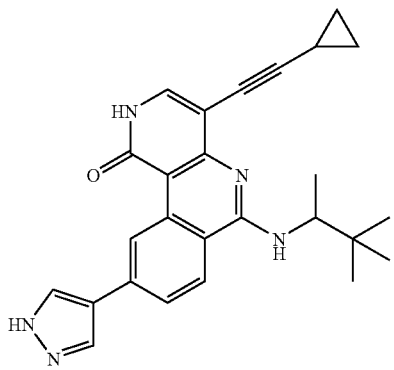

4-(cyclopropylethynyl)-9-(1H-pyrazol-4-yl)-6-[(1,2,2-trimethylpropyl)amino]benzo[c]-1,6-naphthyridin-1(2H)-one 4-(cyclopropylethynyl)-9-bromo-6-[(1,2,2-trimethylpropyl)amino]benzo[c]-1,6-naphthyridin-1(2H)-one (750 mg, 1.711 mmol), 4-(4,4,5,5-tetramethyl-1,3,2-dioxaborolan-2-yl)-1H-pyrazole (664 mg, 3.42 mmol), and PdCl$_2$(dppf)-CH$_2$Cl$_2$ adduct (279 mg, 0.342 mmol) were added to a vial, followed by DMF (1.71E+04 µl) and aqueous sodium carbonate (2M) (1711 µl, 3.42 mmol). The reaction was purged with argon (subsurface bubbling) for 10 min. The reaction mixture was heated in a microwave oven at 130° C. for 45 min. The mixture was then cooled to room temperature and diluted with DMSO (~17 mL) and filtered through a syringe filter (filter was rinsed with DMSO). This solution was purified by preparative HPLC Reverse phase (C-18), eluting with Acetonitrile/Water+0.05% TFA. The fractions were combined, neutralized with NaHCO$_3$ (sat) and extracted with dichloromethane (2×300 mL). The combined organics were washed with water (200 mL), brine (200 mL) dried over anhydrous sodium sulfate, swirled for 10 min with 1 g MP-TMT Pd scavenger resin, filtered and dried under reduced pressure to give the title compound as a yellow solid. $^1$H NMR (500 MHz, CD₃OD) δ 13.10 (s, 1H), 11.28 (d, 1H, J=6.5 Hz), 10.02 (d, 1H, J=1.5 Hz), 8.49 (d, 1H, J=9.0 Hz), 8.28 (s, 1H), 7.96 (s, 1H), 7.83 (dd, 1H, J=8.5, 1.5 Hz), 7.49 (d, 1H, J=6.5 Hz), 7.45 (d, 1H, J=9.0 Hz), 4.87 (m, 1H), 1.53 (m, 1H) 1.21 (d, 3H, J=7 Hz), 0.98 (s, 9H), 0.88 (m, 2H), 0.72 (m, 2H).

LRMS (ESI) calc'd for (C$_{26}$H$_{28}$N$_{5}$O) [M+H]$^{+}$, 426.2; found 426.2.

The compounds listed in Table 14 below were prepared according to Scheme 15, following analogous procedures to those used to prepare Example 306.

TABLE 14

| Ex. | Structure | Name | LRMS [M + H]$^{+}$ |
| --- | --- | --- | --- |
| 307 | 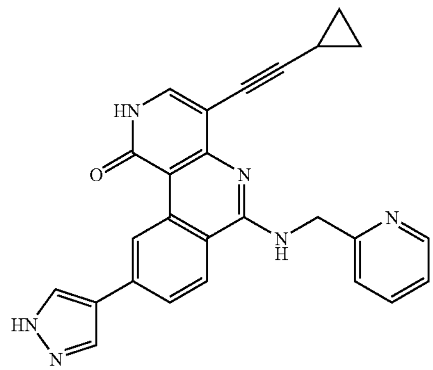 | 4-(cyclopropylethynyl)-9-(1H-pyrazol-4-yl)-6-[(pyridin-2-ylmethyl)amino]benzo[c]-1,6-naphthyridin-1(2H)-one | Calc'd 433.2, found 433.1 |
| 308 | 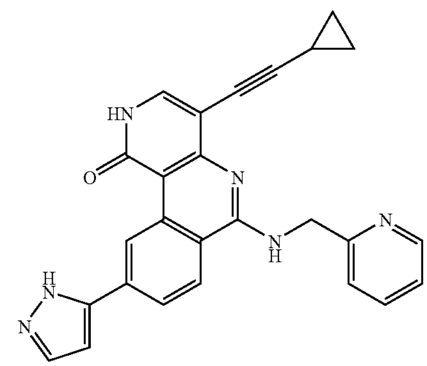 | 4-(cyclopropylethynyl)-9-(1H-pyrazol-5-yl)-6-[(pyridin-2-ylmethyl)amino]benzo[c]-1,6-naphthyridin-1(2H)-one | Calc'd 433.2, found 433.1 |
| 309 | 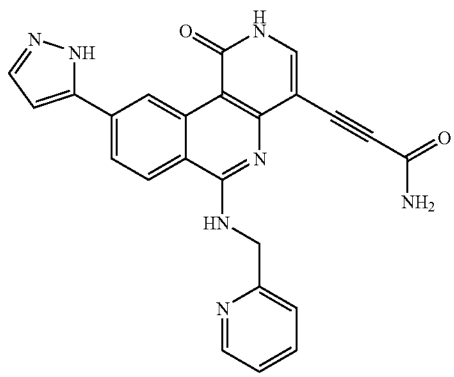 | 3-{1-oxo-9-(1H-pyrazol-5-yl)-6-[(pyridin-2-ylmethyl)amino]-1,2-dihydrobenzo[c]-1,6-naphthyridin-4-yl}prop-2-ynamide | Calc'd 436.1, found 436.2 |
| 310 | 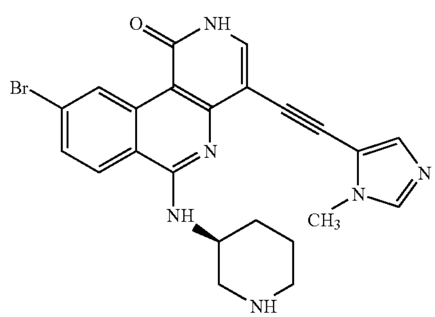 | 9-bromo-4-[(1-methyl-1H-imidazol-5-yl)ethynyl]-6-[(3S)-piperidin-3-ylamino]benzo[c]-1,6-naphthyridin-1(2H)-one | Calc'd 477.1, found 477.0 |

TABLE 14-continued

| Ex. | Structure | Name | LRMS [M + H]+ |
|---|---|---|---|
| 311 | 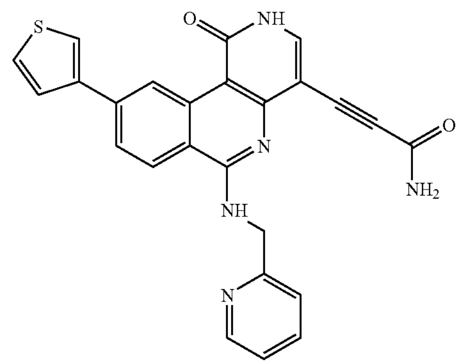 | 3-[1-oxo-6-[(pyridin-2-ylmethyl)amino]-9-(3-thienyl)-1,2-dihydrobenzo[c]-1,6-naphthyridin-4-yl]prop-2-ynamide | Calc'd 452.1, found 452.1 |
| 312 | 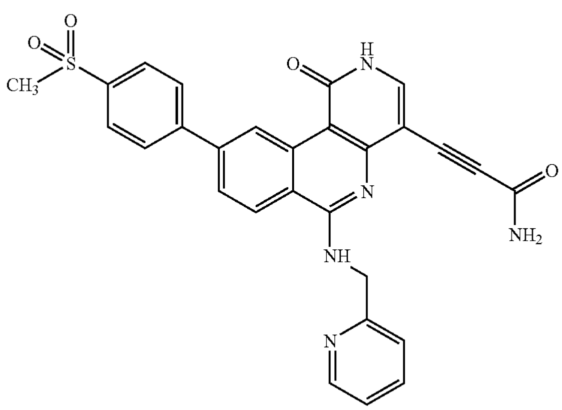 | 3-{9-[4-(ethylsulfonyl)phenyl]-1-oxo-6-[(pyridin-2-ylmethyl)amino]-1,2-dihydrobenzo[c]-1,6-naphthyridin-4-yl}prop-2-ynamide | Calc'd 538.2, found 538.1 |
| 313 | 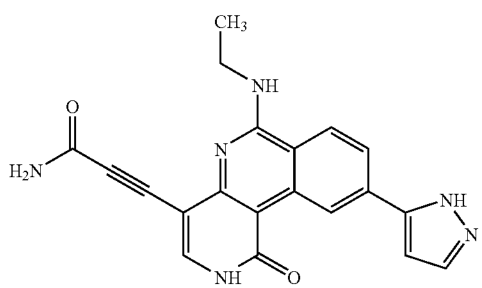 | 3-[6-(ethylamino)-1-oxo-9-(1H-pyrazol-5-yl)-1,2-dihydrobenzo[c]-1,6-naphthyridin-4-yl]prop-2-ynamide | Calc'd 373.1, found 373.1 |
| 314 | 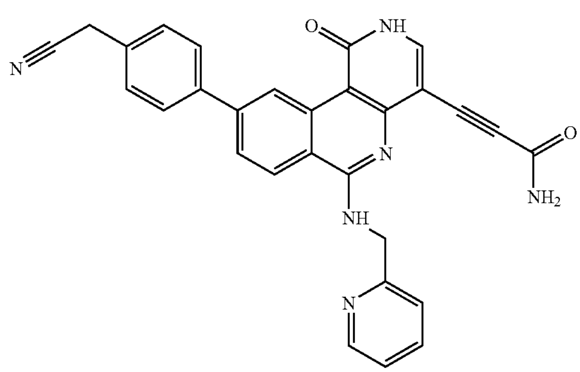 | 3-{9-[4-(cyanomethyl)phenyl]-1-oxo-6-[(pyridin-2-ylmethyl)amino]-1,2-dihydrobenzo[c]-1,6-naphthyridin-4-yl}prop-2-ynamide | Calc'd 485.2, found 485.1 |

TABLE 14-continued

| Ex. | Structure | Name | LRMS [M + H]+ |
|---|---|---|---|
| 315 | 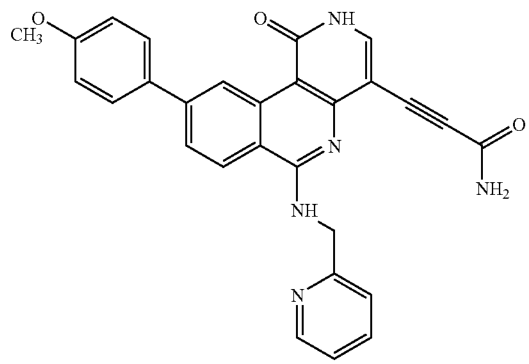 | 3-{9-(4-methoxyphenyl)-1-oxo-6-[(pyridin-2-ylmethyl)amino]-1,2-dihydrobenzo[c]-1,6-naphthyridin-4-yl}prop-2-ynamide | Calc'd 476.2, found 476.2 |
| 316 | 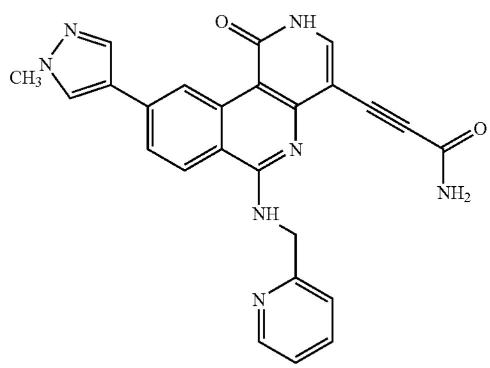 | 3-{9-(1-methyl-1H-pyrazol-4-yl)-1-oxo-6-[(pyridin-2-ylmethyl)amino]-1,2-dihydrobenzo[c]-1,6-naphthyridin-4-yl}prop-2-ynamide | Calc'd 450.2, found 450.0 |
| 317 | 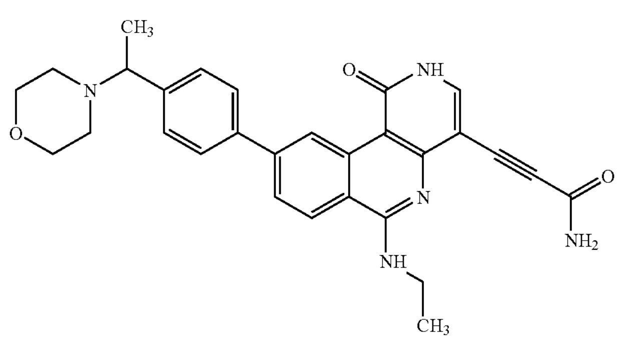 | 3-{6-(ethylamino)-9-[4-(1-morpholin-4-ylethyl)phenyl]-1-oxo-1,2-dihydrobenzo[c]-1,6-naphthyridin-4-yl}prop-2-ynamide | Calc'd 496.2, found 496.1 |
| 318 | 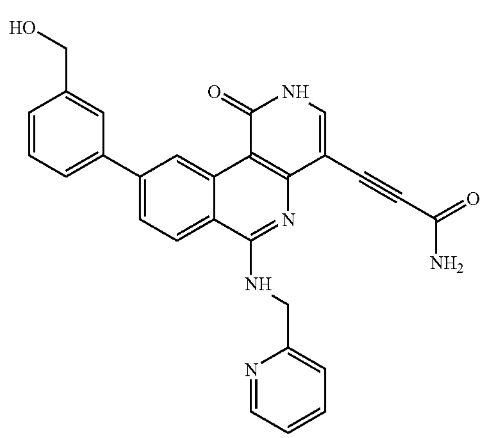 | 3-{9-[3-(hydroxymethyl)phenyl]-1-oxo-6-[(pyridin-2-ylmethyl)amino]-1,2-dihydrobenzo[c]-1,6-naphthyridin-4-yl}prop-2-ynamide | Calc'd 476.2, found 476.2 |

TABLE 14-continued

| Ex. | Structure | Name | LRMS [M + H]+ |
|---|---|---|---|
| 319 | 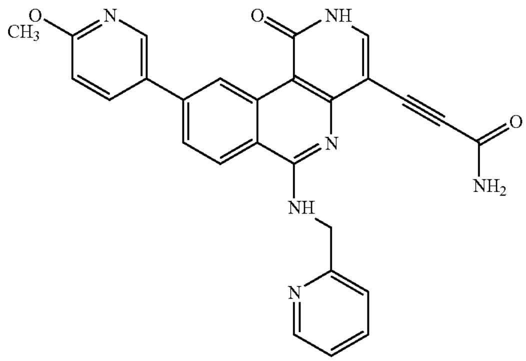 | 3-{9-(6-methoxpyridin-3-yl)-1-oxo-6-[(pyridin-2-ylmethyl)amino]-1,2-dihydrobenzo[c]-1,6-naphthyridin-4-yl}prop-2-ynamide | Calc'd 477.2, found 477.1 |
| 320 | 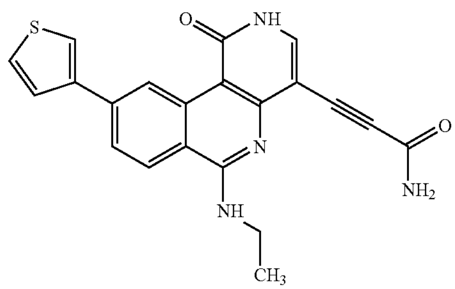 | 3-[6-(ethylamino)-1-oxo-9-(3-thienyl)-1,2-dihydrobenzo[c]-1,6-naphthyridin-4-yl]prop-2-ynamide | Calc'd 389.1, found 389.1 |
| 321 | 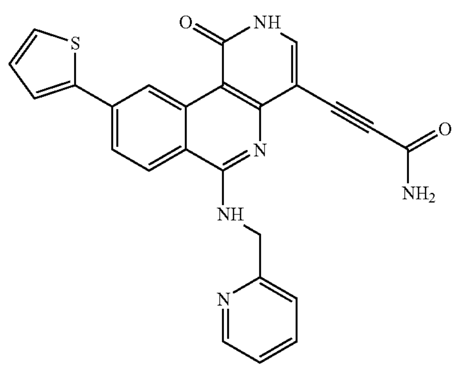 | 3-[1-oxo-6-[(pyridin-2-ylmethyl)amino]-9-(2-thienyl)-1,2-dihydrobenzo[c]-1,6-naphthyridin-4-yl]prop-2-ynamide | Calc'd 452.1, found 452.1 |
| 322 | 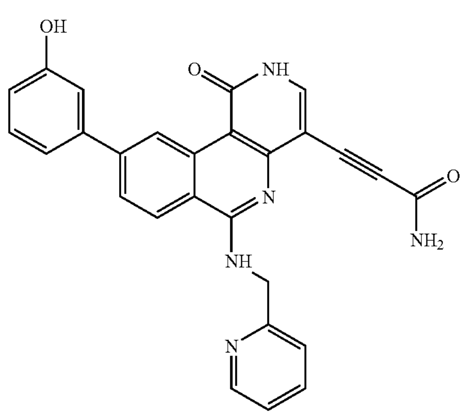 | 3-{9-(3-hydroxyphenyl)-1-oxo-6-[(pyridin-2-ylmethyl)amino]-1,2-dihydrobenzo[c]-1,6-naphthyridin-4-yl}prop-2-ynamide | Calc'd 462.2, found 462.2 |

TABLE 14-continued

| Ex. | Structure | Name | LRMS [M + H]+ |
|---|---|---|---|
| 323 | 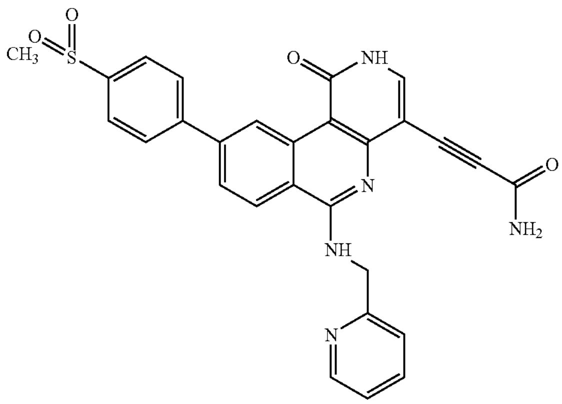 | 3-{9-[4-(methylsulfonyl)phenyl]-1-oxo-6-[(pyridin-2-ylmethyl)amino]-1,2-dihydrobenzo[c]-1,6-naphthyridin-4-yl}prop-2-ynamide | Calc'd 524.1, found 524.1 |
| 324 | 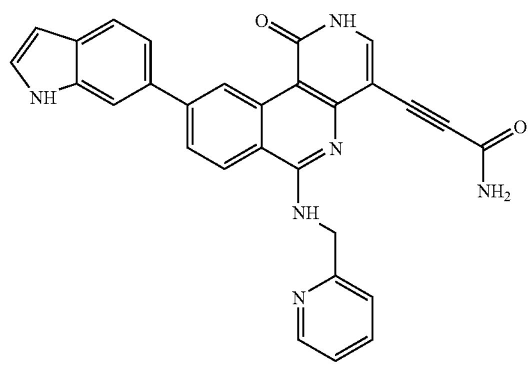 | 3-{9-(1H-indol-6-yl)-1-oxo-6-[(pyridin-2-ylmethyl)amino]-1,2-dihydrobenzo[c]-1,6-naphthyridin-4-yl}prop-2-ynamide | Calc'd 485.2, found 485.2 |
| 325 | 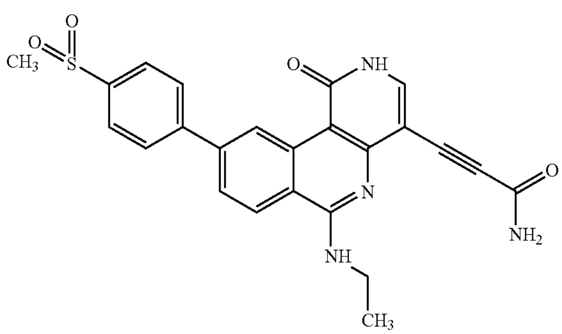 | 3-{6-(ethylamino)-9-[4-(methylsulfonyl)phenyl]-1-oxo-1,2-dihydrobenzo[c]-1,6-naphthyridin-4-yl}prop-2-ynamide | Calc'd 461.1, found 461.0 |
| 326 | 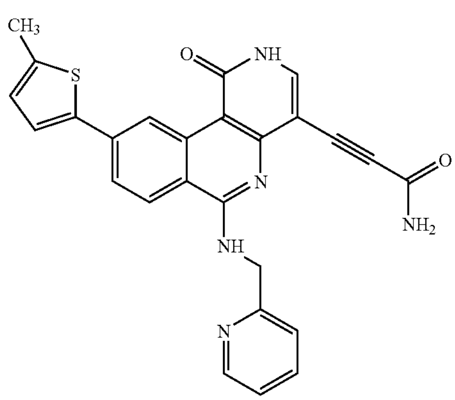 | 3-{9-(5-methyl-2-thienyl)-1-oxo-6-[(pyridin-2-ylmethyl)amino]-1,2-dihydrobenzo[c]-1,6-naphthyridin-4-yl}prop-2-ynamide | Calc'd 466.1, found 466.1 |

TABLE 14-continued

| Ex. | Structure | Name | LRMS [M + H]+ |
|---|---|---|---|
| 327 | 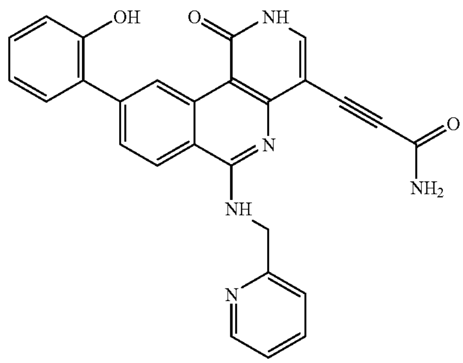 | 3-{9-(2-hydroxyphenyl)-1-oxo-6-[(pyridin-2-ylmethyl)amino]-1,2-dihydrobenzo[c]-1,6-naphthyridin-4-yl}prop-2-ynamide | Calc'd 462.2, found 462.1 |
| 328 | 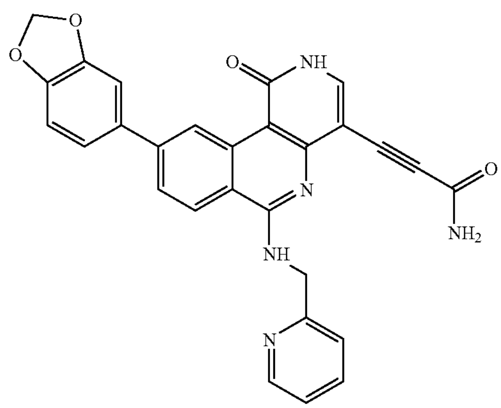 | 3-{9-(1,3-benzodioxol-5-yl)-1-oxo-6-[(pyridin-2-ylmethyl)amino]-1,2-dihydrobenzo[c]-1,6-naphthyridin-4-yl}prop-2-ynamide | Calc'd 490.1, found 490.2 |
| 329 | 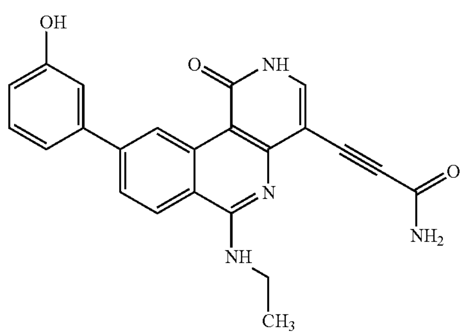 | 3-[6-(ethylamino)-9-(3-hydroxyphenyl)-1-oxo-1,2-dihydrobenzo[c]-1,6-naphthyridin-4-yl]prop-2-ynamide | Calc'd 399.1, found 399.2 |
| 330 | 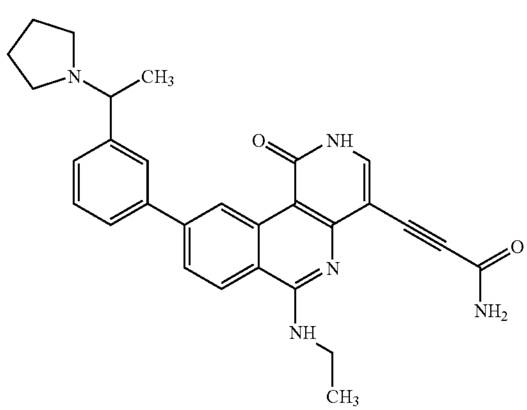 | 3-{6-(ethylamino)-1-oxo-9-[3-(1-pyrrolidin-1-ylethyl)phenyl]-1,2-dihydrobenzo[c]-1,6-naphthyridin-4-yl}prop-2-ynamide | Calc'd 480.2, found 480.2 |

TABLE 14-continued

| Ex. | Structure | Name | LRMS [M + H]+ |
|---|---|---|---|
| 331 | 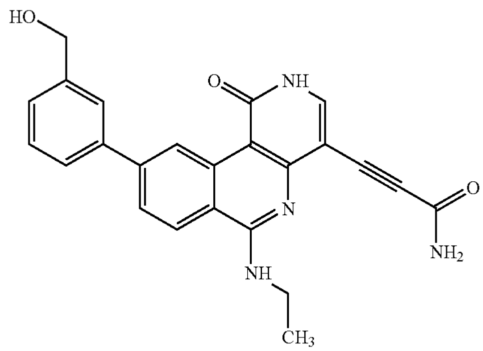 | 3-{6-(ethylamino)-9-[3-(hydroxymethyl)phenyl]-1-oxo-1,2-dihydrobenzo[c]-1,6-naphthyridin-4-yl}prop-2-ynamide | Calc'd 413.2, found 413.2 |
| 332 | 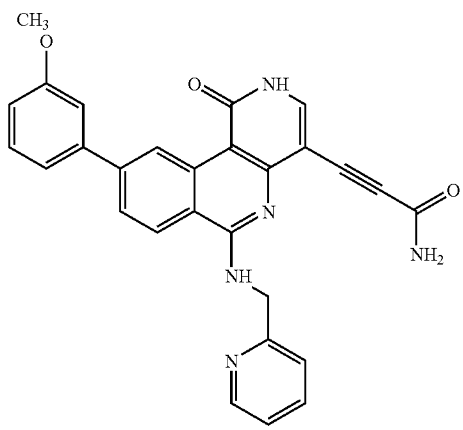 | 3-{9-(3-methoxyphenyl)-1-oxo-6-[(pyridin-2-ylmethyl)amino]-1,2-dihydrobenzo[c]-1,6-naphthyridin-4-yl}prop-2-ynamide | Calc'd 476.2, found 476.2 |
| 333 | 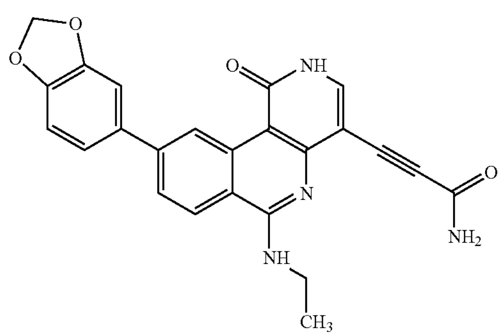 | 3-[9-(1,3-benzodioxol-5-yl)-6-(ethylamino)-1-oxo-1,2-dihydrobenzo[c]-1,6-naphthyridin-4-yl]prop-2-ynamide | Calc'd 427.1, found 427.1 |
| 334 | 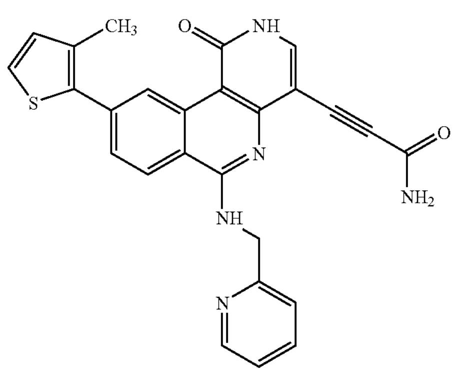 | 3-{9-(3-methyl-2-thienyl)-1-oxo-6-[(pyridin-2-ylmethyl)amino]-1,2-dihydrobenzo[c]-1,6-naphthyridin-4-yl}prop-2-ynamide | Calc'd 466.1, found 466.1 |

TABLE 14-continued

| Ex. | Structure | Name | LRMS [M + H]+ |
|---|---|---|---|
| 335 | 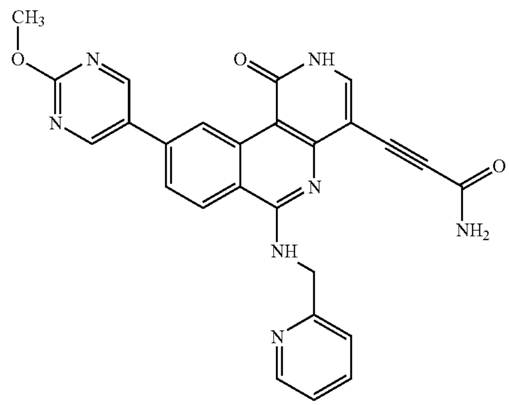 | 3-{9-(2-methoxypyrimidin-5-yl)-1-oxo-6-[(pyridin-2-ylmethyl)amino]-1,2-dihydrobenzo[c]-1,6-naphthyridin-4-yl}prop-2-ynamide | Calc'd 478.2, found 478.2 |
| 336 | 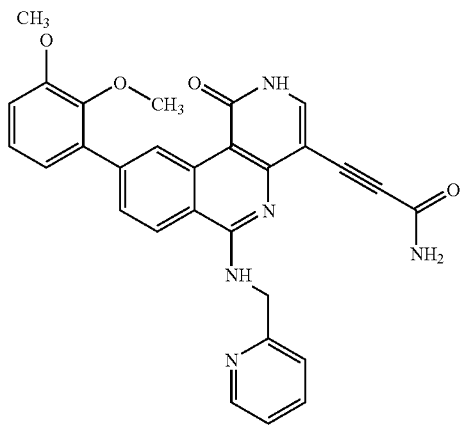 | 3-{9-(2,3-dimethoxyphenyl)-1-oxo-6-[(pyridin-2-ylmethyl)amino]-1,2-dihydrobenzo[c]-1,6-naphthyridin-4-yl}prop-2-ynamide | Calc'd 506.2, found 506.2 |
| 337 | 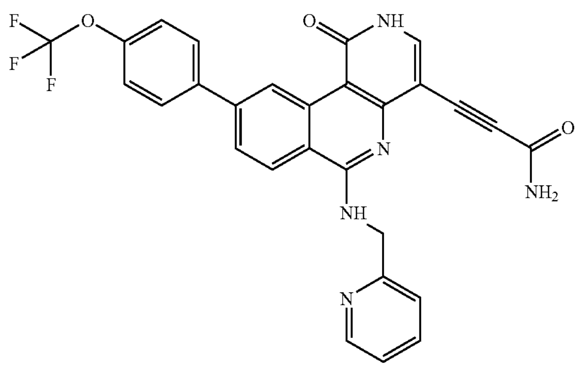 | 3-{1-oxo-6-[(pyridin-2-ylmethyl)amino]-9-[4-(trifluoromethoxy)phenyl]-1,2-dihydrobenzo[c]-1,6-naphthyridin-4-yl}prop-2-ynamide | Calc'd 530.1, found 530.1 |
| 338 | 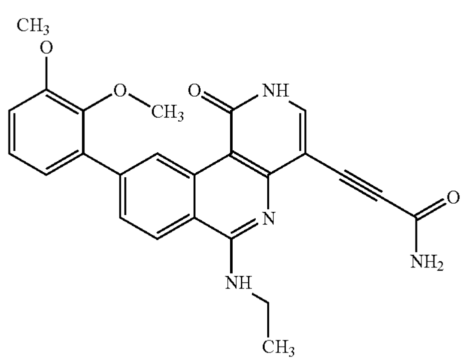 | 3-[9-(2,3-dimethoxyphenyl)-6-(ethylamino)-1-oxo-1,2-dihydrobenzo[c]-1,6-naphthyridin-4-yl]prop-2-ynamide | Calc'd 443.2, found 443.2 |

TABLE 14-continued

| Ex. | Structure | Name | LRMS [M + H]+ |
|---|---|---|---|
| 339 | 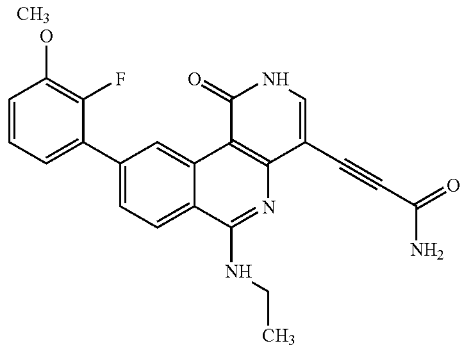 | 3-[6-(ethylamino)-9-(2-fluoro-3-methoxyphenyl)-1-oxo-1,2-dihydrobenzo[c]-1,6-naphthyridin-4-yl]prop-2-ynamide | Calc'd 431.1, found 431.1 |
| 340 | 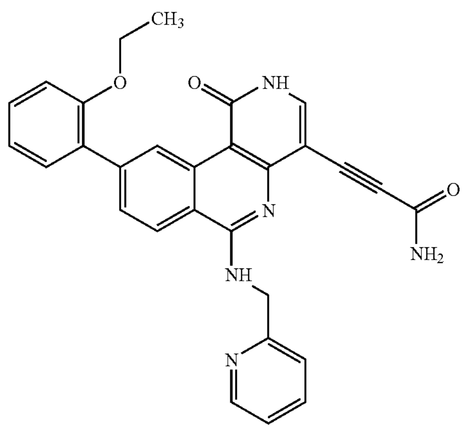 | 3-{9-(2-ethoxyphenyl)-1-oxo-6-[(pyridin-2-ylmethyl)amino]-1,2-dihydrobenzo[c]-1,6-naphthyridin-4-yl}prop-2-ynamide | Calc'd 490.2, found 490.2 |
| 341 | 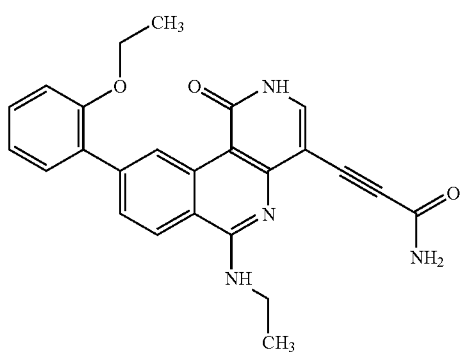 | 3-[9-(2-ethoxyphenyl)-6-(ethylamino)-1-oxo-1,2-dihydrobenzo[c]-1,6-naphthyridin-4-yl]prop-2-ynamide | Calc'd 427.2, found 427.2 |
| 342 | 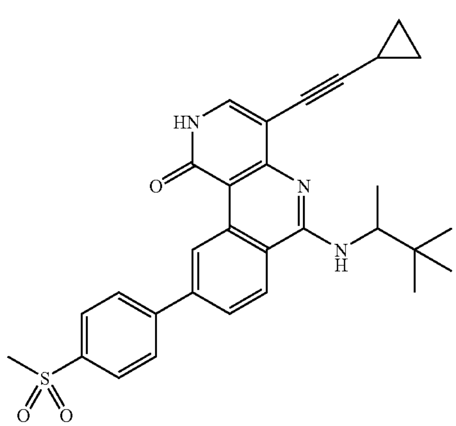 | 4-(cyclopropylethynyl)-9-[4-(methylsulfonyl)phenyl]-6-[(1,2,2-trimethylpropyl)amino]benzo[c]-1,6-naphthyridin-1(2H)-one | Calc'd 514.2, found 514.1 |

TABLE 14-continued

| Ex. | Structure | Name | LRMS [M + H]+ |
|---|---|---|---|
| 343 | 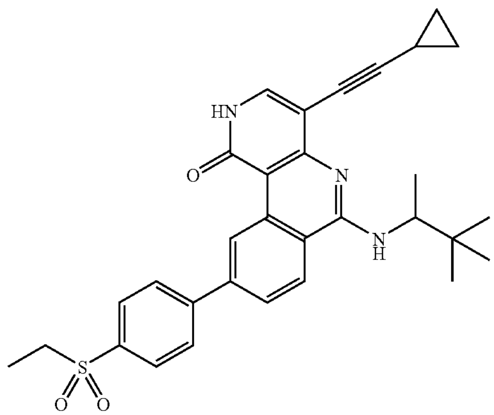 | 4-(cyclopropylethynyl)-9-[4-(ethylsulfonyl)phenyl]-6-[(1,2,2-trimethylpropyl)amino]benzo[c]-1,6-naphthyridin-1(2H)-one | Calc'd 528.2, found 528.2 |
| 344 | 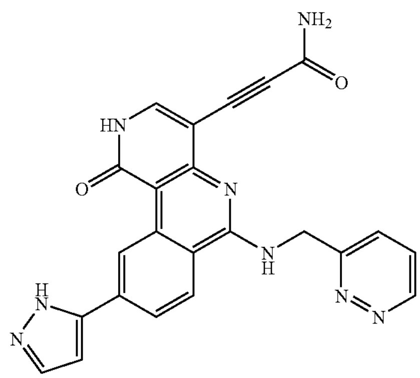 | 3-{1-oxo-9-(1H-pyrazol-5-yl)-6-[(pyridazin-3-ylmethyl)amino]-1,2-dihydrobenzo[c]-1,6-naphthyridin-4-yl}prop-2-ynamide | Calc'd 437.1, found 437.1 |
| 345 | 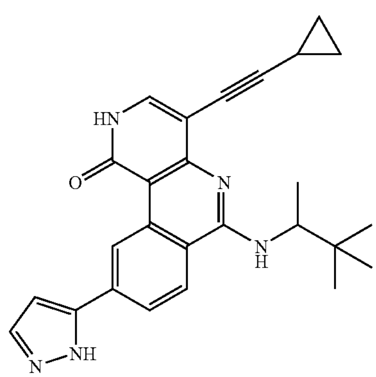 | 4-(cyclopropylethynyl)-9-(1H-pyrazol-5-yl)-6-[(1,2,2-trimethylpropyl)amino]benzo[c]-1,6-naphthyridin-1(2H)-one | Calc'd 426.2, found 426.1 |
| 346 | 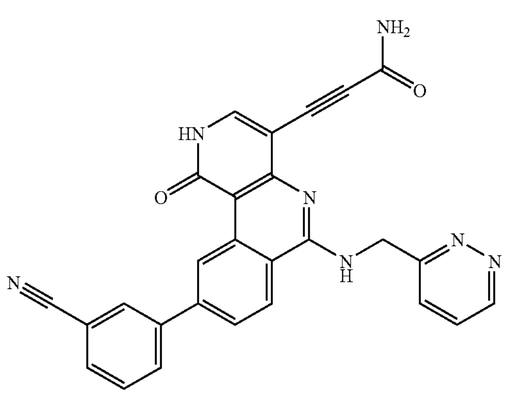 | 3-{9-(3-cyanophenyl)-1-oxo-6-[(pyridazin-3-ylmethyl)amino]-1,2-dihydrobenzo[c]-1,6-naphthyridin-4-yl}prop-2-ynamide | Calc'd 472.2, found 472.0 |

TABLE 14-continued

| Ex. | Structure | Name | LRMS [M + H]+ |
|---|---|---|---|
| 347 | 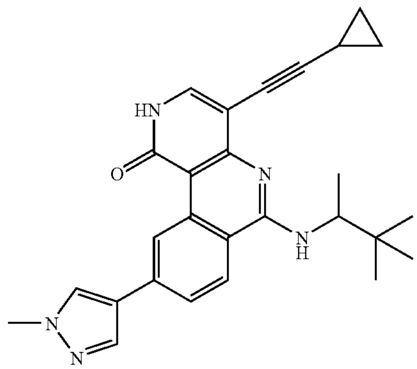 | 4-(cyclopropylethynyl)-9-(1-methyl-1H-pyrazol-4-yl)-6-[(1,2,2-trimethylpropyl)amino]benzo[c]-1,6-naphthyridin-1(2H)-one | Calc'd 440.2, found 440.2 |
| 348 | 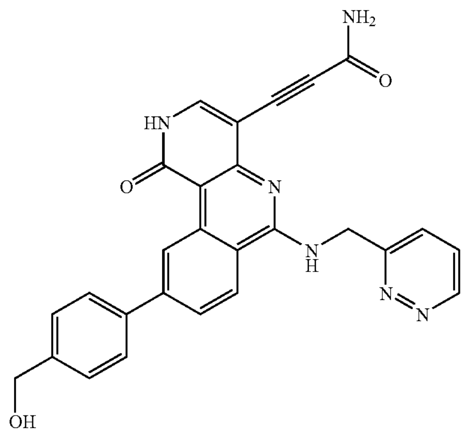 | 3-{9-[4-(hydroxymethyl)phenyl]-1-oxo-6-[(pyridazin-3-ylmethyl)amino]-1,2-dihydrobenzo[c]-1,6-naphthyridin-4-yl}prop-2-ynamide | Calc'd 477.2, found 478.0 |
| 349 | 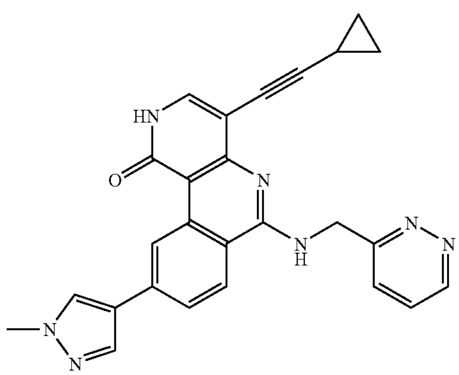 | 4-(cyclopropylethynyl)-9-(1-methyl-1H-pyrazol-4-yl)-6-[(pyridazin-3-ylmethyl)amino]benzo[c]-1,6-naphthyridin-1(2H)-one | Calc'd 448.2, found 448.1 |
| 350 | 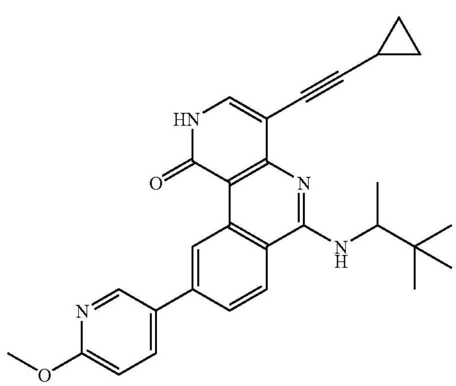 | 4-(cyclopropylethynyl)-9-(6-methoxypyridin-3-yl)-6-[(1,2,2-trimethylpropyl)amino]benzo[c]-1,6-naphthyridin-1(2H)-one | Calc'd 467.2, found 467.2 |

TABLE 14-continued

| Ex. | Structure | Name | LRMS [M + H]+ |
|---|---|---|---|
| 351 | 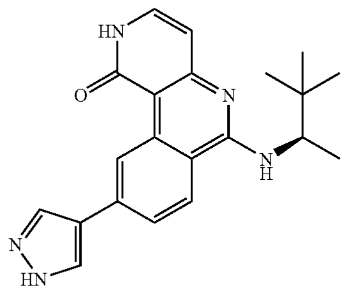 | 9-(1H-pyrazol-4-yl)-6-{[(1R)-1,2,2-trimethylpropyl]amino}benzo[c]-1,6-naphthyridin-1(2H)-one | Calc'd 362.2, found 362.1 |
| 352 | 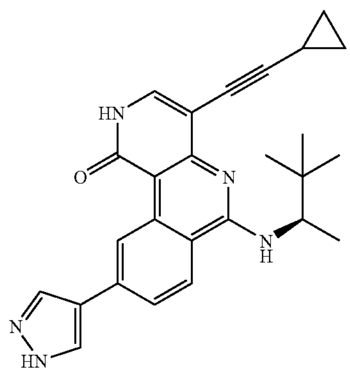 | 4-(cyclopropylethynyl)-9-(1H-pyrazol-4-yl)-6-{[(1R)-1,2,2-trimethylpropyl]amino}benzo[c]-1,6-naphthyridin-1(2H)-one | Calc'd 426.2, found 426.2 |
| 353 | 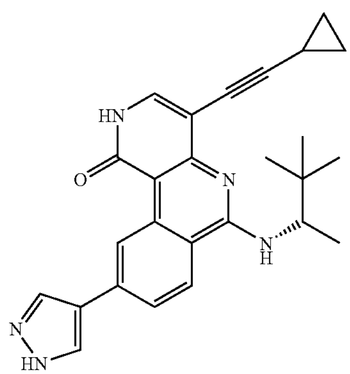 | 4-(cyclopropylethynyl)-9-(1H-pyrazol-4-yl)-6-{[(1S)-1,2,2-trimethylpropyl]amino}benzo[c]-1,6-naphthyridin-1(2H)-one | Calc'd 426.2, found 426.2 |

Example 354

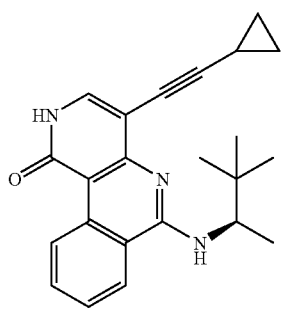

Step 1: 4-(cyclopropylethynyl)-6-{[(1R)-1,2,2-trimethylpropyl]amino}benzo[c]-1,6-naphthyridin-1(2H)-one To a mixture of 9-bromo-4-(cyclopropylethynyl)-6-{[(1R)-1,2,2-trimethylpropyl]amino}benzo[c]-1,6-naphthyridin-1(2H)-one (104 mg, 0.237 mmol), 4-(4,4,5,5-tetramethyl-1,3,2-dioxaborolan-2-yl)-1H-pyrazole (92 mg, 0.474 mmol) and 1,1'-bis(dipheylphosphino)ferrocene-palladium (II)dichloride dichloromethane complex (38.7 mg, 0.047 mmol) was added DMF (2.4 mL) and the mixture was stirred under an argon atmosphere for five minutes. Sodium carbonate (2N) (0.237 mL, 0.474 mmol) was added, and the mixture was further degassed with argon. The reaction was then heated to 130° C. for 35 minutes using microwave irradiation, then quenched with the dropwise addition to a dilute aqueous NaHCO$_3$ solution. The crude product mixture was filtered and purified via silica gel chromatography using 0.5-10% CH$_3$OH in CH$_2$Cl$_2$ as eluent to afford the title compound 4-(cyclopropylethynyl)-6-{[(1R)-1,2,2-trimethylpropyl]

amino}benzo[c]-1,6-naphthyridin-1(2H)-one. LRMS (APCI) calc'd ($C_{23}H_{25}N_3O$) [M+H]$^+$, 360.2; found 360.2. $^1$H NMR (500 MHz, DMSO-d$_6$) δ 11.33 (d, 1H), 9.80 (d, 1H), 8.51 (d, 1H), 7.75 (t, 1H), 7.58 (t, 1H), 7.49 (d, 2H), 4.88 (m, 1H), 1.54 (m, 1H), 1.21 (d, 3H), 0.98 (s, 9H), 0.87 (m, 2H), 0.70 (m, 2H).

Example 355

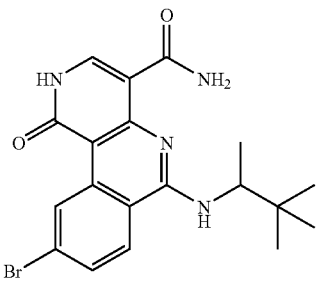

9-bromo-1-oxo-6-[(1,2,2-trimethylpropyl)amino]-1,2-dihydrobenzo[c]-1,6-naphthyridine-4-carboxamide 9-bromo-4-iodo-6-[(1,2,2-trimethylpropyl)amino]benzo[c]-1,6-naphthyridin-1(2H)-one (100 mg, 0.20 mmol), acetic hydrazide (16.3 mg, 0.220 mmol), Mo(CO)$_6$ (52.8 mg, 0.200 mmol), t-butylphosphine HBF$_4$ salt (5.80 mg, 0.020 mmol), and trans-di-mu-acetatobis[2-(di-o-tolylphosphino)benzyl]dipalladium(II) (9.38 mg, 10.00 mmol) were added to a microwave vial and flushed with nitrogen. Dioxane (2000 μl) was added followed by Hunig's base (34.9 μl 0.200 mmol) and degassed for 10 min with subsurface N$_2$ bubbling. The reaction flask was then sealed and heated to 100° C. for 2 h. The crude reaction mixture was then diluted with DMSO and purified by preparative HPLC Reverse phase (C-18), eluting with Acetonitrile/Water+0.05% TFA, to give the title compound as a white solid and also N'-acetyl-9-bromo-1-oxo-6-[(1,2,2-trimethylpropyl)amino]-1,2-dihydrobenzo[c]-1,6-naphthyridine-4-carbohydrazide as a white solid. $^1$H NMR (500 MHz, CD$_3$OD) δ 11.88 (d, 1H, J=6.0 Hz), 10.14 (d, 1H, J=2.0 Hz), 10.03 (d, 1H, J=4.0 Hz), 8.56 (d, 1H, J=9.0 Hz), 8.20 (d, 1H, J=7.0 Hz), 7.85 (m, 3H), 4.21 (m, 1H), 1.22 (d, 3H, J=13.5 Hz), 0.96 (s, 9H). LRMS (ESI) calc'd for ($C_{19}H_{22}BrN_4O_2$) [M+H]$^+$, 417.1; found 417.0.

The compounds listed in Table 15 below were prepared according to Scheme 16, following analogous procedures to those sued to prepare Example 355.

TABLE 15

| Ex. | Structure | Name | LRMS [M + H]$^+$ |
|---|---|---|---|
| 356 | 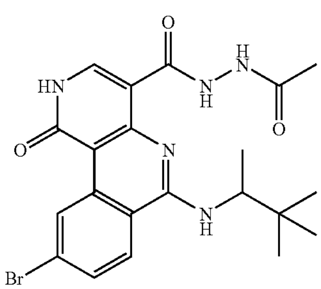 | N'-acetyl-9-bromo-1-oxo-6-[(1,2,2-trimethylpropyl)amino]-1,2-dihydrobenzo[c]-1,6-naphthyridine-4-carbohydrazide | Calc'd 476.1, found 476.0 |
| 357 | 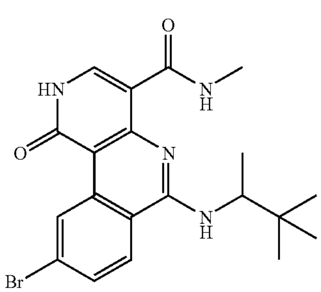 | 9-bromo-N-methyl-1-oxo-6-[(1,2,2-trimethylpropyl)amino]-1,2-dihydrobenzo[c]-1,6-naphthyridine-4-carboxamide | Calc'd 433.1, found 431.1 |
| 358 | 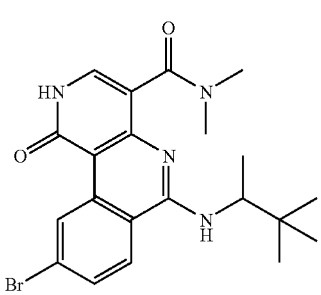 | 9-bromo-N-methyl-1-oxo-6-[(1,2,2-trimethylpropyl)amino]-1,2-dihydrobenzo[c]-1,6-naphthyridine-4-carboxamide | Calc'd 447.1, found 447.0 |

TABLE 15-continued

| Ex. | Structure | Name | LRMS [M + H]+ |
|---|---|---|---|
| 359 | 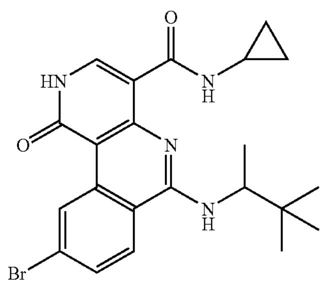 | 9-bromo-N-cyclopropyl-1-oxo-6-[(1,2,2-trimethylpropyl)amino]-1,2-dihydrobenzo[c]-1,6-naphthyridine-4-carboxamide | Calc'd 459.1, found 459.0 |
| 360 | 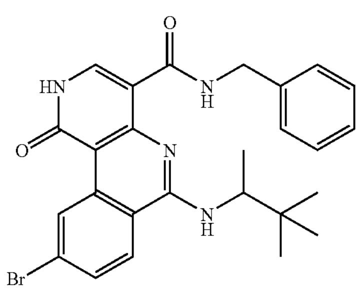 | N-benzyl-9-bromo-1-oxo-6-[(1,2,2-trimethylpropyl)amino]-1,2-dihydrobenzo[c]-1,6-naphthyridine-4-carboxamide | Calc'd 507.1, found 507.1 |

Example 361

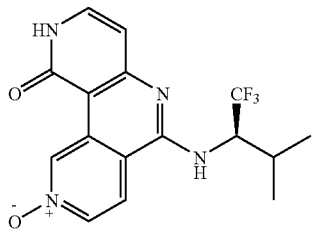

6-{[(1R)-2-methyl-1-(trifluoromethyl)propyl]amino}pyrido[4,3-c]-1,6-naphthyridin-1(2H)-one 9-oxide To a solution of 6-{[(1R)-2-methyl-1-(trifluoromethyl)propyl]amino}pyrido[4,3-c]-1,6-naphthyridin-1(2H)-one (20 mg, 0.059 mmol) in $CH_2Cl_2$ (8 mL) at 0° C. was added m-CPBA (60 mg, 0.268 mmol, 77% max) and allowed to stir for 2 hr. 10% sodium thiosulfate and sat. sodium bicarbonate were added to the reaction solution and stirred for 30 min. The layers were separated, the organic layer was dried with $MgSO_4$, filtered, and concentrated. The residue was purified on reverse phase HPLC 100% $H_2O$ to 100% MeCN to afford 6-{[(1R)-2-methyl-1-(trifluoromethyl)propyl]amino}pyrido[4,3-c]-1,6-naphthyridin-1(2H)-one 9-oxide. $^1$H NMR (600 MHz, $CD_3OD$) δ 10.80 (s, 1H), 8.50 (d, 1H), 8.35 (d, 1H), 7.48 (d, 1H), 6.60 (d, 1H), 5.39 (m, 1H), 2.33 (m, 1H), 1.14 (d, 3H), 1.06 (d, 3H). LRMS (ESI) calc'd for ($C_{16}H_{16}F_3N_4O_2$) [M+H]+, 353.1; found 353.1.

Example 362

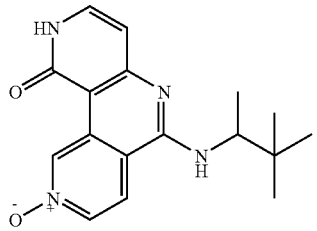

6-[(1,2,2-trimethylpropyl)amino]pyrido[4,3-c]-1,6-naphthyridin-1(2H)-one 9-oxide 6-[(1,2,2-trimethylpropyl)amino]pyrido[4,3-c]-1,6-naphthyridin-1(2H)-one 9-oxide was synthesized using the same procedure as 6-{[(1R)-2-methyl-1-(trifluoromethyl)propyl]amino}pyrido[4,3-c]-1,6-naphthyridin-1(2H)-one 9-oxide. LRMS (ESI) calc'd for ($C_{17}H_{21}F_3N_4O_2$) [M+H]+, 313.2; found 313.1. amino}pyrido[4,3-c]-1,6-naphthyridin-1(2H)-one 9-oxide. LRMS (ESI) calc'd for ($C_{17}H_{21}F_3N_4O_2$) [M+H]+, 313.2; found 313.1.

Example 363

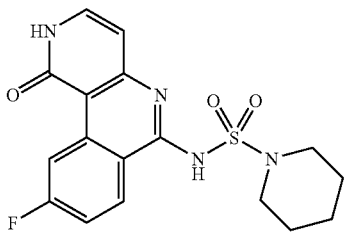

N-(9-fluoro-1-oxo-1,2-dihydrobenzo[c]-1,6-naphthyridin-6-yl)piperidine-1-sulfonamide To a solution of 1,6-dichloro-9-fluorobenzo[c]-1,6-naphthyridine (30 mg, 0.11 mmol) in dioxane (3 mL) were added cesium carbonate (128 mg, 0.39 mmol), piperidine-1-sulfonamide (18.4 mg, 0.11 mmol), Xantphos, (9,9-dimethyl-9H-xanthene-4,5-diyl)bis(diphenylphosphine), (10 mg, 0.02 mmol), and $Pd_2(dba)_3$ (5.14 mg, 5.62 μmol). The solution was degassed by bubbling $N_2$ for 5 min and heated 80° C. overnight and worked up with EtOAc and $H_2O$. The organic layers were dried with $MgSO_4$, filtered, and concentrated by rotary evaporation to afford an oily residue. Silica gel column chromatography 100% $CH_2Cl_2$ to 25% MeOH afforded N-(1-chloro-9-fluorobenzo[c]-1,6-naphthyridin-6-yl)piperidine-1-sulfonamide. This intermediate was taken up in 6 N HCl (2 mL) and THF (2 mL) and heated to 85° C. for 2 hr. The reaction mixture was concentrated and purified by reverse phase HPLC 100% $H_2O$ to 100% MeCN to afford N-(9-fluoro-1-oxo-1,2-dihydrobenzo[c]-1,6-naphthyridin-6-yl)piperidine-1-sulfonamide. LRMS (ESI) calc'd for ($C_{17}H_{18}FN_4O_3S$) [M+H]$^+$, 377.1; found 377.1.

Example 364

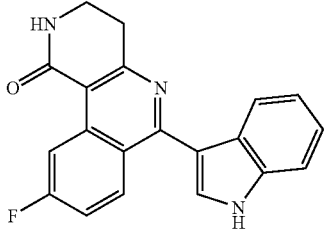

9-fluoro-6-(1H-indol-3-yl)benzo[c]-1,6-naphthyridin-1(2H)-one

To a solution of 1,6-dichloro-9-fluorobenzo[c]-1,6-naphthyridine (20 mg, 0.075 mmol) in THF (2 mL) and 2.0 M $Na_2CO_3$ (500 μL) were added [1-(tert-butoxycarbonyl)-1H-indol-3-yl]boronic acid (23.5 mg, 0.09 mmol). The solution was degassed by bubbling $N_2$ for 5 min heated to 150° C. for 1 hr in a microwave reactor. The reaction solution was extracted with EtOAc and water, the organic layers were dried with $MgSO_4$, filtered, and concentrated by rotary evaporation. Silcia gel column chromatography with 100% $CH_2Cl_2$ to 25% MeOH provided the 9-fluoro-6-(1H-indol-3-yl)benzo[c]-1,6-naphthyridin-1(2H)-one. LRMS (ESI) calc'd for ($C_{20}H_{13}FN_3O$) [M+H]$^+$, 330.1; found 330.1

Example 365

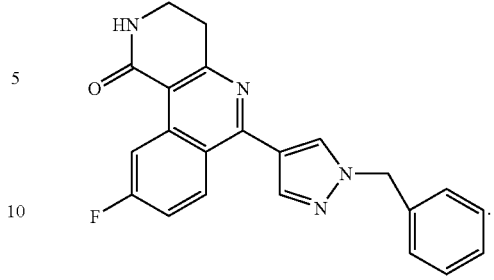

6-(1-benzyl-1H-pyrazol-4-yl)-9-fluorobenzo[c]-1,6-naphthyridin-1(2H)-one 6-(1-benzyl-1H-pyrazol-4-yl)-9-fluorobenzo[c]-1,6-naphthyridin-1(2H)-one was prepared using the same procedure as example 9-fluoro-6-(1H-indol-3-yl)benzo[c]-1,6-naphthyridin-1(2H)-one. LRMS (ESI) calc'd for ($C_{22}H_{16}FN_4O$) [M+H]$^+$, 371.1; found 371.1

Example 366

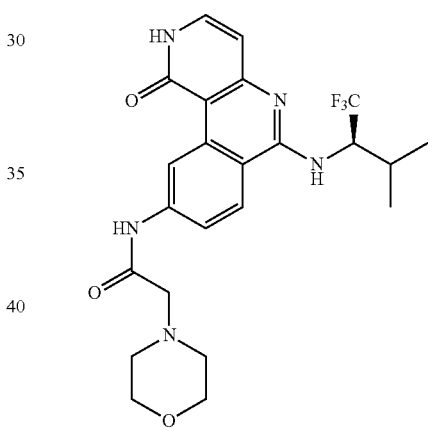

N-(6-{[(1R)-2-methyl-1-(trifluoromethyl)propyl]amino}-1-oxo-1,2-dihydrobenzo[c]-1,6-naphthyridin-9-yl)-2-morpholin-4-ylacetamide To a solution of 9-bromo-6-{[(1R)-2-methyl-1-(trifluoromethyl)propyl]amino}benzo[c]-1,6-naphthyridin-1(2H)-one (30 mg, 0.07 mmol) in dioxane (1 mL) were added cesium carbonate (83 mg, 0.25 mmol), 2-morpholin-4-ylacetamide (10 mg, 0.07 mmol), Xantphos, (9,9-dimethyl-9H-xanthene-4,5-diyl)bis(diphenylphosphine), (8.3 mg, 0.01 mmol), and $Pd_2(dba)_3$ (6.63 mg, 7.24 μmol). The solution was degassed by bubbling nitrogen gas for 5 min and heated to 100° C. for 2 hr. The solution was filtered and purified using reverse phase chromatography 100% $H_2O$ to 100% MeCN. LRMS (ESI) calc'd for ($C_{23}H_{27}F_3N_5O_3$) [M+H]$^+$, 478.2; found 478.1.

The compounds listed in Table 16 below were prepared according to Scheme 17, following analogous procedures to those sued to prepare Example 366.

TABLE 16

| Ex. | Structure | Name | LRMS [M + H]+ |
|---|---|---|---|
| 367 | 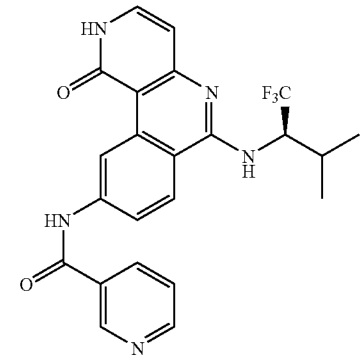 | N-(6-{[(1R)-2-methyl-1-(trifluoromethyl)propyl]amino}-1-oxo-1,2-dihydrobenzo[c]-1,6-naphthyridin-9-yl)nicotinamide | Calc'd 456.2, found 456.1 |
| 368 | 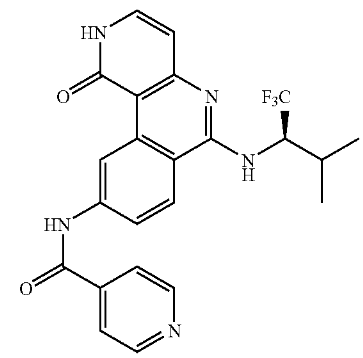 | N-(6-{[(1R)-2-methyl-1-(trifluoromethyl)propyl]amino}-1-oxo-1,2-dihydrobenzo[c]-1,6-naphthyridin-9-yl)isonicotinamide | Calc'd 456.2, found 456.1 |

Example 369

9-bromo-3-methyl-6-[(pyridin-2-ylmethyl)amino]benzo[c]-1,6-naphthyridin-1(2H)-one

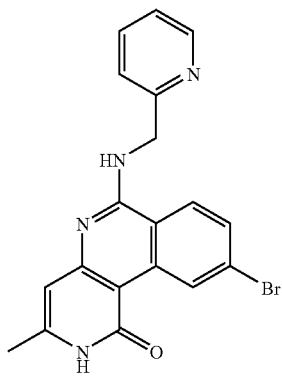

Step 1: 2-chloro-6-methylpyridine 1-oxide

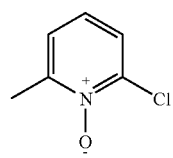

To a solution of 2-chloro-6-methylpyridine (60.0 g, 0.47 mol) in $CH_2Cl_2$ (500 mL) was added m-CPBA (122 g, 0.700 mol), and the reaction mixture was stirred at 40° C. for 8 hours. The reaction was quenched with sodium thiosulfate and adjusted to pH=7.5 with sodium bicarbonate solution. The organic layer was washed with water, dried over sodium sulfate and the solvent was evaporated to afford 2-chloro-6-methylpyridine 1-oxide. $^1$H NMR (300 MHz, CDCl$_3$) δ 7.37 (dd, J1=8.1 Hz, J2=1.5 Hz, 1H), 7.18 (dd, J1=7.8 Hz, J2=1.5 Hz, 1H), 7.07 (t, J=7.8 Hz, 1H), 2.54 (s, 3H). LRMS calc'd for ($C_6H_6ClNO$) [M+H]+, 144; found 144.

Step 2: 2-chloro-6-methyl-4-nitropyridine 1-oxide

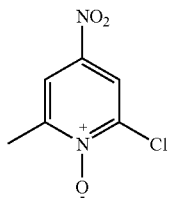

2-chloro-6-methylpyridine 1-oxide (60 g, 0.42 mol) was dissolved in 98% sulfuric acid (60 mL) at 0° C., then a solution of $HNO_3$ (50 mL) and $H_2SO_4$ (50 mL) was added dropwise at the same temperature. After the addition was complete, the reaction was stirred at 90° C. for 3 h. The reaction was poured into ice-water, neutralized with $NaHCO_3$, and then extracted with ethyl acetate (3×500 mL). The combined organic layers were washed with brine (500 mL), dried over magnesium sulfate, filtered and concentrated to afford 2-chloro-6-methyl-4-nitropyridine 1-oxide which was used without further purification. $^1H$ NMR (300 MHz, CDCl3) δ 8.27 (d, J=2.7 Hz, 1H), 8.07 (d, J=0.6 Hz, 1H), 2.62 (s, 3H). LRMS calc'd for ($C_6H_6ClNO$) [M+H]+, 189; found 189.

Step 3: 2-chloro-6-methylpyridin-4-amine

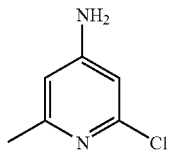

A solution of 2-chloro-6-methyl-4-nitropyridine 1-oxide (52 g, 0.27 mol) in EtOH and $H_2O$ was treated with powdered iron (46 g, 0.83 mol) and $NH_4Cl$ (44 g, 0.83 mol). The mixture was stirred at 90° C. for 3 h. After cooling to room temperature the reaction mixture was filtered, and the filtrate was extracted with ethyl acetate (3×500 mL). The combined organic layers were washed with brine (500 mL), dried over magnesium sulfate, filtered and concentrated to afford 2-chloro-6-methylpyridin-4-amine. $^1H$ NMR (400 MHz, $CDCl_3$) δ 6.36 (d, J=1.5 Hz, 1H), 6.28 (d, J=1.2 Hz, 1H), 4.30 (m, 2H), 2.34 (s, 3H). LRMS calc'd for ($C_6H_7ClN_2$) [M+H]+, 143; found 143.

Step 4: 2-butoxy-6-methylpyridin-4-amine

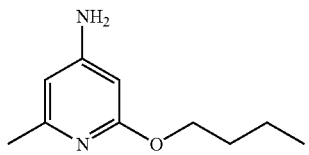

2-chloro-6-methylpyridin-4-amine (36 g, 0.25 mol) and sodium hydroxide (24 g, 1 mol) were dissolved in 1-butanol (400 mL). The solution was heated at reflux for 10 h, and then cooled to rt. The reaction mixture was diluted with water (300 mL) and then extracted with ethyl acetate (3×500 mL). The combined organic layers were washed with brine (500 mL), dried over sodium sulfate, and concentrated to afford 2-butoxy-6-methylpyridin-4-amine. $^1H$ NMR (400 MHz, CDCl3) δ 6.05 (d, J=0.6 Hz, 1H), 5.75 (d, J=0.6 Hz, 1H), 4.18 (t, J=6.4 Hz, 1H), 2.30 (s, 3H), 1.71 (m, 2H), 1.48 (m, 2H), 0.98 (t, J=7.6 Hz, 3H). LRMS calc'd for ($C_{10}H_{16}N_2O$) [M+H]+, 181; found 181.

Step 5: 2-butoxy-3-iodo-6-methylpyridin-4-amine

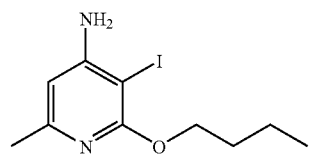

2-butoxy-6-methylpyridin-4-amine (31 g, 0.17 mol) was dissolved in THF (500 mL), and then N-iodosuccinimide (32 g, 0.14 mol) was added portionwise at −78° C. The reaction mixture was stirred at the same temperature for 2 min. The reaction was quenched by addition of water, and the resulting mixture was extracted with ethyl acetate (2×600 mL). The combined organic layers were washed with brine (500 mL), dried over sodium sulfate, and concentrated. The crude was purified by silica gel column chromatography (petroleum ether) to afford 2-butoxy-3-iodo-6-methylpyridin-4-amine. $^1H$ NMR (400 MHz, CDCl3): δ 6.10 (s, 1H), 4.49 (m, 2H), 4.29 (t, J=6.4 Hz, 2H), 2.284 (s, 1H), 1.75 (m, 2H), 1.50 (m, 2H), 0.98 (t, J=7.6 Hz, 3H). LRMS calc'd for ($C_{10}H_{15}1N_2O$) [M+H]+, 307; found 307.

Step 6: 4-bromo-N,N-diisopropylbenzamide

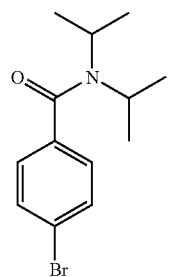

A mixture of 4-bromobenzoic acid (200 g, 1 mol) and thionyl chloride (300 mL) was refluxed for 3 hours. The mixture was concentrated in vacuo to remove excessive thionyl chloride, and then azeotroped with toluene (3×). The crude residue was dissolved in $CH_2Cl_2$ (2 L) and cooled in ice-water bath. To the resulting solution was added dropwise a mixture of triethylamine (330 mL, 2.38 mol) and diisopropylamine (168 mL, 1.19 mol) over 1 hour. The solution was allowed to stir overnight, and then washed with 1N HCl, followed by brine. The organic layer was dried over $MgSO_4$, filtered, and concentrated to afford 4-bromo-N,N-diisopropylbenzamide. LRMS calc'd for ($C_{13}H_{18}BrNO$) [M+H]+, 284; found 284.

Step 7: {5-bromo-2-[(diisopropylamino)carbonyl]phenyl}boronic acid

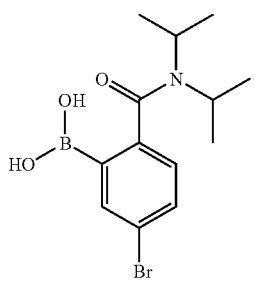

To a solution of 4-bromo-N,N-diisopropylbenzamide (1.0 g, 35 mmol) and triisopropyl borate (0.79 g, 4.2 mmol) in THF (20 mL) was added a freshly prepared solution of LDA in THF (4.6 mL, 4.6 mmol) dropwise at 20° C. over a 1 hour period under nitrogen. The reaction mixture was stirred overnight, quenched with saturated aqueous $NH_4Cl$ solution (20 mL), and extracted with ethyl acetate (3×30 mL). The combined organic layers were washed with brine (20 mL), dried over magnesium sulfate, filtered and concentrated to afford {5-bromo-2-[(diisopropylamino)carbonyl]phenyl}boronic acid that was used without further purification.

Step 8: 2-(4-amino-2-butoxy-6-methylpyridin-3-yl)-4-bromo-N,N-diisopropylbenzamide

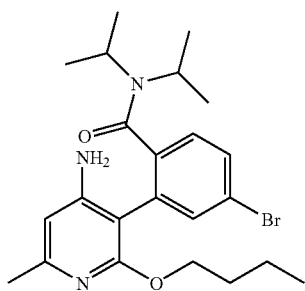

To a stirred solution of {5-bromo-2-[(diisopropylamino)carbonyl]phenyl}boronic acid (0.26 g, 0.8 mmol) in dioxane (10 mL) was added 2-butoxy-3-iodo-6-methylpyridin-4-amine (0.24 g, 0.8 mmol), $Cs_2CO_3$ (0.78 g, 2.4 mmol) and Pd(dppf)Cl$_2$ (40 mg) under a nitrogen atmosphere. The reaction mixture was stirred under reflux for 3 h, and then diluted with water (10 mL). The resulting mixture was extracted with ethyl acetate (20 mL×3). The combined extracts were washed with brine (10 mL), dried over $Na_2SO_4$, evaporated. Column chromatography (EtOAc/petroleum ether) was used for purification to afford 2-(4-amino-2-butoxy-6-methylpyridin-3-yl)-4-bromo-N,N-diisopropylbenzamide. $^1$HNMR (300 MHz, CDCl$_3$) δ 7.50 (dd, J=7.9 Hz, 1.9 Hz, 1H), 7.38 (d, J=1.9 Hz, 1H), 7.13 (d, J=8.3 Hz, 1H), 6.12 (s, 1H), 4.12 (m, 2H), 3.64 (m, 1H), 3.31 (m, 1H), 1.53 (m, 2H), 1.47 (d, J=6.8 Hz, 3H), 1.29 (m, 2H), 1.17 (d, J=6.8 Hz, 3H), 0.99 (d, J=6.8 Hz, 3H), 0.87 (t, J=7.6 Hz, 3H), 0.76 (d, J=6.4 Hz, 3H). LRMS calc'd for ($C_{23}H_{32}BrN_3O_2$) [M+H]+, 462; found 462.

Step 9: 9-bromo-1-butoxy-3-methylbenzo[c]-1,6-naphthyridin-6(5H)-one

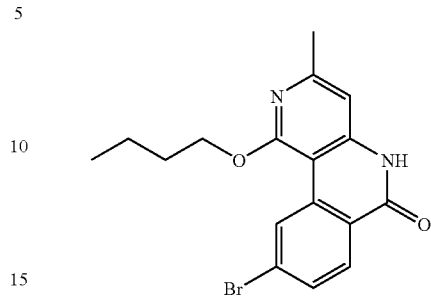

To a solution of 2-(4-amino-2-butoxy-6-methylpyridin-3-yl)-4-bromo-N,N-diisopropylbenzamide (50 mg, 0.10 mmol) in THF (50 mL) was added dropwise a solution of NaHMDS in THF (0.40 mL, 0.20 mmol) at room temperature over 1 h. The resulting mixture was quenched with saturated aqueous $NH_4Cl$ solution (3 mL) and extracted with ethyl acetate (3×10 mL). The combined organic layers were washed with brine (5 mL), dried over magnesium sulfate, filtered and concentrated to afford a crude solid. The crude material was triturated with diethyl ether (5 mL) and filtered to afford 9-bromo-1-butoxy-3-methylbenzo[c]-1,6-naphthyridin-6(5H)-one. $^1$H-NMR (300 MHz, DMSO) δ 9.13 (d, J=5.7 Hz, 1H), 8.17 (d, J=8.7 Hz, 1H), 7.47 (dd, J1=8.4 Hz, J2=1.8 Hz, 1H), 4.41 (t, J=6.3 Hz, 2H), 2.27 (s, 3H), 1.82 (m, 2H), 1.60 (m, 2H), 1.00 (t, J=7.5 Hz, 3H). LRMS calc'd for ($C_{17}H_{17}BrN_2O_2$) [M+H]+, 361; found 362.

Step 10: 9-bromo-1,6-dichloro-3-methylbenzo[c]-1,6-naphthyridine

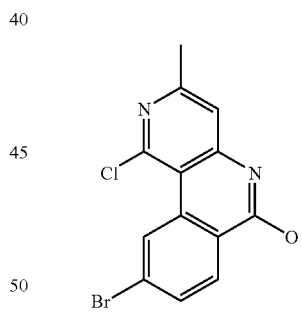

To a solution of 9-bromo-1-butoxy-3-methyl-5H-benzo[c][1,6]naphthyridin-6-one (0.20 g, 0.55 mMol) in anhydrous CH$_3$CN (1.5 mL) was added freshly distilled POCl$_3$ (0.5 mL, 5.5 mMol). The resulting suspension was heated in a sealed tube at 120° C. for 16 hours. The precipitate was filtered and the resulting solid was dissolved in CHCl$_3$ (8 mL), cooled to 0° C. and Et$_3$N was added until the solution became slightly alkaline. The solution was then washed with cold water (3×5 mL), brine (1×10 mL), dried over MgSO$_4$ and concentrated to afford 9-bromo-1,6-dichloro-3-methylbenzo[c]-1,6-naphthyridine. $^1$H NMR (400 MHz, DMSO-d6) δ 10.02 (d, 1H), 8.45 (d, 1H), 7.98-7.95 (dd, 1H), 7.74 (s, 1H), 2.74 (s, 3H). LRMS calculated for $C_{13}H_7BrCl_2N_2$ [M+H]+, 343.0; found 343.0.

Step 11: 9-bromo-1-chloro-3-methyl-N-(pyridin-2-ylmethyl)benzo[c1,6-naphthyridin-6-amine

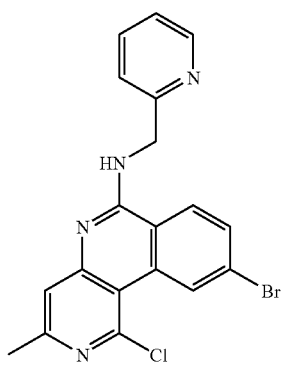

To a solution of 9-bromo-1,6-dichloro-3-methyl-benzo[c][1,6]naphthyridine (0.12 g, 0.35 mMol) in anhydrous dioxane (4 mL) was added anhydrous Et$_3$N (0.07 mL, 0.53 mMol), followed by 2-aminomethylpyridine (0.038 g, 0.35 mMol). The resulting reaction mixture was heated in a sealed tube at 120° C. for 5 hours. The reaction mixture was concentrated to a crude solid that was redissolved in EtOAc (10 mL). The EtOAc layer was washed with water (2×5 mL), brine (1×10 mL) and dried over MgSO$_4$. The filtrate was concentrated and the resulting residue was purified by flash chromatography using an EtOAc/Hexanes gradient to afford 9-bromo-1-chloro-3-methyl-N-(pyridin-2-ylmethyl)benzo[c]-1,6-naphthyridin-6-amine. $^1$H NMR (400 MHz, DMSO-d6) δ 9.88 (d, 1H), 8.65 (bs, 1H), 7.97 (d, 1H), 7.83-7.80 (dd, 1H), 7.75 (t, 1H), 7.64 (bs, 1H), 7.43 (s, 1H), 7.41 (s, 1H), 7.27 (s, 1H), 4.99 (d, 2H), 2.62 (s, 3H). LRMS calculated for C$_{19}$H$_{14}$BrClN$_4$ [M+H]+, 415.0; found 415.1.

Step 12: 9-bromo-3-methyl-6-[(pyridin-2-ylmethyl)amino]benzo[c]-1,6-naphthyridin-1(2H)-one Water (0.20 mL) and NaOAc (0.015 g, 0.18 mMol) were added to a solution 9-bromo-1-chloro-3-methyl-benzo[c][1,6]naphthyridin-6-yl)-pyridin-2-ylmethylamine (0.05 g, 0.12 mMol) in acetic acid (1 mL). The resulting mixture was heated to 120° C. for 2.5 hours. The reaction mixture was then cooled to 0° C., and then made slightly alkaline by the dropwise addition of a 10% NaHCO$_3$ solution. The resulting solution was washed with EtOAc (4×6 mL). The combined EtOAc layers were washed with brine (1×10 mL), dried with MgSO$_4$ and concentrated. The crude residue was purified by preparative reverse phase HPLC using an acetonitrile/water (with 0.1% formic acid modifier) gradient to afford 9-bromo-3-methyl-6-[(pyridin-2-ylmethyl)amino]benzo[c]-1,6-naphthyridin-1(2H)-one. $^1$H NMR (400 MHz, DMSO-d6) δ 11.43 (s, 1H), 10.08 (d, 1H), 8.95 (bt, 1H), 8.56 (d, 1H), 8.34 (d, 1H), 7.86 (t, 1H), 7.79-7.77 (dd, 1H), 7.48 (d, 1H), 7.37 (t, 1H), 6.15 (s, 1H), 4.93 (d, 2H), 2.20 (s. 3H). LRMS calculated for C$_{19}$H$_{15}$BrN$_4$O [M+H]+, 397.0; found 397.1.

Example 370

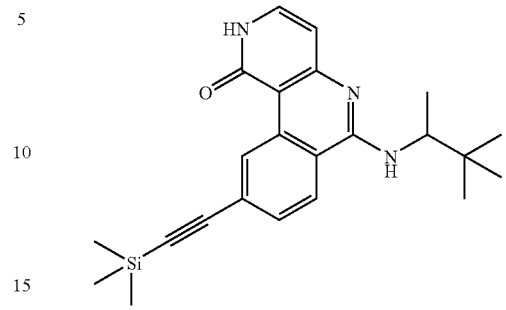

6-[(1,2,2-trimethylpropyl)amino]-9-[(trimethylsilyl)ethynyl]benzo[c]-1,6-naphthyridin-1(2H)-one To a stirred solution of 9-bromo-6-[(1,2,2-trimethylpropyl)amino]benzo[c]-1,6-naphthyridin-1(2H)-one (20 mg, 0.05 mmol) in Et$_3$N (3.0 mL) was added Pd$_2$(dba)$_3$ (10 mg) and BINAP (10 mg) in Schlenk tube under argon. Trimethylsiylacetylene (16 mg, 0.15 mmol) was added into the tube and the mixture was stirred at 60-70° C. for 20 h under an argon atmosphere. After cooling to room temperature, the mixture was diluted with water (5 ml) and extracted with ethyl acetate (3×5 mL). The combined organic layers were washed with brine (5 mL), dried over magnesium sulfate, filtered, and concentrated to a crude solid that was purified by preparative TLC to afford 6-[(1,2,2-trimethylpropyl)amino]-9-[(trimethylsilyl)ethynyl]benzo[c]-1,6-naphthyridin-1(2H)-one. $^1$H NMR (400 MHz, CDCl$_3$) δ 10.08 (s, 1H), 7.67 (d, J=8.6 Hz, 1H), 7.58 (d, J=10.1 Hz, 1H), 7.33 (s, 1H), 6.59 (s, 1H), 3.11 (s, 1H), 1.25 (m, 3H), 1.03 (s, 9H), 0.29 (s, 9H). LRMS calculated for C$_{23}$H$_{29}$N$_3$OSi [M+H]+, 392; found 392.

Example 371

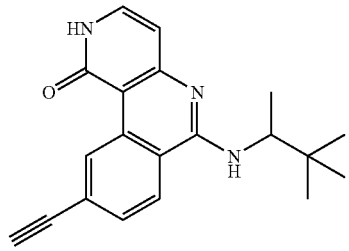

9-ethynyl-6-[(1,2,2-trimethylpropyl)amino]benzo[c]-1,6-naphthyridin-1(2H)-one

To a stirred solution of 6-[(1,2,2-trimethylpropyl)amino]-9-[(trimethylsilyl)ethynyl]benzo[c]-1,6-naphthyridin-1(2H)-one (20 mg, 0.05 mmol) in MeOH (3.0 mL) was added KOH (6.0 mg, 0.09 mmol). The resulting mixture was stirred at room temperature for 3 h. The reaction mixture was diluted with water (5 mL) and extracted with ethyl acetate (3×5 mL). The combined organic layers were washed with brine (5 mL), dried over magnesium sulfate, filtered, concentrated to afford 9-ethynyl-6-[(1,2,2-trimethylpropyl)amino]benzo[c]-1,6-naphthyridin-1(2H)-one. $^1$H NMR (300 MHz, CDCl$_3$) δ 10.15 (s, 1H), 7.69 (d, J=8.3 Hz, 1H), 7.62 (d, J=10.1 Hz, 1H), 7.31 (s, 1H), 6.62 (s, 1H), 3.23 (s, 1H), 1.25 (m, 3H), 1.04 (s, 9H). LRMS calculated for C$_{20}$H$_{21}$N$_3$O [M+H]+, 320; found 320.

Example 372

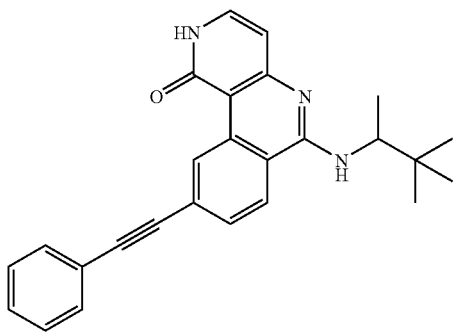

9-(phenylethynyl)-6-[(1,2,2-trimethylpropyl)amino]benzo[c]-1,6-naphthyridin-1(2H)-one To a solution of 9-bromo-6-[(1,2,2-trimethylpropyl)amino]benzo[c]-1,6-naphthyridin-1(2H)-one (150 mg, 0.040 mmol) in Et$_3$N (3.0 mL) was added the phenylacetylene (50 mg, 0.05 mmol), CuI (10 mg) and PdCl$_2$(PPh$_3$)$_2$ (10 mg). The mixture was stirred under reflux and N$_2$ atmosphere for 12 h. After cooling to room temperature, the mixture was diluted with water (5 mL) and extracted with ethyl acetate (3×5 mL). The combined organic layers were washed with brine (5 mL), dried over magnesium sulfate, filtered, and concentrated to a crude residue that was purified by preparative TLC to afford 9-(phenylethynyl)-6-[(1,2,2-trimethylpropyl)amino]benzo[c]-1,6-naphthyridin-1(2H)-one. $^1$H-NMR (300 MHz, MeOH): δ 10.03 (s, 1H), 8.26 (d, J=8.3 Hz, 1H), 7.70 (d, J=9.0 Hz, 1H) 7.39 (m, 1H), 6.62 (m, 4H), 3.30 (s, 1H), 1.27 (d, J=6.9 Hz, 2H), 1.03 (s, 9H). LRMS calculated for C$_{26}$H$_{25}$N$_3$O [M+H]+, 396; found 396.

Example 373

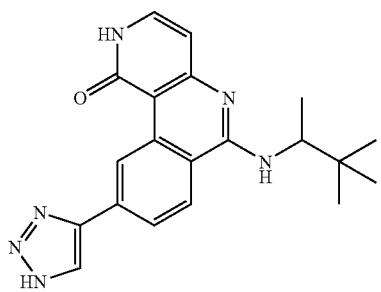

9-(1H-1,2,3-triazol-4-yl)-6-[(1,2,2-trimethylpropyl)amino]benzo[c]-1,6-naphthyridin-1(2H)-one 9-ethynyl-6-[(1,2,2-trimethylpropyl)amino]benzo[c]-1,6-naphthyridin-1(2H)-one (150 mg, 0.47 mmol) was dissolved in DMF/MeOH (2.0 mL) in a sealed tube. To the solution was added CuI (5.0 mg, 0.020 mmol) and azidotrimethylsilane (270 mg, 2.4 mmol) under an argon atmosphere. The mixture was stirred at 100° C. in a sealed tube for 8 h. The resulting solution was diluted with water (5 mL) and extracted with ethyl acetate (3×5 mL). The combined organic layers were washed with brine (5 mL), dried over magnesium sulfate, filtered, and purified by preparative TLC to afford 9-(1H-1,2,3-triazol-4-yl)-6-[(1,2,2-trimethylpropyl)amino]benzo[c]-1,6-naphthyridin-1(2H)-one. $^1$H NMR (400 MHz, MeOD) δ 10.28 (s, 1H), 8.38 (d, J=8.4 Hz, 2H), 8.30 (d, J=6.4 Hz, 1H), 7.38 (d, J=7.2 Hz, 1H), 6.64 (d, J=7.2 Hz, 1H), 4.78 (m, 1H), 1.28 (d, J=6.8 Hz, 3H), 1.04 (s, 9H). LRMS calculated for C$_{20}$H$_{22}$N$_6$O [M+H]+, 363; found 363.

Example 374

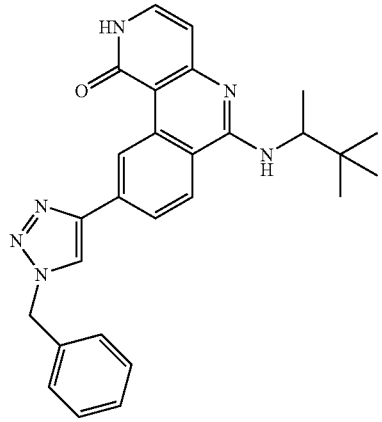

9-(1-benzyl-1H-1,2,3-triazol-4-yl)-6-[(1,2,2-trimethylpropyl)amino]benzo[c]-1,6-naphthyridin-1(2H)-one 9-ethynyl-6-[(1,2,2-trimethylpropyl)amino]benzo[c]-1,6-naphthyridin-1(2H)-one (150 mg, 0.47 mmol) was dissolved in DMF/MeOH (2 mL) in a sealed tube. To the solution was added CuI (5.0 mg, 0.020 mmol) and Bn—N$_3$ (310 mg, 2.4 mmol) under an argon atmosphere. The mixture was stirred at 100° C. for 8 h, then the resulting solution was filtered and purified by reverse phase HPLC to afford 9-(1-benzyl-1H-1,2,3-triazol-4-yl)-6-[(1,2,2-trimethylpropyl)amino]benzo[c]-1,6-naphthyridin-1(2H)-one. $^1$H NMR (400 MHz, MeOD) δ 10.30 (s, 1H), 8.64 (m, 2H), 8.30 (d, J=8.4 Hz, 1H), 7.65 (d, J=6.8 Hz, 1H), 7.40 (m, 5H), 6.93 (d, J=7.2 Hz, 1H), 5.70 (s, 2H), 4.46 (m, 1H), 1.46 (d, J=6.8 Hz, 3H), 1.09 (s, 9H). LRMS calculated for C$_{27}$H$_{28}$N$_6$O [M+H]+, 453; found 454.

Example 375

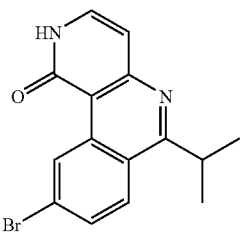

9-bromo-6-isopropylbenzo[c]-1,6-naphthyridin-1(2H)-one

Step 1: tert-butyl 2-(9-bromo-1-chlorobenzo[c]-1,6-naphthyridin-6-yl)-2-methylpropanoate

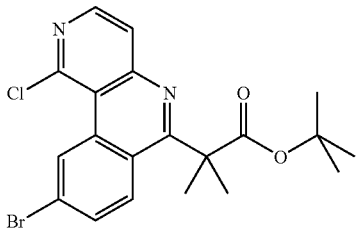

To a stirred suspension of 9-bromo-1,6-dichlorobenzo[c]-1,6-naphthyridine (5 g, 15.24 mmol) in Toluene (50 ml) was added tert-butyl 2-methylpropanoate (2.64 g, 18.29 mmol). The reaction mixture was cooled to 0° C. A solution of NaHMDS (1M in THF, 3.35 g, 18.29 mmol) was added dropwise, and the reaction mixture was allowed to warm to room temperature. After 5 hours, the reaction was quenched with aqueous saturated ammonium chloride (50 mL), and extracted with EtOAc (1×100 mL). The organic layer was dried over sodium sulfate, filtered and concentrated. The residue was adsorbed on to silica gel and purified by column chromatography on silica gel, eluting with an EtOAc/Hexanes gradient to afford tert-butyl 2-(9-bromo-1-chlorobenzo[c]-1,6-naphthyridin-6-yl)-2-methylpropanoate. LRMS (ESI) calc'd for ($C_{20}H_{20}BrClN_2O_2$) [M+H]$^+$, 437.0; found 437.0.

Step 2: 9-bromo-6-isopropylbenzo[c]-1,6-naphthyridin-1(2H)-one

To a stirred solution of tert-butyl 2-(9-bromo-1-chlorobenzo[c]-1,6-naphthyridin-6-yl)-2-methylpropanoate (3.32 g, 7.62 mmol) in dichloromethane (30 ml) was added TFA (30 ml). The solution was stirred for 12 hrs, then concentrated to a crude oil. EtOAc was added (20 mL), and the resulting solids were collected by vacuum filtration to afford 9-bromo-6-isopropylbenzo[c]-1,6-naphthyridin-1(2H)-one. The filtrate was concentrated, EtOAc was added, and a second crop of product was obtained by vacuum filtration. $^1$H NMR (500 MHz, DMSO-D6) δ 11.91 (br d, 1H), 10.28 (d, 1H), 8.41 (d, 1H), 7.89 (dd, 1H), 7.58 (t, 1H), 6.77 (d, 1H), 4.05 (septet, 1H), 1.36 (d, 6H). LRMS (ESI) calc'd for ($C_{15}H_{13}BrN_2O$) [M+H]$^+$, 317.0; found 317.0.

The following compounds in Table 17 (isolated as the free base unless otherwise noted) were prepared according to Scheme 20 following analogous procedures to those described to prepare Example 375. In the cases where the starting tert-butyl esters were not available commercially, one of the following two methods was used for their synthesis.

Method A: tert-butyl tetrahydro-2H-pyran-4-carboxylate

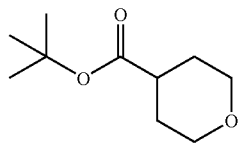

Tetrahydro-2H-pyran-4-carboxylic acid (10 g, 77 mmol) and EDC (17.68 g, 92 mmol) were added to a flask, followed by DCM (200 ml). To the resulting suspension was added Et$_3$N (16 ml, 115 mmol), tBuOH (16.1 ml, 169 mmol) and DMAP (9.39 g, 77 mmol). The reaction mixture was stirred at 40° C. for 18 hr. The reaction mixture was diluted with DCM (100 Ml) and washed with 1N NaOH (1×100 Ml) followed by 1M citric acid solution (1×100 Ml). The organic layer was dried over sodium sulfate, filtered and concentrated to afford tert-butyl tetrahydro-2H-pyran-4-carboxylate. $^1$H NMR (500 MHz, CDCl$_3$) δ 3.90 (dt, 2H), 3.37 (dt, 2H), 2.38 (septet, 1H), 1.77-1.67 (m, 4H), 1.40 (s, 9H).

Method B: tert-butyl 2-methylbutanoate

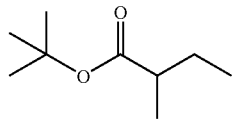

To a stirred solution of 2-methylbutanoic acid (1.029 Ml, 8.29 mmol) in DCM (10 Ml) was added potassium tert-butoxide (20 wt % in THF) (4.66 Ml, 8.29 mmol) dropwise at 0° C. The resulting suspension was allowed to warm to room temperature, and stirred for 1.5 hr. The reaction mixture was diluted with DCM (10 Ml), MP-®Trisamine Resin (3.86 g, 3.22 mMol/g; Argonaut Technologies, Inc.) was added, and the resulting suspension was stirred at room temperature for 1.5 hours. The resin was removed by vacuum filtration, and the resulting filtrate was washed with 1 N NaOH (1×20 Ml). The organic layer was dried over magnesium sulfate, filtered, and concentrated to afford tert-butyl 2-methylbutanoate. $^1$H NMR (500 MHz, CDCl$_3$) δ 2.24 (sextet, 1H), 1.61 (m, 1H), 1.44-1.39 (overlapping s, m, 10H), 1.09 (d, 3H), 0.90 (t, 3H).

TABLE 17

| Ex. | Structure | Name | Ester synthesis | LRMS |
|---|---|---|---|---|
| 376 | 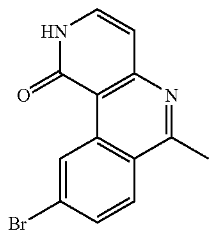 | 9-bromo-6-methylbenzo[c]-1,6-naphthyridin-1(2H)-one | | Calc'd 289.0, found 289.0 |
| 377 | 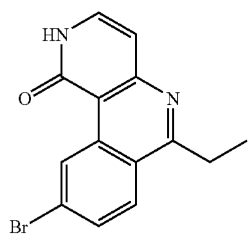 | 9-bromo-6-ethylbenzo[c]-1,6-naphthyridin-1(2H)-one | | Calc'd 303.1, found 303.0 |
| 378 | 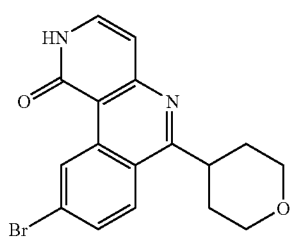 | 9-bromo-6-(tetrahydro-2H-pyran-4-yl)benzo[c]-1,6-naphthyridin-1(2H)-one | Method A | Calc'd 359.0, found 359.0 |
| 379 | 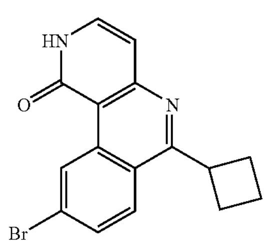 | 9-bromo-6-cyclobutylbenzo[c]-1,6-naphthyridin-1(2H)-one | Method B | Calc'd 329.0, found 329.0 |

TABLE 17-continued

| Ex. | Structure | Name | Ester synthesis | LRMS |
|---|---|---|---|---|
| 380 | 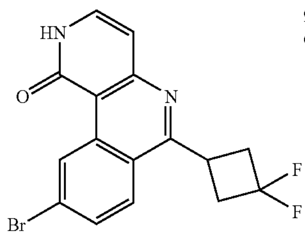 | 9-bromo-6-(3,3-difluorocyclobutyl)benzo[c]-1,6-naphthyridin-1(2H)-one | Method A | Calc'd 365.0, found 364.9 |
| 381 | 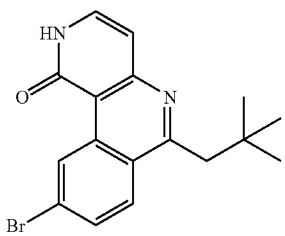 | 9-bromo-6-(2,2-dimethylpropyl)benzo[c]-1,6-naphthyridin-1(2H)-one | Method B | Calc'd 345.1, found 345.1 |
| 382 | 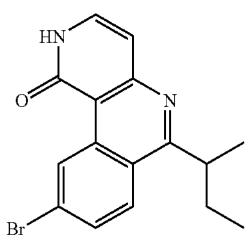 | 9-bromo-6-sec-butylbenzo[c]-1,6-naphthyridin-1(2H)-one | Method B | Calc'd 331.0, found 331.0 |
| 383 | 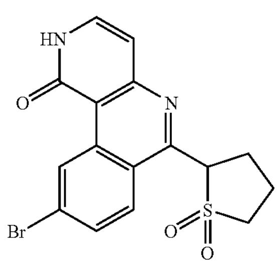 | 9-bromo-6-(1,1-dioxidotetrahydro-2-thienyl)benzo[c]-1,6-naphthyridin-1(2H)-one | | Calc'd 393.0, found 392.9 |

INTERMEDIATE 11

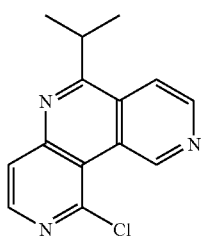

1-chloro-6-isopropylpyrido[4,3-c]-1,6-naphthyridine

To a solution of 1,6-dichloropyrido[4,3-c]-1,6-naphthyridine (50 mg, 0.200 mmol) and 1,2-bis(diphenylphosphino)ethanenickel(II) chloride (1.056 mg, 1.999 µmol) in THF (0.4 mL). The mixture was cooled to −10° C. in a methanol-ice bath, and isopropylmagnesium bromide (220 µl 0.220 mmol, 1 M in THF) was added dropwise. The reaction mixture was stirred at −10° C. for 30 min. The mixture was then allowed to warm to room temperature and then stirred for 30 min. The reaction mixture was quenched with aqueous ammonium chloride (saturated), and the aqueous layer was extracted with ethyl acetate. The combined organic extracts were dried over sodium sulfate and concentrated under reduced pressure to afford 1-chloro-6-isopropylpyrido[4,3-c]-1,6-naphthyridine as a red solid. LRMS (APCI) calc'd for ($C_{14}H_{13}ClN_3$) [M+H]+, 258.1; found 258.0.

Example 384

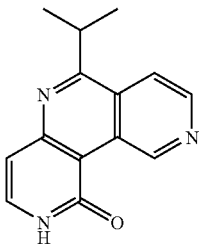

6-isopropylpyrido[4,3-c]-1,6-naphthyridin-1(2H)-one 1-chloro-6-isopropylpyrido[4,3-c]-1,6-naphthyridine was converted to 6-isopropylpyrido[4,3-c]-1,6-naphthyridin-1(2H)-one by the procedure used to make 9-bromo-6-{[(1R)-2-methyl-1-(trifluoromethyl)propyl]amino}benzo[c]-1,6-naphthyridin-1(2H)-one. LRMS (APCI) calc'd for ($C_{14}H_{14}N_3O$) [M+H]+, 240.1; found 240.1.

INTERMEDIATE 12

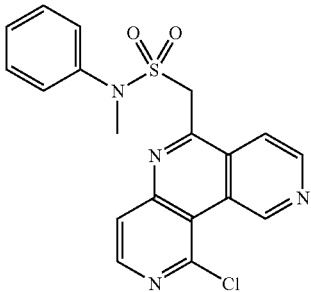

1-(1-chloropyrido[4,3-c]-1,6-naphthyridin-6-yl)-N-methyl-N-phenylmethanesulfonamide To a mixture of methyl {[methyl(phenyl)amino]sulfonyl}acetate (1021 mg, 4.20 mmol) and 1,6-dichloropyrido[4,3-c]-1,6-naphthyridine (350 mg, 1.400 mmol) in toluene (14.0 mL) at 0° C., LHMDS (4.20 mL, 4.20 mmol, 1 M in THF) was added dropwise. The reaction was allowed to warm to room temperature and was stirred for 5 h. The reaction mixture was then heated to 50° C. for 1 h. The reaction mixture was then stirred at room temperature for 72 h. To the reaction mixture, LHMDS (1.400 mL, 1.400 mmol, 1 M in THF) was added, and the reaction was stirred at room temperature overnight. This mixture was poured into aqueous ammonium chloride (saturated). The aqueous layer was extracted with ethyl acetate. The combined organic extracts were filtered through a frit, dried over sodium sulfate, and concentrated under reduced pressure. The residue was purified by column chromatography on silica gel, eluting with ethyl acetate/hexanes, to afford 1-(1-chloropyrido[4,3-c]-1,6-naphthyridin-6-yl)-N-methyl-N-phenylmethanesulfonamide as a brown solid. LRMS (APCI) calc'd for ($C_{19}H_{16}ClN_4O_2S$) [M+H]+, 399.1; found 399.0.

Example 385

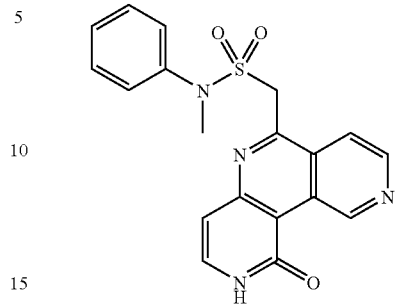

N-methyl-1-(1-oxo-1,2-dihydropyrido[4,3-c]-1,6-naphthyridin-6-yl)-N-phenylmethanesulfonamide A mixture of 1-(1-chloropyrido[4,3-c]-1,6-naphthyridin-6-yl)-N-methyl-N-phenylmethanesulfonamide (45 mg, 0.113 mmol) in acetic acid (2790 µl) and water (1196 µl) was heated to 100° C. and stirred for 2 h. After cooling to room temperature, the reaction mixture was added to aqueous sodium hydroxide (1M). The aqueous layer was extracted with ethyl acetate. The combined organic extracts were dried over sodium sulfate and concentrated under reduced pressure. The residue was purified by preparative HPLC Reverse phase (C-18), eluting with Acetonitrile/Water+0.05% TFA, to afford N-methyl-1-(1-oxo-1,2-dihydropyrido[4,3-c]-1,6-naphthyridin-6-yl)-N-phenylmethanesulfonamide as a yellow solid. $^1$H NMR (500 MHz, $C_2D_6SO$) δ 12.17 (s, 1H), 11.19 (s, 1H), 8.87 (d, 1H), 8.30 (d, 1H), 7.71 (t, 1H), 7.48 (d, 2H), 7.38 (t, 2H), 7.29 (t, 1H), 6.95 (d, 1H), 5.36 (s, 2H), 3.22 (s, 3H). LRMS (APCI) calc'd for ($C_{14}H_{14}N_3O$) [M+H]+, 381.1; found 381.0.

Example 386

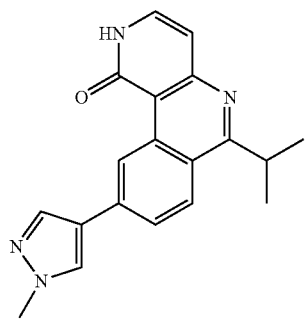

6-isopropyl-9-(1-methyl-1H-pyrazol-4-yl)benzo[c]-1,6-naphthyridin-1(2H)-one 9-bromo-6-isopropylbenzo[c]-1,6-naphthyridin-1(2H)-one (50 mg, 0.16 mmol), 1-methyl-4-(4,4,5,5-tetramethyl-1,3,2-dioxaborolan-2-yl)-1H-pyrazole (66 mg, 0.32 mmol), PdCl$_2$(dppf)-CH$_2$Cl$_2$ adduct (26 mg, 0.032 mmol), DMF (1.7 ml), and 2 M aqueous sodium carbonate (0.16 ml, 0.32 mmol) were combined in a microwave vial and sparged with argon for 5 minutes. The reaction mixture was heated in a microwave reactor at 100° C. for 30 min. The reaction mixture was diluted with MeOH and purified directly by preparative reverse phase HPLC eluting with an acetonitrile/water (with 0.05% TFA modifier) gradient to afford 6-isopropyl-9-(1-methyl-1H-pyrazol-4-yl)benzo[c]-1,6-naphthyridin-1(2H)-one. $^1$H NMR (500 MHz, DMSO D-6) δ 11.69 (br d, 1H), 10.20 (d, 1H), 8.42 (d, 1H), 8.32 (s, 1H), 7.97 (s, 1H), 7.94 (dd, 1H), 7.51 (t, 1H), 6.73 (d, 1H), 4.06 (septet, 1H), 3.92 (s, 3H), 1.37 (d, 6H). LRMS (ESI) calc'd for ($C_{19}H_{18}N_4O$) [M+H]$^+$, 319.1; found 319.1.

The following compounds in Table 18 were prepared according to Scheme 22, using analogous procedures to those used to prepare Example 386.

TABLE 18

| Ex. | Structure | Name | LRMS |
| --- | --- | --- | --- |
| 387 | 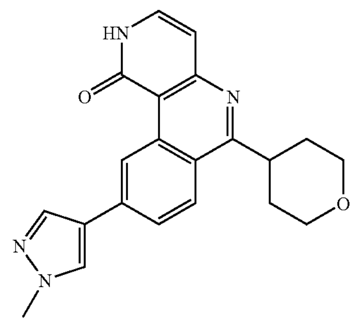 | 9-(1-methyl-1H-pyrazol-4-yl)-6-(tetrahydro-2H-pyran-4-yl)benzo[c]-1,6-naphthyridin-1(2H)-one | Calc'd 361.2, found 361.2 |
| 388 | 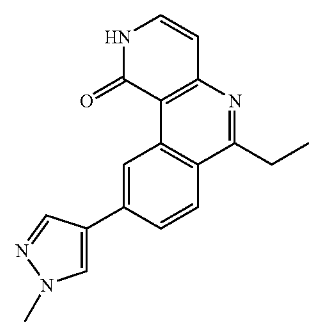 | 6-ethyl-9-(1-methyl-1H-pyrazol-4-yl)benzo[c]-1,6-naphthyridin-1(2H)-one | Calc'd 305.1, found 305.1 |
| 389 | 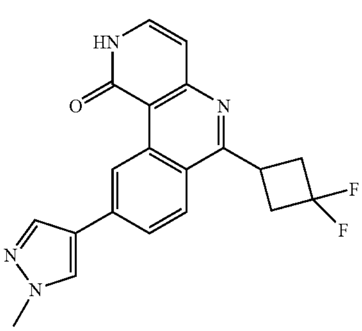 | 6-(3,3-difluorocyclobutyl)-9-(1-methyl-1H-pyrazol-4-yl)benzo[c]-1,6-naphthyridin-1(2H)-one | Calc'd 367.1, found 367.0 |

Example 390

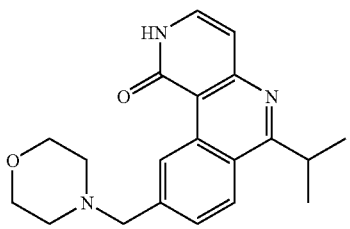

6-isopropyl-9-(morpholin-4-ylmethyl)benzo[c]-1,6-naphthyridin-1(2H)-one

Example 391

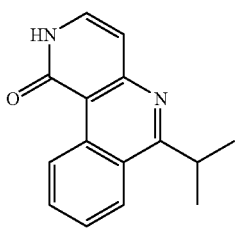

6-isopropylbenzo[c]-1,6-naphthyridin-1(2H)-one 9-bromo-6-isopropylbenzo[c]-1,6-naphthyridin-1(2H)-one (65 mg, 0.21 mmol), potassium 4-trifluoroboratomethylmorpholine (85 mg, 0.41 mmol; prepared according to Molander, G. A.; Sandrock, S. L. *Org. Lett.* 2007, 9, 1597-1600), 2-dicyclohexylphosphino-2',4',6'-triisopropyl-1,1'-biphenyl (20 mg, 0.041 mmol), PdOAc$_2$ (4.6 mg, 0.020 mmol), and cesium carbonate (200 mg, 0.62 mmol) were added to a vial, followed by THF (2.0 ml) and water (0.20 ml). The reaction was purged with argon (subsurface bubbling) for 5 min. The vial was sealed, and the reaction mixture was stirred at 80° C. for 18 hr. The reaction mixture was cooled to room temperature, diluted with ACN and DMF, and purified directly by preparative reverse phase HPLC, eluting with an acetonitrile/water (with 0.05% TFA as a modifier) gradient, to afford 6-isopropyl-9-(morpholin-4-ylmethyl)benzo[c]-1,6-naphthyridin-1(2H)-one as the major product, along with 6-isopropylbenzo[c]-1,6-naphthyridin-1(2H)-one as the minor product.

6-isopropyl-9-(morpholin-4-ylmethyl)benzo[c]-1,6-naphthyridin-1(2H)-one $^1$H NMR (500 MHz, DMSO D-6) δ 11.71 (br s, 1-1), 9.95 (s, 1H), 8.42 (d, 1H), 7.72 (d, 1H), 7.51 (d, 1H), 6.74 (d, 1H), 4.06 (septet, 1H), 3.69 (s, 2H), 3.58 (br m, 4H), 2.41 (br s, 4H), 1.37 (d, 6H). LRMS (ESI) calc'd for (C$_{20}$H$_{23}$N$_3$O$_2$) [M+H]$^+$, 338.2; found 338.1.

6-isopropylbenzo[c]-1,6-naphthyridin-1(2H)-one $^1$H NMR (500 MHz, DMSO D-6) δ 11.76 (br s, 1H), 10.04 (d, 1H), 8.45 (d, 2H), 7.91 (t, 1H), 7.74 (t, 1H), 7.53 (d, 1H), 6.76 (d, 1H), 4.09 (septet, 1H), 1.37 (d, 6H). LRMS (ESI) calc'd for (C$_{15}$H$_{14}$N$_2$O) [M+H]$^+$, 239.1; found 239.1.

The following compound in Table 19 (free base) was prepared according to Scheme 23 using the above procedure for Example 390.

TABLE 19

| Ex. | Structure | Name | LRMS |
|---|---|---|---|
| 392 | 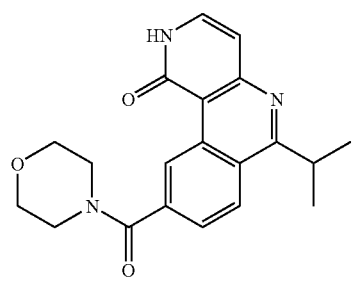 | 6-isopropyl-9-(pyrrolidin-1-ylmethyl)benzo[c]-1,6-naphthyridin-1(2H)-one | Calc'd 322.2, found 322.1 |

Example 393

6-isopropyl-9-(morpholin-4-ylcarbonyl)benzo[c]-1,6-naphthyridin-1(2H)-one 9-bromo-6-isopropylbenzo[c]-1,6-naphthyridin-1(2H)-one (50 mg, 0.16 mmol), molybdenum hexacarbonyl (0.042 g, 0.16 mmol), trans-di-mu-acetatobis[2-(di-o-tolylphosphino)benzyl]dipalladium(II) (7.4 mg, 7.9 mmol), and tri-(t-butyl)phosphonium HBF$_4$ salt (4.6 mg, 0.016 mmol) were added to a vial, followed by dioxane (1.0 ml), DBU (0.095 ml, 0.63 mmol) and morpholine (0.027 ml, 0.32 mmol). The resulting suspension was purged with argon (subsurface bubbling) for 5 min. The reaction mixture was stirred at 100° C. for 16 hr in a sealed vial. The reaction mixture was diluted with ACN, MeOH, and DMSO and purified directly by preparative reverse phase HPLC, eluting with an acetonitrile/water (0.05% TFA modifier) gradient to afford 6-isopropyl-9-(morpholin-4-ylcarbonyl)benzo[c]-1,6-naphthyridin-1(2H)-one. $^1$H NMR (500 MHz, DMSO D-6) δ 11.86 (d, 1H), 10.07 (d, 1H), 8.53 (d, 1H), 7.74 (dd, 1H), 7.57 (t, 1H), 6.78 (dd, 1H), 4.10 (septet, 1H), 3.70 (br s, 4H), 3.55 (br s, 2H), 3.35 (br s, 2H), 1.38 (d, 6H). LRMS (ESI) calc'd for (C$_{20}$H$_{21}$N$_3$O$_3$) [M+H]$^+$, 352.2; found 352.1.

The following compounds in Table 20 were prepared according to Scheme 24 using procedures analogous to those used to prepare Example 393. Example 396 was isolated as a side product in the preparation of Example 395.

For Example 396: $^1$H NMR (500 MHz, CDCl$_3$) δ 11.88 (s, 1H), 10.60 (s, 1H), 8.34 (d, 1H), 8.21 (overlapping m, 2H), 7.58 (t, 1H), 6.88 (d, 1H), 3.98 (m, 1H), 3.57 (t, 2H), 3.51 (q, 2H), 3.29 (dd, 2H), 2.54 (dd, 2H), 1.83 (m, 2H), 1.71-1.62 (overlapping m, 6H), 1.46 (d, 6H)

Example 397

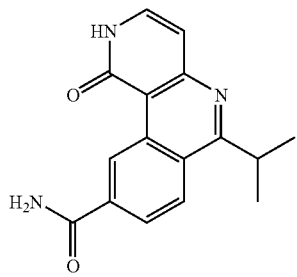

TABLE 20

| Ex. | Structure | Name | LRMS |
|---|---|---|---|
| 394 | 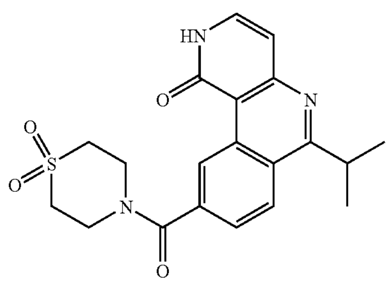 | 9-[(1,1-dioxidothiomorpholin-4-yl)carbonyl]-6-isopropylbenzo[c]-1,6-naphthyridin-1(2H)-one | Calc'd 400.1, found 400.1 |
| 395 | 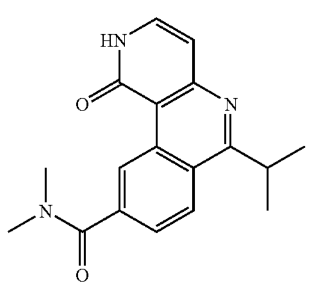 | 6-isopropyl-N,N-dimethyl-1-oxo-1,2-dihydrobenzo[c]-1,6-naphthyridine-9-carboxamide | Calc'd 310.2, found 310.1 |
| 396 | 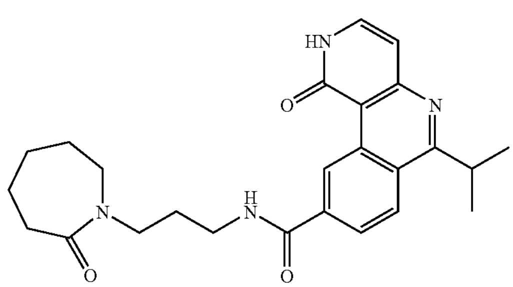 | 6-isopropyl-1-oxo-N-[3-(2-oxoazepan-1-yl)propyl]-1,2-dihydrobenzo[c]-1,6-naphthyridine-9-carboxamide | Calc'd 435.2, found 435.2 |

6-isopropyl-1-oxo-1,2-dihydrobenzo[c]-1,6-naphthyridine-9-carboxamide

Step 1: 6-isopropyl-1-oxo-1,2-dihydrobenzo[c]-1,6-naphthyridine-9-carboxylic acid 9-bromo-6-isopropylbenzo[c]-1,6-naphthyridin-1(2H)-one (200 mg, 0.631 mmol), molybdenum hexacarbonyl (166 mg, 0.631 mmol), trans-di-mu-acetatobis[2-(di-o-tolylphosphino)benzyl]dipalladium(II) (29.6 mg, 0.0320 mmol), and tri-(t-butyl)phosphonium $HBF_4$ salt (18.3 mg, 0.0630 mmol) were added to a vial, followed by dioxane (2 ml), DBU (0.38 ml, 2.52 mmol) and water (0.114 mL, 6.31 mmol). The resulting suspension was purged with argon (subsurface bubbling) for 5 min, the heated at 100° C. for 18 hr. The reaction mixture was cooled to room temperature, diluted with water (25 mL), and LiOH (45.3 mg) was added. The aqueous layer was washed with ethyl acetate (25 mL). The aqueous layer was acidified with 1 M citric acid (2.5 mL), and the resulting solid was collected by vacuum filtration, then dried under high vacuum at 50° C. for 2 hours to afford 6-isopropyl-1-oxo-1,2-dihydrobenzo[c]-1,6-naphthyridine-9-carboxylic acid. LRMS (ESI) calc'd for ($C_{16}H_{14}N_2O_3$) $[M+H]^+$, 283.1; found 283.0.

Step 2: 6-isopropyl-1-oxo-1,2-dihydrobenzo[c]-1,6-naphthyridine-9-carboxamide To a stirred suspension of 6-isopropyl-1-oxo-1,2-dihydrobenzo[c]-1,6-naphthyridine-9-carboxylic acid (78 mg, 0.28 mmol) in DMF (1.0 mL) was added 1,1'-carbonylbis(1H-imidazole) (CDI, 68 mg, 0.42 mmol). The reaction mixture was stirred for 1 hour at room temperature. Ammonium hydroxide (0.19 mL, 1.3 mmol) was added, and the resulting mixture was stirred for 15 minutes. The reaction mixture was diluted with DMF and purified directly by preparative reverse phase HPLC, eluting with an acetonitrile/water (with 0.05% TFA modifier) gradient to afford 6-isopropyl-1-oxo-1,2-dihydrobenzo[c]-1,6-naphthyridine-9-carboxamide. $^1$H NMR (500 MHz, DMSO-D6) δ 11.86 (s, 1H), 10.46 (s, 1H), 8.50 (d, 1H), 8.20 (s, 1H), 8.09 (d, 1H), 7.61 (s, 1H), 7.56 (t, 1H), 6.78 (d, 1H), 4.12 (septet, 1H), 1.37 (d, 6H). LRMS (ESI) calc'd for ($C_{16}H_{15}N_3O_2$) $[M+H]^+$, 282.1; found 282.1.

Example 398

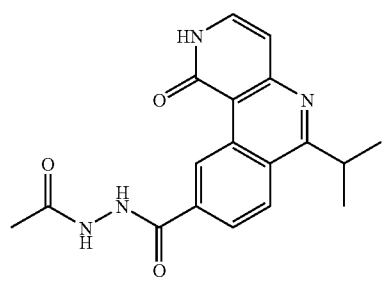

N'-acetyl-6-isopropyl-1-oxo-1,2-dihydrobenzo[c]-1,6-naphthyridine-9-carbohydrazide 9-bromo-6-isopropylbenzo[c]-1,6-naphthyridin-1(2H)-one (100 mg, 0.32 mmol), acetichydrazide (47 mg, 0.63 mmol), molybdenum hexacarbonyl (83 mg, 0.32 mmol), trans-di-mu-acetatobis[2-(di-o-tolylphosphino)benzyl]dipalladium(II) (15 mg, 0.016 mmol), and tri-(t-butyl)phosphonium $HBF_4$ salt (9.2 mg, 0.032 mmol) were combined in a vial, followed by dioxane (2.0 ml), DMA (1.0 ml) and N,N-diisopropylethylamine (0.22 ml, 1.3 mmol). The resulting suspension was purged with argon (subsurface bubbling) for 10 min, and then stirred at 100° C. in a sealed vial for 3 hours. The reaction mixture was cooled to room temperature, diluted with EtOAc (3 mL), and filtered to afford N-acetyl-6-isopropyl-1-oxo-1,2-dihydrobenzo[c]-1,6-naphthyridine-9-carbohydrazide. $^1$H NMR (500 MHz, DMSO-D6) δ 11.88 (d, 1H), 10.53 (s, 1H), 10.47 (d, 1H), 9.97 (s, 1H), 8.56 (d, 1H), 8.06 (dd, 1H), 7.57 (t, 1H), 6.79 (d, 1H), 4.12 (septet, 1H), 1.94 (s, 3H), 1.38 (d, 6H). LRMS (ESI) calc'd for ($C_{18}H_{18}N_4O_3$) $[M+H]^+$, 339.1; found 339.1.

Example 399

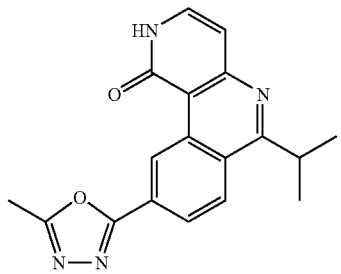

6-isopropyl-9-(5-methyl-1,3,4-oxadiazol-2-yl)benzo[c]-1,6-naphthyridin-1(2H)-one

Step 1: 1-chloro-6-isopropyl-9-(5-methyl-1,3,4-oxadiazol-2-yl)benzo[c]-1,6-naphthyridine

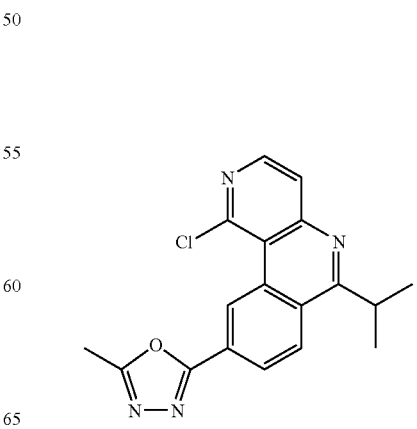

To a stirred suspension of N'-acetyl-6-isopropyl-1-oxo-1,2-dihydrobenzo[c]-1,6-naphthyridine-9-carbohydrazide (30 mg, 0.089 mmol) in ACN (1.0 mL) was added POCl$_3$ (1.0 ml). The resulting suspension was stirred at 100° C. in a sealed vial for 3 hr. The solution was diluted with additional acetonitrile (10 mL), and then added to cooled 6N NaOH (20 mL). The resulting mixture was extracted with EtOAc (1×25 mL). The organic layer was dried over sodium sulfate, filtered and concentrated to afford crude 1-chloro-6-isopropyl-9-(5-methyl-1,3,4-oxadiazol-2-yl)benzo[c]-1,6-naphthyridine that was used directly without further purification. LRMS (ESI) calc'd for (C$_{18}$H$_{15}$ClN$_4$O) [M+H]$^+$, 339.1; found 339.1.

Step 2: 6-isopropyl-9-(5-methyl-1,3,4-oxadiazol-2-yl)benzo[c]-1,6-naphthyridin-1(2H)-one To a stirred solution of 1-chloro-6-isopropyl-9-(5-methyl-1,3,4-oxadiazol-2-yl)benzo[c]-1,6-naphthyridine (50 mg, 0.15 mmol) in dichloromethane (1.0 ml) was added TFA (1.0 mL). The reaction mixture was stirred at room temperature for 3 h. The solution was concentrated to remove most of the solvent (leaving some TFA to promote solubility), diluted with DMF, and purified directly by preparative reverse phase HPLC eluting with an acetonitrile/water (with 0.05% TFA as a modifier) gradient to afford 6-isopropyl-9-(5-methyl-1,3,4-oxadiazol-2-yl)benzo[c]-1,6-naphthyridin-1(2H)-one. $^1$H NMR (500 MHz, DMSO-D6) δ 11.93 (d, 1H), 10.70 (s, 1H), 8.65 (d, 1H), 8.29 (d, 1H), 7.60 (t, 1H), 6.81 (d, 1H), 4.12 (septet, 1H), 2.66 (s, 3H), 1.39 (d, 6H). LRMS (ESI) calc'd for (C$_{18}$H$_{16}$N$_4$O$_2$) [M+H]$^+$, 321.1; found 321.1.

The following example in Table 20 was prepared in analogy to the above Example 399:

3-(9-bromo-6-isopropyl-1-oxo-1,2-dihydrobenzo[c]-1,6-naphthyridin-4-yl)prop-2-ynamide

Step 1: 9-bromo-4-iodo-6-isopropylbenzo[c]-1,6-naphthyridin-1(2H)-one

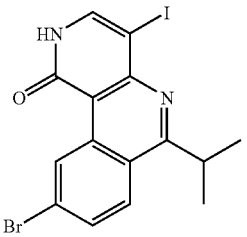

To a stirred suspension of 9-bromo-6-isopropylbenzo[c]-1,6-naphthyridin-1(2H)-one (81 mg, 0.26 mmol) in DMF (1.5 ml) was added NIS (86 mg, 0.38 mmol), and stirred for 24 hours at room temperature. The reaction mixture was diluted with EtOAc until a solution was formed, and washed with a mixture of 10% aqueous sodium thiosulfate and 1N NaOH. The organic layer was dried over sodium sulfate, filtered and concentrated. The crude material was adsorbed on to silica gel and purified by silica gel chromatography using an EtOAc/Hexanes gradient to afford 9-bromo-4-iodo-6-isopropylbenzo[c]-1,6-naphthyridin-1(2H)-one. LRMS (ESI) calc'd for (C$_{15}$H$_{12}$BrIN$_2$O) [M+H]$^+$, 442.9; found 442.8.

TABLE 20

| Ex. | Structure | Name | LRMS |
| --- | --- | --- | --- |
| 400 | 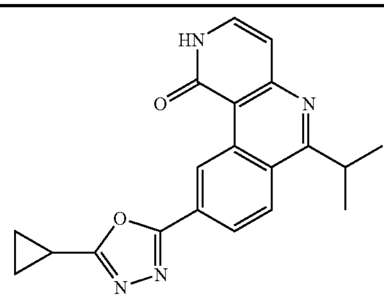 | 9-(5-cyclopropyl-1,3,4-oxadiazol-2-yl)-6-isopropylbenzo[c]-1,6-naphthyridin-1(2H)-one | Calc'd 347.1, found 347.1 |

Example 401

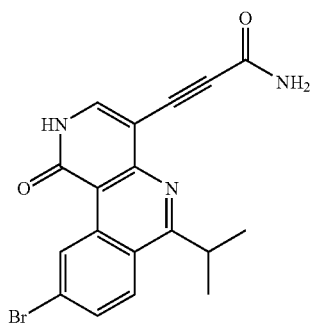

Step 2: 3-(9-bromo-6-isopropyl-1-oxo-1,2-dihydrobenzo[c]-1,6-naphthyridin-4-yl)prop-2-ynamide 9-bromo-4-iodo-6-isopropylbenzo[c]-1,6-naphthyridin-1(2H)-one (140 mg, 0.32 mmol), propynoic acid amide (26 mg, 0.38 mmol), copper (I) iodide (9.0 mg, 0.047 mmol), and Pd(Ph$_3$P)$_4$ (37 mg, 0.032 mmol) were added to a vial, followed by DMF (1.5 ml) and TEA (0.13 ml, 0.95 mmol). The resulting suspension was purged with argon (subsurface bubbling) for 10 min, and then stirred for 15 hr at room temperature. The reaction mixture was diluted with DMF and purified directly by reverse phase preparative HPLC using an acetonitrile/water (with 0.05% TFA as a modifier) gradient to afford 3-(9-bromo-6-isopropyl-1-oxo-1,2-dihydrobenzo[c]-1,6-naphthyridin-4-yl)prop-2-ynamide. $^1$H NMR (500 MHz, DMSO-D6) δ 12.33 (br s, 1H), 10.21 (d, 1H), 8.46 (d, 1H), 8.04 (s, 1H), 7.93 (dd, 1H), 7.91 (br s, 1H), 7.58 (s, 1H), 4.07

(septet, 1H), 1.40 (d, 6H). LRMS (ESI) calc'd for (C₁₈H₁₄BrN₃O₂) [M+H]⁺, 384.0; found 384.0.

Example 402

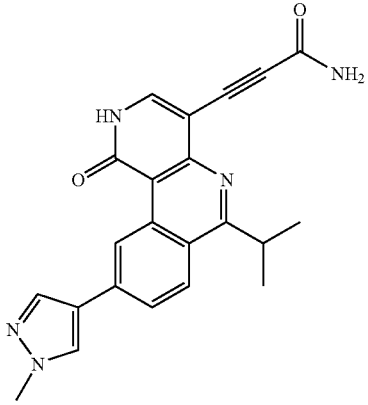

3-[6-isopropyl-9-(1-methyl-1H-pyrazol-4-yl)-1-oxo-1,2-dihydrobenzo[c]-1,6-naphthyridin-4-yl]prop-2-ynamide 3-(9-bromo-6-isopropyl-1-oxo-1,2-dihydrobenzo[c]-1,6-naphthyridin-4-yl)prop-2-ynamide (57 mg, 0.15 mmol), 1-methyl-4-(4,4,5,5-tetramethyl-1,3,2-dioxaborolan-2-yl)-1H-pyrazole (62 mg, 0.30 mmol), and PdCl₂(dppp-CH₂Cl₂ adduct (24 mg, 0.030 mmol) were added to a vial, followed by DMF (1.8 ml) and aqueous sodium carbonate (2M) (0.15 ml, 0.30 mmol). The resulting suspension was purged with argon (subsurface bubbling) for 10 min, then heated in a microwave reactor at 100° C. for 30 min. The mixture was cooled, diluted with DMF, and filtered to remove salts. The solution was purified directly by preparative reverse phase HPLC eluting with an acetonitrile/water (with 0.05% TFA as a modifier) gradient, to afford 3-[6-isopropyl-9-(1-methyl-1H-pyrazol-4-yl)-1-oxo-1,2-dihydrobenzo[c]-1,6-naphthyridin-4-yl]prop-2-ynamide. ¹H NMR (500 MHz, DMSO-D6) δ 12.15 (br s, 1H), 10.15 (s, 1H), 8.46 (d, 1H), 8.34 (s, 1H), 8.01-7.98 (overlapping m, 3H), 7.89 (br s, 1H), 7.56 (br s, 1H), 4.08 (septet, 1H), 3.92 (s, 3H), 1.41 (d, 6H). LRMS (ESI) calc'd for (C₂₂H₁₉N₅O₂) [M+H]⁺, 386.2; found 386.1.

Example 403

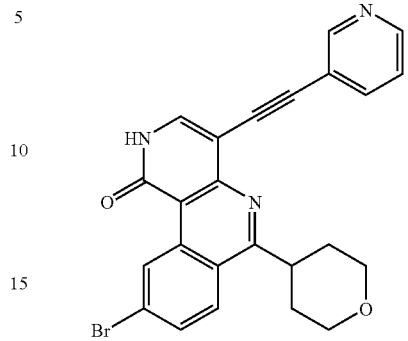

9-bromo-4-(pyridin-3-ylethynyl)-6-(tetrahydro-2H-pyran-4-yl)benzo[c]-1,6-naphthyridin-1(2H)-one The starting material 9-bromo-4-iodo-6-(tetrahydro-2H-pyran-4-yl)benzo[c]-1,6-naphthyridin-1(2H)-one was prepared in analogy to the preparation of 9-bromo-4-iodo-6-isopropylbenzo[c]-1,6-naphthyridin-1(2H)-one required for the synthesis of Example 403.

9-bromo-4-iodo-6-(tetrahydro-2H-pyran-4-yl)benzo[c]-1,6-naphthyridin-1(2H)-one (50 mg, 0.10 mmol), di-mu-chlorobis[(eta-allyl)palladium(II)] (2.3 mg, 6.2 µmol), copper iodide (2.4 mg, 0.012 mmol) and tri(2-furyl)phosphine (2.9 mg, 0.012 mmol) were added to a vial, followed by acetonitrile (1.0 mL), diisopropylamine (44 uL, 0.71 mmol) and 2-ethynyl pyridine (32 mg, 0.31 mmol). The resulting suspension was heated to 45° C. and stirred for four hours. The reaction mixture was diluted with 4 mL DMF and 100 uL TFA, then purified directly by preparative reverse phase HPLC eluting with an acetonitrile/water gradient (with 0.05% TFA as a modifier) to afford 9-bromo-4-(pyridin-3-ylethynyl)-6-(tetrahydro-2H-pyran-4-yl)benzo[c]-1,6-naphthyridin-1(2H)-one. ¹H NMR (500 MHz, DMSO-D6) δ 12.38 (br s, 1H), 10.28 (s, 1H), 8.75 (s, 1H), 8.56 (d, 1H), 8.54 (d, 1H), 8.09 (s, 1H), 7.93 (overlapping t, 2H), 7.49 (dd, 1H), 4.02 (overlapping m, 3H), 3.65 (t, 2H), 2.11 (m, 2H), 1.89 (d, 2H). LRMS (ESI) calc'd for (C₂₄H₁₈BrN₃O₂) [M+H]⁺, 460.1; found 460.0.

The following examples in Table 21 were prepared according to Scheme 25 using analogous procedures to those used to prepare Examples 401-402.

TABLE 21

| Ex. | Structure | Name | LRMS |
|---|---|---|---|
| 404 | 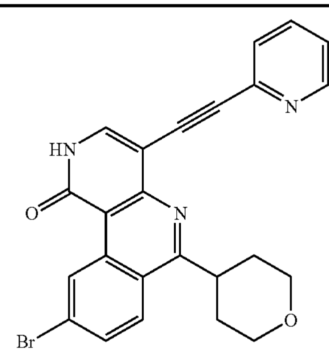 | 9-bromo-4-(pyridin-2-ylethynyl)-6-(tetrahydro-2H-pyran-4-yl)benzo[c]-1,6-naphthyridin-1(2H)-one | Calc'd 460.1, found 460.0 |

TABLE 21-continued

| Ex. | Structure | Name | LRMS |
|---|---|---|---|
| 405 | 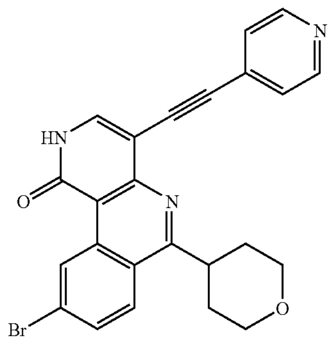 | 9-bromo-4-(yridine-4-ylethynyl)-6-(tetrahydro-2H-pyran-4-yl)benzo[c]-1,6-naphthyridin-1(2H)-one | Calc'd 460.0, found 460.0 |

Example 406

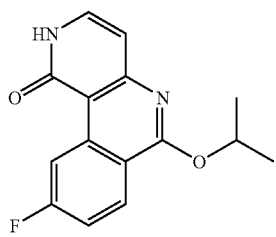

9-fluoro-6-isopropoxybenzo[c]-1,6-naphthyridin-1(2H)-one

Step 1: 1-chloro-9-fluoro-6-isopropoxybenzo[c]-1,6-naphthyridine

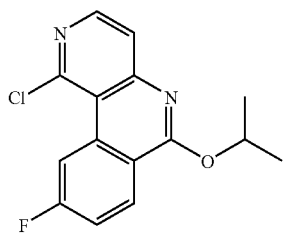

To a stirred suspension of 1-chloro-9-fluoro-6-isopropoxybenzo[c]-1,6-naphthyridine (200 mg, 0.75 mmol) and isopropyl alcohol (0.060 mL, 0.82 mmol) in DMF (3.0 mL) was added NaH (36 mg, 0.90 mmol) in one portion at 0° C. The cooling bath was removed and the reaction mixture was allowed to warm to room temperature. After 1 hour, and additional portion of isopropanol (0.5 eq, 0.030 mL) and NaH (15 mg) were added, and the reaction mixture was stirred for 1 hour. The reaction mixture was diluted with ethyl acetate, and quenched with water (slowly, gas evolution). The organic layer was washed with brine (30 mL), dried over sodium sulfate, filtered and concentrated. The crude material was adsorbed on to silica gel and purified by silica gel chromatography using an EtOAc/Hexanes gradient to afford 1-chloro-9-fluoro-6-isopropoxybenzo[c]-1,6-naphthyridine. LRMS (ESI) calc'd for $(C_{15}H_{12}ClFN_2O)$ $[M+H]^+$, 291.1; found 291.0.

Step 2: 9-fluoro-6-isopropoxybenzo[c]-1,6-naphthyridin-1(2H)-one 1-chloro-9-fluoro-6-isopropoxybenzo[c]-1,6-naphthyridine (107 mg, 0.368 mmol), potassium hydroxide (83.0 mg, 1.47 mmol), 2-di-t-butylphosphino-2',4',6'-tri-1-propyl-1,1'-biphenyl (31.3 mg, 0.0740 mmol), and $Pd_2(dba)_3$ (33.7 mg, 0.0370 mmol) were combined in a vial. 1,4-Dioxane (2.2 mL) and water (1.5 mL), were added, and the resulting suspension was degassed with argon for 10 min. The reaction mixture was heated to 100° C. and stirred for 16 h. After cooling to room temperature, the reaction mixture was added to saturated aqueous ammonium chloride (40 mL). The aqueous layer was extracted with ethyl acetate (2×40 mL). The combined organic extracts were dried over $Na_2SO_4$, filtered and concentrated to a crude residue. The crude material was purified by preparative reverse phase HPLC eluting with an acetonitrile/water (with 0.05% TFA as a modifier) gradient, to afford 9-fluoro-6-isopropoxybenzo[c]-1,6-naphthyridin-1(2H)-one. $^1$H NMR (500 MHz, DMSO-D6) δ 11.74 (s, 1H), 9.55 (d, 1H), 8.33 (dd, 1H), 7.53 (overlapping m, 2H), 6.56 (d, 1H), 5.64 (septet, 1H), 1.43 (d, 6H). LRMS (ESI) calc'd for $(C_{15}H_{13}FN_2O_2)$ $[M+H]^+$, 273.1; found 273.0.

The following examples in Table 22 were prepared according to Scheme 26 in analogy to the procedures used to prepare Example 406.

TABLE 22

| Ex. | Structure | Name | LRMS |
|---|---|---|---|
| 407 | 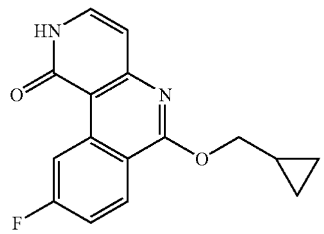 | 6-(cyclopropylmethoxy)-9-fluorobenzo[c]-1,6-naphthyridin-1(2H)-one | Calc'd 285.1, found 285.0 |
| 408 | 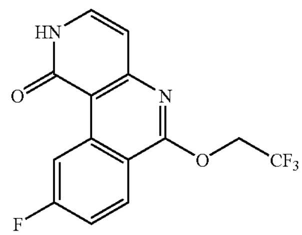 | 9-fluoro-6-(2,2,2-trifluoroethoxy)benzo[c]-1,6-naphthyridin-1(2H)-one | Calc'd 313.1, found 313.0 |
| 409 | 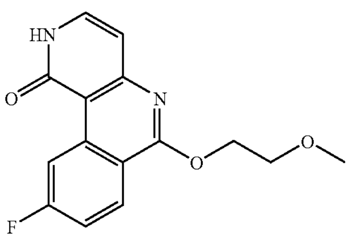 | 9-fluoro-6-(2-methoxyethoxy)benzo[c]-1,6-naphthyridin-1(2H)-one | Calc'd 289.1, found 289.0 |

Example 410

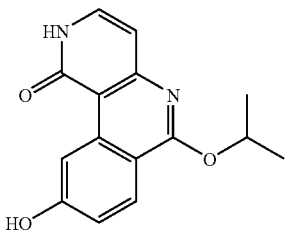

9-hydroxy-6-isopropoxybenzo[c]-1,6-naphthyridin-1(2H)-one

Step 1: 9-bromo-1-chloro-6-isopropoxybenzo[c]-1,6-naphthyridine

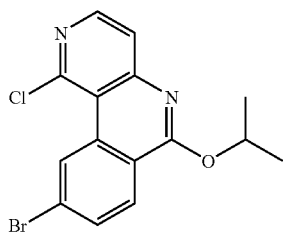

9-bromo-1-chloro-6-isopropoxybenzo[c]-1,6-naphthyridine was prepared in analogy to Example 406, starting from 9-bromo-1,6-dichlorobenzo[c]-1,6-naphthyridine. LRMS (ESI) calc'd for ($C_{15}H_{12}BrClN_2O$) [M+H]$^+$, 351.0; found 350.9.

Step 2: 9-hydroxy-6-isopropoxybenzo[c]-1,6-naphthyridin-1(2H)-one 9-bromo-1-chloro-6-isopropoxybenzo[c]-1,6-naphthyridine 1 (80 mg, 0.23 mmol), potassium hydroxide (51 mg, 0.91 mmol), 2-di-t-butylphosphino-2',4',6'-tri-1-propyl-1,1'-biphenyl (39 mg, 0.091 mmol), and Pd$_2$(dba)$_3$ (42 mg, 0.046 mmol) were combined in a vial. 1,4-Dioxane (1.4 mL) and water (0.91 mL) were added, and the mixture was degassed with argon for 10 min. The resulting suspension was heated at 100° C. for 30 min. The reaction was cooled to room temperature, then added to saturated aqueous ammonium chloride (40 mL). The aqueous layer was extracted with ethyl acetate (2×40 mL). The combined organic extracts were dried over sodium sulfate, filtered and concentrated. The crude residue was purified by preparative reverse phase HPLC, eluting with an acetonitrile/water (with 0.05% TFA modifier) gradient, to afford 9-hydroxy-6-isopropoxybenzo[c]-1,6-naphthyridin-12H)-one. $^1$H NMR (500 MHz, DMSO-D6) δ 11.51 (br d, 1H), 10.41 (br s, 1H), 9.21 (d, 1H), 8.10 (d, 1H), 7.41 (t, 1H), 7.09 (dd, 1H), 6.48 (d, 1H), 5.60 (septet, 1H), 1.40 (d, 6H). LRMS (ESI) calc'd for ($C_{15}H_{14}N_2O_3$) [M+H]$^+$, 271.1; found 271.0.

Example 411

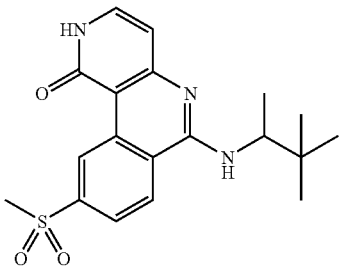

9-(methylsulfonyl)-6-[(1,2,2-trimethylpropyl)amino]benzo[c]-1,6-naphthyridin-1(2H)-one Step 1: 9-iodo-6-[(1,2,2-trimethylpropyl)amino]benzo[c]-1,6-naphthyridin-1(2H)-one

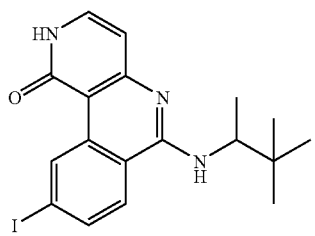

9-iodo-6-[(1,2,2-trimethylpropyl)amino]benzo[c]-1,6-naphthyridin-1(2H)-one was prepared from 9-bromo-6-[(1,2,2-trimethylpropyl)amino]benzo[c]-1,6-naphthyridin-1(2H)-one utilizing a procedure found in the following reference: Klapars, A.; Buchwald, *J. Am. Chem. Soc.* 2002, 14844-14845.

9-bromo-6-[(1,2,2-trimethylpropyl)amino]benzo[c]-1,6-naphthyridin-1(2H)-one (120 mg, 0.31 mmol), copper(I) iodide (5.9 mg, 0.031 mmol), and sodium iodide (93 mg, 0.62 mmol) were combined in a vial. Butan-1-ol (1.0 ml) and trans-(1R,2R)—N,N-bismethyl-1,2-cyclohexanediamine (9.9 µl, 0.062 mmol) were added, and the resulting suspension was purged with argon (subsurface bubbling) for 5 min. The reaction mixture was heated to 130° C., and stirred for 22 hours. After cooling to room temperature, the reaction mixture was partitioned between ethyl acetate (40 mL) and brine (40 mL). The organic layer was washed with additional brine (1×40 ml). The first aqueous layer was back-extracted with ethyl acetate (1×40 mL). The combined organics were dried over sodium sulfate, filtered and concentrated. The residue was purified by column chromatography on silica gel (solid $SiO_2$ loading) using an EtOAc/Hexanes gradient to afford 9-iodo-6-[(1,2,2-trimethylpropyl)amino]benzo[c]-1,6-naphthyridin-1(2H)-one. LRMS (ESI) calc'd for ($C_{18}H_{20}IN_3O$) [M+H]+, 422.1; found 422.0.

Step 2: 9-(methylsulfonyl)-6-[(1,2,2-trimethylpropyl)amino]benzo[c]-1,6-naphthyridin-1(2H)-one 9-(methylsulfonyl)-6-[(1,2,2-trimethylpropyl)amino]benzo[c]-1,6-naphthyridin-1(2H)-one was prepared from 9-iodo-6-[(1,2,2-trimethylpropyl)amino]benzo[c]-1,6-naphthyridin-1(2H)-one utilizing a procedure found in the following reference: Zhu, W.; Ma, D. *J. Org. Chem.* 2005, 70, 2696-2700.

9-Iodo-6-[(1,2,2-trimethylpropyl)amino]benzo[c]-1,6-naphthyridin-1(2H)-one (130 mg, 0.31 mmol), copper(I) iodide (5.9 mg, 0.031 mmol), L-proline (7.1 mg, 0.062 mmol), sodium hydroxide (2.5 mg, 0.062 mmol), and methanesulfinic acid sodium salt (41 mg, 0.40 mmol) were combined in a vial. DMSO (2.0 ml) was added, and the resulting suspension was purged with argon (subsurface bubbling) for 5 min. The reaction mixture was stirred at 95° C. for 24 h. The crude material was precipitated out of solution by adding 2 mL of MeOH, followed by 1.5 mL of water. The solids were collected by vacuum filtration, and purified by preparative reverse phase HPLC, eluting with an acetonitrile/water (with 0.05% TFA as a modifier) gradient, to afford 9-(methylsulfonyl)-6-[(1,2,2-trimethylpropyl)amino]benzo[c]-1,6-naphthyridin-1(2H)-one. $^1$H NMR (500 MHz, DMSO-D6) δ 11.33 (br s, 1H), 10.45 (s, 1H), 8.74 (d, 1H), 8.01 (dd, 1H), 7.59 (br d, 1H), 7.36 (d, 1H), 6.36 (d, 1H), 4.71 (pentet, 1H), 3.25 (s, 3H), 1.17 (d, 3H), 0.93 (s, 9H). LRMS (ESI) calc'd for ($C_{19}H_{23}N_3O_3S$) [M+H]+, 374.1; found 374.1.

Example 412

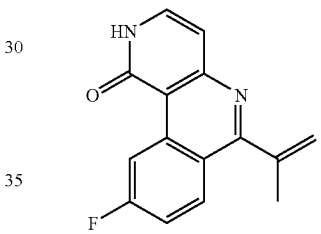

9-fluoro-6-isopropenylbenzo[c]-1,6-naphthyridin-1(2H)-one

Step 1: 1-butoxy-9-fluorobenzo[c]-1,6-naphthyridin-6-yl trifluoromethanesulfonate

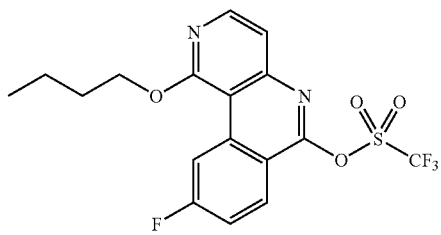

To a stirred suspension of 1-butoxy-9-fluorobenzo[c]-1,6-naphthyridin-6(5H)-one (2.00 g, 6.99 mmol) in THF (80 mL) was added N-phenylbis(trifluoromethansulfonimide) (9.98 g, 27.9 mmol), and cesium carbonate (9.10 g, 27.9 mmol). The reaction mixture was stirred at 65° C. for 30 minutes. The reaction was cooled and diluted with EtOAc (50 mL), water (50 mL), and saturated aqueous sodium carbonate (100 mL). The organic layer was dried over sodium sulfate, filtered, and concentrated to a crude residue that was adsorbed on to silica gel. The solid mixture was purified by column chromatography on silica gel eluting with an EtOAc/hexanes gradient to afford 1-butoxy-9-fluorobenzo[c]-1,6-naphthyridin-6-yl trifluoromethanesulfonate contaminated with approximately an equimolar amount of unreacted N-phenylbis(trifluoromethansulfonimide). The level of this impurity can be reduced if necessary by using the following procedure:

To a stirred solution of the crude material in DCM (50 mL) was added 10 grams of PL-OH® MP-resin (1.92 mMol/gram loading, from Varian PolymerLabs). The resulting suspension was stirred overnight at room temperature. The resin was removed by vacuum filtration, and the resulting filtrate was concentrated to afford 1-butoxy-9-fluorobenzo[c]-1,6-naphthyridin-6-yl trifluoromethanesulfonate. LRMS (ESI) calc'd for $(C_{17}H_{14}F_4N_2O_4S)$ $[M+H]^+$, 419.1; found 419.0.

Step 2: 1-butoxy-9-fluoro-6-isopropenylbenzo[c]-1,6-naphthyridine

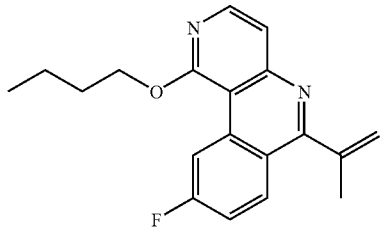

1-butoxy-9-fluorobenzo[c]-1,6-naphthyridin-6-yl trifluoromethanesulfonate (1.00 g, 2.39 mmol), potassium phosphate tribasic (1.52 g, 7.17 mmol), palladium(II) acetate (0.0540 g, 0.239 mmol), and tricyclohexylphosphine (0.134 g, 0.478 mmol) were combined in pressure vessel. Toluene (20 ml), water (6.67 ml), and isopropenylboronic acid pinacol ester (0.899 ml, 4.78 mmol) were added. The resulting suspension was purged with argon (subsurface bubbling) for 10 min. The reaction mixture was stirred in a sealed pressure vessel at 100° C. for 2.5 h. After cooling the reaction mixture was diluted with EtOAc, and washed with aqueous ammonium chloride. The organic layer was dried over sodium sulfate, filtered, and concentrated to a crude residue that was adsorbed on to silica gel and purified by column chromatography on silica gel eluting with an EtOAc/hexane gradient to afford 1-butoxy-9-fluoro-6-isopropenylbenzo[c]-1,6-naphthyridine. LRMS (ESI) calc'd for $(C_{19}H_{19}FN_2O)$ $[M+H]^+$, 311.1; found 311.1.

Step 3: 9-fluoro-6-isopropenylbenzo[c]-1,6-naphthyridin-1(2H)-one

To a stirred suspension of 1-butoxy-9-fluoro-6-isopropenylbenzo[c]-1,6-naphthyridine (30 mg, 0.097 mmol) in water (0.5 ml) was added sulfuric acid (0.5 ml) (CAUTION: EXOTHERM). The reaction mixture was stirred for 15 h at 100° C. The reaction was diluted with EtOAc (30 mL) and water (30 mL). To the resulting biphasic mixture was added NaOH (0.85 g, 21 mmol) portionwise to make the aqueous layer basic. The organic layer was dried over sodium sulfate, filtered and concentrated. The crude residue was dissolved in 3 ml DMF and 100 uL of TFA, and purified by preparative reverse phase HPLC eluting with an acetonitrile/water+(with 0.05% TFA as a modified) gradient, to afford 9-fluoro-6-isopropenylbenzo[c]-1,6-naphthyridin-1(2H)-one. $^1$H NMR (500 MHz, DMSO-D6) δ 11.92 (br s, 1H), 9.74 (dd, 1H), 8.41 (dd, 1H), 7.64-7.60 (overlapping m, 2H), 6.78 (d, 1H), 5.70 (s, 1H), 5.22 (s, 1H), 2.25 (s, 3H). LRMS (ESI) calc'd for $(C_{15}H_{11}FN_2O)$ $[M+H]^+$, 255.1; found 255.0.

Example 413

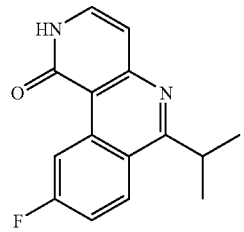

9-fluoro-6-isopropylbenzo[c]-1,6-naphthyridin-1(2H)-one (HCl salt)

Step 1: 1-butoxy-9-fluoro-6-isopropylbenzo[c]-1,6-naphthyridine

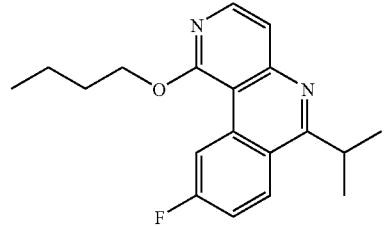

1-butoxy-9-fluoro-6-isopropenylbenzo[c]-1,6-naphthyridine (50 mg, 0.161 mmol) and 5% Pd on Carbon; Type A470129-5® (Johnson Matthey) (5 mg, 0.161 mmol) were combined in a vial. The vial was flushed with nitrogen for several minutes, and then EtOH (1.0 ml) was added. The reaction mixture was stirred under hydrogen (balloon pressure) for 6 hr. The reaction mixture was flushed with nitrogen, diluted with EtOAc (5 mL), and then filtered through a syringe filter to remove Pd/C. The filtrate was concentrated, and the resulting residue was adsorbed on to silica gel, then purified by column chromatography on silica gel eluting with an EtOAc/hexanes gradient to afford 1-butoxy-9-fluoro-6-isopropylbenzo[c]-1,6-naphthyridine. LRMS (ESI) calc'd for $(C_{19}H_{21}FN_2O)$ $[M+H]^+$, 313.2; found 313.1.

Step 2: 9-fluoro-6-isopropylbenzo[c]-1,6-naphthyridin-1(2H)-one

To a stirred solution of 1-butoxy-9-fluoro-6-isopropylbenzo[c]-1,6-naphthyridine (33 mg, 0.11 mmol) in tetrahydrofuran (1.0 ml) was added 6N HCl (1.0 ml). The reaction mixture was stirred at 100° C. for 2 h, and then cooled to room temperature. The yellow precipitate was collected by vacuum filtration (rinsing the filter cake with THF) to afford 9-fluoro-6-isopropylbenzo[c]-1,6-naphthyridin-1(2H)-one (HCl salt). $^1$H NMR (500 MHz, DMSO-D6) δ 11.89 (br s, 1H), 9.76 (dd, 1H), 8.59 (dd, 1H), 7.63 (dt, 1H), 7.59 (t, 11-1), 6.79 (d, 1H), 6.33 (br peak, HCL/H$_2$O), 4.09 (septet, 1H), 1.37 (d, 6H). LRMS (ESI) calc'd for (C$_{15}$H$_{13}$FN$_2$O) [M+H]$^+$, 257.1; found 257.1.

Example 414

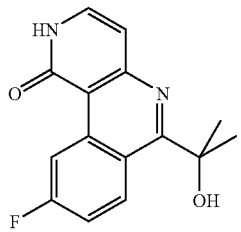

9-fluoro-6-(1-hydroxy-1-methylethyl)benzo[c]-1,6-naphthyridin-1(2H)-one (HBr salt)

Step 1: 1-(1-butoxy-9-fluorobenzo[c]-1,6-naphthyridin-6-yl)ethanone

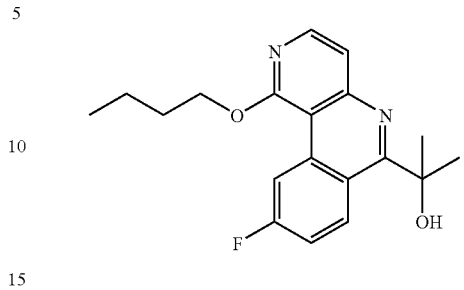

To a stirred solution of 1-butoxy-9-fluoro-6-isopropenyl-benzo[c]-1,6-naphthyridine (100 mg, 0.320 mmol) in tetrahydrofuran (1.0 ml) and water (0.25 ml) was added 4-methylmorpholine 4-oxide (NMO) (39.6 mg, 0.338 mmol) followed by osmium tetroxide (525 uL of a 4 wt % aqueous solution. The reaction mixture was stirred at room temperature for 1 hr. Additional tetrahydrofuran (1.0 ml) and water (0.25 ml) were added, followed by an additional portion of NMO (39.6 mg, 0.338 mmol). The reaction mixture was partitioned between EtOAc and water. The organic layer was dried over sodium sulfate, filtered, and concentrated to a crude residue that was adsorbed on to silica gel and purified by silica gel chromatography eluting with an EtOAc/hexanes gradient to afford 1-(1-butoxy-9-fluorobenzo[c]-1,6-naphthyridin-6-yl)ethanone. LRMS (ESI) calc'd for (C$_{18}$H$_{17}$FN$_2$O$_2$) [M+H]$^+$, 313.1; found 313.1.

Step 2: 2-(1-butoxy-9-fluorobenzo[c]-1,6-naphthyridin-6-yl)propan-2-ol

To a stirred solution of 1-(1-butoxy-9-fluorobenzo[c]-1,6-naphthyridin-6-yl)ethanone (59 mg, 0.19 mmol) in tetrahydrofuran (2.0 ml) was added methylmagnesium bromide (1.4 M in toluene/THF 75:25; 0.202 ml, 0.283 mmol) dropwise at –78° C. The cooling bath was removed, and the resulting suspension was allowed to warm to room temperature. The reaction mixture was stirred for 30 minutes, and then quenched with saturated aqueous ammonium chloride (5 mL). Water was added, and the mixture extracted with EtOAc. The organic layer was dried over sodium sulfate, filtered and concentrated to a crude solid that was adsorbed on to silica gel and purified by column chromatography on silica gel eluting with an EtOAc/hexanes gradient to afford 2-(1-butoxy-9-fluorobenzo[c]-1,6-naphthyridin-6-yl)propan-2-ol. LRMS (ESI) calc'd for (C$_{19}$H$_{21}$FN$_2$O$_2$) [M+H]$^+$, 329.2; found 329.1.

Step 3: 9-fluoro-6-(1-hydroxy-1-methylethyl)benzo[c]-1,6-naphthyridin-1(2H)-one (HBr salt)

A suspension of 2-(1-butoxy-9-fluorobenzo[c]-1,6-naphthyridin-6-yl)propan-2-ol (30 mg, 0.091 mmol) in HBr/acetic acid (33% wt) (1.0 ml) was stirred for 22 hr at room temperature. The resulting solution was concentrated to a crude oil that solidified on standing. Acetonitrile (5 ml) was added, and then concentrated to dryness in an attempt to drive off all acetic acid. The resulting solids were triturated with EtOAc (1 mL). Collection of the solids by vacuum filtration affords 9-fluoro-6-(1-hydroxy-1-methylethyl)benzo[c]-1,6-naphthyridin-1(2H)-one (HBr salt). $^1$H NMR (500 MHz, DMSO-D6) δ 11.90 (br d, 1H), 9.80 (dd, 1H), 9.40 (dd, 1H), 7.61-7.57 (overlapping m, 2H), 6.77 (d, 1H), 6.46 (br peak, HBr/H$_2$O, possibly OH peak), 1.71 (s, 6H). LRMS (ESI) calc'd for (C$_{15}$H$_{13}$FN$_2$O$_2$) [M+H]$^+$, 273.1; found 273.0.

Example 415

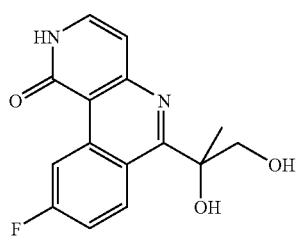

6-(1,2-dihydroxy-1-methylethyl)-9-fluorobenzo[c]-1,6-naphthyridin-1(2H)-one (HCl salt)

Step 1: 2-(1-butoxy-9-fluorobenzo[c]-1,6-naphthyridin-6-yl)propane-1,2-diol

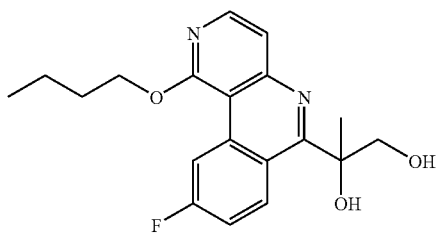

To a stirred solution of 1-butoxy-9-fluoro-6-isopropenyl-benzo[c]-1,6-naphthyridine (50 mg, 0.16 mmol) in tetrahydrofuran (1.0 ml) and water (0.25 ml) was added a solution of osmium tetroxide (4 wt % in water; 10.2 uL, 0.41 mg of osmium tetroxide, 1.6 μmol). NMO (0.20 g, 0.17 mmol) was added, and the reaction mixture was stirred at room temperature for 15 hr. Added 60 uL of additional osmium tetroxide solution, and continued stirring at room temperature for an additional 24 hr. The reaction mixture was quenched with aqueous saturated sodium sulfite (40 mL), and extracted with EtOAc (40 mL). The organic layer was dried over sodium sulfate, filtered, and concentrated to a crude residue that was adsorbed on to silica gel. The resulting residue was purified by column chromatography on silica gel eluting with an EtOAc/hexanes gradient to afford 2-(1-butoxy-9-fluorobenzo[c]-1,6-naphthyridin-6-yl)propane-1,2-diol. LRMS (ESI) calc'd for ($C_{19}H_{21}FN_2O_3$) [M+H]$^+$, 345.2; found 345.1.

Step 2: 6-(1,2-dihydroxy-1-methylethyl)-9-fluorobenzo[c]-1,6-naphthyridin-1(2H)-one (HCl salt)

The same procedure to prepare 9-fluoro-6-isopropylbenzo[c]-1,6-naphthyridin-1(2H)-one was used to furnish 6-(1,2-dihydroxy-1-methylethyl)-9-fluorobenzo[c]-1,6-naphthyridin-1(2H)-one (HCl salt). $^1$H NMR (500 MHz, DMSO-D6) δ 11.91 (br d, 1H), 9.80 (dd, 1H), 9.36 (dd, 1H), 7.61-7.57 (overlapping m, 2H), 6.80 (d, 1H) 5.91 (br peak, HCl, H$_2$O, OH's), 3.91 (d, 1H), 3.83 (d, 1H), 1.67 (s, 3H). LRMS (ESI) calc'd for ($C_{15}H_{13}FN_2O_3$) [M+H]$^+$, 289.1; found 289.0.

Example 416

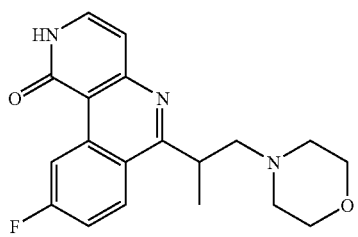

9-fluoro-6-(1-methyl-2-morpholin-4-ylethyl)benzo[c]-1,6-naphthyridin-1(2H)-one Step 1: 6-(2-bromo-1-methylethyl)-9-fluorobenzo[c]-1,6-naphthyridin-1(2H)-one (HBr salt)

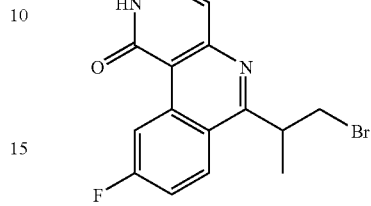

A solution of 1-butoxy-9-fluoro-6-isopropenylbenzo[c]-1,6-naphthyridine (26 mg, 0.063 mmol) in HBr/acetic acid (33% wt) (1.0 ml) was stirred for 18 hr at room temperature. The reaction mixture was concentrated to a crude solid that was taken up into acetonitrile (5 mL) and concentrated again in an attempt to drive off more acetic acid. The resulting solid was triturated with EtOAc (1 mL), then collected by vacuum filtration to afford 6-(2-bromo-1-methylethyl)-9-fluorobenzo[c]-1,6-naphthyridin-1(2H)-one (HBr salt). LRMS (ESI) calc'd for ($C_{15}H_{12}BrFN_2O$) [M+H]$^+$, 335.0; found 335.0.

Step 2: 9-fluoro-6-(1-methyl-2-morpholin-4-ylethyl)benzo[c]-1,6-naphthyridin-1(2H)-one A suspension of 6-(2-bromo-1-methylethyl)-9-fluorobenzo[c]-1,6-naphthyridin-1(2H)-one (HBr salt) (25 mg, 0.060 mmol) in morpholine (1.0 mL) was stirred at 100° C. for 1 h. After cooling to room temperature, acetonitrile was added, and the resulting solution was concentrated to a crude residue. The resulting crude residue was purified by preparative reverse phase HPLC eluting with an acetonitrile/water (with 0.05% TFA as a modifier) gradient to afford 9-fluoro-6-(1-methyl-2-morpholin-4-ylethyl)benzo[c]-1,6-naphthyridin-1(2H)-one. $^1$H NMR (500 MHz, DMSO-D6). δ 11.86 (br d, 1H), 9.76 (dd, 1H), 8.63 (dd, 1H), 7.62 (br t, 1H), 7.57 (br t, 1H), 6.76 (d, 1H), 4.20 (br m, 1H), 3.47 (br s, 4H), 2.80 (br dd, 1H), 2.65 (br m, 1H), 2.43 (br s, 4H), 1.33 (d, 3H). LRMS (ESI) calc'd for ($C_{19}H_{20}FN_3O_2$) [M+H]$^+$, 342.2; found 342.1.

Pharmaceutical Composition

As a specific embodiment of this invention, 100 mg of 9-bromo-6-{[(1R)-2-methyl-1-(trifluoromethyl)propyl]amino}benzo[c]-1,6-naphthyridin-1(2H)-one, is formulated with sufficient finely divided lactose to provide a total amount of 580 to 590 mg to fill a size 0, hard-gelatin capsule.

Biological Assays

JAK1 Enzyme Assay

For the JAK1 enzyme assay, reactions (50 uL) contained 5×IVGN buffer (50 mM Hepes, pH 7.5, 10 mM MgCl$_2$, 0.01% Brij-35, 1 mM EGTA, 0.1 mg/ml BSA), 2 mM DTT, 2.0 μM peptide substrate, 25 μM MgATP, 400 pM JAK1 enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103) Peptide substrate is amino hexanoyl biotin-EQEDEPEGDY-FEWLE-NH$_2$ (SEQ. ID NO.: 1); in DMSO.

JAK2 Kinase Activity Inhibition Assay and Determination of IC$_{50}$

The kinase activity was measured using a modified version of the homogeneous time-resolved tyrosine kinase assay described in Park et al. *Anal. Biochem.* 269, 94-104 (1999).

The procedure for determining the potency of a compound to inhibit JAK2 kinase comprises the following steps:
1. prepare 3-fold serial diluted compound/inhibitor solutions in 100% (DMSO) at 20× of the final desired concentrations in a 96 well plate;
2. prepare a master reaction mix containing 6.67 mM MgCl$_2$, 133.3 mM NaCl, 66.7 mM Tris-HCl (pH 7.4), 0.13 mg/ml BSA, 2.67 mM dithiothreitol, 0.27 recombinant JAK2 and 666.7 nM biotinylated synthetic peptide substrate (biotin-ahx-EQEDEPEGDYFEWLE-CONH$_2$) (SEQ. ID NO.: 1);
3. in a black assay plate, add 2.5 µl compound/inhibitor (or DMSO) and 37.5 µl master reaction mix per well; initiate the kinase reaction by adding 10 µl of 75 µM MgATP per well, allow the reactions to proceed for 80 minutes at room temperate; (the final conditions for the reactions are: 50 nM JAK2 JH1 domain (Upstate), 2.0 µM substrate, 15 µM MgATP, 5 mM MgCl$_2$, 100 mM NaCl, 2 mM DTT, 0.1 mg/ml BSA, 50 mM Tris (pH 7.4) and 5% DMSO);
4. stop the kinase reaction with 50 µl of Stop/Detection buffer containing 10 mM EDTA, 25 mM HEPES, 0.1% TRITON X-100, 0.126 µg/ml Eu-chelate labeled anti-phosphotyrosine antibody PY20 (cat. # AD0067, PerkinElmer) and 45 µg/ml Streptavidin-allophycocyanin conjugate (cat. # PJ25S, Prozyme); and
5. read HTRF signals on a Victor reader (PerkinElmer) in HTRF mode after 60 minutes.

IC$_{50}$ was obtained by fitting the observed relationship between compound/inhibitor concentration and HTRF signal with a 4-parameter logistic equation.

Compounds of the instant invention are potent inhibitors of recombinant purified JAK2 kinase activity with an IC$_{50}$ of approximately 0.1 nM20 µM.

JAK3 Enzyme Assay

For the JAK3 enzyme assay, reactions (50 uL) contained 5×IVGN buffer (50 mM Hepes, pH 7.5, 10 mM MgCl$_2$, 0.01% Brij-35, 1 mM EGTA, 0.1 mg/ml BSA), 2 mM DTT, 2.0 µM peptide substrate, 25 µM MgATP, 400 pM JAK3 enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103) Peptide substrate is amino hexanoyl biotin-EQEDEPEGDY-FEWLE-NH2 (SEQ. ID NO.: 1); in DMSO.

TYK2 Enzyme Assay

For the TYK2 enzyme assay, reactions (50 uL) contained 5×IVGN buffer (50 mM Hepes, pH 7.5, 10 mM MgCl$_2$, 0.01% Brij-35, 1 mM EGTA, 0.1 mg/ml BSA), 2 mM DTT, 2.0 µM peptide substrate, 15 µM MgATP, 125 µM enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103)

Peptide substrate is amino hexanoyl biotin-EQEDEPEGDY-FEWLE-NH2 (SEQ. ID NO.: 1); in DMSO.

Assay for JAK Family Protein Kinase Activity

Materials: Streptavidin•allophycocyanin conjugate (SA•APC) and Europium•cryptate (Eu•K) were from Packard Instrument Company. Eu•K conjugated pY20 was produced as described in Cummings, R. T.; McGovern, H. M.; Zheng, S.; Park, Y. W. and Hermes, J. D. Use Of A Phosphotyrosine-Antibody Pair As A General Detection Method In Homogeneous Time Resolved Fluorescence-Application To Human Immunodeficiency Viral Protease. *Analytical Biochemistry* 1999, 33, 79-93. Homogenous time resolved fluorescence (HTRF) measurements were made using the Discovery instrument from Packard. T-stim Culture Supplement was from Collaborative Biomedical Research. Recombinant mouse IL2 was from Pharmingen or R & D.

JAK family kinase expression: JAK3, TYK2 and JAK2 kinase domains with N-terminal "Flag" affinity tags were expressed in Sf9 cells using standard baculovirus methods. The human JAK3 gene and the human TYK2 gene can be purchased from Update (now part of Millpore Corporation). Human JAK2 kinase domain was cloned from a MOLT4 cDNA library (Clonetech).

Assay for JAK family protein kinase activity: Tyrosine kinase activity was measured by detection of the tyrosine phosphorylated peptide amino hexanoyl biotin-EQEDEPEGDY-FEWLE-NH2 (SEQ. ID NO.: 1); (S, hereafter) detected by time-resolved fluorescence using a europium labeled antibody to phosphotyrosine (pY20). The JAK3 (JH1) catalyzed phosphorylation reactions were carried out in a 30 uL total reaction volume. The compound was run at 5% DMSO and preincubated with enzyme buffer (EB). The EB comprised Invitrogen 5× kinase buffer (50 mM Hepes, pH 7.5, 10 mM MgCl$_2$, 0.01% Brij-35, 1 mM EGTA, 0.1 mg/ml BSA), 2 mM (final) DTT, 2 µM (final) S, and 250 µM (final) JAK3 enzyme. The assay was run at ATP K$_m$ (5 µM final) for 40 to 80 minutes. Reactions were run at ambient temperature and quenched with an equal volume of quench buffer (QB) (10 mM EDTA, 25 mM HEPES, 0.1% TRITON X-100) containing 50 µg/mL SA•APC conjugate and 0.75 nM Eu•K conjugated pY20. This mixture was incubated at ambient temperature for at least 60 minutes and read on an optimized fluorescent reader at Ex=320 nm and Em$_1$=665 nm (SA-APC) and Em$_2$=615 nM (Eu). The data was analyzed by using a standard 4P fit on the ratio of the Em results: (EM$_1$÷EM$_2$)* 10,000.

JAK2 384-Well HEL irf1-bla AlphaScreen™ SureFire™ p-STAT5 Assay:

Principle: When JAK2 is activated and dimerized, it phosphorylates STAT5 which translocates to the nucleus and actives the transcription of target genes. AlphaScreen™ SureFire™ p-STAT5 assay (Perkin Elmer and TGR Biosciences) uses both biotinylated anti-phospho-STAT5 antibody, which is captured by Streptavidin-coated Donor beads, and anti-total STAT5 antibody, which is captured by Protein A conjugated Acceptor beads. The irf1-bla HEL CellSensor™ cell line was created by transducing parental HEL 92.1.7 cells (ATCC) with the pLenti-bsd/irf1-bla CellSensor™ vector. When both antibodies bind to phospho-STAT5 proteins released from HEL irf1-bla cells, the Donor and Acceptor beads are brought into the close proximity (<=200 nm) and a cascade of chemical reactions is initiated to produce a greatly amplified signal. Upon laser excitation, a photosensitizer in the donor bead converts ambient oxygen to a more excited singlet state. The singlet state oxygen molecules diffuse across to react with a chemiluminescer in the acceptor bead that further activates fluorophores contained within the same bead. The fluorophores subsequently emit light at 520-620 nm. The emitted light intensity is directly proportional to the amount of phospho-STATS proteins released from HEL irf1-bla cells.

Growth Medium: RPMI Medium 1640 (Invitrogen) with 10% dialyzed FBS (Invitrogen), 1 µg/ml blasticidin, 0.1 mM NEAA, 1 mM sodium pyruvate and 1% Pen-Strep.

Method: On day 1, split HEL irf1-bla cells at density of 500,000 cells/ml. Incubate cells in a tissue culture flask at 37° C., 5% $CO_2$ overnight. On day 2, harvest cells and wash the once with HBSS (Invitrogen) containing 0.5% dialyzed FBS. Next, seed cells at a density of 100,000 cells/well in 8 ul of HBSS w/0.5% dialyzed FBS in 384-well microtiter plates. Temporarily put these cell plates in a 37° C., 5% $CO_2$ incubator. To prepare a compound plate, prepare serially diluted compounds in DMSO at a 500× stock concentration. Transfer 2 uL of the serially diluted compounds from the compound plate to an intermediate dilution plate containing 198 uL of HBSS w/0.5% dialyzed FBS. Next, transfer 2 uL of intermediately diluted compounds to each well of the cell plate to get 1:500 final dilution of each test compound and controls. Incubate the cell plates at 37° C., 5% $CO_2$ for 1 hr. Add 2.5 ul/well of 5× lysis buffer from the kit to cell plates. Gently agitate the plates for 5-10 min.

Make detection reagent mixture A by adding together 800 uL reaction buffer, 20 uL acceptor beads, and 200 uL activation buffer. Add 15 uL/well of detection mixture A to the cell plates and gently agitate the plates for 1-2 min. Seal the plates with an adhesive cover and incubate at room temperature for 2 hr, avoiding exposure to light. Make detection mixture B by adding together 400 uL dilution buffer and 20 uL donor beads. Add 6 uL/well of mixture B to the cell plates and gently agitate the plates for 1-2 mM. Seal the plates with an adhesive cover and incubate at room temperature for 2 hr, avoiding exposure to light. Read the plates on an AlphaScreen-capable plate reader.

Compounds of the instant invention are potent inhibitors of pSTAT5 in the HEL irf1-bla AlphaScreen™ SureFire™ p-STAT5 Assay activity with an $IC_{50}$ of <250 nM.

Cellular proliferation assays: CTLL-2 cells (ATCC) were maintained in 6% T-stim Culture Supplement (source of IL2) in RPMI-1640 supplemented with 10% fetal bovine serum, 1 mM sodium pyruvate, 50 µM β-mercaptoethanol, 1.4 mM L-glutamine, 10 mM HEPES, 1 mg/ml dextrose, 0.04 mM essential amino acids, 0.02 mM nonessential amino acids, penicillin and streptomycin (H10). The day before use in the proliferation assay, cells were washed and resuspended in 0.2% Tstim at a cell concentration of $5 \times 10^5$/ml. The next day, cells were washed and plated at $0.2-1 \times 10^5$ cells/well in a 96 well tissue culture plate (CoStar). 0.05 ng/ml mouse recombinant IL2 (Pharmingen), with or without a test compound, or 20 ng/ml PMA (Sigma) and 1 µCi/well [$^3$H]-thymidine were added. After overnight culture, cells were harvested with a glass fiber Filtermat (Wallac) and a Tomtek cell harvester. Tritium incorporation was measured by liquid scintillation counting on a Topcount scintillation counter (Packard).

Compounds of the instant invention are potent inhibitors of recombinant purified JAK3 kinase activity with an $IC_{50}$ of approximately 0.1 nM-20 µM.

In Vitro PDK1 Kinase Assay

Activated recombinant full-length mT(Glu-Glu-Phe) tagged human PDK1 is used to determine whether the compounds of the instant invention modulate the enzymatic activity of this kinase.

The cDNA, encoding full-length PDK1, is subcloned into a baculovirus expression vector pBlueBac4.5 (Invitrogen), containing an in frame middle T tag (MEYMPME) at its N-terminus. Soluble activated recombinant full-length mT(Glu-Glu-Phe) tagged human PDK1 is expressed in a baculovirus-infected Sf9 insect cells (Kemp Biotechnologies), according to the protocol recommended by the manufacturer. Immunoaffinity purification of the PDK1 kinase from the insect cell lysate is performed using a middle Tag antibody bound to Protein G-EE column. Upon elution using 50 mM Tris pH 7.4, 1 mM EDTA, 1 mM EGTA, 0.5 mM $Na_3VO_4$, 1 mM DTT, 50 mM NaF, Na Pyrophospate, Na-β-glycerophosphate, 10% glycerol, Complete, 1 µM microcystein, and 50 µg/ml EYMPME peptide, fractions containing PDK1 protein are pooled together, based on SDS-PAGE and western blot analyses, and then analyzed for protein concentration using BCA Protein Assay (Pierce) with BSA as standard. The final product was aliquoted and flash frozen in liquid nitrogen before being stored at −80° C. Resulting PDK1 protein has MW of 64 kDa, is phosphorylated 'by default' and purifies as an activated kinase from insect cells.

The procedure for determining the potency of a compound to inhibit PDK1 kinase comprises the following steps:
1. Prepare 3-fold serial diluted compound solutions in 100% dimethyl sulfoxide (DMSO) at 20× of the desired final concentrations in a 384-well plate.
2. Prepare a master reaction mix containing 62.5 mM HEPES (pH 7.5), 12.5 mM $MgCl_2$, 0.013% Brij-35, 1.25 mM EGTA, 2.5 mM dithiothreitol, 1.25 nM recombinant PDK1 and 375 nM biotinylated synthetic peptide substrate (Biotin-GGDGATMKTFCGGTPSDGDP-DGGEFTEF-COOH) (SEQ. ID NO.: 2).
3. In a black assay plate, add 2.5 µl of compound solution (or DMSO) and 22.5 µl of master reaction mix per well. Pre-incubate for 10 mM. Initiate the kinase reaction by adding 6 µl of 0.25 mM MgATP per well. Allow the reactions to proceed for 25 mM at room temperature. The final conditions for the reaction are 1 nM PDK1, 300 nM peptide substrate, 5 µM MgATP, 10 mM $MgCl_2$, 2 mM DTT, 50 mM HEPES (pH 7.5), 0.01% Brij-35, 1 mM EGTA and 5% DMSO.
4. Stop the kinase reaction with 30 µl of Stop/Detection buffer containing 10 mM EDTA, 1× Lance Detection Buffer (cat. # CR97-100, PerkinElmer), 1% Super-Blocking in TBS (cat. #37535, Pierce), 5 nM phospho-Akt(T308) monoclonal antibody (cat. #4056, Cell Signaling Technologies), 5 nM Lance labeled Eu-Anti-rabbit IgG (cat. # AD0083, PerkinElmer), and 100 nM Streptavidin-allophycocyanin conjugate (cat. # PJ25S, Prozyme).
5. Read HTRF signals on an Envision reader (PerkinElmer) in HTRF mode after 60 min.
6. IC50 is determined by fitting the observed relationship between compound concentration and HTRF signal with a 4-parameter logistic equation.

The compounds 1 to 419 in the Examples were tested in the above assay and found to have an $IC_{50}$ 50 µM.

Cell Biochemical Assay for PDK1 Inhibition

Objective: To determine the inhibitory potency of PDK1 inhibitors on the PI3'K pathway in PC3 cells using Odyssey Western Blot Analysis and a cocktail of Phosphospecific antibodies to two direct PDK1 substrates RSK(Ser221) and AKT (Thr308) and the downstream effector molecule S6RP(235/236).

Cells: PC-3 cells grown in Earle's MEM with 10% FBS, 1×L-Glutamine, 1× Non Essential Amino Acids, 1× NaPyruvate and 1× Hepes. Other cells may be used.

Reagents:
  Primary Antibodies:
    P*Akt 308—Cell Signalling, Cat. #4056
    P*RSKS221—Biosource Cat. #44 924G
    P*S6RP235/236—Cell Signalling Cat#2211
    P*-p44/42 MAP kinase (Thre202/Tyr204)—Cell signaling Cat. #9101
    Total eIF4E—Cell signaling Cat. #9742
  Secondary Antibody:
    Infrared (1R)-labeled goat anti-mouse IRDye 600 (LI-COR Cat. #926-32221)
    Infrared (1R)-labeled goat anti-rabbit IRDye 800CW (LI-COR Cat. #926-32210)
  Reference Compounds (Pathway Inhibitors)
    Rapamycin—Calbiochem, 553211
    LY294002—Calbiochem, 440204
    Protease Inhibitor Tablets—Roche 11836145001
    PageRuler Prestained Protein Ladder—Fermentas, SM0671
    Nitrocellulose membrane
Buffers/Solutions
  Lysis Stock (Store at 4° C.)
  20 mM TrisHCl, pH 7.5
  150 mM NaCl
  15% Glycerol
  1% Igepal
  Complete Lysis Buffer
  1.25 mL of 1M β-Glycerolphosphate
  5 mL of 0.5M NaF
  5 mL of 0.1M NaPPi
  0.5 mL of 100 mM Sodium Orthovanadate
  1 protease inhibitor tablet
  Fill to 50 mL with Lysis Stock, make 10 mL aliquots and freeze. To one aliquot, add 100 uL of 200 mM PMSF before use.
  TBS-Tween
  20 mM TrisHCl, pH 7.5
  150 mM NaCl
  0.05% Tween-20
  TBS
  20 mM TrisHCl, pH 7.5
  150 mM NaCl
  Blocking Buffer
  Odyssey Blocking Buffer (LI-COR, Cat. #927-40000)
  Primary Diluent
  4% BSA fractions in PBS
  0.02% Tween-20
  0.5% Sodium Azide
  4×SDS Sample Buffer
Sample Protocol
Seed Cells 24 Hours Before Compound Stimulation in Full Growth Medium
  1. Allow PC-3 cell growth in a T150 flask using standard tissue culture procedures until cells reach near confluence ($1.0 \times 10^7$).
  2. Remove growth media, wash cells with sterile 1×PBS, and trypsinised cells for displacement using 3 ml Trypsin
  3. Neutralize displaced cells with 30 ml of culture media and transfer to a 50 ml tube.
  4. Vortex briefly the tube to resuspend and mix cell suspension thoroughly.
  5. Count cells and dilute with media to a conc of 150,000 cells per mL.
  6. Dispense 1 ml of the cell suspension to each well in a 12 well plate using a repeat pipetter and incubate for 24 hours in 37° C., 5% $CO_2$.

Compound Stimulation
  1. Make a 3 fold dilution series of PDK1 inhibitors in DMSO using a 96 well master plate (7 different compound concentrations and a no compound DMSO control). Concentration should be 200× of the final conc used in the assay.
  2. To stimulate cells, add 5 uL compound/DMSO to each well with cells and incubate for 24 hours in 37° C., 5% CO2.
Cell Lysis
  1. The following day, remove growth media, wash with cold 1×PBS and remove PBS completely before adding 100 uL of lysis buffer to each well.
  2. Shake plates on shaker for 10 min in the cold room
  3. Collect lysate from each well and transfer to 1.5 mL eppendorf tube standing on ice.
  4. Spin down at 13,000 rpm at 4° C. for 5 min.
  5. Transfer 90 uL of lysate into new eppendorf tube containing 30 uL of 4×SDS loading buffer.
  6. Place tube in 70° C. heat block for 7 min and store sample at −80° C.
Western Blot Detection
  1. Run samples on 18 well 10% or 4-20% Tris-Glycine Biorad gels (70V, constat 40 min) loading 30 uL sample per well and 2 uL pre-stained molecular weight marker. Load ladder in the first and ninth well
  2. Blot onto nitrocellulose using Bio-Rad system (70V, 350 mA, 40 min)
  3. Block the membrane for non-specific binding in Odessy Blocking buffer for 1 hr at RT.
  4. Dilute the primary antibodies in Odyssey blocking buffer containing 0.1% Tween 20. (i.e. make a cocktail of the three antibodies (P*AKT, P*S6RP and P*RSK) by diluting each 1:1000). Incubate shaking overnight in cold room
  5. Wash membrane 4×5 min at RT in PBS with 0.1% Tween 20.
  6. Dilute the fluorescently-labeled secondary antibodies (1:10,000) in Odessey Blocking Buffer containing 0.1% Tween
  7. Incubate blote in secondary antibody for 60-90 min at RT. Avoid prolonged exposure to light.
  8. Wash membrane 4×5 min at RT in PBS with 0.1% Tween 20. Protect from light.
  9. Rinse membrane in PBS to remove residual Tween-20. The membrane is now ready to scan.
Scan Membrane
  1. Scan in the appropriate channels and protect the membrane from light until it has been scanned. The signal will be stable for several months, if protected from light. Membrane may be stores in PBS buffer at 4° C. or stored dry.
  2. Quantify the bands using the Odessy software and normalize to loading control (mab)
Cellular proliferation assays. CTLL-2 cells (ATCC) were maintained in 6% T-stim Culture Supplement (source of IL2) in RPMI-1640 supplemented with 10% fetal bovine serum, 1 mM sodium pyruvate, 50 µM β-mercaptoethanol, 1.4 mM L-glutamine, 10 mM HEPES, 1 mg/ml dextrose, 0.04 mM essential amino acids, 0.02 mM nonessential amino acids, penicillin and streptomycin (H10). The day before use in the proliferation assay, cells were washed and resuspended in 0.2% Tstim at a cell concentration of $5 \times 10^5$/ml. The next day, cells were washed and plated at $0.2$-$1 \times 10^5$ cells/well in a 96 well tissue culture plate (CoStar). 0.05 ng/ml mouse recombinant IL2 (Pharmingen), with or without a test compound, or 20 ng/ml PMA (Sigma) and 1 µCi/well [$^3$H]-thymidine were added. After overnight culture, cells were harvested with a glass fiber Filtermat (Wallac) and a Tomtek cell harvester. Tritium incorporation was measured by liquid scintillation counting on a Topcount scintillation counter (Packard).

Compounds of the instant invention are potent inhibitors of recombinant purified JAK3 kinase activity with an $IC_{50}$ of approximately 0.1 nM-20 µM.

PC3 Cell Proliferation Assay

Growth Medium: F12 Kaighn's (Gibco #21127) with 10% FBS and 1% HEPES

Method:

Day 1: Seed PC-3 cells in 36 ul of Growth Medium at 1000 cells/well in Costar black clear bottom 384-well plates (Corning 3712). Incubate Cell Plates at 37° C. overnight.

Day 2: 1. Complete the Compound Plate (the low volume 384-well round bottom plate, Corning 3672) which has 20 ul of 10 mM cherry picked compounds in wells of column 3, B3-O3 and column 13, B13-O13, (highest final concentration of each compound in cells is 50 uM).
  1.) Add 7 ul DMSO (High Control, 0% inhibition, final concentration in cells is 0.5%) in column 2, B2-H2 and column 23, I23-O23.
  2.) Add 7 ul of 200 uM Stautosporine (Low Control, 100% inhibition, final concentration in cells is 1 uM) in column 2, I2-O2 and column 23, B23-H23.
  3.) Add 20 ul of 3 internal controls in the last three wells of the Compound Plate, which are a PDK1 inhibitor, 200 uM Staurosporine, (highest final concentration in cells is 1 uM), and 400 uM Taxol (highest final concentration in cells is 2 uM).
2. Make half-log serial dilution in DMSO for Compound Plate 3. Transfer 5 ul of serially diluted compounds from Compound Plate to Intermediate Dilution Plate (Greiner Bio-One 781281) containing 95 ul of Growth Medium to get 1:20 intermediate dilution, and then transfer 4 ul of intermediately diluted compounds to duplicated Cell Plates to get 1:200 final dilution of each compound and control.

The final concentration series of test compounds in cells with 10-point half-log serial dilution are 50000 nM, 15000 nM, 5000 nM, 1500 nM, 500 nM, 150 nM, 50 nM, 15 nM, 5 nM, and 1.5 nM.

4. Incubate the Cell Plates at 37° C. for 72 hr.

Day 5: Perform ViaLight Proliferation Assay from ViaLight Plus kit (Cambrex LT07-321) for Cell Plates after 72 hr compound treatment.
  1. Bring all ViaLight reagents to room temperature before use. Reconstitute ATP Monitoring Reagent Plus (AMR PLUS) in supplied Assay Buffer. Let equilibrate to room temperature for at least 1 hr.
  2. Remove 72 hr compound treated Cell Plates from incubator and equilibrate to room temperature for at least 5 min.
  3. Transfer 10 ul of ViaLight Cell Lysis Reagent to each well. Incubate plates at room temperature for 10 min.
  4. Transfer 30 ul of Assay Buffer to each well. Incubate plates at room temperature for 2 min.
  5. Read plates by Perkin Elmer Viewlux.

While a number of embodiments of this invention have been described, it is apparent that the basic examples may be altered to provide other embodiments, encompassed by the present invention. Therefore, it will be appreciated that the scope of this invention is to be defined by the appended claims rather than by the specific embodiments, which have been represented by way of example.

What is claimed is:
1. A compound of formula I

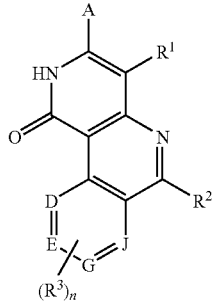

wherein D is CH;
E is N;
G is CH;
J is CH;
$R^1$ is
hydrogen or halogen;
$R^2$ is $NR^5R^6$;
$R^3$ is
- (a) hydrogen;
- (b) $C_{1-6}$ alkyl, which is optionally substituted with halo, hydroxyl, amino, phenyl, heterocyclyl, $C_{1-6}$ alkyl or $R^{10}$;
- (c) $C_{2-6}$ alkenyl, which is optionally substituted with halo, hydroxyl, amino, phenyl, heterocyclyl or $C_{1-6}$ alkyl;
- (d) $C_{2-6}$ alkynyl, which is optionally substituted with one or two substituents independently selected from halo, hydroxyl, amino, phenyl (which is optionally substituted with $C_{1-6}$ alkyl), heterocyclyl, heteroaryl, $C_{1-6}$ alkyl or $Si(CH_3)_3$;
- (e) $C_{3-10}$ cycloalkyl, which is optionally substituted with $C_{1-6}$ alkyl, $-OR^{13}$, $-NR^{13}R^{14}$, phenyl (which is optionally substituted with $C_{1-6}$ alkyl, $-OR^{13}$ or $-NR^{13}R^{14}$), halo, $R^{10}$ or heterocyclyl;
- (f) $-(C=O)R^{11}$;
- (g) $-(C=O)NR^9R^{13}$;
- (h) $-(C=O)NHNH(C=O)R^{11}$;
- (i) $C_{4-10}$ heterocyclyl, which is optionally substituted on either the carbon or the heteroatom with $C_{1-6}$ alkyl, halo, $R^{10}$, $-OR^{13}$, $-NR^{13}R^{14}$, phenyl (which is optionally substituted with $C_{1-6}$ alkyl, $OR^{13}$ or $NR^{13}R^{14}$), $-(C=O)R^9$ or $-(C=O)NR^{13}R^{14}$;
- (j) $-OR^{13}$;
- (k) $-NH(C=O)R^{11}$;
- (l) halo;
- (m) Aryl, which is optionally substituted with one to three groups independently selected from $C_{1-6}$ alkyl (which is optionally substituted with one to three halo, cyano or heterocyclyl), halo, heterocyclyl, or $R^{10}$;
- (n) Heteroaryl, which is optionally substituted on either the carbon or the heteroatom with one to three groups independently selected from $C_{1-6}$ alkyl (which is optionally substituted with one to three halo or hydroxy), halo, heterocyclyl, $R^{10}$ or $R^{11}$;
- (o) $-O(aryl)$, which is optionally substituted with one to three groups independently selected from $C_{1-6}$ alkyl, halo or $R^{10}$;
- (p) $-O(C_{1-6}$ alkyl), which is optionally substituted with one to three groups independently selected from $C_{1-6}$ alkyl, halo or $R^{10}$;
- (q) $-SO_m(C_{1-6}$ alkyl); or
- (r) $-SO_m(aryl)$;

$R^4$ is
- (a) hydrogen;
- (b) $C_{1-6}$ alkyl, which is optionally substituted with halo, hydroxyl, amino, aryl or heterocyclyl;

$R^5$ is
- (a) $C_{1-6}$ alkyl, which is optionally substituted with one to three substituents independently selected from halo, cyano, $C_{1-6}$ alkyl, $C_{3-10}$ cycloalkyl, $C_{1-6}$ haloalkyl, aryl, $-NR^{13}R^{14}$, $Si(CH_3)_3$, $SO_m(C_{1-6}$ alkyl), $-(C=O)OR^{13}$, $OR^{13}$ or hydroxyl;
- (b) $C_{3-10}$ cycloalkyl, which is optionally substituted with one to three substituents independently selected from halo, aryl, $(C_{1-6}$ alkyl)OH or $C_{1-6}$ alkyl;
- (c) aryl, which is optionally substituted with one to three substituents independently selected from halo, $C_{1-6}$ alkyl, aryl, hydroxyl, O(heteroaryl), $C_{1-6}$ haloalkyl or heteroaryl;
- (d) heteroaryl;
- (e) $(C_{1-6}$ alkyl)(aryl), which is optionally substituted on the alkyl and aryl groups with one to three substituents independently selected from halo, cyano, $C_{1-6}$ alkyl, $C_{1-6}$ haloalkyl, $C_{3-10}$ cycloalkyl or $O(C_{1-6}$ alkyl);
- (f) $(C_{1-6}$ alkyl)(heteroaryl), which is optionally substituted on the alkyl and heteroaryl groups with one to three substituents independently selected from halo, $C_{1-6}$ haloalkyl or $C_{1-6}$ alkyl;
- (g) $(C_{1-6}$ alkyl)(heterocyclyl);
- (h) heterocyclyl, which is optionally substituted with one to four substituents independently selected from halo, $R^7$, $(C_{1-6}$ alkyl)$R^7$, $(C=O)R^7$, $(C=O)OR^7$, $(C=O)NHR^7$, $(SO_m)R^9$
- (i) $C_{1-6}$ alkyl)$(C_{3-10}$ cycloalkyl) which is optionally substituted on the alkyl with aryl;
- (j) $C_{1-6}$ alkyl$(C=O)OH$;

$R^6$ is
hydrogen;
$R^7$ is
- (a) hydrogen;
- (b) $C_{1-6}$ alkyl, which is optionally substituted with halo, cyano, hydroxyl, amino, aryl (which is optionally substituted with halo, $C_{1-6}$ alkyl, $O(C_{1-6}$ alkyl) or $NR^8R^9$), heterocyclyl, $C_{3-10}$ cycloalkyl, $C_{1-6}$ haloalkyl, $NH(C=O)R^{13}$, $SO_mNR^{13}R^{14}$ or $NR^{13}R^{14}$;
- (c) $C_{3-10}$ cycloalkyl, which is optionally substituted with one to three substituents independently selected from halo, hydroxyl, $C_{1-6}$ alkyl, $C_{1-6}$ haloalkyl, $-OR^4$, $-NR^8R^4$ or phenyl (which is optionally substituted with $C_{1-6}$ alkyl, $-OR^4$, $-NR^8R^4$, heterocyclyl, $-(CO)R^8$ or $-(CO)NR^8R^9$);
- (d) $C_{4-10}$ heterocyclyl which is optionally substituted on either the carbon or the heteroatom with one to three substituents independently selected from halo, $C_{1-6}$ alkyl, $-OR^{13}$, $-NR^{13}R^{14}$, phenyl (which is optionally substituted with $C_{1-6}$ alkyl, $-OR^{13}$, $-NR^{13}R^{14}$, heterocyclyl, $-(CO)R^9$ or $-(CO)-NR^{13}R^{14}$);
- (e) Aryl, which is optionally substituted with one to three substituents independently selected from halo, $NR^{13}R^{14}$ or $C_{1-6}$ haloalkyl;
- (f) Heteroaryl, which is optionally substituted on either the carbon or heteroatom with $NR^{13}R^{14}$;

$R^8$ is hydrogen, $C_{1-6}$ alkyl, $(C_{1-6}$ alkyl)aryl, $(C_{1-6}$ alkenyl) aryl, $(C_{1-6}$ alkyl)$OR^9$, $-OR^{13}$, $-NR^{13}R^{14}$, $-(CO)$ NR$^{13}$R$^{14}$, heterocyclyl or phenyl (which is optionally substituted with C$_{1-6}$ alkyl, —OR$^{13}$, —NR$^{13}$R$^{14}$, heterocyclyl, —(CO)R$^9$ or —(CO)—NR$^{13}$R$^{14}$);

R$^9$ is hydrogen, C$_{1-6}$ alkyl, (C$_{1-6}$ alkyl)aryl, (C$_{1-6}$ alkyl)heterocyclyl, heteroaryl, heterocyclyl, C$_{3-6}$ cycloalkyl or —NR$^{13}$NR$^{14}$;

R$^{10}$ is:
(a) hydrogen;
(b) —OR$^{11}$;
(c) —O(C$_{1-6}$ haloalkyl);
(b) —CO$_2$R$^{11}$;
(c) —(C=O)R$^{11}$;
(d) —NHR$^{11}$;
(e) —NR$^{11}$R$^{12}$;
(f) —NHS(O)$_2$R$^{11}$;
(g) —NH(C=O)R$^{11}$;
(h) —NH(C=O)OR$^{11}$;
(i) —NH—C=(NH)NH$_2$;
(j) —NH(C=O)NH$_2$;
(k) —NH(C=O)NHR$^{11}$;
(l) —NH(C=O)NR$^{11}$R$^{12}$;
(m) —NHC$_{3-6}$cycloalkyl;
(n) —(C=O)NHR$^{11}$;
(o) —(C=O)NR$^{11}$R$^{12}$;
(p) —SO$_2$NHR$^{11}$;
(q) —SO$_2$NH(C=O)R$^{12}$; or
(r) —SO$_2$R$^{11}$;
(s) heterocyclyl;

R$^{11}$ is selected from the group consisting of:
(a) hydrogen,
(b) C$_{3-6}$cycloalkyl, which is optionally substituted with aryl, heteroaryl or one to five halo;
(c) C$_{1-6}$alkyl, which is optionally substituted with aryl, heteroaryl, heterocyclyl, cyano, NR$^{13}$R$^{14}$, OR$^{13}$ or one to five halo;
(d) Aryl, which is optionally substituted with one to five halo;
(e) Heteroaryl (wherein the heteroaryl has 5 or 6 members in which 1, 2, 3 or 4 of the atoms is a heteroatom selected from N, S and O), which is optionally substituted on either the carbon or the heteroatom with one to five halo;
(f) Heterocyclyl, which is optionally substituted with (C$_{1-6}$alkyl)OH;

R$^{12}$ is selected from the group consisting of:
(a) hydrogen,
(b) C$_{1-6}$alkyl, which is optionally substituted with aryl, heteroaryl or one to five halo;
(c) C$_{3-6}$cycloalkyl, which is optionally substituted with aryl, heteroaryl or one to five halo;
(d) Aryl, which is optionally substituted with one to five halo;
(e) Heteroaryl (wherein the heteroaryl has 5 or 6 members in which 1, 2 3 or 4 of the atoms is a heteroatom selected from N, S and O), which is optionally substituted on either the carbon or the heteroatom with one to five halo;

R$^{13}$ is hydrogen or C$_{1-6}$ alkyl;
R$^{14}$ is hydrogen or C$_{1-6}$ alkyl;
A is
hydrogen;
(o)
m is 0, 1 or 2;
n is 0;
or a pharmaceutically acceptable salt or stereoisomer thereof.

2. The compound of claim 1 wherein R$^5$ is
(a) C$_{1-6}$ alkyl, which is optionally substituted with one to three substituents independently selected from halo, C$_{1-6}$ alkyl, C$_{3-6}$ cycloalkyl, C$_{1-6}$ haloalkyl, aryl, —NR$^{13}$R$^{14}$ or hydroxyl; or
(b) aryl, which is optionally substituted with one to three substituents independently selected from halo, C$_{1-6}$ alkyl, aryl, hydroxyl, —O(heteroaryl) or heteroaryl;
or a pharmaceutically acceptable salt or stereoisomer thereof.

3. The compound of claim 2 wherein R$^5$ is C$_{1-6}$ alkyl, which is substituted with one to three substituents independently selected from halo or C$_{1-6}$ haloalkyl; or a pharmaceutically acceptable salt or stereoisomer thereof.

4. The compound of claim 3 wherein R$^5$ is C$_{1-6}$ alkyl, which is substituted with trifluoromethyl; or a pharmaceutically acceptable salt or stereoisomer thereof.

5. A compound which is
6-{[(1R)-2-methyl-1-(trifluoromethyl)propyl]amino}pyrido[4,3-c]-1,6-naphthyridin-1(2H)-one;
6-{[1-(2,4-dichloro-5-fluorophenyl)ethyl]amino}pyrido[4,3-c]-1,6-naphthyridin-1(2H)-one;
6-[(2,2,2-trifluoroethyl)amino]pyrido[4,3-c]-1,6-naphthyridin-1(2H)-one;
6-[(3-thienylmethyl)amino]pyrido[4,3-c]-1,6-naphthyridin-1(2H)-one;
6-[(1,3-thiazol-2-ylmethyl)amino]pyrido[4,3-c]-1,6-naphthyridin-1(2H)-one;
6-[(pyridin-2-ylmethyl)amino]pyrido[4,3-c]-1,6-naphthyridin-1(2H)-one;
6-{[(5-methylisoxazol-3-yl)methyl]amino}pyrido[4,3-c]-1,6-naphthyridin-1(2H)-one;
tert-butyl (3S)-3-[(1-oxo-1,2-dihydropyrido[4,3-c]-1,6-naphthyridin-6-yl)amino]piperidine-1-carboxylate;
6-(benzylamino)pyrido[4,3-c]-1,6-naphthyridin-1(2H)-one;
6-(methylamino)pyrido[4,3-c]-1,6-naphthyridin-1(2H)-one;
6-(dimethylamino)pyrido[4,3-c]-1,6-naphthyridin-1(2H)-one;
6-(benzylamino)pyrido[4,3-c]-1,6-naphthyridin-1(2H)-one;
6-{[(1R)-1,2,2-trimethylpropyl]amino}pyrido[4,3-c]-1,6-naphthyridin-1(2H)-one;
6-{[(1S)-1,2,2-trimethylpropyl]amino}pyrido[4,3-c]-1,6-naphthyridin-1(2H)-one;
4-iodo-6-[(1,2,2-trimethylpropyl)amino]pyrido[4,3-c]-1,6-naphthyridin-1(2H)-one;
4-iodo-6-[(1,3-thiazol-2-ylmethyl)amino]pyrido[4,3-c]-1,6-naphthyridin-1(2H)-one;
4-iodo-6-[(2,2,2-trifluoroethyl)amino]pyrido[4,3-c]-1,6-naphthyridin-1(2H)-one;
4-iodo-6-{[(5-methylisoxazol-3-yl)methyl]amino}pyrido[4,3-c]-1,6-naphthyridin-1(2H)-one;
tert-butyl (3S)-3-[(4-iodo-1-oxo-1,2-dihydropyrido[4,3-c]-1,6-naphthyridin-6-yl)amino]piperidine-1-carboxylate;
4-iodo-6-[(pyridin-2-ylmethyl)amino]pyrido[4,3-c]-1,6-naphthyridin-1(2H)-one;
or a pharmaceutically acceptable salt or stereoisomer thereof.

6. A pharmaceutical composition comprising a pharmaceutically effective amount of the compound according to claim 1, and a pharmaceutically acceptable carrier.

7. A method of treating a myeloproliferative disorder in a mammal in need thereof with a therapeutically effective amount of a compound of claim 1, wherein the myeloproliferative disorder is selected from polycythemia vera (PV), essential thrombocythemia (ET), myeloid metaplasia with myelofibrosis (MMM), chronic myelogenous leukemia (CML), myelomonocytic leukemia (CMML), hypereosinophilic syndrome (HES), juvenile myelomonocytic leukemia (JMML), or systemic mast cell disease (SMCD).

8. A pharmaceutical composition comprising a pharmaceutically effective amount of the compound according to claim 5, and a pharmaceutically acceptable carrier.

9. A method of treating a myeloproliferative disorder in a mammal in need thereof with a therapeutically effective amount of a compound of claim 5, wherein the myeloproliferative disorder is selected from polycythemia vera (PV), essential thrombocythemia (ET), myeloid metaplasia with myelofibrosis (MMM), chronic myelogenous leukemia (CML), myelomonocytic leukemia (CMML), hypereosinophilic syndrome (HES), juvenile myelomonocytic leukemia (JMML), or systemic mast cell disease (SMCD).

* * * * *

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Completely synthetic
<220> FEATURE:
<221> NAME/KEY: AMIDATION
<222> LOCATION: (1)...(1)

<400> SEQUENCE: 1

Glu Gln Glu Asp Glu Pro Glu Gly Asp Tyr Phe Glu Trp Leu Glu
1               5                   10                  15

<210> SEQ ID NO 2
<211> LENGTH: 28
<212> TYPE: PRT
<213> ORGANISM: Artificial Sequence
<220> FEATURE:
<223> OTHER INFORMATION: Completely synthetic

<400> SEQUENCE: 2

Gly Gly Asp Gly Ala Thr Met Lys Thr Phe Cys Gly Gly Thr Pro Ser
1               5                   10                  15

Asp Gly Asp Pro Asp Gly Gly Glu Phe Thr Glu Phe
            20                  25
```